(12) United States Patent
Eastham et al.

(10) Patent No.: US 8,445,711 B2
(45) Date of Patent: May 21, 2013

(54) METAL COMPLEXES

(75) Inventors: Graham Ronald Eastham, Durham (GB); Neil Tindale, Cleveland (GB)

(73) Assignee: Lucite International UK Limited, Southhampton Hampshire (GB)

( * ) Notice: Subject to any disclaimer, the term of this patent is extended or adjusted under 35 U.S.C. 154(b) by 901 days.

(21) Appl. No.: 12/297,023

(22) PCT Filed: Apr. 10, 2007

(86) PCT No.: PCT/GB2007/050189
§ 371 (c)(1),
(2), (4) Date: Mar. 20, 2009

(87) PCT Pub. No.: WO2007/119079
PCT Pub. Date: Oct. 25, 2007

(65) Prior Publication Data
US 2009/0312561 A1  Dec. 17, 2009

(30) Foreign Application Priority Data
Apr. 13, 2006 (GB) .................................. 0607494.2

(51) Int. Cl.
C07F 9/02 (2006.01)
C07F 15/00 (2006.01)
(52) U.S. Cl.
USPC .................................. 556/19; 556/9; 549/206
(58) Field of Classification Search
USPC ........................................ 556/9, 19; 549/206
See application file for complete search history.

(56) References Cited

U.S. PATENT DOCUMENTS

| | | |
|---|---|---|
| 3,131,204 A | 4/1964 | Sisler et al. |
| 3,564,020 A | 2/1971 | Fenton |
| 4,245,115 A | 1/1981 | Butter |
| 4,377,708 A | 3/1983 | Morris |
| 4,500,727 A | 2/1985 | Kitamura et al. |
| 4,504,684 A | 3/1985 | Fox et al. |
| 4,517,061 A | 5/1985 | Fauvarque |
| 4,786,443 A | 11/1988 | Drent et al. |

(Continued)

FOREIGN PATENT DOCUMENTS

| | | |
|---|---|---|
| AU | 2003259322 A1 | 2/2004 |
| CN | 1478071 A | 2/2004 |

(Continued)

OTHER PUBLICATIONS

Andrews et al., Inorganic Chemistry, vol. 35, No. 19, pp. 5478-5483 (1996).*

(Continued)

*Primary Examiner* — Porfirio Nazario Gonzalez
(74) *Attorney, Agent, or Firm* — Venable LLP; Keith G. Haddaway; Lars H. Genieser

(57) ABSTRACT

The invention concerns metal complexes and their preparation, in particular a metal complex MLnXm, where M is a metal of group 8, 9 or 10 and X is a halide, HCO3-, NO3-, CO32- or carboxylate. n is a number equal to or less than the coordination number of the metal and m is 1 or 2 and is equal to the oxidation state of the metal. The ligand L may be a bidentate phosphine of formula (I), (II), (III) or (IV) as set out herein. The process of production comprises reacting an ammine compound of metal M with a complexing compound, which is preferably a phosphine.

16 Claims, 1 Drawing Sheet

U.S. PATENT DOCUMENTS

| | | |
|---|---|---|
| 4,818,810 A | 4/1989 | Drent |
| 4,835,250 A | 5/1989 | Drent |
| 4,868,282 A | 9/1989 | Van Broekhoven et al. |
| 4,880,903 A | 11/1989 | Van Broekhoven et al. |
| 4,900,413 A | 2/1990 | Sakakura et al. |
| 4,950,703 A | 8/1990 | Smutny |
| 4,960,926 A | 10/1990 | Drent |
| 4,960,949 A | 10/1990 | Devon et al. |
| 5,028,576 A | 7/1991 | Drent et al. |
| 5,099,062 A | 3/1992 | Drent et al. |
| 5,103,043 A | 4/1992 | Drent et al. |
| 5,149,868 A | 9/1992 | Drent |
| 5,158,921 A | 10/1992 | Drent et al. |
| 5,166,116 A | 11/1992 | Drent et al. |
| 5,177,253 A | 1/1993 | Drent et al. |
| 5,179,225 A | 1/1993 | Drent et al. |
| 5,189,003 A | 2/1993 | Klusener et al. |
| 5,210,280 A | 5/1993 | Drent |
| 5,245,098 A | 9/1993 | Summers et al. |
| 5,246,558 A | 9/1993 | Chevigne et al. |
| 5,258,546 A | 11/1993 | Klusener et al. |
| 5,350,876 A | 9/1994 | Drent et al. |
| 5,369,074 A | 11/1994 | Drent |
| 5,436,356 A | 7/1995 | Drent et al. |
| 5,563,308 A | 10/1996 | Spindler et al. |
| 5,710,344 A | 1/1998 | Breikss et al. |
| 5,719,313 A | 2/1998 | Drent et al. |
| 5,760,264 A | 6/1998 | Brieden |
| 5,773,661 A | 6/1998 | Unruh et al. |
| 5,783,715 A | 7/1998 | Pugin |
| 5,962,732 A | 10/1999 | Burke |
| 6,015,919 A | 1/2000 | Pugin |
| 6,156,934 A | 12/2000 | Suykerbuyk et al. |
| 6,169,192 B1 | 1/2001 | Pugin et al. |
| 6,191,284 B1 | 2/2001 | Knochel et al. |
| 6,232,262 B1 | 5/2001 | Sielcken et al. |
| 6,258,979 B1 | 7/2001 | Kagan et al. |
| 6,284,919 B1 | 9/2001 | Pearson et al. |
| 6,284,925 B1 | 9/2001 | Knochel et al. |
| 6,307,065 B1 | 10/2001 | Tjaden et al. |
| 6,335,471 B1 | 1/2002 | Eastham et al. |
| 6,337,406 B1 | 1/2002 | Zhang |
| 6,348,621 B1 | 2/2002 | Wang et al. |
| 6,391,818 B1 | 5/2002 | Bonsel et al. |
| 6,462,095 B1 | 10/2002 | Bonsel et al. |
| 6,476,255 B1 | 11/2002 | Hadden et al. |
| 6,521,769 B1 | 2/2003 | Zhang |
| 6,706,912 B2 | 3/2004 | Drent et al. |
| 6,723,882 B2 | 4/2004 | Slany et al. |
| 6,743,911 B2 | 6/2004 | Drent et al. |
| 6,753,450 B2 | 6/2004 | Ahlers et al. |
| 6,844,463 B2 * | 1/2005 | Slany et al. ............ 558/357 |
| 6,916,954 B2 | 7/2005 | Schafer et al. |
| 6,982,357 B2 | 1/2006 | Crabtree et al. |
| 6,984,668 B1 | 1/2006 | Eastham et al. |
| 7,026,473 B2 | 4/2006 | Drent et al. |
| 7,129,367 B2 * | 10/2006 | Suzuki et al. ............ 556/21 |
| 7,148,176 B2 | 12/2006 | Beller et al. |
| 7,265,240 B2 | 9/2007 | Eastham et al. |
| 7,371,705 B2 | 5/2008 | Eastham et al. |
| 2001/0044556 A1 | 11/2001 | Drent et al. |
| 2001/0051745 A1 | 12/2001 | Pearson et al. |
| 2002/0016484 A1 | 2/2002 | Drent et al. |
| 2002/0045748 A1 | 4/2002 | Drent et al. |
| 2003/0191339 A1 | 10/2003 | Schfer et al. |
| 2004/0110989 A1 | 6/2004 | Slany et al. |
| 2004/0115475 A1 | 6/2004 | Hashimoto |
| 2004/0162440 A1 | 8/2004 | Bunel et al. |
| 2005/0090694 A1 | 4/2005 | Drent et al. |
| 2006/0106259 A1 | 5/2006 | Eastham et al. |
| 2006/0122435 A1 | 6/2006 | Eastham et al. |
| 2006/0128985 A1 | 6/2006 | Eastham et al. |
| 2006/0235241 A1 | 10/2006 | Drent et al. |
| 2006/0252935 A1 | 11/2006 | Eastham et al. |
| 2008/0086015 A1 | 4/2008 | Eastham |
| 2008/0269459 A1 | 10/2008 | Drent et al. |
| 2008/0269520 A1 | 10/2008 | Drent et al. |
| 2009/0163724 A1 | 6/2009 | Eastham et al. |
| 2009/0216041 A1 | 8/2009 | Eastham et al. |
| 2009/0234126 A1 | 9/2009 | Hartwig et al. |
| 2009/0312561 A1 | 12/2009 | Eastham et al. |
| 2010/0030036 A1 | 2/2010 | Mottram et al. |
| 2010/0197958 A1 | 8/2010 | Eastham et al. |
| 2010/0324332 A1 | 12/2010 | Carrington-Smith et al. |

FOREIGN PATENT DOCUMENTS

| | | |
|---|---|---|
| CN | 101137611 A | 3/2008 |
| CN | 101142162 A | 3/2008 |
| DE | 19745904 A1 | 4/1999 |
| DE | 19754304 A1 | 6/1999 |
| DE | 10023470 A1 | 11/2001 |
| DE | 10037961 A1 | 2/2002 |
| EP | 0055875 A1 | 7/1982 |
| EP | 0106379 A1 | 4/1984 |
| EP | 121965 A2 | 10/1984 |
| EP | 0144118 | 6/1985 |
| EP | 181014 A1 | 5/1986 |
| EP | 213671 A1 | 3/1987 |
| EP | 0227160 A2 | 7/1987 |
| EP | 0235864 A1 | 9/1987 |
| EP | 0274795 A2 | 7/1988 |
| EP | 0282142 A1 | 9/1988 |
| EP | 0305089 A1 | 3/1989 |
| EP | 0375573 A1 | 6/1990 |
| EP | 0386833 A1 | 9/1990 |
| EP | 0441447 A1 | 8/1991 |
| EP | 0489472 A2 | 6/1992 |
| EP | 0495347 A1 | 7/1992 |
| EP | 0495348 A1 | 7/1992 |
| EP | 0495547 A2 | 7/1992 |
| EP | 0495548 A2 | 7/1992 |
| EP | 0499329 A1 | 8/1992 |
| EP | 0577205 A2 | 1/1994 |
| EP | 0683764 A1 | 11/1995 |
| EP | 0728733 A1 | 8/1996 |
| EP | 0879642 A2 | 11/1998 |
| EP | 1330309 A1 | 7/2003 |
| FR | 2034147 A5 | 12/1970 |
| GB | 2006208 A | 5/1979 |
| JP | 06-065148 A | 3/1994 |
| JP | 08 134218 A | 5/1996 |
| JP | 08134218 A | 5/1996 |
| JP | 10 339929 A | 12/1998 |
| JP | 2001-517218 A | 10/2001 |
| JP | 2003-528849 A | 9/2003 |
| JP | 2004-515487 A * | 5/2004 |
| JP | 2004-515537 A | 5/2004 |
| JP | 2009-533409 A | 9/2009 |
| KR | 2000-0076427 | 12/2000 |
| KR | 10-0851423 B1 | 8/2008 |
| TW | 552257 B | 9/2003 |
| TW | 200416212 | 9/2004 |
| TW | 200404773 | 4/2010 |
| WO | WO-96/19434 | 6/1996 |
| WO | WO-9708124 A1 | 3/1997 |
| WO | WO-98/41495 | 9/1998 |
| WO | WO-98/42717 | 10/1998 |
| WO | WO-98/45040 | 10/1998 |
| WO | WO-99/47528 A1 | 9/1999 |
| WO | WO-00/56695 A1 | 9/2000 |
| WO | WO-01/10551 | 2/2001 |
| WO | WO-01/28972 A1 | 4/2001 |
| WO | WO-01/65583 A1 | 9/2001 |
| WO | WO-01/68583 A2 | 9/2001 |
| WO | WO-0168583 A2 | 9/2001 |
| WO | WO-0170659 | 9/2001 |
| WO | WO-01/72697 | 10/2001 |
| WO | WO-01/85662 A2 | 11/2001 |
| WO | WO-0187899 A1 | 11/2001 |
| WO | WO-0212161 | 2/2002 |
| WO | WO 02/046143 A1 * | 6/2002 |
| WO | WO-02/48094 A1 | 6/2002 |
| WO | WO-03/040159 | 5/2003 |
| WO | WO-03/070370 A1 | 8/2003 |
| WO | WO-03070370 A1 | 8/2003 |
| WO | WO-2004/014552 A1 | 2/2004 |
| WO | WO-2004/014834 A1 | 2/2004 |

| WO | WO-2004/024322 A2 | 3/2004 |
| --- | --- | --- |
| WO | WO-2004/028689 A2 | 4/2004 |
| WO | WO-2004/050599 A1 | 6/2004 |
| WO | WO-2004050599 A1 | 6/2004 |
| WO | WO 2004/072088 A2 * | 8/2004 |
| WO | WO-2004/103948 | 12/2004 |
| WO | WO-2004/103948 A1 | 12/2004 |
| WO | WO-2005/003070 A1 | 1/2005 |
| WO | WO-2005/079981 A1 | 9/2005 |
| WO | WO-2005/082830 | 9/2005 |
| WO | WO-2005082830 A1 | 9/2005 |
| WO | WO-2005118519 A1 | 12/2005 |
| WO | WO-2006/062467 A1 | 6/2006 |
| WO | WO-2006/084892 A2 | 8/2006 |
| WO | WO-2007/020379 A1 | 2/2007 |
| WO | WO-2007109365 A2 | 9/2007 |
| WO | WO-2007/119079 A1 | 10/2007 |
| WO | WO-2007119079 A1 | 10/2007 |
| WO | WO-2008/075108 A1 | 6/2008 |
| WO | WO-2008145976 A1 | 12/2008 |
| WO | WO-2009010782 A1 | 1/2009 |

OTHER PUBLICATIONS

Examination Report issued from the State Intellectual Property Office of P.R. China issued in Application No. GCC/P/2007/9585, dated Jan. 20, 2012.*
] Notice of Reason for Rejection issued from the Japanese Office Action in Japanese Application No. 2006-553662, dated Sep. 25, 2012 (including English Translation).*
Notice of Reason for Rejection issued from the Japanese Office Action in Japanese Application No. 2008-525618, dated Sep. 25, 2012 (including English Translation).*
Notice of Reasons for Rejection issued from the Japanese Patent Office in Japanese Application No. 2009-504833, dated Jul. 31, 2012 (including English Translation).*
Notice of Reexamination issued from the Patent Reexamination Board of State Intellectual Property Office of P.R. China in Chinese Application No. 200580011699.0 dated Jul. 30, 2012.*
Office Action issued from the Eurasian Patent Organization issued in Application No. 200970528/28 dated Aug. 15, 2012 (including English Translation).*
Tolman, "Phosphorous Ligand Exchange Equilibria on Zerovalent Nickel. A Dominant Role for Steric Effects," Journal of the American Chemical Society, vol. 92, No. 10, pp. 2956-2965.
Tolman, "Steric Effects of Phosphorous Ligands in Organometallic Chemistry and Homogeneous Catalysis," Chemical Reviews, vol. 77, No. 3, pp. 313-348.
Grimmer, et al., "Zirconium bis-cyclopentadienyl compounds: An investigation into the influence of substituent effects on the ethene polymerisation behaviour of $(CpR)_2ZrCl_2$/MAO catalysts," Journal of Molecular Catalysis A: Chemical, vol. 188, No. 1-2, pp. 105-113, 2002.
Machine Translation of JP 08-134218, May 28, 1996.
Office Action for U.S. Appl. No. 11/597,787, issued by the USPTO on Oct. 8, 2008.
Office Action for U.S. Appl. No. 11/597,787, issued by the USPTO on Oct. 8, 2009.
Office Action for U.S. Appl. No. 11/597,787, issued by the USPTO on May 20, 2009.
Office Action for U.S. Appl. No. 10/561,912, issued by the USPTO on Aug. 25, 2008.
Office Action for U.S. Appl. No. 10/561,912, issued by the USPTO on Sep. 2, 2009.
Office Action for U.S. Appl. No. 10/561,912, issued by the USPTO on Jan. 14, 2008.
Office Action for U.S. Appl. No. 10/561,912, issued by the USPTO on Feb. 11, 2009.
Office Action for U.S. Appl. No. 10/536,801, issued by the USPTO on Apr. 8, 2008.
Office Action for U.S. Appl. No. 10/536,801, issued by the USPTO on Jan. 7, 2010.
Office Action for U.S. Appl. No. 10/536,801, issued by the USPTO on Jun. 17, 2009.

Wang et al., "Polymer-Bound Bidentate-Phosphine-Pallalium Complex as a Catalyst in the Heck Arylation", J. Org. Chem, vol. 59, No. 18, 1994, pp. 5358-5364.
Hofmann et al., "Bis(Di-T-Butylphosphino)Methane Complexes of Rhodium: Homogeneous Alkyne Hydrosilylation by Catalyst-Dependent Alkyne Insertion Into Rh-Si or Rh-H Bonds. Molecular Structures of the Dimer $[(dtbpm) RHcL]_2$ and of the Silyl Complex $(dtbpm) Rh[Si(OEt)^{31(PMe}3)$", Journal of Organometallic Chemistry, vol. 490, 1995, pp. 51-70.
Lindner et al., "Catalytic Activity of Cationic Diphospalladium (II) Complexes in the Alkene/CO Copolymerization in Organic Solvents and Water in Dependence on the Length of the Alkyl Chain at the Phosphine Ligands", Journal of Organometallic Chemistry, vol. 602, 2000, pp. 173-187.
Richmond et al., "Preparation of New Catalysts by the Immobilization of Palladium(II) Species Onto Silica: An Investigation of Their Catalytic Activity for the Cyclization of Aminoalkynes", J. Am Chem. Soc., vol. 123, 2001, pp. 10521-10525.
Tamao et al., "Alkyl Group Isomerization in the Cross-Coupling Reaction of Secondary Alkyl Grignard Reagents With Organic Halides in the Presence of Nickel-Phosphine Complexes as Catalysts", Journal of the American Chemical Society, vol. 94, 1972, pp. 9268-9269.
Jones et al, "Rhodium-Catalyzed Activation and Functionalization of the C-C Bond of Biphenylene", Organometallics, vol. 20, 2001, pp. 5745-5750.
Vavasori et al., "Highly active $[Pd(AcO)_2(dppp(]$ catalyst for the $CO-C_2H_4$ copolymerization in $H_2O-CH_3COOH$ solvent [dppp = 1,3-bis (diphenylphosphino)propane]"', Journal of Molecular Cat. A. Chem., vol. 204-205, 2003, pp. 295-303.
Seayad et al., "Hydroesterification of styrene using an in situ formed $Pd(OTs)_2(PPh_3)_2$ complex catalyst", Journal of Molecular Cat. A. Chem., vol. 151, 2000, pp. 47-59.
Vavasori et al. "Carbon monoxide-ethylene copolymerization catalyzed by a $Pd(AcO)_2/dpppTsOH^1$ system: the promoting effect of water and of the acid", Journal of Molecular Cat. A. Chem., vol. 110, 1996, pp. 13-23.
Kirk Othmer Encyclopaedia of Chemical Terminology, vol. 9, 4th Ed., p. 783, Hydrolysis of Organic Esters, pp. 783-785 and 787, John Wiley & Sons, Jan. 1994.
Masters, Christopher, "Homogeneous Transition Metal Catalysis," p. 4-21, Chapman and Hall, Feb. 1981.
Lide et al., Handbook of Chem and Phys., 76th Ed., CRC Press, 1995, p. 8-141 6-155 to 5-17; 15-16 to 15-25.
Clegg, W. et al: "Highly active and selective catalysts for the production of methl propanoate via the methoxycarbonylation of ethene" Chem. Commun., 1999, pp. 1877-1878.
Knight et al: "Remarkable Differences in Catalyst Activity and Selectivity fo rthe production of Methyl Propanoate versus CO-Ethylene Copolymer by a Series of palladium Complexes of Related $C_4$-Bridged Diphosphines" Organometallics 2000, 19 4957-4967.
Rucklidge et al.: "Methoxycarbonylation f vinyl acetate catalysed by palladium comlexes of bis )ditertiarybutylphosphinomethyl) benzene and related ligands" Chem. Commun., 2005, pp. 1176-1178.
Pugh, R. I. et al. "Tandem isomerisation-carbonylation catalysis: highly active palladium(II) catalysts for the selective methoxycarbonylation of internal alkenes to linear esters", Chemical Communications—CHEMCOM, Royal Society of Chemistry, GB, No. 16, (Aug. 21, 2001), pp. 1476-1477.
Cullen et al, "Structure of the Hydrogenation Catalyst $[(PP)Rh(NBD)]ClO_4$, $(PP)=(\eta^5-[(CH_3)_3C]_2PC_5H_4)_2Fe$, and Some Comparative Rate Studies," Organometallics, vol. 2, pp. 714-719, 1983.
Abbenhuis et al., "Successful Application of a "Forgotten" Phosphine in Asymmetric Catalysis: A 9-Phosphabicyclo[3.3.1]non-9-yl Ferrocene Derivative as a Chiral Ligand," Organometallics, vol. 14, pp. 759-766, 1995.
Hartwig, et al. "Structure and reactions of oxametallacyclobutanes and oxametallacyclobutenes of ruthenium", Organometallics, vol. 10, No. 9, pp. 3344-3362 (1991).
Andrews et al. "Syntheses, spectra and structures of (diphosphine)platinum(II) carbonate complexes" Inorganic Chemistry, No. 35, pp. 5478-5483, (1996).

Latif et al. "Square planar platinum(II) complexes, crystal structures of cis-bis(triphenylphosphine) hydro(triphenylstannyl) platinum(II) and cis-bis(triphenylphosphine) hydro(triphenylsilyl) platinum(II)", Journal of Organometallic Chemistry, No. 474, pp. 217-221, (1994).
Becker et al. "Synthesis and characterization of chiral diphosphine platinum(II) VANOL and VAPOL complexes", Organometallics, No. 22, pp. 3245-3249, (2003).
Becker et al. "Imprinting chiral information into rigidified dendrimers", Organometallics, No. 22, pp. 4984-4998, (2003).
Tudor et al. "Diasteroisomer interconversion in chiral BiphepPtX$_2$ complexes", Organometallics, No. 19, pp. 4376-4384, (2000).
Related U.S. Appl. No. 10/524,023, filed Nov. 17, 2005, Eastham et al.
Olah, George A., et al., "AlCl$_3$-Catalyzed Dichlorophosphorylation of Saturated Hydrocarbons with PCl$_3$ in Methylene Chloride Solution," *J. Org. Chem.*, 1990, 55, 1224-1227.
Wei-Yong Yu, et al., "Preparation of Polymer-Protected Pt/Co Bimetallic Colloid and its Catalytic Properties in Selective Hydrogenation of Cinnamaldehyde to Cinnamyl Alcohol," Polymers for Advanced Technologies, GB, John Wiley and Sons, Chichester, Aug. 1, 1996, 719-722, vol. 7, No. 8.
Brunkan et al. "Effect of chiral cavities associated with molecularly imprinted platinum centers on the selectivity of ligand-exchange reactions at platinum", Journal of American Chemical Society, No. 22, pp. 6217-6225, (2000).
Brunkan et al. "Unorthodox C,O binding mode of Me$_2$BINOL in Pt(II) complexes", Journal of American Chemical Society, No. 120, pp. 11002-11003, (1998).
Andrews et al. "Regioselective complexation of unprotected carbohydrates by Platinum(II): Synthesis, structure, complexation equilibria, and hydrogen-bonding in carbonate-derived bis(phosphine)platinum(II) diolate and alditolate complexes", Journal of American Chemical Society, No. 116, pp. 5730-5740, (1994).
Hartwig, et al. "Structure and reactions of oxametallacyclobutanes and oxametallacyclobutenes of ruthenium", Journal of American Chemical Society, vol. 10, No. 9, pp. 3344-3362 (1991).
Konno et al. "Preparation and spectroscopic characteristics of geometrical isomers of bis[1,2-bis(dimethylphosphino)ethane]cobalt(III) complexes with thiolate ligands", The Chemical Society of Japan, No. 62, pp. 3475-3478, (1989).
Cecconi et al. "Palladium complexes with the tripodal phosphine tris(2-diphenylphosphinoethyl)amine. Synthesis and structure of trigonal, tetrahedral, trigonal bipyramidal, and square planar complexes", J. Chem. Soc. Dalton Trans., issue 1, pp. xvii-xx. (1989).
Miskowski et al. "Preparation and spectroscopic properties of Cobalt(III) complexes containing phosphine ligands. The electronic structural description of side-bonded dioxygen", Journal of American Chemical Society, vol. 98, No. 9, pp. 2477-2483, (1976).
Hayward et al. "Some reactions of peroxobis(triphenylphosphine)platinum(II) and analogs with carbon dioxide, carbon disulfide, and other unsaturated molecules", Journal of American Chemical Society, vol. 92, issue 20, pp. 5873-5878, (1970).
Osman, Serindag "Synthesis of some platinum(II) diphosphine complexes of the type [PtX$_2$(P-P)] (X$_2$ = $_{CO3}$; X = CH$_3$COO, CF$_3$COO, NCO)", Synth. React. Inorg. Met.-Org. Chem., vol. 27. No. 1, pp. 69-76, (1997).
Andrews et al. "Syntheses, spectra and structures of (diphosphine)platinum(II) carbonate complexes" Journal of American Chemical Society, No. 35, pp. 5478-5483, (1996).
Latif et al. "Square planar platinum(II) complexes. Crystal structures of cis-bis(triphenylphosphine) hydro(triphenylstannyl) platinum(II) and cis-bis(triphenylphosphine) hydro(triphenylsilyl) platinum(II)", Journal of Organic Chemistry, No. 474, pp. 217-221, (1994).
Becker et al. "Synthesis and characterization of chiral diphosphine platinum(II) VANOL and VAPOL complexes", Journal of American Chemical Society, No. 22, pp. 3245-3249, (2003).
Becker et al. "Imprinting chiral information into rigidified dendrimers", Journal of American Chemical Society, No. 22, pp. 4984-4998, (2003).
Peng et al. "Chiral rodlike platinum complexes, double helical chains and potential asymmetric hydrogenation ligand based on "linear" building blocks: 1,8,9,16-tetrahydroxytetraphenylene and 1,8,9,16-tetrakis(diphenylphosphino)tetraphenylene" Journal of American Chemical Society, No. 127, pp. 9603-9611, (2005).
Wen et al. "Synthesis, resolution, and applications of 1,16-dihydroxytetraphenylene as a novel building block in molecular recognition and assembly", Journal of Organic Chemistry, No. 68, pp. 8918-8931, (2003).
Mikami et al. "Molecular design of DABNTf as a highly efficient resolving reagent for racemic Pd complex with *tropos* biphenylphosphine (BIPHEP) ligand: circular dichroism (CD) spectra of enantiopure BIPHEP-Pd complex", Chirality, No. 15, pp. 105-107, (2003).
Tudor et al. "Diasteroisomer interconversion in chiral BiphepPtX$_2$ complexes", Journal of American Chemical Society, No. 19, pp. 4376-4384, (2000).
Office Action for U.S. Appl. No. 11/990,272, issued by the USPTO on Jul. 12, 2011.
Office Action for U.S. Appl. No. 10/589,971, issued by the USPTO on Mar. 22, 2011.
Bellabarba et al., "Synthesis, X-ray characterization and reactions of a trigonal planar palladium( )) carbonyl complex", Chemical Communications, No. 15, pp. 1916-1917, (2003).
Clegg et al., "Synthesis and reactivity of palladium hydrido-solvento complexes, including a key intermediate in the catalytic methoxycarbonylation of ethane to methypropanoate", Journal of the Chemical Society, Dalton Transactions, No. 17, pp. 3300-3308 (2002).
Clegg et al., "Characterisation and dynamics of [Pd(L-L)H(solv)]+, [Pd(L-L(CH2CH3)]+ and [Pd(L-L)(C(0)Et)(THF)]+ (L-L = 1,2-(CH2PBut2)2C6H4): key intermediates in the catalytic methoxycarbonylation of ethane to methylpropanoate", Organometallics, vol. 21, No. 9, pp. 1832-1840 (2002).
Edelbach at al., "Catalytic hydrogenolysis of biphenylene with platinum, palladium, and nickelphosphine complexes", Organometallics, vol. 17, No. 22, pp. 4784-4794 (1998).
Kim et al., "Synthesis and theoretical study of palladium (II) complexes with aminophosphines as 7-membered chelate rings", Bulletin of the Korean Chemical Society, vol. 18, No. 11, pp. 1162-1166 (1997).
Reddy et al., "Unexpected cross-metathesis between Si-C and Si-Si bonds", Chemical Communications, No. 16, pp. 1865-1866 (1996).
Uchimaru et al., "Ring-opening polymerization of 1,1,2,2-tetramethyl-1,2-disilacyclopentane via palladium complex-catalysed Si-Si bond metathesis", Chemistry Letters, No. 2, p. 164 (1995).
Portnoy et al., "Reactions of electron-rich arylpalladium complexes with olefins. Origin of the chelate effect in vinylation catalysis", Organometallics, vol. 13, No. 9, pp. 3465-3479 (1994).
Wurst et al., "Synthesis and structure of the platinum (0) compounds [(dipb)Pt]2(COD) and (dipb)3Pt2 and of the cluster Hg6[Pt(dipb)]4 (dipb = (iPr)2P(CH2)4P(i-Pr)2)", Zeitschrift Für Anorganische Und Allgemeine Chemie, vol. 395, pp. 239-250 (1991).
Tanaka et al., "Synthesis of ketones via carbonylation of organic halides. II. Palladium-catalysed carbonylation of organic halides with terminal acetylenes in the presence of amines. Novel acetylenic ketone synthesis", Nippon Kagaku Kaishi, No. 3, pp. 537-546 (1985).
Molander et al., "Synthesis and application of chiral cyclopropane-based ligands in palladium-catalyzed allylic alkylation", Journal of Organic Chemistry, vol. 69, No. 23, pp. 8062-8069 (2004).
Brauer et al., "Reactions of coordinated ligands. XIV. Synthesis of a tetradentate phosphorus macrocycle in a palladium (II) template", Chemische Berichte, vol. 119, No. 1, pp. 349-365 (1986).
Dias et al., "Synthesis and characterization of .eta.5-monocyclopentadienyl (p-nitrobenzonitrile)ruthenium(II) salts: second harmonic generation powder efficiencies", Journal of Organometallic Chemistry, vol. 475, No. 1-2, pp. 241-245 (1994).
Office Action issued by the USPTO for U.S. Appl. No. 10/589,971 on Jul. 27, 2010.
Office Action issued by the USPTO in U.S. Appl. No. 12/518,320 on Dec. 8, 2010.
Oblad et al., Catalysis and Catalysts. In McKetta ed, *Encyclopedia of Chemical Processing and Design*, pp. 420-490, 1978.

Hartley, Supported Metal Complexes: A New Generation of Catalysts, Section 1.3, pp. 1, 9, 1985.
Armor, "Perspective: Do you really have a better catalyst?," Applied Catalysis A: General, vol. 282, pp. 1-4, 2005.
Hagen, "Industrial Catalysis: A Practical Approach," pp. v-xvii and 1-6, 2006.
Office Action for U.S. Appl. No. 12/084,575, issued by the USPTO on Aug. 29, 2011.
Doherty et al., "Selectivity for the methoxycarbonylation of ethylene versus CO-ethylene copolymerization with catalysts based on C4-bridged bidentate phosphines and phospholes," Journal of Organometallic Chemistry, vol. 640, pp. 182-196, 2001.
Dörwald, Side Reactions in Organic Synthesis: A Guide to Successful Synthesis Design, Weinheim—Wiley-VCH, pp. ix, 1-16, 2005.
Office Action for European Application No. 07848735.2, issued by the EPO on Sep. 9, 2011.
Office Action for Australian Application No. 2006314268, issued by the Australian Patent Office on Nov. 11, 2010.
Office Action for European Application No. 07824927.3, issued by the EPO on Mar. 30, 2011.
Office Action for GCC Application No. GCC/P/2007/8136 issued by the State Intellectual Property Office of the P.R. China on Nov. 5, 2010.
Office Action for Chinese Application No. 200580011699.0 issued by the State Intellectual Property Office of the P.R. China on Jun. 23, 2011.
Office Action for Japanese Application based on International Application No. PCT/GB2005/000569 issued by the Patent Office of Japan on Jun. 21, 2011.
Office Action for U.S. Appl. No. 11/990,272, issued by the USPTO on Oct. 28, 2011.
Office Action for U.S. Appl. No. 12/518,320, issued by the USPTO on Dec. 6, 2011.
Office Action for Taiwanese Application No. 094104929 issued by the Intellectual Property Office of Taiwan on Sep. 21, 2011.
Argouarch, et al., "Synthesis of Some Ferrocene-Based 1,3(phosphanes) with Planar Chirality as the Sole Source of Chirality", European Journal of Organic Chemistry, 2000, vol. 16 pp. 2885-2891.
Examination Report issued by the State Intellectual Property Office of the P.R. China in Application No. GCC/P/2007/8136 dated Nov. 5, 2010.
Examiner's First Report issued in Australian Application No. 2007327051 dated May 9, 2012.
Gray et al., "The Di-*t*-Butylphosphinyl Directed *ortho* Metalation Group, Synthesis of Hindered Dialkylarylphosphines," Synlett Letters, vol. 4, pp. 422-424 (1998).
Godard, et al., "Systematic Study of the Asymmetric Methoxycarbonylation of Styrene Catalyzed by Palladium Systems Containing Chiral Ferrocenyl Diphosphine Ligands", Helvetica Chimica Acta, 2006 vol. 89(8) pp. 1610-1622.
International Preliminary Report on Patentability issued in Application No. PCT/GB2010/052093 dated Jun. 28, 2012.
International Search Report issued in International Application No. PCT/GB2009/050780 dated Oct. 15, 2009.
International Search Report issued in International Application No. PCT/GB2010/052093 dated Apr. 8, 2011.
International Search Report issued in International Application No. PCT/GB2010/052214 dated Mar. 30, 2011.
Japanese Notice of Reasons for Rejection issued in Application No. 2008-525618 dated Apr. 3, 2012.
Japanese Notice of Reasons for Rejection issued in Application No. 2008-540675 dated May 22, 2012.
Kraatz et al., "The reactions of tridentate cationic palladium (II) complexes with olefins and nucleophiles," The Journal of Organometallic Chemistry, vol. 488, No. 1, pp. 223-232 (1995).
Ooka et al., "Highly active and selective palladium catalyst for hydroesterification of styrene and vinyl acetate promoted by polymeric sulfonic acids," Chemical Communications, pp. 1173-1175 (2005).
Rucklidge, et al., "Methoxycarbonylation of vinyl acetate catalysed by palladium complexes of bis(ditertiarybutylphosphinomethyl) benzene and related ligands", Chemical Communications, 2005, vol. 9 pp. 1176-1178.
Russian Office Action issued in Application No. 201170142/28 dated Apr. 20, 2012.
United Kingdom Search Report issued in Application No. GB1000078.4 dated May 6, 2010.
United Kingdom Search Report issued in Application No. GB0921876.9 dated Oct. 29, 2010.
United Kingdom Search Report issued in Application No. GB0812297.0 dated Jun. 17, 2009.
Wang, et al., "Synthesis and Use in Asymmetric Hydrogenations of Solely Planar Chiral 1,2-Disubstituted and 1,2,3-Trisubstituted Ferrocenyl Diphosphines: A Comparative Study", Organometallics, 2007, vol. 26, pp. 3530-3540.
Written Opinion of the International Searching Authority issued in International Application No. PCT/GB2009/050780 dated Oct. 15, 2009.
Written Opinion of the International Searching Authority issued in International Application No. PCT/GB2010/052093 dated Apr. 8, 2011.
Written Opinion of the International Searching Authority issued in International Application No. PCT/GB2010/052214 dated Mar. 30, 2011.
Office Action for U.S. Appl. No. 12/084,575, issued by the USPTO on Mar. 19, 2012.
Office Action issued in Korean Patent Office on Jan. 12, 2012, English translation.
Office Action for U.S. Appl. No. 11/990,272, issued by the USPTO on May 2, 2012.
Office Action for U.S. Appl. No. 12/517,215, issued by the USPTO on Feb. 27, 2012.
Office Action issued in Chinese Application No. 200580011699.0 dated Jan. 14, 2013.
Office Action issued in Japanese Application No. 2009-538795 dated Feb. 19, 2013.
Office Action issued in Taiwanese Application No. 095128759 dated Jan. 3, 2013.
Office Action issued in Taiwanese Application No. 096113047 dated Jan. 22, 2013.
Office Action issued in U.S. Appl. No. 11/990,272 dated Feb. 6, 2013.

* cited by examiner

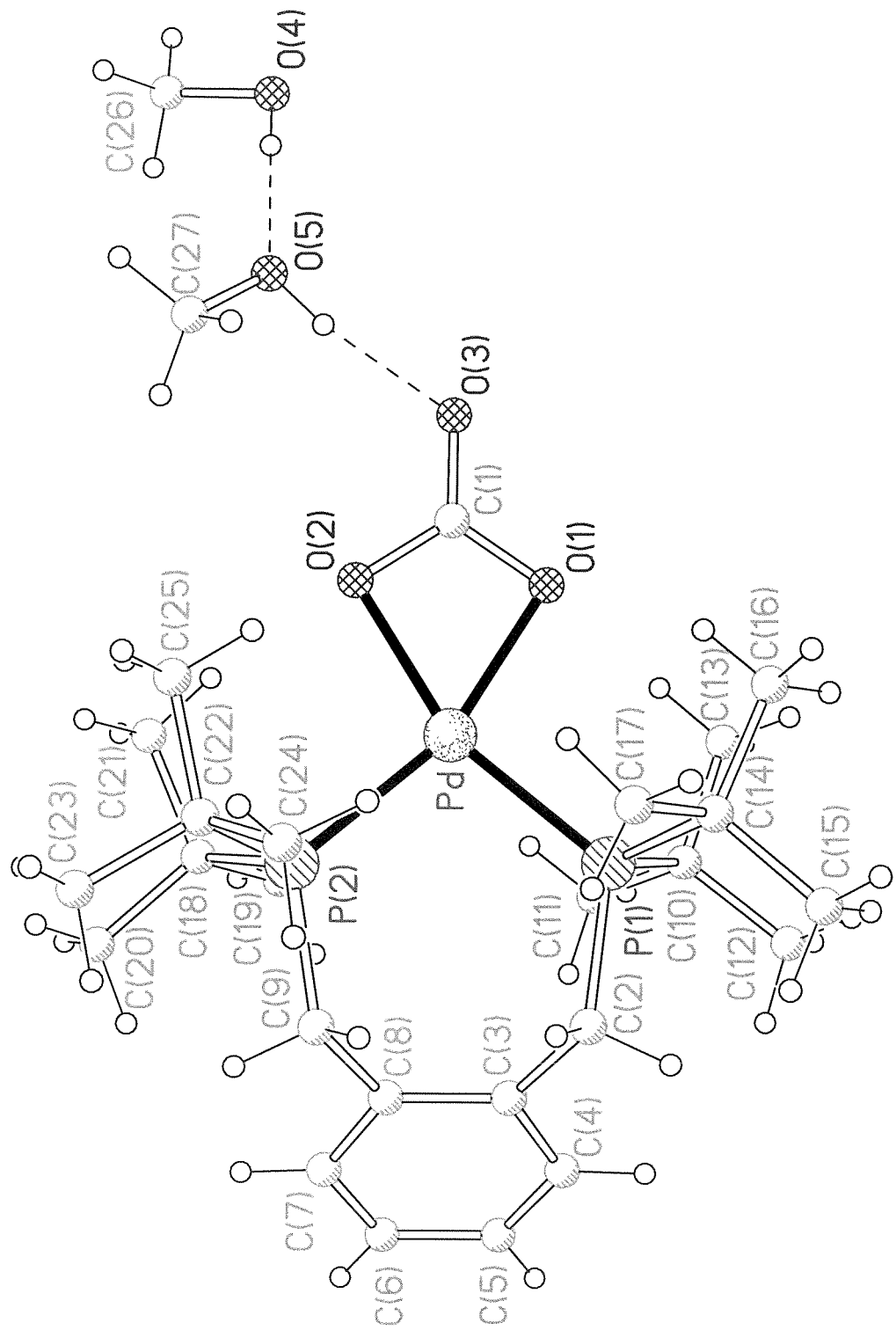

METAL COMPLEXES

The present invention relates to stable metal complexes useful in the carbonylation of ethylenically unsaturated compounds and to their preparation.

The present invention also relates to novel catalyst systems incorporating such complexes.

The carbonylation of ethylenically unsaturated compounds using carbon monoxide in the presence of an alcohol or water and a catalyst system comprising a group 6, 8, 9 or 10 metal, for example, palladium, and a phosphine ligand, for example an alkyl phosphine, cycloalkyl phosphine, aryl phosphine, pyridyl phosphine or bidentate phosphine, has been described in numerous European patents and patent applications, for example EP-A-0055875, EP-A-04489472, EP-A-0106379, EP-A-0235864, EP-A-0274795, EP-A-0499329, EP-A-0386833, EP-A-0441447, EP-A-0489472, EP-A-0282142, EP-A-0227160, EP-A-0495547 and EP-A-0495548. In particular, EP-A-0227160, EP-A-0495547 and EP-A-0495548 disclose that bidentate phosphine ligands provide catalyst systems which enable high reaction rates to be achieved. C3 alkyl bridges between the phosphorous atoms are exemplified in EP0495548 together with tertiary butyl substituents on the phosphorous.

WO96/19434 subsequently disclosed that a particular group of bidentate phosphine compounds having a substituted aryl bridge could provide remarkably stable catalysts which require little or no replenishment; that use of such bidentate catalysts leads to reaction rates which are significantly higher than those previously disclosed; and that little or no impurities are produced at high conversions.

WO 01/68583 discloses rates for the same process as WO 96/19434 when used for higher alkenes and when in the presence of an externally added aprotic solvent.

EP0495548B1 gives an example of vinyl acetate carbonylation employing the C3 bridged phosphine 1,3bis (di-tert-butylphosphino)propane. The rates quoted are 200 moles product per mole of Pd per hour and the result is the production of 1 and 2-acetoxy methyl propanoate in a ratio of 40:60 (linear:branched).

WO 98/42717 discloses a modification to the bidentate phosphines used in EP0495548 wherein one or both phosphorous atoms are incorporated into an optionally substituted 2-phospha-tricyclo[3.3.1.1{3,7}]decyl group or a derivative thereof in which one or more of the carbon atoms are replaced by heteroatoms("2-PA" group). The examples include a number of alkoxycarbonylations of ethene, propene and some higher terminal and internal olefins. In addition, hydroformylation of vinyl acetate giving a branched: linear product ratio of 10:1 is also disclosed. Notably, no alkoxy or hydroxy-carbonylation of vinyl acetate is disclosed.

WO 03/070370 extends the teaching of WO 98/42717 to bidentate phosphines having 1, 2 substituted aryl bridges of the type disclosed in WO96/19434. The suitable olefin substrates disclosed include several types having various substituents. Notably, vinyl esters are not mentioned either generally or specifically.

WO 04/103948 describes both the above types of ligand bridges as useful for butadiene carbonylation and WO 05/082830 describes a selection of WO 04/103948 where the tertiary carbon substituents are different on the respective phosphorous atoms.

Nevertheless, all the above systems require the production of the metal ligand complex from the ligand and the metal or metal compound under carefully controlled conditions as the ligand-metal complex is unstable in air. However, the use of stable metal compounds provides a potential source of catalyst poisoning or, at least, a waste product in the form of the metal anion and/or salt. In time, this agent which has provided a stable source of the metal builds up in the catalyst system and needs to be periodically removed. The present invention solves this problem by providing a stable catalyst metal complex with easily handleable by-products.

According to a first aspect of the present invention there is provided metal complex $ML_nX_m$, where M is a metal of group 8, 9 or 10, L is a ligand, X is a halide, $HCO_3^-$, $NO_3^-$, $CO_3^{2-}$ or carboxylate, n is a number equal to or less than the coordination number of the metal, m is 1 or 2 and is equal to the oxidation state of the metal.

For the avoidance of doubt, references to group 8, 9 or 10 metals herein should be taken to include Groups 8, 9 and 10 in the modern periodic table nomenclature. By the term "Group 8, 9 or 10" we preferably select metals such as Ru, Rh, Os, Ir, Pt and Pd. Preferably, the metals are selected from Ru, Pt and Pd. More preferably, the metal is Pd.

Typically, the number n is between 1-6, more typically, 1-4, especially 1 or 2, more especially, 2. An especially preferred metal complex is one in which the ammonia groups have been removed. Surprisingly and conveniently, it has been found that this is possible when further heating the di-hydrogencarbonate complex during complexation with the metal. It was found that after heating, the di-hydrogen carbonate complex may internally re-arrange to generate ammonium carbonate salt and the bidentate carbonate species. Advantageously, this produces the metal complex $ML_n$ X where X is a bidentate carbonate ligand and M L and n are defined herein.

The ligand L is preferably a phosphine so that the complexing compound is a phosphine. The phosphine may be a monodentate or a bidentate phosphine. Tertiary phosphines are preferred and, in addition to those generally of formulas (I)-(V) herein, may be selected from triphenylphosphine; 2,2'-Bis[bis(3,5-dimethylphenyl)phosphino]-1,1'-binaphthyl; 1,4-Bis[bis(3,5-dimethylphenyl)phosphino]butane; 1,2-Bis[bis(3,5-dimethylphenyl)phosphino]ethane; Bis[bis(3,5-dimethylphenyl)phosphino]methane; 1,3-Bis[bis(3,5-dimethylphenyl)phosphino]propane; 2,2'-Bis[bis(3,5-ditrifluoromethylphenyl)phosphino]-1,1'-binaphthyl; 1,4-Bis[bis(3,5-ditrifluoromethylphenyl)phosphino]butane; 1,3-Bis[bis(3,5-ditrifluoromethylphenyl)phosphino]propane; 1,2-Bis[bis(3,5-ditrifluoromethylphenyl)phosphino]ethane; tri(tert-butyl)phosphine;1,2-bis(di-tertbutylphosphinomethyl) benzene; 1,2-Bis(di-tert-butylphosphino) benzene; 2,2'-Bis(di-tert-butylphosphino) biphenyl; 1,4-Bis(di-tert-butylphosphino)butane; 1,3-bis(di-tertbutylphosphinomethyl)propane; 1,3-Bis(di-tert-butylphosphino)propane; 1,2-Bis(di-tert-butylphosphino)ethane; 1,1'-Bis(di-tert-butylphosphino)ferrocene; Bis(di-tert-butylphosphino)methane; 1,3-Bis(di-tert-butylphosphinomethyl)benzene; tris(p-tolyl)phosphine; tris(o-tolyl)phosphine; tricyclohexylphosphine; 1,2-Bis(dicyclohexylphosphino)benzene; 2,2'-Bis(dicyclohexylphosphino)biphenyl; 1,4-Bis(dicyclohexylphosphino)butane; 1,3-Bis(dicyclohexylphosphino)propane; 1,2-Bis(dicyclohexylphosphino)ethane; 1,1'-Bis(dicyclohexylphosphino) ferrocene; 1,1'-Bis(diisopropylphosphino)ferrocene; 1,2-Bis(diisopropylphosphino)benzene; 1,3-Bis(diisopropylphosphino)propane; 1,2-Bis(diisopropylphosphino)ethane; 1,4-Bis(dimethylphosphino) butane; 1,3-Bis(dimethylphosphinomethyl)benzene; 1,2-Bis(dimethylphosphino)benzene; 2,2'-Bis(dimethylphosphino)biphenyl; 1,3-Bis(dimethylphosphino)propane; 1,2-Bis(dimethylphosphino)ethane; 1,1'-Bis(dimethylphosphino)ferrocene; 1,4-Bis(dimethylphosphino)butane; 1,2-bis(diphenylphosphinomethyl)benzene; 1,3-Bis(diethylphosphinomethyl)benzene; 1,2-Bis(diethylphosphino)benzene; 2,2'-Bis(diethylphosphino)biphenyl; 1,3-Bis(diethylphosphino)propane; 1,2-Bis (diethylphosphino)ethane; 1,1'-bis(diphenylphosphino)ferrocene; and 1,1'-Bis(diethylphosphino)ferrocene.

Especially preferred is when the ligand L is a bidentate phosphine ligand, more especially a bidentate phosphine ligand of formula (I), (II), (III), (IV) or (V) as will be more particularly set out herein. In addition, as set out above, a particularly preferred bidentate phosphine ligand in this context is ML-LX where L-L is the bidentate phosphine ligand, M is the metal and X is a bidentate carbonate. An especially preferred metal in this context is palladium.

According to a second aspect of the present invention there is provided a process for the carbonylation of ethylenically unsaturated compounds comprising reacting said compound with carbon monoxide in the presence of a co-reactant having an active hydrogen such as a source of hydroxyl groups and of a catalyst system, the catalyst system derived from a metal complex according to the first aspect of the present invention.

Advantageously, such complexes have (1) no heavies build Up, (2) no air Sensitivity and (3) reduced catalyst preparation time.

1. NO Heavies Build Up

In a Pd(0) generated system such as Pd(dba) catalyst system the dba is an innocent ligand. It plays a role in the stabilisation of the palladium zero precursor but has no function in the catalysis. Activation of the catalyst employing a sulphonic acid leads to the liberation of the dba into the process solution. The concentration in the reactor builds up and ultimately a purge of the catalyst recycle stream is required to stop levels building up to a point where they have a deleterious effect on the process. The combined palladium ligand salts (specifically the bicarbonate, carbonate, acetate and lactate) do not generate a heavy component on activation with a suitable acid such as a sulphonic acid. The most preferred options i.e. the bicarbonate and carbonate salts generate $CO_2$ and water on activation both of which do not interfere with the process chemistry at the potential levels envisaged.

2. No Air Sensitivity

In any full scale process design there would need to be a catalyst preparation system in which the ligand is combined with a palladium salt and acid before being fed to the reactor. The phosphine ligands in the above mentioned prior art processes are extremely air sensitive in solution and hence to avoid unwanted oxidation of the phosphine highly degassed solvents are required. The efficient removal of oxygen from organic solvents down to the sub ppm levels required and subsequent analysis is a challenge at large scale. The combined ligand palladium salts of the present invention are not air sensitive and can be dissolved in less rigouously degassed solvents.

3. Reduced Catalyst Preparation Time

The complexation and activation of a Pd(0) generated system such as a Pd(dba) catalyst system takes approximately 48 hours. During the first 24 hours of this process there is free ligand present and the system is sensitive to oxidation. The catalyst solutions employing the combined palladium ligand salts of the invention can be generated in 1-2 hours simply by slurrying the complex in MeP/MeOH and adding a suitable acid such as a sulphonic acid. The catalyst species formed in this process is identical to that formed from the Pd(dba) catalyst system.

The metal complexes of the present invention have also been found to be more air stable than the equivalent metal dba complex and also exist in the catalytically active state whereas the metal dba complex is in the non-catalytic oxidation state. A problem with the prior art catalysts is the necessity to add the phosphine ligand separately to the reaction chamber in the presence of degassed solvents. The phosphine ligands are highly air sensitive so the solvents used in a continuous process must be thoroughly de-gassed beforehand so that the phosphine is not oxidised prior to metal complexation. If the phosphine ligand is oxidised then the ligand becomes inactive and will not complex to the metal to form an active catalyst. By forming the stable complexes of the present invention, it is therefore possible to avoid these additional steps in the use of catalyst in the industrial processes.

According to a further aspect of the present invention there is provided a catalyst system capable of carbonylating an ethylentically unsaturated compound, the catalyst system comprising a metal complex according to the first aspect of the present invention.

Suitable acids for the catalyst system of the present invention are those know to the skilled person. Suitable acids include nitric acid; sulphuric acid; lower alkanoic (up to $C_{12}$) acids such as acetic acid and propionic acid; sulphonic acids such as methane sulphonic acid, chlorosulphonic acid, fluorosulphonic acid, trifluoromethane sulphonic acid, benzene sulphonic acid, naphthalene sulphonic acid, toluene sulphonic acid, e.g. p-toluene sulphonic acid, t-butyl sulphonic acid, and 2-hydroxypropane sulphonic acid; sulphonated ion exchange resins (including low acid level sulphonic resins) perhalic acid such as perchloric acid; halogenated carboxylic acids such as trichloroacetic acid and trifluoroacetic acid; orthophosphoric acid; phosphonic acids such as benzenephosphonic acid; and acids derived from interactions between Lewis acids and Broensted acids.

In an alkoxycarbonylation reaction, the acid may have a pKa measured in aqueous solution at 18° C. of less than 4, more preferably, less than 3. Suitable acids include the acids, other than unsubstituted carboxylates, listed supra In an hydroxycarbonylation reaction, the acid may have a pKa measured in aqueous solution at 18° C. of less than 6, more preferably, less than 5. Suitable acids include the acids listed supra.

In one particular preferred embodiment, the acid in the hydroxycarbonylation reaction may be derived from a carboxylic acid. The carboxylic acid is preferably any optionally substituted $C_1$-$C_{30}$ organic compound having at least one carboxylic acid group, more preferably any C1 to C16 organic compound having at least one carboxylic acid group. The pKa of the acid is preferably greater than about 2 measured in an aqueous solution at 18° C. The pKa is preferably less than about 5.0 measured in an aqueous solution at 18° C. The organic compound may be substituted with one or more of the following: hydroxy groups, $C_1$-$C_4$ alkoxy groups such as, for example, methoxy; amine or halogenide groups such as, for example Cl, I and Br. Examples of suitable carboxylic acids include but are not restricted to benzoic acid, substituted benzoic acids, acetic acid, propionic acid, valeric acid, butanoic acid cyclohexylpropionic acid, 2, 3, or 4-pentenoic acid, adipic acid or nonanoic acid.

Examples of suitable sterically hindered carboxylic acids which may be used in the hydroxycarbonylation reaction include but are not restricted to sterically hindered benzoic acids, including, for example, $C_1$-$C_4$ alkyl substituted benzoic acids such as for example, 2,6-dimethylbenzoic acid or 2,4,6-trimethyl benzoic acid. These also include hydroxy substituted benzoic acids such as, for example, meta- and parahydroxybenzoic acid and other substituted benzoic acids such as, for example, 2,6-difluorobenzoic acid or 2,4,6-tribromobenzoic acid.

Particularly preferred acid promoters for an alkoxycarbonylation are the sulfonic acids and sulfonated ion exchange resins listed supra. The low level acid ion exchange resins that may be used preferably provide a level of $SO_3H/Pd$ ratio in the reaction of less than 35 mol/mol, more preferably less than 25 mol/mol, most preferably less than 15 mol/mol. Typical ranges for the $SO_3H$ concentration provided by the resin are in the range 1-40 mol/mol Pd, more typically, 2-30 mol/mol Pd, most typically 3-20 mol/mol Pd.

Preferably, in an hydroxycarbonylation reaction, the solvent may be an acid having a pKa less than 5, more preferably, having a pKa greater than 3 and less than 5. Suitable acid solvents may be selected from the acids listed supra, more preferably, the lower alkanoic (up to $C_{12}$) acids such as acetic and propanoic, most preferably acetic acid.

In an alkoxycarbonylation reaction, the quantity of acid present is not critical to the catalytic behaviour of the catalyst system. The molar ratio of acid to Group 8, 9 or 10 metal or compound may be from 1:1 to 500:1, preferably from 2:1 to 100:1 and particularly from 3:1 to 30:1. Preferably, the ratio of acid to group 8, 9 or 10 metal is preferably, at least 1:1 mol ($H^+$)/mol ($C^{2+}$) and preferably, less than at least 5:1 mol ($H^+$)/mol ($C^{2+}$), more preferably, the ratio is at least 2:1 and preferably, less than at least 3:1; most preferably, around a 2:1 ratio is preferred. By $H^+$ is meant the amount of active acidic sites so that a mole of monobasic acid would have 1 mole of $H^+$ whereas a mole of dibasic acid would have 2 moles of $H^+$ and tribasic acids etc should be interpreted accordingly. Similarly, by $C^{2+}$ is meant moles of metal having a $2^+$ cationic charge so that for $M^+$ ions the ratio of the metal cation should be adjusted accordingly. For example, an $M^+$ cation should be taken as having 0.5 moles of $C^{2+}$ per mole of $M^+$.

In an hydroxycarbonylation reaction, the quantity of acid present is not critical to the catalytic behaviour of the catalyst system. The molar ratio of acid to Group 8, 9 or 10 metal/compound may be from 1:1 to 10000:1, preferably from 2:1 to 1000:1 and particularly from 3:1 to 100:1.

In an alkoxycarbonylation reaction, preferably, the ratio of bidentate ligand to acid is at least 1:2 mol/mol($H^+$) and preferably, the ratio of bidentate ligand to group 8, 9 or 10 metal is at least 1:1 mol/mol($C^{2+}$). Preferably, the ligand is in excess of metal mol/mol($C^2$) and preferably in excess of a ratio of 1:2 mol/mol($H^+$) with the acid. Excess ligand is advantageous as the ligand itself may act as a base to buffer the acid levels in the reaction and prevent degradation of substrate. On the other hand the presence of acid activates the reaction mix and improves the overall rate of reaction.

In an hydroxycarbonylation reaction, preferably, the ratio of bidentate ligand to acid is at least 1:2 mol/mol($H^+$) and preferably, the ratio of bidentate ligand to group 8, 9 or 10 metal is at least 1:1 mol/mol ($C^{2+}$). Preferably, the ligand is in excess of metal mol/mol($C^{2+}$). Excess ligand may be advantageous as the ligand itself may act as a base to buffer the acid levels in the reaction and prevent degradation of substrate. On the other hand the presence of acid activates the reaction mix and improves the overall rate of reaction.

According to a further aspect of the present invention there is provided a process for the carbonylation of an ethylenically unsaturated compound comprising the steps of reacting said compound with carbon monoxide and a co-reactant having an active hydrogen in the presence of a solvent system comprising a carboxylic acid, preferably an aromatic carboxylic acid, a catalyst system and, optionally, a source of hydrogen, the catalyst system comprising a metal complex according to the first aspect of the present invention.

The co-reactant of the present invention may be any compound having a mobile hydrogen atom, and capable of reacting as a nucleophile with the diene under catalytic conditions. The chemical nature of the co-reactant determines the type of product formed. An especially advantageous co reactant is water so that hydroxcarbonylation is especially preferred.

However, other co-reactants are also possible and may be advantageous such as a carboxylic acid, alcohol, ammonia or an amine, a thiol, or a combination thereof. If the co-reactant is water, the product obtained will be an unsaturated carboxylic acid. In the case of carboxylic acids the product is an unsaturated anhydride. For an alcohol co reactant, the product of the carbonylation is an ester.

Similarly, the use of ammonia ($NH_3$) or a primary or secondary amine $R^{81}NH_2$ or $R^{82}R^{83}NH$ will produce an amide, and the use of a thiol $R^{81}SH$ will produce a thioester. In the above-defined coreactants, $R^{81}$ $R^{82}$ and/or $R^{83}$ represent alkyl, alkenyl or aryl groups which may be unsubstituted or may be substituted by one or more substituents selected from halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $SR^{29}$, $C(O)SR^{30}$, $C(S)NR^{27}R^{28}$, aryl or Het, wherein $R^{19}$ to $R^{30}$ are defined herein, and/or be interrupted by one or more oxygen or sulphur atoms, or by silano or dialkylsilcon groups.

If ammonia or amines are employed, a small portion of co-reactants will react with acid present in the reaction to form an amide and water. Therefore, in the case of ammonia or amine-co-reactants, water is present.

Preferably the carboxylic acid co-reactant has the same number of carbon atoms as the diene reactant, plus one.

Preferred amine co-reactants have from 1 to 22, more preferably having 1 to 8 carbon atoms per molecule, and diamine co-reactants—having 2-22, more preferably 2 to 10 carbon atoms per molecule. The amines can be cyclic, part-cyclic, acylic, saturated or unsaturated (including aromatic), unsubstituted or substituted by one or more substituents selected from halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $SR^{29}$, $C(O)SR^{30}$, $C(S)NR^{27}R^{28}$, aryl, alkyl, Het, wherein $R^{19}$ to $R^{30}$ are as defined herein and/or be interrupted by one or more (preferably less than a total of 4) oxygen, nitrogen, sulphur, silicon atoms or by silano or dialkyl silicon groups or mixtures thereof.

The thiol co-reactants can be cyclic, part-cyclic, acylic, saturated or unsaturated(including aromatic), unsubstituted or substituted by one or more substituents selected from halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $SR^{29}$, $C(O)SR^{30}$, $C(S)NR^{27}R^{28}$, aryl, alkyl, Het, wherein $R^{19}$ to $R^{30}$ are as defined herein and/or be interrupted by one or more (preferably less than a total of 4) oxygen, nitrogen, sulphur, silicon atoms or by silano or dialkyl silicon groups or mixtures thereof. Preferred thiol co-reactants are aliphatic thiols with 1 to 22, more preferably with 1 to 8 carbon atoms per molecule, and aliphatic dithiols with 2-22, more preferably 2 to 8 carbon atoms per molecule.

If a co-reactant should react with the acid, then the amount of the acid to co-reactant should be chosen such that a suitable amount of free acid is present. Generally, a large surplus of acid over the co-reactant is preferred due to the enhanced-reaction rates.

The carboxylic acid used in this aspect of the the present invention may be any optionally substituted $C_1$-$C_{30}$ compound having, in addition, at least one carboxylic acid group, more preferably any $C_1$ to $C_{16}$ compound having at least one carboxylic acid group. The pKa of the acid is preferably greater than about 2 measured in dilute aqueous solution at 18° C. The pKa is preferably less than about 6 measured in dilute aqueous solution at 18° C. Examples of suitable carboxylic acids include: optionally substituted $C_1$-$C_{12}$alkanoic acids such as acetic acid, propionic acids, butyric acids, pentanoic acids, hexanoic acids, nonanoic acids; $C_1$-$C_{12}$ alkenoic acids such as propenoic acids such as acrylic acid, butenoic acids such as methacrylic acid, pentenoic acids, hexenoic acids and heptenoic acids; lactic acid; which may all where possible be linear or branched, cyclic, part cyclic, or acyclic and apart from that they may be interrupted with hetero atoms may be unsubstituted or substituted with one or more further substituents selected from aryl, alkyl, hetero (preferably oxygen), Het, halo, cyano, nitro, —OR$^{19}$, —OC(O)R$^{20}$, —C(O)R$^{21}$, —C(O)OR$^{22}$, —N(R$^{23}$)R$^{24}$, C(O)N(R$^{25}$)R$^{26}$, —SR$^{29}$, —C(O)SR$^{30}$, —C(S)N(R$^{27}$)R$^{28}$ or —CF$_3$ wherein R$^{19}$-R$^{28}$ are as defined herein.

A particularly preferred carboxylic acid is the acid product of the carbonylation reaction.

The aromatic carboxylic acid used in the carbonylation reaction such as a hydroxycarbonylation reaction is preferably any optionally substituted $C_1$-$C_{30}$ aromatic compound such as those based on phenyl, napthyl, cyclopentadienyl anion(s), indenyl, pyridinyl, and pyrollyl groups and having at least one carboxylic acid group associated with the aromatic ring, more preferably any $C_1$ to $C_{16}$ aromatic compound having at least one carboxylic acid group. The pKa of the acid is preferably greater than about 2 measured in dilute aqueous solution at 18° C. The pKa is preferably less than about 6 measured in dilute aqueous solution at 18° C., more preferably, less than 5.

The carboxylic acid group means a —COOH group and this may be attached directly to a cyclic ring atom of the aromatic ring but may also be attached to an c or β carbon to the ring, more preferably either attached to an c carbon or directly to the ring, most preferably, attached directly to the ring.

The aromatic compound may be substituted with one or more of the following: alkyl groups; aryl groups; hydroxy groups; alkoxy groups such as, for example, methoxy; amino groups or halo groups such as, for example F, Cl, I and Br.

The aromatic ring of the carboxylic acid may substituted on any available carbon atom. Preferably, the aromatic ring is mono- or di-substituted. Examples of suitable aromatic carboxylic acids include benzoic acids; naphthoic acids; and cyclopentadenyl acids, particularly preferred are substituted aromatic acids, including for example, $C_1$-$C_4$ alkyl substituted benzoic acids, such as 2,4,6-trimethyl benzoic acid, or 2,6-dimethyl benzoic acid and o-toluic acid (2-methyl benzoic acid), 2-nitrobenzoic acid, 6-chloro-2-methylolbenzoic acid, 4-aminobenzoic acid, 2-chloro-6-hydroxybenzoic acid, 2-cyanobenzoic acid, 3-cyanobenzoic acid, 4-cyanobenzoic acid 2,4dihydroxybenzoic acid, 3-nitrobenzoic acid, 2-phenylbenzoic acid, 2-tert-butylbenzoic acid, 2-napthoic acid, 1-napthoic acid, 2,4-dimethylbenzoic acid, 3-methylbenzoic acid, 3,5-dimethylbenzoic acid, 4-hydroxybenzoic acid, 2-fluorobenzoic acid, 3-propoxybenzoic acid, 3-ethoxybenzoic acid, 2-propoxybenzoic acid, 2,2-diphenylpropionic acid, 2-meyhoxyphenylacetic acid, ortho-anisic acid, meta-anisic acid, 4-tert-butylbenzoic acid and 2-ethoxybenzoic acid.

Preferably, the aromatic carboxylic acid is substituted by only one group in addition to the group bearing the carboxylic acid. Preferably, an alkyl group substitutes the aromatic ring of the carboxylic acid. An especially preferred compound is o-toluic acid.

Preferably, when the solvent system comprises a carboxylic acid as defined above (preferably an aromatic carboxylic acid), at least one co-solvent is also used. Suitable co-solvents include the aprotic solvents mentioned herein.

The present invention also concerns the preparation of the metal complex, in particular a precious metal phosphine complex.

Precious metal β-diketonates such as palladium (II) acetylacetonate are used in many chemical processes as catalysts or as components of catalyst systems. Palladium (II) acetylacetonate has been manufactured from palladium (II) chloride. For example, GB-A-1475834 describes a process comprising dissolving $PdCl_2$ or a complex tetrachloro-palladinate in hydrochloric acid, reacting the resulting solution with an at least stoichiometric amount of acetylacetone, stirring the mixture to a clear solution, then adjusting the pH to from 7 to 8 by gradual addition of aqueous alkali metal hydroxide, separating off the precipitated Pd(II) acetylacetonate, and washing and drying it.

The process of the invention provides a process for the preparation of a metal complex which does not use metal dichloride as a starting material. Since $MCl_2$ is generally made from an ammine by calcining/reduction to metal sponge followed by reaction with chlorine and hydrochloric acid, the use of the process of the invention avoids these additional process steps and has environmental benefits.

It is an object of the present invention to provide an alternative process for the preparation of precious metal complexes such as precious metal phosphines.

According to a further aspect of the invention there is provided a process for the preparation of a metal complex $ML_nX_m$, where M is a metal atom, L is a ligand, X is a halide, $HCO_3^-$, $NO_3^-$, $CO_3^{2-}$ or carboxylate, n is a number equal to or less than the coordination number of the metal, m is 0, 1 or 2 and is equal to the oxidation state of the metal, comprises reacting an ammine compound of metal M with a complexing compound.

When M is palladium, it may be Pd(II) or Pd(0). m is therefore 2 or 0 in the case of Palladium complex production.

The metal ammine compound may be an ionic compound. In this case, the anion is preferably selected from a halide (preferably chloride), bicarbonate, carbonate, carboxylate (e.g. acetate, lactate or citrate), or nitrate. Suitable palladium ammine compounds include $Pd(NH3)_2Cl_2$, $Pd(NH_3)_4(HCO_3)_2$, $Pd(NH_3)_4(CH_3CO_2)_2$, $Pd(NH_3)_4(NO_3)_2$. $Pd(NH_3)_2Cl_2$, $Pd(NH_3)_4(HCO_3)_2$, and $Pd(NH_3)_4(CH_3CO_2)_2$, are particularly preferred metal ammine compounds.

Particularly preferred is the reaction of $Pd(NH_3)_4(HCO_3)_2$ with a ligand as defined herein such as the bidentate ligands set out below. In a preferred reaction, the bidentate ligand is reacted with the $Pd(NH_3)_4(HCO_3)_2$ complex in a suitable solvent such as methanol and heated for several hours, typically more than 2 hours and less than 12 hours, more typically, 4-8 hrs. This extended heating causes the bidentate carbonate to form with liberation of the ammonia, typically as the ammonium hydrogen carbonate. The ammonium hydrogen carbonate may be left in solution with precipitation of the desired metal complex or may be removed by water washing or extraction because the ammonium hydrogen carbonate is soluble in water. Advantageously, improvements in TON for such metal complexes have been found and this may be due to the absence of ammonia in the final metal complex.

As mentioned herein, in one set of embodiments of the present invention, the bidentate phosphine ligand is of general formula (I)

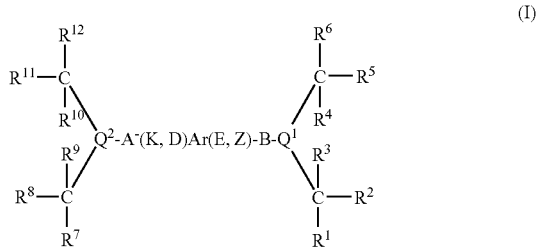

wherein:

Ar is a bridging group comprising an optionally substituted aryl moiety to which the phosphorus atoms are linked on available adjacent carbon atoms;

A and B each independently represent lower alkylene;

K, D, E and Z are substituents of the aryl moiety (Ar) and each independently represent hydrogen, lower alkyl, aryl, Het, halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $C(S)R^{25}R^{26}$, $SR^{27}$, $C(O)SR^{27}$, or $-J-Q^3(CR^{13}(R^{14})(R^{15})CR^{16}(R^{17})(R^{18})$ where J represents lower alkylene; or two adjacent groups selected from K, Z, D and E together with the carbon atoms of the aryl ring to which they are attached form a further phenyl ring, which is optionally substituted by one or more substituents selected from hydrogen, lower alkyl, halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $C(S)R^{25}R^{26}$, $SR^{27}$ or $C(O)SR^{27}$;

$R^{13}$ to $R^{18}$ each independently represent hydrogen, lower alkyl, aryl, or Het, preferably each independently represent lower alkyl, aryl, or Het;

$R^{19}$ to $R^{27}$ each independently represent hydrogen, lower alkyl, aryl or Het;

$R^1$ to $R^{12}$ each independently represent hydrogen, lower alkyl, aryl, or Het, preferably each independently represent lower alkyl, aryl, or Het;

$Q^1$, $Q^2$ and $Q^3$ (when present) each independently represent phosphorous, arsenic or antimony and in the latter two cases references to phosphine or phosphorous above are amended accordingly, with preferably both $Q^1$ and $Q^2$ representing phosphorus, more preferably all of $Q^1$, $Q^2$ and $Q^3$ (when present) representing phosphorus.

Suitably, the bidentate phosphines of the invention should preferably be capable of bidentate coordination to the Group VIB or Group VIIIB metal or compound thereof, more preferably to the preferred palladium.

Preferably, when K, D, E or Z represent $-J-Q^3(CR^{14})(R^{14})(R^{15}))CR^{16}(R^{17})(R^{18})$, the respective K, D, E or Z is on the aryl carbon adjacent the aryl carbon to which A or B is connected or, if not so adjacent, is adjacent a remaining K, D, E or Z group which itself represents $-J-Q^3(CR^{13}(R^{14})(R^{15}))CR^{16}(R^{17})(R^{18})$.

Specific but non-limiting examples of bidentate ligands within this embodiment include the following: 1,2-bis-(di-tert-butylphosphinomethyl)benzene, 1, 2-bis-(di-tert-pentylphosphinomethyl)benzene, 1, 2-bis-(di-tert-butylphosphinomethyl)naphthalene. Nevertheless, the skilled person in the art would appreciate that other bidentate ligands can be envisaged without departing from the scope of the invention.

The term "Ar" or "aryl" when used herein, includes five-to-ten-membered, preferably, six-to-ten membered carbocyclic aromatic groups, such as phenyl and naphthyl, which groups are optionally substituted with, in addition to K, D, E or Z, one or more substituents selected from aryl, lower alkyl (which alkyl group may itself be optionally substituted or terminated as defined below), Het, halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $SR^{27}$, $C(O)SR^{27}$ or $C(S)NR^{25}R^{26}$ wherein $R^{19}$ to $R^{27}$ each independently represent hydrogen, aryl or lower alkyl (which alkyl group may itself be optionally substituted or terminated as defined below). Furthermore, the aryl moiety may be a fused polycyclic group, e.g. naphthalene, biphenylene or indene.

By the term "a metal of Group VIB or Group VIIIB" in a compound of formula I we include metals such as Cr, Mo, W, Fe, Co, Ni, Ru, Rh, Os, Ir, Pt and Pd. Preferably, the metals are selected from Ni, Pt and Pd. More preferably, the metal is Pd. For the avoidance of doubt, references to Group VIB or VIIIB metals herein should be taken to include Groups 6, 8, 9 and 10 in the modern periodic table nomenclature.

The term "Het", when used herein, includes four-to-twelve-membered, preferably four-to-ten-membered ring systems, which rings contain one or more heteroatoms selected from nitrogen, oxygen, sulphur and mixtures thereof, and which rings may contain one or more double bonds or be non-aromatic, partly aromatic or wholly aromatic in character. The ring systems may be monocyclic, bicyclic or fused. Each "Het" group identified herein is optionally substituted by one or more substituents selected from halo, cyano, nitro, oxo, lower alkyl (which alkyl group may itself be optionally substituted or terminated as defined below) $OR^{19}$, $OC(O)R^{20}$, $C(O)R^{21}$, $C(O)OR^{22}$, $NR^{23}R^{24}$, $C(O)NR^{25}R^{26}$, $SR^{27}$, $C(O)SR^{27}$ or $C(S)NR^{25}R^{26}$ wherein $R^{19}$ to $R^{27}$ each independently represent hydrogen, aryl or lower alkyl (which alkyl group itself may be optionally substituted or terminated as defined below). The term "Het" thus includes groups such as optionally substituted azetidinyl, pyrrolidinyl, imidazolyl, indolyl, furanyl, oxazolyl, isoxazolyl, oxadiazolyl, thiazolyl, thiadiazolyl, triazolyl, oxatriazolyl, thiatriazolyl, pyridazinyl, morpholinyl, pyrimidinyl, pyrazinyl, quinolinyl, isoquinolinyl, piperidinyl, pyrazolyl and piperazinyl. Substitution at Het may be at a carbon atom of the Het ring or, where appropriate, at one or more of the heteroatoms. "Het" groups may also be in the form of an N oxide.

The term "lower alkyl" when used herein, means $C_1$ to $C_{10}$ alkyl and includes methyl, ethyl, propyl, butyl, pentyl, hexyl and heptyl groups. Unless otherwise specified, alkyl groups may, when there is a sufficient number of carbon atoms, be linear or branched, be saturated or unsaturated, be cyclic, acyclic or part cyclic/acyclic, and/or be substituted or terminated by one or more substituents selected from halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $SR^{27}$, $C(O)SR^{27}$, $C(S)NR^{25}R^{26}$, aryl or Het, wherein $R^{19}$ to $R^{27}$ each independently represent hydrogen, aryl or lower alkyl, and/or be interrupted by one or more oxygen or sulphur atoms, or by silano or dialkylsilcon groups.

Lower alkyl groups or alkyl groups which $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, K, D, E and Z may represent and with which aryl and Het may be substituted, may, when there is a sufficient number of carbon atoms, be linear or branched, be saturated or unsaturated, be cyclic, acyclic or part cyclic/acyclic, and/or be interrupted by one or more of oxygen or sulphur atoms, or by silano or dialkylsilicon groups, and/or be substituted by one or more substituents selected from halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $SR^{27}$, $C(O)SR^{27}$, $C(S)NR^{25}R^{26}$, aryl or Het wherein $R^{19}$ to $R^{27}$ each independently represent hydrogen, aryl or lower alkyl.

Similarly, the term "lower alkylene" which A, B and J (when present) represent in a compound of formula I, when used herein, includes $C_1$ to $C_{10}$ groups which are bonded to other moieties at least at two places on the group and is otherwise defined in the same way as "lower alkyl".

Halo groups with which the above-mentioned groups may be substituted or terminated include fluoro, chloro, bromo and iodo.

Where a compound of a formula herein contains an alkenyl group, cis (E) and trans (Z) isomerism may also occur. The present invention includes the individual stereoisomers of the compounds of any of the formulas defined herein and, where appropriate, the individual tautomeric forms thereof, together with mixtures thereof. Separation of diastereoisomers or cis and trans isomers may be achieved by conventional techniques, e.g. by fractional crystallisation, chromatography or H.P.L.C. of a stereoisomeric mixture of a compound one of the formulas or a suitable salt or derivative thereof. An individual enantiomer of a compound of one of the formulas may also be prepared from a corresponding optically pure intermediate or by resolution, such as by H.P.L.C. of the corresponding racemate using a suitable chiral support or by fractional crystallisation of the diastereoisomeric salts formed by reaction of the corresponding racemate with a suitable optically active acid or base, as appropriate.

All stereoisomers are included within the scope of the process of the invention.

It will be appreciated by those skilled in the art that the compounds of formula I may function as ligands that coordinate with the Group VIB or Group VIIIB metal or compound thereof in the formation of the catalyst system of the invention. Typically, the Group VIB or Group VIIIB metal or compound thereof coordinates to the one or more phosphorous, arsenic and/or antimony atoms of the compound of formula I.

Preferably, $R^1$ to $R^{18}$ each independently represent lower alkyl or aryl. More preferably, $R^1$ to $R^{18}$ each independently represent $C_1$ to $C_6$ alkyl, $C_1$-$C_6$ alkyl phenyl (wherein the phenyl group is optionally substituted as defined herein) or phenyl (wherein the phenyl group is optionally substituted as defined herein). Even more preferably, $R^1$ to $R^{18}$ each independently represent $C_1$ to $C_6$ alkyl, which is optionally substituted as defined herein. Most preferably, $R^1$ to $R^{18}$ each represent non-substituted $C_1$ to $C_6$ alkyl such as methyl, ethyl, n-propyl, iso-propyl, n-butyl, iso-butyl, tert-butyl, pentyl, hexyl and cyclohexyl.

Alternatively, or additionally, each of the groups $R^1$ to $R^3$, $R^4$ to $R^6$, $R^7$ to $R^9$, $R^{10}$ to $R^{12}$, $R^{13}$ to $R^{15}$ or $R^{16}$ to $R^{18}$ together independently may form cyclic structures such as 1-norbornyl or 1-norbornadienyl. Further examples of composite groups include cyclic structures formed between $R^1$-$R^{18}$. Alternatively, one or more of the groups may represent a solid phase to which the ligand is attached.

In a particularly preferred embodiment of the present invention $R^1$, $R^4$, $R^7$, $R^{10}$, $R^{13}$ and $R^{16}$ each represent the same lower alkyl, aryl or Het moiety as defined herein, $R^2$, $R^5$, $R^8$, $R^{11}$, $R^{14}$ and $R^{17}$ each represent the same lower alkyl, aryl or Het moiety as defined herein, and $R^3$, $R^6$, $R^9$, $R^{12}$, $R^{15}$ and $R^{18}$ each represent the same lower alkyl, aryl or Het moiety as defined herein. More preferably $R^1$, $R^4$, $R^7$, $R^{10}$, $R^{13}$ and $R^{16}$ each represent the same $C_1$-$C_6$ alkyl, particularly non-substituted $C_1$-$C_6$ alkyl, such as methyl, ethyl, n-propyl, iso-propyl, n-butyl, iso-butyl, tert-butyl, pentyl, hexyl or cyclohexyl; $R^2$, $R^5$, $R^8$, $R^{11}$, $R^{14}$ and $R^{17}$ each independently represent the same $C_1$-$C_6$ alkyl as defined above; and $R^3$, $R^6$, $R^9$, $R^{12}$, $R^{15}$ and $R^{18}$ each independently represent the same $C_1$-$C_6$ alkyl as defined above. For example: $R^1$, $R^4$, $R^7$, $R^{10}$, $R^{13}$ and $R^{16}$ each represent methyl; $R^2$, $R^5$, $R^8$, $R^{11}$, $R^{14}$ and $R^{17}$ each represent ethyl; and, $R^3$, $R^6$, $R^9$, $R^{12}$, $R^{15}$ and $R^{18}$ each represent n-butyl or n-pentyl.

In an especially preferred embodiment of the present invention each $R^1$ to $R^{18}$ group represents the same lower alkyl, aryl, or Het moiety as defined herein. Preferably, each $R^1$ to $R^{18}$ represents the same $C_1$ to $C_6$ alkyl group, particularly non-substituted $C_1$-$C_6$ alkyl, such as methyl, ethyl, n-propyl, iso-propyl, n-butyl, iso-butyl, tert-butyl, pentyl, hexyl and cyclohexyl. Most preferably, each $R^1$ to $R^{18}$ represents methyl.

In the compound of formula I, preferably each $Q^1$, $Q^2$ and $Q^3$ (when present) are the same. Most preferably, each $Q^1$, $Q^2$ and $Q^3$ (when present) represents phosphorous.

Preferably, in the compound of formula I, A, B and J (when present) each independently represent $C_1$ to $C_6$ alkylene which is optionally substituted as defined herein, for example with lower alkyl groups. Preferably, the lower alkylene groups which A, B and J (when present) represent are non-substituted. A particular preferred lower alkylene which A, B and J may independently represent is —$CH_2$— or —$C_2H_4$—. Most preferably, each of A, B and J (when present) represent the same lower alkylene as defined herein, particularly —$CH_2$—.

Preferably, in the compound of formula I when K, D, E or Z does not represent -J-$Q^3$($CR^{13}$($R^{14}$)($R^{15}$))$CR^{16}$($R^{17}$)($R^{18}$), K, D, E or Z represents hydrogen, lower alkyl, phenyl or lower alkylphenyl. More preferably, K, D, E or Z represent hydrogen, phenyl, $C_1$-$C_6$ alkylphenyl or $C_1$-$C_6$ alkyl, such as methyl, ethyl, propyl, butyl, pentyl and hexyl. Most preferably, K, D, E or Z represents hydrogen.

Preferably, in the compound of formula I when K, D, E and Z together with the carbon atoms of the aryl ring to which they are attached do not form a phenyl ring, K, D, E and Z each independently represent hydrogen, lower alkyl, phenyl or lower alkylphenyl. More preferably, K, D, E and Z each independently represent hydrogen, phenyl, $C_1$-$C_6$ alkylphenyl or $C_1$-$C_6$ alkyl, such as methyl, ethyl, propyl, butyl, pentyl and hexyl. Even more preferably, K, D, E and Z represent the same substituent. Most preferably, they represent hydrogen.

Preferably, in the compound of formula I when K, D, E or Z does not represent -J-$Q^3$($CR^{13}$($R^{14}$)($R^{15}$))$CR^{16}$($R^{17}$)($R^{18}$) and K, D, E and Z together with the carbon atoms of the aryl ring to which they are attached do not form a phenyl ring, each of K, D, E and Z represent the same group selected from hydrogen, lower alkyl, aryl, or Het as defined herein; particularly hydrogen or $C_1$-$C_6$ alkyl (more particularly unsubstituted $C_1$-$C_6$ alkyl), especially hydrogen.

Preferably, in the compound of formula I when two of K, D, E and Z together with the carbon atoms of the aryl ring to which they are attached form a phenyl ring, then the phenyl ring is optionally substituted with one or more substituents selected from aryl, lower alkyl (which alkyl group may itself be optionally substituted or terminated as defined below), Het, halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $SR^{27}$, $C(O)SR^{27}$ or $C(S)NR^{25}R^{26}$ wherein $R^{19}$ to $R^{27}$ each independently represent hydrogen or lower alkyl (which alkyl group may itself be optionally substituted or terminated as defined herein). More preferably, the phenyl ring is not substituted by any substituents i.e. it bears hydrogen atoms only.

Preferred compounds of formula I include those wherein:

A and B each independently represent unsubstituted $C_1$ to $C_6$ alkylene;

K, D, Z and E each independently represent hydrogen, $C_1$-$C_6$ alkyl, phenyl, $C_1$-$C_6$ alkylphenyl or -J-$Q^3$($CR^{13}$($R^{14}$)($R^{15}$))$CR^{16}$($R^{17}$)($R^{18}$) where J represents unsubstituted $C_1$ to $C_6$ alkylene; or two of K, D, Z and E together with the carbon atoms of the aryl ring to which they are attached form a phenyl ring which is optionally substituted by one or more substituents selected from lower alkyl, phenyl or lower alkylphenyl.

$R^1$ to $R^{18}$ each independently represent $C_1$ to $C_6$ alkyl, phenyl or $C_1$ to $C_6$ alkylphenyl.

Further preferred compounds of formula I include those wherein:

A and B both represent —$CH_2$— or $C_2H_4$, particularly $CH_2$;

K, D, Z and E each independently represent hydrogen, $C_1$-$C_6$ alkyl phenyl or $C_1$-$C_6$ alkyl or -J-$Q^3$ ($CR^{13}$($R^{14}$)($R^{15}$))$CR^{16}$($R^{17}$)($R^{18}$) where J is the same as A; or two of K, D, E and Z together with the carbon atoms of the aryl ring to which they are attached form an unsubstituted phenyl ring;

$R^1$ to $R^{18}$ each independently represent $C_1$ to $C_6$ alkyl;

Still further preferred compounds of formula I include those wherein:

$R^1$ to $R^{18}$ are the same and each represents $C_1$ to $C_6$ alkyl, particularly methyl.

Still further preferred compounds of formula I include those wherein:

K, D, Z and E are each independently selected from the group consisting of hydrogen or $C_1$ to $C_6$ alkyl, particularly where each of K, D, Z and E represent the same group, especially where each of K, D, Z and E represent hydrogen; or K represents —$CH_2$-$Q^3(CR^{13}(R^{14})(R^{15}))CR^{16}(R^{17})(R^{18})$ and D, Z and E are each independently selected from the group consisting of hydrogen or $C_1$ to $C_6$ alkyl, particularly where both D and E represent the same group, especially where D, Z and E represent hydrogen.

Especially preferred specific compounds of formula I include those wherein:

each $R^1$ to $R^{12}$ is the same and represents methyl;
A and B are the same and represent —$CH_2$—;
K, D, Z and E are the same and represent hydrogen.

In a still further embodiment, at least one ($CR^xR^yR^z$) group attached to $Q^1$ and/or $Q^2$, i.e. $CR^1R^2R^3$, $CR^4R^5R^6$, $CR^7R^8R^9$, or $CR^{10}R^{11}R^{12}$, may instead be represented by the group (Ad) wherein:

Ad each independently represent an optionally substituted adamantyl or congressyl radical bonded to the phosphorous atom via any one of its tertiary carbon atoms, the said optional substitution being by one or more substituents selected from hydrogen, lower alkyl, halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $C(S)R^{25}R^{26}$, $SR^{27}$ or $C(O)SR^{27}$; or both ($CR^xR^yR^z$) groups attached to either or both $Q^1$ and/or $Q^2$, or $Q^3$ (if present), form an optionally substituted 2-phospha-tricyclo[3.3.1.1{3,7}]decyl group (also termed a 2-phospha-adamantyl group (2-PA-group)) or derivative thereof as more particularly defined hereinafter, or form a ring system of formula

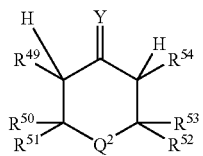

wherein $R^{49}$, and $R^{54}$, each independently represent hydrogen, lower alkyl or aryl;

$R^{50}$ to $R^{53}$, when present, each independently represent hydrogen, lower alkyl, aryl or Het; and Y represents oxygen, sulfur or N—$R^{55}$; and $R^{55}$, when present, represents hydrogen, lower alkyl or aryl.

In this embodiment, formula I may be represented as:

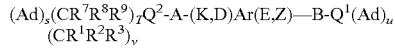

wherein Ar, A, B, K, D, E and Z, $Q^1$, $Q^2$, and $Q^3$, and $R^1$ to $R^{27}$ are as defined hereinbefore except that K, D, E and Z may represent -J-$Q^3(Ad)_w(CR^{13}(R^{14})(R^{15}))_x$ instead of -J-$Q^3(CR^{13}(R^{14})(R^{15}))CR^{16}(R^{17})(R^{18})$ and Ad is as defined above, S & U=0, 1 or 2 provided that S+U≧1;
T & V=0, 1 or 2 provided that T+V≦3;
W & X=0, 1 or 2.

In addition to the preferred embodiments for $R^1$ to $R^{18}$, $Q^1$ to $Q^3$, A, B, J (when present), K, D, E or Z, $R^{19}$ to $R^{27}$, noted hereinbefore, all of which equally apply to the present embodiment where at least one (Ad) group is present, the following also applies.

Further preferred compounds of formula I include those wherein:

A and B both represent —$CH_2$— or —$C_2H_4$—, particularly —$CH_2$—;

K, D, Z and E each independently represent hydrogen, $C_1$-$C_6$ alkyl phenyl or $C_1$-$C_6$ alkyl or -J-$Q^3(Ad)_w(CR^{13}(R^{14})(R^{15}))_x$ where J is the same as A; or two of K, D, E and Z together with the carbon atoms of the aryl ring to which they are attached form an unsubstituted phenyl ring;

$R^1$ to $R^3$, $R^7$ to $R^9$, and $R^{13}$ to $R^{15}$ (when present) each independently represent $C_1$ to $C_6$ alkyl, and the total number of (Ad) groups attached to $Q^1$ and $Q^2$ is ≧3, i.e. S+U≧3, and W and X=0, 1 or 2.

Still further preferred compounds of formula I include those wherein:

$R^1$ to $R^3$, $R^7$ to $R^9$ and $R^{13}$ to $R^{15}$ (when present) are the same and each represents $C_1$ to $C_6$ alkyl, particularly methyl, and the total number of (Ad) groups attached to $Q^1$ and $Q^2$ is ≧3, i.e. S+U≧3.

Still further preferred compounds of formula I include those wherein:

K, D, Z and E are each independently selected from the group consisting of hydrogen or $C_1$ to $C_6$ alkyl, particularly where each of K, D, Z and E represent the same group, especially where each of K, D, Z and E represent hydrogen; or K represents —$CH_2$-$Q^3(Ad)_w(CR^{13}(R^{14})(R^{15}))_x$ and D, Z and E are each independently selected from the group consisting of hydrogen or $C_1$ to $C_6$ alkyl, particularly where both D and E represent the same group, especially where D, Z and E represent hydrogen, wherein W and X=0, 1 or 2.

Especially preferred specific compounds of formula I include those wherein:

each $R^1$ to $R^3$, and $R^7$ to $R^9$ is the same and represents methyl or the total number of (Ad) groups attached to $Q^1$ and $Q^2$ is 2, i.e. S+U=2;

A and B are the same and represent —$CH_2$—;
K, D, Z and E are the same and represent hydrogen.

Especially preferred specific compounds of formula I include those wherein Ad is joined to $Q_1$ or $Q_2$ at the same position in each case. Preferably S≧1 and U≧1, more preferably, S=2 and U≧1 or vice versa, most preferably S & U=2, wherein S is the number of (Ad) groups attached to $Q^2$ and U is the number of (Ad) groups attached to $Q^1$.

Specific but non-limiting examples of bidentate ligands within this embodiment include the following: 1,2 bis(diadamantylphosphinomethyl)benzene, 1,2 bis(di-3,5-dimethyladamantylphosphinomethyl)benzene, 1,2 bis(di-5-tert-butyladamantylphosphinomethyl)benzene, 1,2 bis(1-adamantyl tert-butyl-phosphinomethyl)benzene, 1-(diadamantylphosphinomethyl)-2-(di-tert-butylphosphinomethyl) benzene, 1-(di-tert-butylphosphinomethyl)-2-(dicongressylphosphinomethyl)benzene, 1-(di-tert-butylphosphinomethyl)-2-(phospha-adamantyl-P-methyl)benzene, 1-(diadamantylphosphinomethyl)-2-(phospha-adamantyl-P-methyl) benzene, 1-(tert-butyladamantylphosphinomethyl)-2-(diadamantylphosphinomethyl)benzene and 1-[(P-(2,2,6,6,-tetra-methylphosphinan-4-one)phosphinomethyl)]-2-(phospha-adamantyl-P-methyl)benzene, wherein "phospha-adamantyl" is selected from 2-phospha-1,3,5,7-tetramethyl-6,9,10-trioxadamantyl, 2-phospha-1,3,5-trimethyl-6,9,10 trioxadamantyl, 2-phospha-1,3,5,7-tetra(trifluoromethyl)-6,9,10-trioxadamantyl or 2-phospha-1,3,5-tri(trifluoromethyl)-6,9,10-trioxadamantyl. Nevertheless, the skilled person in the art would appreciate that other bidentate ligands can be envisaged without departing from the scope of the invention.

As mentioned herein, in a yet further set of embodiments, the bidentate phosphine ligand is of general formula (II).

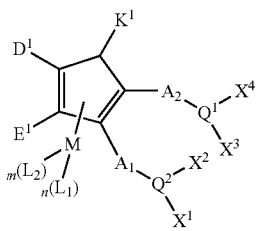

(II)

wherein:

$A_1$ and $A_2$, and $A_3$, $A_4$ and $A_5$ (when present), each independently represent lower alkylene;

$K^1$ is selected from the group consisting of hydrogen, lower alkyl, aryl, Het, halo, cyano, nitro, —$OR^{19}$, —$OC(O)R^{20}$, —$C(O)R^{21}$, —$C(O)OR^{22}$, —$N(R^{23})R^{24}$, —$C(O)N(R^{25})R^{26}$, —$C(S)(R^{27})R^{28}$, —$SR^{29}$, —$C(O)SR^{30}$, —$CF_3$ or -$A_3$-$Q^3$($X^5$)$X^6$;

$D^1$ is selected from the group consisting of hydrogen, lower alkyl, aryl, Het, halo, cyano, nitro, —$OR^{19}$, —$OC(O)R^{20}$, —$C(O)R^{21}$, —$C(O)OR^{22}$, —$N(R^{23})R^{24}$, —$C(O)N(R^{25})R^{26}$, —$C(S)(R^{27})R^{28}$, —$SR^{29}$, —$C(O)SR^{30}$, —$CF_3$ or -$A_4$-$Q^4$($X^7$)$X^8$;

$E^1$ is selected from the group consisting of hydrogen, lower alkyl, aryl, Het, halo, cyano, nitro, —$OR^{19}$, —$OC(O)R^{20}$, —$C(O)R^{21}$, —$C(O)OR^{22}$, —$N(R^{23})R^{24}$, —$C(O)N(R^{25})R^{26}$, —$C(S)(R^{27})R^{28}$, —$SR^{29}$, —$C(O)SR^{30}$, —$CF_3$ or -$A_5$-$Q^5$($X^9$)$X^{10}$;

or both $D^1$ and $E^1$ together with the carbon atoms of the cyclopentadienyl ring to which they are attached form an optionally substituted phenyl ring:

$X^1$ represents $CR^1(R^2)(R^3)$, congressyl or adamantyl, $X^2$ represents $CR^4(R^5)(R^6)$, congressyl or adamantyl, or $X^1$ and $X^2$ together with $Q^2$ to which they are attached form an optionally substituted 2-phospha-tricyclo[3.3.1.1{3,7}]decyl group or derivative thereof, or $X^1$ and $X^2$ together with $Q^2$ to which they are attached form a ring system of formula IIIa

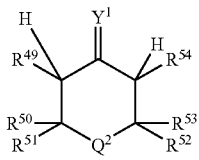

(IIIa)

$X^3$ represents $CR^7(R^8)(R^9)$, congressyl or adamantyl, $X^4$ represents $CR^{10}(R^{11})(R^{12})$, congressyl or adamantyl, or $X^3$ and $X^4$ together with $Q^1$ to which they are attached form an optionally substituted 2-phospha-tricyclo[3.3.1.1{3,7}]decyl group or derivative thereof, or $X^3$ and $X^4$ together with $Q^1$ to which they are attached form a ring system of formula IIIb

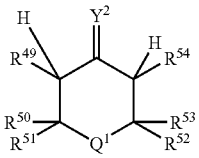

(IIIb)

$X^5$ represents $CR^{13}(R^{14})(R^{15})$, congressyl or adamantyl, $X^6$ represents $CR^{16}(R^{17})(R^{18})$, congressyl or adamantyl, or $X^5$ and $X^6$ together with $Q^3$ to which they are attached form an optionally substituted 2-phospha-tricyclo[3.3.1.1{3,7}]decyl group or derivative thereof, or $X^5$ and $X^6$ together with $Q^3$ to which they are attached form a ring system of formula IIIc

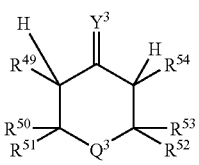

(IIIc)

$X^7$ represents $CR^{31}(R^{32})(R^{33})$ congressyl or adamantyl, $X^8$ represents $CR^{34}(R^{35})(R^{36})$, congressyl or adamantyl, or $X^7$ and $X^8$ together with $Q^4$ to which they are attached form an optionally substituted 2-phospha-tricyclo[3.3.1.1{3,7}]decyl group or derivative thereof, or $X^7$ and $X^8$ together with $Q^4$ to which they are attached form a ring system of formula IIId

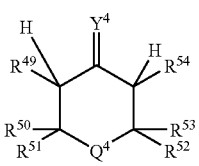

(IIId)

$X^9$ represents $CR^{37}(R^{38})(R^{39})$, congressyl or adamantyl, $X^{10}$ represents $CR^{40}(R^{41})(R^{42})$, congressyl or adamantyl, or $X^9$ and $X^{10}$ together with $Q^5$ to which they are attached form an optionally substituted 2-phospha-tricyclo[3.3.1.1.{3,7}]decyl group or derivative thereof, or $X^9$ and $X^{10}$ together with $Q^5$ to which they are attached form a ring system of formula IIIe

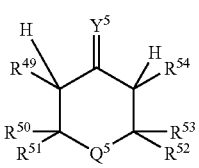

(IIIe)

and in this yet further embodiment, $Q^1$ and $Q^2$, and $Q^3$, $Q^4$ and $Q^5$ (when present), each independently represent phosphorus, arsenic or antimony;

M represents a Group VIB or VIIIB metal or metal cation thereof;

$L_1$ represents an optionally substituted cyclopentadienyl, indenyl or aryl group;

$L_2$ represents one or more ligands each of which are independently selected from hydrogen, lower alkyl, alkylaryl, halo, CO, $P(R^{43})(R^{44})R^{45}$ or $N(R^{46})(R^{47})R^{48}$;

$R^1$ to $R^{18}$ and $R^{31}$ to $R^{42}$, when present, each independently represent hydrogen, lower alkyl, aryl, halo or Het;

$R^{19}$ to $R^{30}$ and $R^{43}$ to $R^{48}$, when present, each independently represent hydrogen, lower alkyl, aryl or Het;

$R^{49}$, $R^{54}$ and $R^{55}$, when present, each independently represent hydrogen, lower alkyl or aryl;

$R^{50}$ to $R^{53}$, when present, each independently represent hydrogen, lower alkyl, aryl or Het;

$Y^1$, $Y^2$, $Y^3$, $Y^4$ and $Y^5$, when present, each independently represent oxygen, sulfur or N—$R^{55}$;

n=0 or 1;

and m=0 to 5;

provided that when n=1 then m equals 0, and when n equals 0 then m does not equal 0.

Preferably in a compound of formula II when both $K^1$ represents -$A_3$-$Q^3(X^5)X^6$ and $E^1$ represents -$A_5$-$Q^5(X^9)X^{10}$, then $D^1$ represents -$A_4$-$Q^4(X^7)X^8$.

Preferably, in this embodiment, $R^1$ to $R^{18}$ and $R^{31}$to $R^{42}$, when present, each independently represent hydrogen, optionally substituted $C_1$ to $C_6$ alkyl, $C_1$-$C_6$ alkyl phenyl (wherein the phenyl group is optionally substituted as defined herein), trifluoromethyl or phenyl (wherein the phenyl group is optionally substituted as defined herein). Even more preferably, $R^1$ to $R^{18}$ and $R^{31}$ to $R^{42}$, when present, each independently represent hydrogen, $C_1$ to $C_6$ alkyl, which is optionally substituted as defined herein, trifluoromethyl or optionally substituted phenyl. Even more preferably, $R^1$ to $R^{18}$ and $R^{31}$ to $R^{42}$, when present each independently represent hydrogen, non-substituted $C_1$ to $C_6$ alkyl or phenyl which is optionally substituted with one or more substituents selected from non-substituted $C_1$ to $C_6$ alkyl or $OR^{19}$ where $R^{19}$ represents hydrogen or unsubstituted $C_1$ to $C_6$ alkyl. More preferably, $R^1$ to $R^{18}$ and $R^{31}$ to $R^{42}$, when present, each independently represent hydrogen or non-substituted $C_1$ to $C_6$ alkyl such as methyl, ethyl, n-propyl, iso-propyl, n-butyl, iso-butyl, tert-butyl, pentyl, hexyl and cyclohexyl, especially methyl. Most preferably, $R^1$ to $R^{18}$ and $R^{31}$ to $R^{42}$ when present, each independently represent non-substituted $C_1$ to $C_6$ alkyl such as methyl, ethyl, n-propyl, iso-propyl, n-butyl, iso-butyl, tert-butyl, pentyl, hexyl and cyclohexyl, especially methyl.

Alternatively, or additionally, one or more of the groups $R^1$ to $R^3$, $R^4$ to $R^6$, $R^7$ to $R^9$, $R^{10}$ to $R^{12}$, $R^{13}$ to $R^{15}$, $R^{16}$ to $R^{18}$, $R^{31}$ to $R^{33}$, $R^{34}$ to $R^{36}$, $R^{37}$ to $R^{39}$ or $R^{40}$ to $R^{42}$ (when present) together with the carbon atom to which they are attached independently may form cyclic alkyl structures such as 1-norbornyl or 1-norbornadienyl.

Alternatively, or additionally, one or more of the groups $R^1$ and $R^2$, $R^4$ and $R^5$, $R^7$ and $R^8$, $R^{10}$ and $R^{11}$, $R^{13}$ and $R^{14}$, $R^{16}$ and $R^{17}$, $R^{31}$ and $R^{32}$, $R^{34}$ and $R^{35}$, $R^{37}$ and $R^{38}$ or $R^{40}$ and $R^{41}$ (when present) together with the carbon atom to which they are attached independently may form a cyclic alkyl structures, preferably a $C_5$ to $C_7$ cyclic alkyl structure such as cyclohexyl and cyclopentyl, and $R^3$, $R^6$, $R^9$, $R^{12}$, $R^{15}$, $R^{18}$, $R^{33}$, $R^{36}$, $R^{39}$ and $R^{42}$ (when present) each independently represent hydrogen, lower alkyl, trifluoromethyl or aryl as defined above, particularly non-substituted $C_1$ to $C_6$ alkyl and hydrogen, especially non-substituted $C_1$ to $C_6$ alkyl.

In an especially preferred embodiment, each of $R^1$ to $R^{18}$ and $R^{31}$ to $R^{42}$, when present, do not represent hydrogen. Suitably, such an arrangement means $Q^1$, $Q^2$, $Q^3$, $Q^4$ and $Q^5$ are bonded to a carbon atom of $X^1$ to $X^{10}$, respectively, which bears no hydrogen atoms.

Preferably, $R^1$, $R^4$, $R^7$, $R^{10}$, $R^{13}$, $R^{16}$, $R^{31}$, $R^{34}$, $R^{37}$ and $R^{40}$ (when present), each represent the same substituent as defined herein; $R^2$, $R^5$, $R^8$, $R^{11}$, $R^{14}$, $R^{17}$, $R^{32}$, $R^{35}$, $R^{38}$ and $R^{41}$ (when present), each represent the same substituent as defined herein; and $R^3$, $R^6$, $R^9$, $R^{12}$, $R^{15}$, $R^{18}$, $R^{33}$, $R^{36}$, $R^{39}$ and $R^{42}$ (when present), each represent the same substituent as defined herein. More preferably $R^1$, $R^4$, $R^7$, $R^{10}$, $R^{13}$, $R^{16}$, $R^{31}$, $R^{34}$, $R^{37}$ and $R^{40}$ (when present) each represent the same $C_1$-$C_6$ alkyl, particularly non-substituted $C_1$-$C_6$ alkyl, such as methyl, ethyl, n-propyl, iso-propyl, n-butyl, iso-butyl, tert-butyl, pentyl, hexyl or cyclohexyl, or trifluoromethyl; $R^2$, $R^5$, $R^8$, $R^{11}$, $R^{14}$, $R^{17}$, $R^{32}$, $R^{35}$, $R^{38}$ and $R^{41}$ (when present), each independently represent the same $C_1$-$C_6$ alkyl as defined above, or trifluoromethyl; and $R^3$, $R^6$, $R^9$, $R^{12}$, $R^{15}$, $R^{18}$, $R^{33}$, $R^{36}$, $R^{39}$ and $R^{42}$ (when present), each independently represent the same $C_1$-$C_6$ alkyl as defined above, or trifluoromethyl. For example: $R^1$, $R^4$, $R^7$, $R^{10}$, $R^{13}$ and $R^{16}$ (when present) each represent methyl; $R^2$, $R^5$, $R^8$, $R^{11}$, $R^{14}$ and $R^{17}$ each represent ethyl (when present); and, $R^3$, $R^6$, $R^9$, $R^{12}$, $R^{15}$ and $R^{18}$ (when present) each represent n-butyl or n-pentyl.

In an especially preferred embodiment each $R^1$ to $R^{18}$ and $R^{31}$ to $R^{42}$ group (when present) represents the same substituent as defined herein. Preferably, each $R^1$ to $R^{18}$ and $R^{31}$ to $R^{42}$ group represents the same $C_1$ to $C_6$ alkyl group, particularly non-substituted $C_1$-$C_6$ alkyl, such as methyl, ethyl, n-propyl, iso-propyl, n-butyl, iso-butyl, tert-butyl, pentyl, hexyl and cyclohexyl, or trifluoromethyl. Most preferably, each $R^1$ to $R^{18}$ and $R^{31}$ to $R^{42}$ group represents non-substituted $C_1$-$C_6$ alkyl, particularly methyl.

The term adamantyl when used herein means an adamantyl group which may be bonded to $Q^1$, $Q^2$, $Q^3$, $Q^4$ and $Q^5$, respectively, in position 1 or 2. Tricyclo[3.3.1.1.{3,7}]decyl is the systematic name for an adamantyl group, suitably $Q^1$, $Q^2$, $Q^3$, $Q^4$ and $Q^5$, respectively, may be bonded to the 1 position or 2 position of one or two tricyclo[3.3.1.1.{3,7}]decyl groups. Preferably, $Q^1$ and $Q^2$, and $Q^3$, $Q^4$ and $Q^5$, when present, is bonded to a tertiary carbon of one or more adamantyl groups. Suitably, when the adamantyl group represents unsubstituted adamantyl, $Q^1$ and $Q^2$, and $Q^3$, $Q^4$ and $Q^5$ when present are preferably bonded to the 1 position of one or more tricyclo[3.3.1.1{3,7}]decyl groups i.e. the carbon atom of the adamantyl group bears no hydrogen atom.

The adamantyl group may optionally comprise, besides hydrogen atoms, one or more substituents selected from lower alkyl, —$OR^{19}$, —$OC(O)R^{20}$, halo, nitro, —$C(O)R^{21}$, —$C(O)OR^{22}$, cyano, aryl, —$N(R^{23})R^{24}$, —$C(O)N(R^{25})R^{26}$, —$C(S)(R^{27})R^{28}$, —$CF_3$, —$P(R^{56})R^{57}$, —$PO(R^{58})(R^{59})$, —$PO_3H_2$, —$PO(OR^{60})(OR^{61})$, or —$SO_3R^{62}$, wherein $R^{19}$, $R^{20}$, $R^{21}$, $R^{22}$, $R^{23}$, $R^{24}$, $R^{25}$, $R^{26}$, $R^{27}$, $R^{28}$, lower alkyl, cyano and aryl are as defined herein and $R^{56}$ to $R^{62}$ each independently represent hydrogen, lower alkyl, aryl or Het.

Suitably, when the adamantyl group is substituted with one or more substituents as defined above, highly preferred substituents include unsubstituted $C_1$ to $C_8$ alkyl, —$OR^{19}$, —$OC(O)R^{20}$, phenyl, —$C(O)OR^{22}$, fluoro, —$SO_3H$, —$N(R^{23})R^{24}$, —$P(R^{56})R^{57}$, —$C(O)N(R^{25})R^{26}$ and —$PO(R^{58})(R^{59})$, —$CF_3$, wherein $R^{19}$ represents hydrogen, unsubstituted $C_1$-$C_8$ alkyl or phenyl, $R^{20}$, $R^{22}$, $R^{23}$, $R^{24}$, $R^{25}$, $R^{26}$ each independently represent hydrogen or unsubstituted $C_1$-$C_8$ alkyl, $R^{56}$ to $R^{53}$, $R^{56}$ each independently represent unsubstituted $C_1$-$C_8$ alkyl or phenyl.

Suitably, the adamantyl group may comprise, besides hydrogen atoms, up to 10 substituents as defined above, preferably up to 5 substituents as defined above, more preferably up to 3 substituents as defined above. Suitably, when the adamantyl group comprises, besides hydrogen atoms, one or more substituents as defined herein, preferably each substituent is identical. Preferred substituents are unsubstituted $C_1$-$C_8$ alkyl and trifluoromethyl, particularly unsubstituted $C_1$-$C_8$ alkyl such as methyl. A highly preferred adamantyl group comprises hydrogen atoms only i.e. the adamantyl group is not substituted.

Preferably, when more than one adamantyl group is present in a compound of formula III, each adamantyl group is identical.

By the term 2-phospha-tricyclo[3.3.1.1.{3,7}]decyl group we mean a 2-phospha-adamantyl group formed by the combination of $X^1$ and $X^2$ together with $Q^2$ to which they are attached, a 2-phospha-adamantyl group formed by the combination of $X^3$ and $X^4$ together with $Q^1$ to which they are attached, a 2-phospha-adamantyl group formed by the combination of $X^5$ and $X^6$ together with $Q^3$ to which they are attached, a 2-phospha-adamantyl group formed by the combination of $X^7$ and $X^8$ together with $Q^4$ to which they are attached and a 2-phospha-adamantyl group formed by the combination of $X^9$ and $X^{10}$ together with $Q^5$ to which they are attached, wherein $Q^1$, $Q^2$, $Q^3$, $Q^4$ and $Q^5$ is in the 2-position of the adamantyl group of which it forms an integral part and each of $Q^1$, $Q^2$, $Q^3$, $Q^4$ and $Q^5$ represents phosphorus.

The 2-phospha-tricyclo[3.3.1.1.{3,7}]decyl group (referred to as 2-phospha-adamantyl group herein) may optionally comprise, beside hydrogen atoms, one or more substituents. Suitable substituents include those substituents as defined herein in respect of the adamantyl group. Highly preferred substituents include lower alkyl, particularly unsubstituted $C_1$-$C_8$ alkyl, especially methyl, trifluoromethyl, —$OR^{19}$ wherein $R^{19}$ is as defined herein particularly unsubstituted $C_1$-$C_8$ alkyl or aryl, and 4-dodecylphenyl. When the 2-phospha-adamantyl group includes more than one substituent, preferably each substituent is identical.

Preferably, the 2-phospha-adamantyl group is substituted on one or more of the 1, 3, 5 or 7 positions with a substituent as defined herein. More preferably, the 2-phospha-adamantyl group is substituted on each of the 1, 3 and 5 positions. Suitably, such an arrangement means the phosphorous atom of the 2-phospha-adamantyl group is bonded to carbon atoms in the adamantyl skeleton having no hydrogen atoms. Most preferably, the 2-phospha-adamantyl group is substituted on each of the 1, 3, 5 and 7 positions. When the 2-phospha-adamantyl group includes more than 1 substituent preferably each substituent is identical. Especially preferred substituents are unsubstituted $C_1$-$C_8$ alkyl and trifluoromethyl, particularly unsubstituted $C_1$-$C_8$ alkyl such as methyl.

Preferably, the 2-phospha-adamantyl group includes additional heteroatoms, other than the 2-phosphorous atom, in the 2-phospha-adamantyl skeleton. Suitable additional heteroatoms include oxygen and sulphur atoms, especially oxygen atoms. More preferably, the 2-phospha-adamantyl group includes one or more additional heteroatoms in the 6, 9 and 10 positions. Even more preferably, the 2-phospha-adamantyl group includes an additional heteroatom in each of the 6, 9 and 10 positions. Most preferably, when the 2-phospha-adamantyl group includes two or more additional heteroatoms in the 2-phospha-adamantyl skeleton, each of the additional heteroatoms are identical. An especially preferred 2-phospha-adamantyl group, which may optionally be substituted with one or more substituents as defined herein, includes an oxygen atom in each of the 6, 9 and 10 positions of the 2-phospha-adamantyl skeleton.

Highly preferred 2-phospha-adamantyl groups as defined herein include 2-phospha-1,3,5,7-tetramethyl-6,9,10-trioxadamantyl group, 2-phospha-1,3,5-trimethyl-6,9,10-trioxadamantyl group, 2-phospha-1,3,5,7-tetra(trifluoromethyl)-6,9, 10-trioxadamantyl group, and 2-phospha-1,3,5-tri(trifluoromethyl)-6,9,10-trioxadamantyl group. Most preferably, the 2-phospha-adamantyl is selected from 2-phospha-1,3,5,7-tetramethyl-6,9,10-trioxadamantyl group or 2-phospa-1,3,5,-trimethyl-6,9,10-trioxadamantyl group.

Preferably, when more than one 2-phospha-adamantyl group is present in a compound of formula III, each 2-phospha-adamantyl group is identical.

The above definition of the term "2-phospha-tricyclo [3.3.1.1.{3,7}]decyl group" applies equally to the group when it is present in formula I but wherein $X''$ in formula III, i.e. $X^1$, $X^2$, $X^3$ . . . $X^{10}$, is denoted $CR^xR^yR^z$, i.e. $CR^1R^2R^3$, . . . $CR^{16}R^{17}R^{18}$, in formula I.

The term congressyl when used herein means a congressyl group (also known as diamantyl group) which may be bonded to $Q^1$, $Q^2$, $Q^3$, $Q^4$ and $Q^5$ respectively. Preferably, $Q^1$ and $Q^2$, and $Q^3$, $Q^4$ and $Q^5$, when present, are bonded to one of the tertiary carbon atoms of the congressyl groups. Suitably, when the congressyl group is unsubstituted, $Q^1$ and $Q^2$, and $Q^3$, $Q^4$ and $Q^5$ when present, are preferably bonded to the 1-position of one or more congressyl groups.

The congressyl group may optionally comprise, beside hydrogen atoms, one or more substituents. Suitable substituents include those substituents as defined herein in respect of the adamantyl group. Highly preferred substituents include unsubstituted $C_1$-$C_6$ alkyl groups, particularly methyl, and trifluoromethyl. Most preferably, the congressyl group is unsubstituted and comprises hydrogen atoms only.

Preferably, when more than one congressyl group is present in a compound of formula III, each congressyl group is identical.

Preferably, where one or more ring systems of formula IIIa, IIIb, IIIc, IIId or IIIe are present in a compound of formula III, $R^{50}$ to $R^{53}$ each independently represent lower alkyl, aryl or Het, which groups are optionally substituted and/or terminated as defined herein. Such an arrangement means $Q^2$, $Q^1$, $Q^3$, $Q^4$ and $Q^5$ of the ring system of formula IIIa to IIIe, respectively, is not bonded to a carbon atom bearing a hydrogen atom. Even more preferably, $R^{50}$ to $R^{53}$ each independently represent optionally substituted $C_1$-$C_6$ alkyl, preferably non-substituted $C_1$-$C_6$ alkyl, phenyl optionally substituted with non-substituted $C_1$-$C_6$ alkyl or $OR^{19}$ where $R^{19}$ represents non-substituted $C_1$-$C_6$ alkyl, or trifluoromethyl. Even more preferably $R^{50}$ to $R^{53}$ each represent the same group as defined herein, particularly non-substituted $C_1$-$C_6$ alkyl, especially methyl.

Preferably, where one or more ring system of formula IIIa to IIIe are present in a compound of formula III, $R^{49}$ and $R^{54}$ each independently represent optionally substituted $C_1$-$C_6$ alkyl, preferably non-substituted $C_1$-$C_6$ alkyl, phenyl optionally substituted with non-substituted $C_1$-$C_6$ alkyl or $OR^{19}$ where $R^{19}$ represents non-substituted $C_1$-$C_6$ alkyl, trifluoromethyl or hydrogen. More preferably, $R^{49}$ and $R^{54}$ represent the same group as defined herein, especially hydrogen.

Preferably, where one or more ring systems of formula IIIa to IIIe are present in a compound of formula III, $Y^1$ to $Y^5$ are identical. Most preferably, each of $Y^1$ to $Y^5$ represents oxygen. Preferably, where more than one ring system of formula IIIa to IIIe is present in a compound of formula III, each such ring system is identical.

Preferred embodiments of the present invention include those wherein:

$X^1$ represents $CR^1(R^2)(R^3)$, $X^2$ represents $CR^4(R^5)(R^6)$, $X^3$ represents $CR^7(R^8)(R^9)$ and $X^4$ represents $CR^{10}(R^{11})(R^{12})$;

$X^1$ represents $CR^1(R^2)(R^3)$, $X^2$ represents adamantyl, $X^3$ represents $CR^7(R^8)(R^9)$ and $X^4$ represents adamantyl;

$X^1$ represents $CR^1(R^2)(R^3)$, $X^2$ represents congressyl, $X^3$ represents $CR^7(R^8)(R^9)$ and $X^4$ represents congressyl;

$X^1$ represents $CR^1(R^2)(R^3)$, $X^2$ represents $CR^4(R^5)(R^6)$, and $X^3$ and $X^4$ together with $Q^1$ to which they are attached form a ring system of formula IIIb or a 2-phospha-adamantyl group;

$X^1$ represents $CR^1(R^2)(R^3)$, $X^2$ represents adamantyl, $X^3$ and $X^4$ together with $Q^1$ to which they are attached form a ring system of formula IIIb or a 2-phospha-adamantyl group;

$X^1$ represents $CR^1(R^2)(R^3)$, $X^2$ represents congressyl, $X^3$ and $X^4$ together with $Q^1$ to which they are attached form a ring system of formula IIIb or a 2-phospha-adamantyl group;

$X^1$ to $X^4$ each independently represent adamantyl;

$X^1$ to $X^4$ each independently represent congressyl;

$X^1$ and $X^2$ each independently represent adamantyl and $X^3$ and $X^4$ each independently represent congressyl;

$X^1$ and $X^3$ independently represent adamantyl and $X^2$ and $X^4$ independently represent congressyl;

$X^1$ and $X^2$ independently represent adamantyl, $X^3$ represents $CR^7(R^8)(R^9)$ and $X^4$ represents $CR^{10}(R^{11})(R^{12})$;

$X^1$ and $X^2$ independently represent congressyl, $X^3$ represents $CR^7(R^8)(R^9)$ and $X^4$ represents $CR^{10}(R^{11})(R^{12})$;

$X^1$ and $X^2$ independently represent adamantyl, and $X^3$ and $X^4$ together with $Q^1$ to which they are attached form a ring system of formula IIIb or a 2-phospha-adamantyl group;

$X^1$ and $X^2$ independently represent congressyl, and $X^3$ and $X^4$ together with $Q^1$ to which they are attached form a ring system of formula IIIb or a 2-phospha-adamantyl group;

$X^1$ and $X^2$ together with $Q^2$ to which they are attached form a ring system of formula IIIa, and $X^3$ and $X^4$ together with $Q^1$ to which they are attached form a ring system of formula IIIb;

$X^1$ and $X^2$ together with $Q^2$ to which they are attached form a 2-phospha-adamantyl group, and $X^3$ and $X^4$ together with $Q^1$ to which they are attached form a 2-phospha-adamantyl group;

Highly preferred embodiments of the present invention include those wherein:

$X^1$ represents $CR^1(R^2)(R^3)$, $X^2$ represents $CR^4(R^5)(R^6)$, $X^3$ represents $CR^7(R^8)(R^9)$ and $X^4$ represents $CR^{10}(R^{11})(R^{12})$;

$X^1$ represents $CR^1(R^2)(R^3)$, $X^2$ represents adamantyl, $X^3$ represents $CR^7(R^8)(R^9)$ and $X^4$ represents adamantyl;

$X^1$ represents $CR^1(R^2)(R^3)$, $X^2$ represents congressyl, $X^3$ represents $CR^7(R^8)(R^9)$ and $X^4$ represents congressyl;

$X^1$ to $X^4$ each independently represent adamantyl;

$X^1$ to $X^4$ each independently represent congressyl;

$X^1$ and $X^2$ together with $Q^2$ to which they are attached form a ring system of formula IIIa, and $X^3$ and $X^4$ together with $Q^1$ to which they are attached form a ring system of formula IIIb;

$X^1$ and $X^2$ together with $Q^2$ to which they are attached form a 2-phospha-adamantyl group, and $X^3$ and $X^4$ together with $Q^1$ to which they are attached form a 2-phospha-adamantyl group;

Preferably in a compound of formula III, $X^1$ is identical to $X^3$ and $X^2$ is identical to $X^4$. More preferably, $X^1$ is identical to $X^3$ and $X^5$, $X^7$ and $X^9$ when present, and $X^2$ is identical to $X^4$ and $X^6$, $X^8$ and $X^{10}$ when present. Even more preferably, $X^1$ to $X^4$ are identical. Most preferably, $X^1$ to $X^4$ are identical to each of $X^6$ to $X^{10}$ when present.

Preferably, in the compound of formula III, $X^1$ and $X^2$ represent identical substituents, $X^3$ and $X^4$ represent identical substituents, $X^5$ and $X^6$ (when present) represent identical substituents, $X^7$ and $X^8$ (when present) represent identical substituents, and $X^9$ and $X^{10}$ (when present) represent identical substituents.

Preferably, in a compound of formula III, $K^1$ represents $-A_3-Q^3(X^5)X^6$, hydrogen, lower alkyl, $-CF_3$, phenyl or lower alkyl phenyl. More preferably, $K^1$ represents $-A_3-Q^3$ $(X^5)X^6$, hydrogen, unsubstituted $C_1-C_6$ alkyl, unsubstituted phenyl, trifluoromethyl or $C_1-C_6$ alkyl phenyl.

In a particular preferred embodiment $K^1$ in a compound of formula III represents hydrogen.

In an alternative embodiment where $K^1$ does not represent hydrogen, $K^1$ represents $-A_3-Q^3(X^5)X^6$. Preferably, $X^5$ is identical to $X^3$ or $X^1$, and $X^6$ is identical to $X^2$ or $X^4$. More preferably, $X^5$ is identical to both $X^3$ and $X^1$, and $X^6$ is identical to both $X^2$ and $X^4$. Even more preferably, $-A_3-Q^3(X^5)X^6$ is identical to either $-A_1-Q^2(X^1)X^2$ or $-A_2-Q^1(X^3)X^4$. Most preferably, $-A_3-Q^3(X^5)X^6$ is identical to both $-A_1-Q^2(X^1)X^2$ and $-A_2-Q^1(X^3)X^4$.

Most preferably, $K^1$ represents hydrogen in a compound of formula III.

Preferably, in the compound of formula III, $D^1$ represents $-A_4-Q^4(X^7)X^8$, hydrogen, lower alkyl, $CF_3$, phenyl or lower alkylphenyl, and $E^1$ represents $-A_5-Q^5(X^9)X^{10}$, hydrogen, lower alkyl, $CF_3$, phenyl or lower alkylphenyl, or $D^1$ and $E^1$ together with the carbons of the cyclopentadienyl ring to which they are attached form an optionally substituted phenyl ring. More preferably, $D^1$ represents $-A_4-Q^4(X^7)X^8$, hydrogen, phenyl, $C_1-C_6$ alkylphenyl, unsubstituted $C_1-C_6$ alkyl, such as methyl, ethyl, propyl, butyl, pentyl and hexyl, or $CF_3$; $E^1$ represents $-A_5-Q^5(X^9)X^{10}$, hydrogen, phenyl, $C_1-C_6$ alkylphenyl, unsubstituted $C_1-C_6$ alkyl such as methyl, ethyl, propyl, butyl, pentyl and hexyl, or $-CF_3$; or both $D^1$ and $E^1$ together with the carbon atoms of the cyclopentadienyl ring to which they are attached form a phenyl ring which is optionally substituted with one or more groups selected from phenyl, $C_1-C_6$ alkylphenyl, unsubstituted $C_1-C_6$ alkyl or $-CF_3$.

Suitably, when $D^1$ and $E^1$ together with the carbon atoms of the cyclopentadienyl ring to which they are attached form an optionally substituted phenyl ring, the metal M or cation thereof is attached to an indenyl ring system.

In a particular preferred embodiment, $D^1$ in a compound of formula III, represents hydrogen.

In an alternative embodiment where $D^1$ does not represent hydrogen, $D^1$ represents $-A_4-Q^4(X^7)X^8$. Preferably $X^8$ is identical to $X^4$ or $X^2$, and $X^7$ is identical to $X^1$ or $X^3$. More preferably, $X^8$ is identical to both $X^4$ and $X^2$, and $X^7$ is identical to $X^1$ and $X^3$. Even more preferably, $-A_4-Q^4(X^7)$ $X^8$ is identical to either $-A_1-Q^2(X^1)X^2$ or $-A_2-Q^1(X^3)X^4$. Most preferably, $-A_4-Q^4(X^7)X^8$ is identical to both $-A_2-Q^1(X^3)X^4$, and $-A_3-Q^3(X^5)X^6$ if present.

In a particular preferred embodiment, $E^1$ in a compound of formula III represents hydrogen.

In an alternative embodiment where $E^1$ does not represent hydrogen, $E^1$ represents $-A_5-Q^5(X^9)X^{10}$. Preferably $X^{10}$ is identical to $X^4$ or $X^2$, and $X^9$ is identical to $X^1$ or $X^3$. More preferably, $X^{10}$ is identical to both $X^4$ and $X^2$, and $X^9$ is identical to $X^1$ and $X^3$. Even more preferably, $-A_5-Q^5(X^9)X^{10}$ is identical to either $-A_1-Q^2(X^1)X^2$ or $-A_2-Q^1(X^3)X^4$. Most preferably, $-A_5-Q^5(X^9)X^{10}$ is identical to both $-A_1-Q^2(X^1)X^2$ and $-A_2-Q^1(X^3)X^4$ and $-A_3-Q^3(X^5)X^6$ and $-A_4-Q^4(X^7)X^8$ if present.

Preferably, in the compound of formula III, when $D^1$ and $E^1$ together with the carbon atoms of the cyclopentadienyl ring to which they are attached do not form an optionally substituted phenyl ring, each of $K^1$, $D^1$ and $E^1$ represent an identical substituent.

In an alternative preferred embodiment, $D^1$ and $E^1$ together with the carbons of the cyclopentadienyl ring to which they are attached form an unsubstituted phenyl ring.

Highly preferred embodiments of compounds of formula III include those wherein:

$K^1$, $D^1$ and $E^1$ are identical substituents as defined herein, particularly where $K^1$, $D^1$ and $E^1$ represent hydrogen;

$K^1$ represents hydrogen, and $D^1$ and $E^1$ together with the carbons of the cyclopentadienyl ring to which they are attached form an unsubstituted phenyl ring;

$K^1$ represents $-A_3-Q^3(X^5)X^6$ as defined herein and both $D^1$ and $E^1$ represent H;

$K^1$ represents $-A_3-Q^3(X^5)X^6$ as defined herein and $D^1$ and $E^1$ together with the carbon atoms of the cyclopentadienyl ring to which they are attached form an unsubstituted phenyl ring;

$K^1$ represents $-A_3-Q^3(X^5)X^6$, $D^1$ represents $-A_4-Q^4(X^7)X^8$ and $E^1$ represents $-A_5-Q^5(X^9)X^{10}$.

Especially preferred compounds of formula III include those where both $D^1$ and $E^1$ represent hydrogen or $D^1$ and $E^1$ together with the carbon atoms of the cyclopentadienyl ring to which they are attached form an unsubstituted phenyl ring, particularly those compounds where both $D^1$ and $E^1$ represent hydrogen.

Preferably, in the compound of formula III, $A_1$ and $A_2$, and $A_3$, $A_4$ and $A_5$ (when present), each independently represent $C_1$ to $C_6$ alkylene which is optionally substituted as defined herein, for example with lower alkyl groups. Suitably, $A_1$ and $A_2$, and $A_3$, $A_4$ and $A_5$ (when present) may include a chiral carbon atom. Preferably, the lower alkylene groups which $A_1$ to $A_5$ may represent are non-substituted. A particular preferred lower alkylene, which $A_1$ to $A_5$ independently represent, is $—CH_2—$ or $—C_2H_4—$. Most preferably, each of $A_1$ and $A_2$, and $A_3$, $A_4$ and $A_5$ (when present), represent the same lower alkylene as defined herein, particularly $—CH_2—$.

In the compound of formula III, preferably each $Q^1$ and $Q^2$, and $Q^3$, $Q^4$ and $Q^5$ (when present) are the same. Most preferably, each $Q^1$ and $Q^2$, and $Q^3$, $Q^4$ and $Q^5$ (when present), represents phosphorus.

It will be appreciated by those skilled in the art that the compounds of formula III may function as ligands that coordinate with the Group VIB or Group VIIIB metal or compound thereof in the formation of the catalyst system of the invention. Typically, the Group VIB or Group VIIIB metal or compound thereof coordinates to the one or more phosphorus, arsenic and/or antimony atoms of the compound of formula III. It will be appreciated that the compounds of formula III may be referred to broadly as "metallocenes".

Suitably, when n=1 and $L_1$ represents an optionally substituted cyclopentadienyl or indenyl group, the compounds of formula III may contain either two cyclopentadienyl rings, two indenyl rings or one indenyl and one cyclopentadienyl ring (each of which ring systems may optionally be substituted as described herein). Such compounds may be referred to as "sandwich compounds" as the metal M or metal cation thereof is sandwiched by the two ring systems. The respective cyclopentadienyl and/or indenyl ring systems may be substantially coplanar with respect to each other or they may be tilted with respect to each other (commonly referred to as bent metallocenes).

Alternatively, when n=1 and $L_1$ represents aryl, the compounds of the invention may contain either one cyclopentadienyl or one indenyl ring (each of which ring systems may optionally be substituted as described herein) and one aryl ring which is optionally substituted as defined herein. Suitably, when n=1 and $L_1$ represents aryl then the metal M of the compounds of formula III as defined herein is typically in the form of the metal cation.

In a particularly preferred embodiment of the present invention, in a compound of formula III, n=1, $L_1$ is as defined herein and m=0.

Preferably, when n=1 in the compound of formula III, $L_1$ represents cyclopentadienyl, indenyl or aryl ring each of which rings are optionally substituted by one or more substituents selected from hydrogen, lower alkyl, halo, cyano, nitro, $—OR^{19}$, $—OC(O)R^{20}$, $—C(O)R^{21}$, $—C(O)OR^{22}$, $—N(R^{23})R^{24}$, $—C(O)N(R^{25})R^{26}$, $—C(S)(R^{27})R^{28}$$—SR^{29}$, $—C(O)SR^{30}$, $—CF_3$ or ferrocenyl (by which we mean the cyclopentadienyl, indenyl or aryl ring which $L_1$ may represent is bonded directly to the cyclopentadienyl ring of the ferrocenyl group), wherein $R^{19}$ to $R^{30}$ is as defined herein. More preferably, if the cyclopentadienyl, indenyl or aryl ring which $L_1$ may represent is substituted it is preferably substituted with one or more substituents selected from unsubstituted $C_1$-$C_6$ alkyl, halo, cyano, $—OR^{19}$, $—OC(O)R^{20}$, $—C(O)R^{21}$, $—C(O)OR^{22}$, $—N(R^{23})R^{24}$ where $R^{19}$, $R^{20}$, $R^{21}$, $R^{22}$, $R^{23}$ and $R^{24}$ each independently represent hydrogen or $C_1$-$C_6$ alkyl. Even more preferably, if the cyclopentadienyl, indenyl or aryl ring which $L_1$ may represent is substituted, it is preferably substituted with one or more substituents selected from unsubstituted $C_1$-$C_6$ alkyl.

Preferably, when n=1, $L_1$ represents cyclopentadienyl, indenyl, phenyl or napthyl optionally substituted as defined herein. Preferably, the cyclopentadienyl, indenyl, phenyl or napthyl groups are unsubstituted. More preferably, $L_1$ represents cyclopentadienyl, indenyl or phenyl, each of which rings are unsubstituted. Most preferably, $L_1$ represents unsubstituted cyclopentadienyl.

Alternatively, when n=0, the compounds of the invention contain only one cyclopentadienyl or indenyl ring (each of which ring systems may optionally be substituted as described herein). Such compounds may be referred to as "half sandwich compounds". Preferably, when n=0 then m represents 1 to 5 so that the metal M of the compounds of formula III has an 18 electron count. In other words, when metal M of the compounds of formula III is iron, the total number of electrons contributed by the ligands $L_2$ is typically five.

In a particularly preferred alternative embodiment of the present invention, in a compound of formula III, n=0, $L_2$ is as defined herein and m=3 or 4, particularly 3.

Preferably, when n is equal to zero and m is not equal to zero in a compound of formula III, $L_2$ represents one or more ligands each of which are independently selected from lower alkyl, halo, $—CO$, $—P(R^{43})(R^{44})R^{45}$ or $—N(R^{46})(R^{47})R^{48}$. More preferably, $L_2$ represents one or more ligands each of which are independently selected from unsubstituted $C_1$ to $C_4$ alkyl, halo, particularly chloro, $—CO$, $—P(R^{43})(R^{44})R^{45}$ or $—N(R^{46})(R^{47})R^{48}$, wherein $R^{43}$ to $R^{48}$ are independently selected from hydrogen, unsubstituted $C_1$ to $C_6$ alkyl or aryl, such as phenyl.

Suitably, the metal M or metal cation thereof in the compounds of formula III is typically bonded to the cyclopentadienyl ring(s), the cyclopentadienyl moiety of the indenyl ring(s) if present, the aryl ring if present, and/or the ligands $L_2$ if present. Typically, the cyclopentadienyl ring or the cyclopentadienyl moiety of the indenyl ring exhibits a pentahapto bonding mode with the metal; however other bonding modes between the cyclopentadienyl ring or cyclopentadienyl moiety of the indenyl ring and the metal, such as trihapto coordination, are also embraced by the scope of the present invention.

Most preferably, in a compound of formula III, n=1, m=0 and $L_1$ is defined herein, particularly unsubstituted cyclopentadienyl.

Preferably M represents a Group VIB or VIIIB metal. In other words the total electron count for the metal M is 18.

Preferably, in the compound of formula III, M represents Cr, Mo, Fe, Co or Ru, or a metal cation thereof. Even more preferably, M represents Cr, Fe, Co or Ru or a metal cation thereof. Most preferably, M is selected from a Group VIIIB metal or metal cation thereof. An especially preferred Group VIIIB metal is Fe. Although the metal M as defined herein may be in a cationic form, preferably it carries essentially no residual charge due to coordination with $L_1$ and/or $L_2$ as defined herein.

Especially preferred compounds of formula III include those wherein:

(1) $X^1$ represents $CR^1(R^2)(R^3)$, $X^2$ represents $CR^4(R^5)(R^6)$, $X^3$ represents $CR^7(R^8)(R^9)$, $X^4$ represents $CR^{10}(R^{11})(R^{12})$, wherein each of $R^1$ to $R^{12}$ independently represents unsubstituted $C_1$-$C_6$ alkyl or trifluoromethyl, particularly where each of $R^1$ to $R^{12}$ is identical, especially where each of $R^1$ to $R^{12}$ represents unsubstituted $C_1$-$C_6$ alkyl, particularly methyl;
$A_1$ and $A_2$ are the same and represent —$CH_2$—;
$K^1$, $D^1$ and $E^1$ are the same and represent hydrogen or unsubstituted $C_1$-$C_6$ alkyl, particularly hydrogen;
$Q^1$ and $Q^2$ both represent phosphorus;
M represents Fe;
n=1 and $L_1$ represents cyclopentadienyl, particularly unsubstituted cyclopentadienyl, and m=0.

(2) $X^1$ represents $CR^1(R^2)(R^3)$, $X^2$ represents $CR^4(R^5)(R^6)$, $X^3$ represents $CR^7(R^8)(R^9)$, $X^4$ represents $CR^{10}(R^{11})(R^{12})$;
$K^1$ represents —$CH_2$-$Q^3(X^5)X^6$ wherein $X^5$ represents $CR^{13}(R^{14})(R^{15})$ and $X^6$ represents $CR^{16}(R^{17})(R^{18})$;
each of $R^1$ to $R^{18}$ independently represent unsubstituted $C_1$-$C_6$ alkyl or trifluoromethyl, particularly where each of $R^1$ to $R^{18}$ is identical, especially where each of $R^1$ to $R^{18}$ represents unsubstituted $C_1$-$C_6$ alkyl, particularly methyl;
$A_1$ and $A_2$ are the same and represent —$CH_2$—;
$Q^1$, $Q^2$ and $Q^3$ each represent phosphorus;
$D^1$ and $E^1$ are the same and represent hydrogen or unsubstituted $C_1$-$C_6$ alkyl, particularly hydrogen;
M represents Fe;
n=1 and $L_1$ represents cyclopentadienyl, particularly unsubstituted cyclopentadienyl, and m=0.

(3) $X^1$ represents $CR^1(R^2)(R^3)$, $X^2$ represents $CR^4(R^5)(R^6)$, $X^3$ represents $CR^7(R^8)(R^9)$, $X^4$ represents $CR^{10}(R^{11})(R^{12})$;
$K^1$ represents —$CH_2$-$Q^3(X^5)X^6$ wherein $X^5$ represents $CR^{13}(R^{14})(R^{15})$ and $X^6$ represents $CR^{16}(R^{17})(R^{18})$;
each of $R^1$ to $R^{18}$ independently represent unsubstituted $C_1$-$C_6$ alkyl or trifluoromethyl, particularly where each of $R^1$ to $R^{18}$ is identical, especially where each of $R^1$ to $R^{18}$ represents unsubstituted $C_1$-$C_6$ alkyl, particularly methyl;
$A_1$ and $A_2$ are the same and represent —$CH_2$—;
$Q^1$, $Q^2$ and $Q^3$ each represent phosphorus;
$D^1$ and $E^1$ together with the carbon atoms of the cyclopentadienyl ring to which they are attached form an unsubstituted phenyl ring;
M represents Fe;
n=1 and $L_1$ represents cyclopentadienyl, particularly unsubstituted cyclopentadienyl, and m=0.

(4) $X^1$ represents $CR^1(R^2)(R^3)$, $X^2$ represents $CR^4(R^5)(R^6)$, $X^3$ represents $CR^7(R^8)(R^9)$, $X^4$ represents $CR^{10}(R^{11})(R^{12})$, wherein each of $R^1$ to $R^{12}$ independently represent unsubstituted $C_1$-$C_6$ alkyl or trifluoromethyl, particularly where each of $R^1$ to $R^{12}$ is identical, especially where each of $R^1$ to $R^{12}$ represents unsubstituted $C_1$-$C_6$ alkyl, particularly methyl;
$A_1$ and $A_2$ are the same and represent —$CH_2$—;
$Q^1$ and $Q^2$ both represent phosphorus;
$K^1$ represents hydrogen or $C_1$-$C_6$ alkyl, particularly hydrogen;
$D^1$ and $E^1$ together with the carbon atoms of the cyclopentadienyl ring to which they are attached form an unsubstituted phenyl ring;
M represents Fe;
n=1 and $L_1$ represents cyclopentadienyl, particularly unsubstituted cyclopentadienyl, and m=0.

(5) $X^1$ represents $CR^1(R^2)(R^3)$, $X^2$ represents $CR^4(R^5)(R^6)$, $X^3$ represents $CR^7(R^8)(R^9)$, $X^4$ represents $CR^{10}(R^{11})(R^{12})$;
$E^1$ represents —$CH_2$-$Q^5(X^9)X^{10}$ wherein $X^9$ represents $CR^{37}(R^{38})(R^{39})$ and $X^{10}$ represents $CR^{40}(R^{41})(R^{42})$;
each of $R^1$ to $R^{12}$ and $R^{37}$ to $R^{42}$ independently represent unsubstituted $C_1$-$C_6$ alkyl or trifluoromethyl, particularly where each of $R^1$ to $R^{12}$ and $R^{37}$ to $R^{42}$ is identical, especially where each of $R^1$ to $R^{12}$ and $R^{37}$ to $R^{42}$ represents unsubstituted $C_1$-$C_6$ alkyl, particularly methyl;
$A_1$ and $A_2$ are the same and represent —$CH_2$—;
$Q^1$, $Q^2$ and $Q^5$ each represent phosphorus;
$D^1$ and $K^1$ are the same and represent hydrogen or unsubstituted $C_1$-$C_6$ alkyl, particularly hydrogen;
M represents Fe;
n=1 and $L_1$ represents cyclopentadienyl, particularly unsubstituted cyclopentadienyl, and m=0.

(6) $X^1$ represents $CR^1(R^2)(R^3)$, $X^2$ represents $CR^4(R^5)(R^6)$, $X^3$ represents $CR^7(R^8)(R^9)$, $X^4$ represents $CR^{10}(R^{11})(R^{12})$;
$K^1$ represents —$CH_2$-$Q^3(X^5)X^6$ wherein $X^5$ represents $CR^{13}(R^{14})(R^{15})$ and $X^6$ represents $CR^{16}(R^{17})(R^{18})$;
$D^1$ represents —$CH_2$-$Q^4(X^7)X^8$ wherein $X^7$ represents $CR^{31}(R^{32})(R^{33})$ and $X^8$ represents $CR^{34}(R^{35})(R^{36})$;
$E^1$ represents —$CH_2$-$Q^5(X^9)X^{10}$ wherein $X^9$ represents $CR^{37}(R^{38})(R^{39})$ and $X^{10}$ represents $CR^{40}(R^{41})(R^{42})$;
each of $R^1$ to $R^{18}$ and $R^{31}$ to $R^{42}$ independently represent unsubstituted $C_1$-$C_6$ alkyl or trifluoromethyl, particularly where each of $R^1$ to $R^{18}$ and $R^{31}$ to $R^{42}$ is identical, especially where each of $R^1$ to $R^{18}$ and $R^{31}$ to $R^{42}$ represents unsubstituted $C_1$-$C_6$ alkyl, particularly methyl;
$A_1$ and $A_2$ are the same and represent —$CH_2$—;
$Q^1$, $Q^2$, $Q^3$, $Q^4$ and $Q^5$ each represent phosphorus M represents Fe;
n=1 and $L_1$ represents cyclopentadienyl, particularly unsubstituted cyclopentadienyl, and m=0.

(7) $X^1$, $X^2$, $X^3$ and $X^4$ independently represent adamantyl, especially where $X^1$ to $X^4$ represent the same adamantyl group;
$A_1$ and $A_2$ are the same and represent —$CH_2$—;
$K^1$, $D^1$ and $E^1$ are the same and represent hydrogen or unsubstituted $C_1$-$C_6$ alkyl, particularly hydrogen;
$Q^1$ and $Q^2$ both represent phosphorus;
M represents Fe;
n=1 and $L_1$ represents cyclopentadienyl, particularly unsubstituted cyclopentadienyl, and m=0.

(8) $X^1$, $X^2$, $X^3$ and $X^4$ independently represent adamantyl, especially where $X^1$ to $X^4$ represent the same adamantyl group;
$K^1$ represents —$CH_2$-$Q^3(X^5)X^6$ wherein $X^5$ and $X^6$ independently represent adamantyl, especially where $X^1$ to $X^6$ represent the same adamantyl group;
$A_1$ and $A_2$ are the same and represent —$CH_2$—;
$Q^1$, $Q^2$ and $Q^3$ each represent phosphorus;
$D^1$ and $E^1$ are the same and represent hydrogen or unsubstituted $C_1$-$C_6$ alkyl, particularly hydrogen;
M represents Fe;
n=1 and $L_1$ represents cyclopentadienyl, particularly unsubstituted cyclopentadienyl, and m=0.

(9) $X^1$, $X^2$, $X^3$ and $X^4$ independently represent adamantyl, especially where $X^1$ to $X^4$ represent the same adamantyl group;
$K^1$ represents —$CH_2$-$Q^3(X^5)X^6$ wherein $X^5$ and $X^6$ independently represent adamantyl, especially where $X^1$ to $X^6$ represent the same adamantyl group;
$A_1$ and $A_2$ are the same and represent —$CH_2$—;
$Q^1$, $Q^2$ and $Q^3$ each represent phosphorus;
$D^1$ and $E^1$ together with the carbon atoms of the cyclopentadienyl ring to which they are attached form an unsubstituted phenyl ring;
M represents Fe;
n=1 and $L_1$ represents cyclopentadienyl, particularly unsubstituted cyclopentadienyl, and m=0.

(10) $X^1$, $X^2$, $X^3$ and $X^4$ independently represent adamantyl, especially where $X^1$ to $X^4$ represent the same adamantyl group;
$A_1$ and $A_2$ are the same and represent —$CH_2$—;
$Q^1$ and $Q^2$ both represent phosphorus;
$K^1$ represents hydrogen or unsubstituted $C_1$-$C_6$ alkyl, particularly hydrogen;
$D^1$ and $E^1$ together with the carbon atoms of the cyclopentadienyl ring to which they are attached form an unsubstituted phenyl ring;
M represents Fe;
n=1 and $L_1$ represents cyclopentadienyl, particularly unsubstituted cyclopentadienyl, and m=0.

(11) $X^1$, $X^2$, $X^3$ and $X^4$ independently represent adamantyl;
$K^1$ represents —$CH_2$-$Q^3(X^5)X^6$ wherein $X^5$ and $X^6$ independently represent adamantyl;
$D^1$ represents —$CH_2$-$Q^4(X^7)X^8$ wherein $X^7$ and $X^8$ independently represents adamantyl;
$E^1$ represents —$CH_2$-$Q^5(X^9)X^{10}$ wherein $X^9$ and $X^{10}$ independently represents adamantyl, especially where $X^1$ to $X^{10}$ represent the same adamantyl group;
$A_1$ and $A_2$ are the same and represent —$CH_2$—;
$Q^1$, $Q^2$, $Q^3$, $Q^4$ and $Q^5$ each represent phosphorus;
M represents Fe;
n=1 and $L_1$ represents cyclopentadienyl, particularly unsubstituted cyclopentadienyl, and m=0.

(12) $X^1$ and $X^2$ together with $Q^2$ to which they are attached represents 2-phospha-adamantyl;
$X^3$ and $X^4$ together with $Q^1$ to which they are attached represents 2-phospha-adamantyl;
$A_1$ and $A_2$ are the same and represent —$CH_2$—;
$K^1$, $D^1$ and $E^1$ are the same and represent hydrogen or unsubstituted $C_1$-$C_6$ alkyl, particularly hydrogen;
$Q^1$ and $Q^2$ both represent phosphorus;
M represents Fe;
n=1 and $L_1$ represents cyclopentadienyl, particularly unsubstituted cyclopentadienyl, and m=0.

(13) $X^1$ and $X^2$ together with $Q^2$ to which they are attached represents 2-phospha-adamantyl;
$X^3$ and $X^4$ together with $Q^1$ to which they are attached represents 2-phospha-adamantyl;
$K^1$ represents —$CH_2$-$Q^3(X^5)X^6$ wherein $X^5$ and $X^6$ together with $Q^3$ to which they are attached represents 2-phospha-adamantyl;
$A_1$ and $A_2$ are the same and represent —$CH_2$—;
$Q^1$, $Q^2$ and $Q^3$ each represent phosphorus;
$D^1$ and $E^1$ are the same and represent hydrogen or unsubstituted $C_1$-$C_6$ alkyl, particularly hydrogen;
M represents Fe;
n=1 and $L_1$ represents cyclopentadienyl, particularly unsubstituted cyclopentadienyl, and m=0.

(14) $X^1$ and $X^2$ together with $Q^2$ to which they are attached represents 2-phospha-adamantyl;
$X^3$ and $X^4$ together with $Q^1$ to which they are attached represents 2-phospha-adamantyl;
$K^1$ represents —$CH_2$-$Q^3(X^5)X^6$ wherein $X^5$ and $X^6$ together with $Q^3$ to which they are attached represents 2-phospha-adamantyl;
$A_1$ and $A_2$ are the same and represent —$CH_2$—;
$Q^1$, $Q^2$ and $Q^3$ each represent phosphorus;
$D^1$ and $E^1$ together with the carbon atoms of the cyclopentadienyl ring to which they are attached form an unsubstituted phenyl ring;
M represents Fe;
n=1 and $L_1$ represents cyclopentadienyl, particularly unsubstituted cyclopentadienyl, and m=0.

(15) $X^1$ and $X^2$ together with $Q^2$ to which they are attached represents 2-phospha-adamantyl;
$X^3$ and $X^4$ together with $Q^1$ to which they are attached represents 2-phospha-adamantyl;
$A_1$ and $A_2$ are the same and represent —$CH_2$—;
$Q^1$ and $Q^2$ both represent phosphorus;
$K^1$ represents hydrogen or unsubstituted $C_1$-$C_6$ alkyl, particularly hydrogen;
$D^1$ and $E^1$ together with the carbon atoms of the cyclopentadienyl ring to which they are attached form an unsubstituted phenyl ring;
M represents Fe;
n=1 and $L_1$ represents cyclopentadienyl, particularly unsubstituted cyclopentadienyl, and m=0.

(16) $X^1$ and $X^2$ together with $Q^2$ to which they are attached represents 2-phospha-adamantyl;
$X^3$ and $X^4$ together with $Q^1$ to which they are attached represents 2-phospha-adamantyl;
$K^1$ represents —$CH_2$-$Q^3(X^5)X^6$ wherein $X^5$ and $X^6$ together with $Q^3$ to which they are attached represents 2-phospha-adamantyl;
$D^1$ represents —$CH_2$-$Q^4(X^7)X^8$ wherein $X^7$ and $X^8$ together with $Q^4$ to which they are attached represents 2-phospha-adamantyl;
$E^1$ represents —$CH_2$-$Q^5(X^9)X^{10}$ wherein $X^9$ and $X^{10}$ together with $Q^5$ to which they are attached represents 2-phospha-adamantyl;
$A_1$ and $A_2$ are the same and represent —$CH_2$—;
$Q^1$, $Q^2$, $Q^3$, $Q^4$ and $Q^5$ each represent phosphorus M represents Fe;
n=1 and $L_1$ represents cyclopentadienyl, particularly unsubstituted cyclopentadienyl, and m=0.

(17) $X^1$ and $X^2$ together with $Q^2$ to which they are attached form a ring system of formula IIIa, $X^3$ and $X^4$ together with $Q^1$ to which they are attached form a ring system of formula IIIb, wherein $Y^1$ and $Y^2$ both represent oxygen, $R^{50}$ to $R^{53}$ are independently selected from unsubstituted $C_1$-$C_6$ alkyl or $CF_3$, and $R^{49}$ and $R^{54}$ represent hydrogen;
$A_1$ and $A_2$ are the same and represent —$CH_2$—;
$K^1$, $D^1$ and $E^1$ are the same and represent hydrogen or unsubstituted $C_1$-$C_6$ alkyl, particularly hydrogen;
$Q^1$ and $Q^2$ both represent phosphorus;
M represents Fe;
n=1 and $L_1$ represents cyclopentadienyl, particularly unsubstituted cyclopentadienyl (referred to as puc) and m=0.

(18) $X^1$ and $X^2$ together with $Q^2$ to which they are attached form a ring system of formula IIIa, $X^3$ and $X^4$ together with $Q^1$ to which they are attached form a ring system of formula IIIb, wherein $Y^1$ and $Y^2$ both represent oxygen, $R^{50}$ to $R^{53}$ are independently selected from unsubstituted $C_1$-$C_6$ alkyl or $CF_3$, and $R^{49}$ and $R^{54}$ represent hydrogen;

K¹ represents —CH₂-Q³(X⁵)X⁶ wherein X⁵ and X⁶ together with Q³ to which they are attached form a ring system of formula IIIc, wherein Y³ represents oxygen, R⁵⁰ to R⁵³ are independently selected from hydrogen, unsubstituted $C_1$-$C_6$ alkyl or $CF_3$ and R⁴⁹ and R⁵⁴ represent hydrogen;

$A_1$ and $A_2$ are the same and represent —CH₂—;

Q¹, Q² and Q³ each represent phosphorus;

D¹ and E¹ are the same and represent hydrogen or $C_1$-$C_6$ alkyl, particularly hydrogen;

M represents Fe;

n=1 and $L_1$ represents cyclopentadienyl, particularly unsubstituted cyclopentadienyl, and m=0.

(19) X¹ and X² together with Q² to which they are attached form a ring system of formula IIIa, X³ and X⁴ together with Q¹ to which they are attached form a ring system of formula IIIb, wherein Y¹ and Y² both represent oxygen, R⁵⁰ to R⁵³ are independently selected from unsubstituted $C_1$-$C_6$ alkyl or $CF_3$, and R⁴⁹ and R⁵⁴ represent hydrogen;

K¹ represents —CH₂-Q³(X⁵)X⁶ wherein X⁵ and X⁶ together with Q³ to which they are attached form a ring system of formula IIIc, wherein Y³ represents oxygen, R⁵⁰ to R⁵³ are independently selected from unsubstituted $C_1$-$C_6$ alkyl or $CF_3$, and R⁴⁹ and R⁵⁴ represent hydrogen;

$A_1$ and $A_2$ are the same and represent —CH₂—;

Q¹, Q² and Q³ each represent phosphorus;

D¹ and E¹ together with the carbon atoms of the cyclopentadienyl ring to which they are attached form an unsubstituted phenyl ring;

M represents Fe;

n=1 and $L_1$ represents cyclopentadienyl, particularly unsubstituted cyclopentadienyl, and m=0.

(20) X¹ and X² together with Q² to which they are attached form a ring system of formula IIIa, X³ and X⁴ together with Q¹ to which they are attached form a ring system of formula IIIb, wherein Y¹ and Y² both represent oxygen, R⁵⁰ to R⁵³ are independently selected from unsubstituted $C_1$-$C_6$ alkyl or $CF_3$, and R⁴⁹ and R⁵⁴ represent hydrogen;

$A_1$ and $A_2$ are the same and represent —CH₂—;

Q¹ and Q² both represent phosphorus;

K¹ represents hydrogen or unsubstituted $C_1$-$C_6$ alkyl, particularly hydrogen;

D¹ and E¹ together with the carbon atoms of the cyclopentadienyl ring to which they are attached form an unsubstituted phenyl ring;

M represents Fe;

n=1 and $L_1$ represents cyclopentadienyl, particularly unsubstituted cyclopentadienyl, and m=0.

(21) X¹ and X² together with Q to which they are attached form a ring system of formula IIIa, X³ and X⁴ together with Q¹ to which they are attached form a ring system of formula IIIb, wherein Y¹ and Y² both represent oxygen, R⁵⁰ to R⁵³ are independently selected from unsubstituted $C_1$-$C_6$ alkyl or $CF_3$, and R⁴⁹ and R⁵⁴ represent hydrogen;

K¹ represents —CH₂-Q³(X⁵)X⁶ wherein X⁵ and X⁶ together with Q³ to which they are attached form a ring system of formula IIIc, wherein Y³ represents oxygen, R⁵⁰ to R⁵³ are independently selected from unsubstituted $C_1$-$C_6$ alkyl or $CF_3$, and R⁴⁹ and R⁵⁴ represent hydrogen;

D¹ represents —CH₂-Q⁴(X⁷)X⁸ wherein X⁷ and X⁸ together with Q⁴ to which they are attached form a ring system of formula IIIc, wherein Y³ represents oxygen, R⁵⁰ to R⁵³ are independently selected from unsubstituted $C_1$-$C_6$ alkyl or $CF_3$, and R⁴⁹ and R⁵⁴ represent hydrogen;

E¹ represents —CH₂-Q⁵(X⁹)X¹⁰ wherein X⁹ and X¹⁰ together with Q⁵ to which they are attached form a ring system of formula IIIe, wherein Y⁵ represents oxygen, and R⁵⁰ to R⁵³ are independently selected from unsubstituted $C_1$-$C_6$ alkyl or $CF_3$, and R⁴⁹ and R⁵⁴ represent hydrogen;

$A_1$ and $A_2$ are the same and represent —CH₂—; Q¹, Q², Q³, Q⁴ and Q⁵ each represent phosphorus;

M represents Fe;

n=1 and $L_1$ represents cyclopentadienyl; particularly unsubstituted cyclopentadienyl, and m=0.

(22) X¹, X², X² and X⁴ independently represent congressyl, especially where X¹ to X⁴ represent the same congressyl group;

$A_1$ and $A_2$ are the same and represent —CH₂—;

K¹, D¹ and E¹ are the same and represent hydrogen or unsubstituted $C_1$-$C_6$ alkyl, particularly hydrogen;

Q¹ and Q² both represent phosphorus;

M represents Fe;

n=1 and $L_1$ represents cyclopentadienyl, particularly unsubstituted cyclopentadienyl, and m=0.

(23) X¹, X², X³ and X⁴ independently represent congressyl, especially where X¹ to X⁴ represent the same congressyl group;

K¹ represents —CH₂-Q³(X⁵)X⁶ wherein X⁵ and X⁶ independently represent congressyl, especially where X¹ to X⁶ represent the same congressyl group;

$A_1$ and $A_2$ are the same and represent —CH₂—;

Q¹, Q² and Q³ each represent phosphorus;

D¹ and E¹ are the same and represent hydrogen or unsubstituted $C_1$-$C_6$ alkyl, particularly hydrogen;

M represents Fe;

n=1 and $L_1$ represents cyclopentadienyl, particularly unsubstituted cyclopentadienyl, and m=0.

(24) X¹, X², X³ and X⁴ independently represent congressyl, especially where X¹ to X⁴ represent the same congressyl group;

K¹ represents —CH₂-Q³(X⁵)X⁶ wherein X⁵ and X⁶ independently represent congressyl, especially where X¹ to X⁶ represent the same congressyl group;

$A_1$ and $A_2$ are the same and represent —CH₂—;

Q¹, Q² and Q³ each represent phosphorus;

D¹ and E¹ together with the carbon atoms of the cyclopentadienyl ring to which they are attached form an unsubstituted phenyl ring;

M represents Fe;

n=1 and $L_1$ represents cyclopentadienyl, particularly unsubstituted cyclopentadienyl, and m=0.

(25) X¹, X², X³ and X⁴ independently represent congressyl, especially where X¹ to X⁴ represent the same congressyl group;

$A_1$ and $A_2$ are the same and represent —CH₂—;

Q¹ and Q² both represent phosphorus;

K¹ represents hydrogen or unsubstituted $C_1$-$C_6$ alkyl, particularly hydrogen;

D¹ and E¹ together with the carbon atoms of the cyclopentadienyl ring to which they are attached form an unsubstituted phenyl ring;

M represents Fe;

n=1 and $L_1$ represents cyclopentadienyl, particularly unsubstituted cyclopentadienyl, and m=0.

(26) X¹, X², X³ and X⁴ independently represent congressyl;

K¹ represents —CH₂-Q³(X⁵)X⁶ wherein X⁵ and X⁶ independently represent congressyl;

D¹ represents —CH₂-Q⁴(X⁷)X⁸ wherein X⁷ and X⁸ independently represents congressyl;

$E^1$ represents —CH$_2$-Q$^5$(X$^9$)X$^{10}$ wherein X$^9$ and X$^{10}$ independently represents congressyl, especially where X$^1$ to X$^{10}$ represent the same congressyl group;

A$_1$ and A$_2$ are the same and represent —CH$_2$—;

Q$^1$, Q$^2$, Q$^3$, Q$^4$ and Q$^5$ each represent phosphorus;

M represents Fe;

n=1 and L$_1$ represents cyclopentadienyl, particularly unsubstituted cyclopentadienyl, and m=0.

(27) X$^1$ and X$^3$ independently represent adamantyl, especially where X$^1$ and X$^3$ represent the same adamantyl group;

X$^2$ represents CR$^4$(R$^5$)(R$^6$) and X$^4$ represents CR$^{10}$(R$^{11}$)(R$^{12}$) wherein each of R$^4$, R$^5$, R$^6$, R$^{10}$, R$^{11}$ and R$^{12}$ independently represent C$_1$-C$_6$ alkyl or trifluoromethyl, particularly where each of R$^4$ to R$^6$ and R$^{10}$ to R$^{12}$ is identical, especially where each of R$^4$ to R$^6$ and R$^{10}$ to R$^{12}$ represents unsubstituted C$_1$-C$_6$ alkyl, particularly methyl;

A$_1$ and A$_2$ are the same and represent —CH$_2$—;

K$^1$, D$^1$ and E$^1$ are the same and represent hydrogen or unsubstituted C$_1$-C$_6$ alkyl, particularly hydrogen;

Q$^1$ and Q$^2$ both represent phosphorus;

M represents Fe;

n=1 and L$_1$ represents cyclopentadienyl, particularly unsubstituted cyclopentadienyl, and m=0.

(28) X$^1$ and X$^3$ independently represent adamantyl, especially where X$^1$ and X$^3$ represent the same adamantyl group;

K$^1$ represents —CH$_2$-Q$^3$(X$^5$)X$^6$ wherein X$^5$ represents adamantyl, especially where X$^1$, X$^3$ and X$^5$ represent the same adamantyl group;

X$^2$ represents CR$^4$(R$^5$)(R$^6$), X$^4$ represents CR$^{10}$(R$^{11}$)(R$^{12}$), X$^6$ represents CR$^{16}$(R$^{17}$)(R$^{18}$), wherein each of R$^4$ to R$^6$, R$^{10}$ to R$^{12}$ and R$^{16}$ to R$^{18}$ independently represent unsubstituted C$_1$-C$_6$ alkyl or trifluoromethyl, particularly where each of R$^4$ to R$^6$, R$^{10}$ to R$^{12}$, and R$^{16}$ to R$^{18}$ is identical, especially where each of R$^4$ to R$^6$, R$^{10}$ to R$^{12}$ and R$^{16}$ to R$^{18}$ represents unsubstituted C$_1$-C$_6$ alkyl, particularly methyl;

A$_1$ and A$_2$ are the same and represent —CH$_2$—;

Q$^1$, Q$^2$ and Q$^3$ each represent phosphorus;

D$^1$ and E$^1$ are the same and represent hydrogen or unsubstituted C$_1$-C$_6$ alkyl, particularly hydrogen;

M represents Fe;

n=1 and L$_1$ represents cyclopentadienyl, particularly unsubstituted cyclopentadienyl, and m=0.

(29) X$^1$ and X$^3$ independently represent adamantyl, especially where X$^1$ and X$^3$ represent the same adamantyl group;

K$^1$ represents —CH$_2$-Q$^3$(X$^5$)X$^6$ wherein X$^5$ represents adamantyl, especially where X$^1$, X$^3$ and X$^5$ represent the same adamantyl group;

X$^2$ represents CR$^4$(R$^5$)(R$^6$), X$^4$ represents CR$^{10}$(R$^{11}$)(R$^{12}$), X$^6$ represents CR$^{16}$(R$^{17}$)(R$^{18}$), wherein each of R$^4$ to R$^6$, R$^{10}$ to R$^{12}$ and R$^{16}$ to R$^{18}$ independently represent unsubstituted C$_1$-C$_6$ alkyl or trifluoromethyl, particularly where each of R$^4$ to R$^6$, R$^{10}$ to R$^{12}$, and R$^{16}$ to R$^{18}$ is identical, especially where each of R$^4$ to R$^6$, R$^{10}$ to R$^{12}$ and R$^{16}$ to R$^{18}$ represents unsubstituted C$_1$-C$_6$ alkyl, particularly methyl;

A$_1$ and A$_2$ are the same and represent —CH$_2$—;

Q$^1$, Q$^2$ and Q$^3$ each represent phosphorus;

D$^1$ and E$^1$ together with the carbon atoms of the cyclopentadienyl ring to which they are attached form an unsubstituted phenyl ring;

M represents Fe;

n=1 and L$_1$ represents cyclopentadienyl, particularly unsubstituted cyclopentadienyl, and m=0.

(30) X$^1$ and X$^3$ independently represent adamantyl, especially where X$^1$ and X$^3$ represent the same adamantyl group;

X$^2$ represents CR$^4$(R$^5$)(R$^6$) and X$^4$ represents CR$^{10}$(R$^{11}$)(R$^{12}$) wherein each of R$^4$, R$^5$, R$^6$, R$^{10}$, R$^{11}$ and R$^{12}$ independently represent C$_1$-C$_6$ alkyl or trifluoromethyl, particularly where each of R$^4$ to R$^6$ and R$^{10}$ to R$^{12}$ is identical, especially where each of R$^4$ to R$^6$ and R$^{10}$ to R$^{12}$ represents unsubstituted C$_1$-C$_6$ alkyl, particularly methyl;

A$_1$ and A$_2$ are the same and represent —CH$_2$—;

Q$^1$ and Q$^2$ both represent phosphorus;

K$^1$ represents hydrogen or unsubstituted C$_1$-C$_6$ alkyl, particularly hydrogen;

D$^1$ and E$^1$ together with the carbon atoms of the cyclopentadienyl ring to which they are attached form an unsubstituted phenyl ring;

M represents Fe;

n=1 and L$_1$ represents cyclopentadienyl, particularly unsubstituted cyclopentadienyl, and m=0.

Specific but non-limiting examples of bidentate ligands within this embodiment (II) include the following: 1,2-bis-(dimethylaminomethyl)ferrocene, 1,2-bis-(ditertbutylphosphinomethyl)ferrocene, 1-hydroxymethyl-2-dimethylaminomethylferrocene, 1,2-bis-(ditertbutylphosphinomethyl)ferrocene, 1-hydroxymethyl-2,3-bis-(dimethylaminomethyl)ferrocene, 1,2,3-tris-(ditertbutylphosphinomethyl)ferrocene, 1,2-bis-(dicyclohexylphosphinomethyl)ferrocene, 1,2-bis-(di-isobutylphosphinomethyl)ferrocene, 1,2-bis-(dicyclopentylphosphinomethyl)ferrocene, 1,2-bis-(diethylphosphinomethyl)ferrocene, 1,2-bis(di-isopropylphosphinomethyl)ferrocene, 1,2-bis-(dimethylphosphinomethyl)ferrocene, 1,2-bis-(di-(1,3,5,7-tetramethyl-6,9,10-trioxa-2-phospha-adamantylmethyl))ferrocene, 1,2-bis-(dimethylaminomethyl)ferrocene-bismethyl iodide, 1,2-bis(dihydroxymethylphosphinomethyl)ferrocene, 1,2-bis(diphosphinomethyl)ferrocene, 1,2-bis-c,c-(P-(2,2,6,6,-tetramethylphosphinan-4-one))dimethylferrocene, and 1,2-bis-(di-1,3,5,7-tetramethyl-6,9,10-trioxa-2-phospha-adamantylmethyl))benzene. Nevertheless, the skilled person in the art would appreciate that other bidentate ligands can be envisaged without departing from the scope of the invention.

As mentioned herein, in a still further set of embodiments of the present invention, the ligand L is a bidentate ligand of general formula (III)

$$X^1(X^2)\text{-}Q^2\text{-}A\text{-}R\text{—}B\text{-}Q^1\text{-}X^3(X^4) \qquad (III)$$

wherein:

A and B are as defined for formula (IV) hereinafter

R represents an optionally substituted cycloalkyl moiety to which the Q$^1$ and Q$^2$ atoms are linked on available adjacent cyclic carbon atoms;

the groups X$^1$, X$^2$, X$^3$ and X$^4$ are as defined for formula (IV) hereinafter;

Q$^1$ and Q$^2$ are as defined for formula (IV) hereinafter.

In the above formula (III) unless indicated otherwise, the groups X$^1$, X$^2$, X$^3$ and X$^4$; A and B; and Q$^1$ or Q$^2$ are as defined for formula (IV) herein.

Preferably, the cycloalkyl moiety has from 3 up to 20 cyclic atoms, more preferably from 4 up to 18 cyclic atoms, most preferably from 4 up to 12 cyclic atoms and especially 5 to 8 cyclic atoms and may be monocyclic or polycyclic. The cyclic atoms may be carbon or hetero, wherein references to hetero herein are references to sulphur, oxygen and/or nitrogen. Typically, the cycloalkyl moiety has from 2 up to 20 cyclic carbon atoms, more preferably from 3 up to 18 cyclic carbon atoms, most preferably from 3 up to 12 cyclic carbon atoms and especially 3 to 8 cyclic carbon atoms, may be monocyclic or polycyclic and may or may not be interrupted by one or more hetero atoms. Typically, when the cycloalkyl moiety is polycyclic it is preferably bicyclic or tricyclic. The cycloalkyl moieties as defined herein may include unsaturated bonds insofar as the said adjacent cyclic carbon atoms are saturated and references to unsaturated cycloalkyl moieties should be understood accordingly. By cyclic atom is meant an atom which forms part of the cyclic skeleton.

The cycloalkyl moiety, apart from that it may be interrupted with hetero atoms may be unsubstituted or substituted with one or more further substituents selected from aryl, lower alkyl (which alkyl group may itself be optionally substituted or terminated as defined below), hetero (preferably oxygen), Het, halo, cyano, nitro, —$OR^{19}$, —$OC(O)R^{20}$, —$C(O)R^{21}$, —$C(O)OR^{22}$, —$N(R^{23})R^{24}$, —$C(O)N(R^{25})R^{26}$, —$SR^{29}$, —$C(O)SR^{30}$, —$C(S)N(R^{27})R^{28}$ or —$CF_3$ wherein $R^{19}$-$R^{28}$ are as already defined herein for formula (IV) below.

The cycloalkyl moiety may be selected from cyclohexyl, cyclopentyl, cyclobutyl, cyclopropyl, cycloheptyl, cyclooctyl, cyclononyl, tricyclodecyl, piperidinyl, morpholinyl, norbornyl, isonorbornyl, norbornenyl, isonorbornenyl, bicyclo[2,2,2]octyl, tetrahydrofuryl, dioxanyl, o-2,3-isopropylidene-2,3-dihydroxy-ethyl, cyclopentanonyl, cyclohexanonyl, cyclopentenyl, cyclohexenyl, cyclohexadienyl, cyclobutenyl, cyclopentenonyl, cyclohexenonyl, adamantyl, furans, pyrans, 1,3 dioxane, 1,4 dioxane, oxocene, 7-oxabicyclo[2.2.1]heptane, pentamethylene sulphide, 1,3 dithiane, 1,4 dithiane, furanone, lactone, butyrolactone, pyrone, succinic anhydride, cis and trans 1,2-cyclohexanedicarboxylic anhydride, glutaric anhydride, pyrollidine, piperazine, imidazole, 1,4,7 triazacyclononane, 1,5,9 triazacyclodecane, thiomorpholine, thiazolidine, 4,5-diphenyl-cyclohexyl, 4 or 5-phenyl-cyclohexyl, 4,5-dimethyl-cyclohexyl, 4 or 5-methylcyclohexyl, 1,2-decalinyl, 2,3,3a,4,5,6,7,7a-octahydro-1H-inden-5,6-yl, 3a,4,5,6,7,7a-hexahydro-1H-inden-5,6-yl, 1, 2 or 3 methyl-3a,4,5,6,7,7a hexahydro-1H-inden-5,6-yl, trimethylene norbonanyl, 3a,4,7,7a-tetrahydro-1H-inden-5,6-yl, 1, 2 or 3-dimethyl-3a,4,5,6,7,7a-hexahydro-1H-inden 5,6-yls, 1,3-bis(trimethylsilyl)-3a,4,5,6,7,7a-hexahydro-3H-isobenzofuran.

Particularly preferred combinations in the present set of embodiments include those wherein:—
(1) $X^3$ represents $CR^7(R^8)(R^9)$, $X^4$ represents $CR^{10}(R^{11})(R^{12})$, $X^1$ represents $CR^1(R^2)(R^3)$ and X2 represents $CR^4(R^5)(R^6)$;
A and B are the same and represent —$CH_2$—;
$Q^1$ and $Q^2$ both represent phosphorus;
R represents cis-cyclohexyl.
(2) $X^3$ represents $CR^7(R^8)(R^9)$, $X^4$ represents $CR^{10}(R^{11})(R^{12})$, $X^1$ represents $CR^1(R^2)(R^3)$ and $X^2$ represents $CR^4(R^5)(R^6)$;
A and B are the same and represent —$CH_2$—;
$Q^1$ and $Q^2$ both represent phosphorus;
R represents cis-cyclopentyl.
(3) $X^3$ and $X^4$ together with $Q^1$ to which they are attached form a 2-phospha-adamantyl group, and, $X^1$ and $X^2$ together with $Q^2$ to which they are attached form a 2-phospha-adamantyl group;
A and B are the same and represent —$CH_2$—;
$Q^1$ and $Q^2$ both represent phosphorus;
R represents cis-cyclohexyl.
(4) $X^1$, $X^2$, $X^3$ and $X^4$ represent adamantyl;
A and B are the same and represent —$CH_2$—;
$Q^1$ and $Q^2$ both represent phosphorus;
R represents cis-cyclohexyl.

Still further preferred compounds of formula (III) include those wherein:
$R^1$ to $R^{12}$ are alkyl and are the same and preferably, each represents $C_1$ to $C_6$ alkyl, particularly methyl.

Especially preferred specific compounds of formula (III) include those wherein:
each $R^1$ to $R^{12}$ is the same and represents methyl;
A and B are the same and represent —$CH_2$—;
R represents 4,5 dimethyl-cis-1,2-cyclohexyl.

Examples of suitable bidentate ligands of formula III are cis-1,2-bis(di-t-butylphosphinomethyl)cyclohexane; cis-1,2-bis(di-t-butylphosphinomethyl)cyclopentane; cis-1,2-bis(di-t-butylphosphinomethyl)cyclobutane; cis-1,2-bis(2-phosphinomethyl-1,3,5,7-tetramethyl-6,9,10-trioxa-adamantyl) cyclohexane; cis-1,2-bis(2-phosphinomethyl-1,3,5,7-tetramethyl-6,9,10-trioxa-adamantyl)cyclopentane; cis-1,2-bis(2-phosphinomethyl-1,3,5,7-tetramethyl-6,9,10-trioxa-adamantyl)cyclobutane; cis-1,2-bis(di-adamantylphosphinomethyl)cyclohexane; cis-1,2-bis(di-adamantylphosphinomethyl)cyclopentane; cis-1,2-bis(di-adamantylphosphinomethyl)cyclobutane; cis-1-(P,P-adamantyl, t-butyl-phosphinomethyl)-2-(di-t-butylphosphinomethyl)cyclohexane; cis-1-(P,P-adamantyl, t-butyl-phosphinomethyl)-2-(di-t-butylphosphinomethyl)cyclopentane; cis-1-(P,P-adamantyl, t-butyl-phosphinomethyl)-2-(di-t-butylphosphinomethyl)cyclobutane; cis-1-(2-phosphinomethyl-1,3,5,7-tetramethyl-6,9,10-trioxa-adamantyl)-2-(di-t-butylphosphinomethyl)cyclohexane; cis-1-(2-phosphinomethyl-1,3,5,7-tetramethyl-6,9,10-trioxa-adamantyl)-2-(di-t-butylphosphinomethyl)cyclopentane; cis-1-(2-phosphinomethyl-1,3,5,7-tetramethyl-6,9,10-trioxa-adamantyl)-2-(di-t-butylphosphinomethyl)cyclobutane; cis-1-(2-phosphinomethyl-1,3,5,7-tetramethyl-6,9,10-trioxa-adamantyl)-2-(diadamantylphosphinomethyl)cyclohexane; cis-1-(2-phosphinomethyl-1,3,5,7-tetramethyl-6,9,10-trioxa-adamantyl)-2-(diadamantylphosphinomethyl)cyclopentane; cis-1-(2-phosphinomethyl-1,3,5,7-tetramethyl-6,9,10-trioxa-adamantyl)-2-(diadamantylphosphinomethyl)cyclobutane; cis-1-(di-t-butylphosphinomethyl)-2-(diadamantylphosphinomethyl)cyclohexane; cis-1-(di-t-butylphosphinomethyl)-2-(diadamantylphosphinomethyl)cyclopentane; cis-1-(di-t-butylphosphinomethyl)-2-(diadamantylphosphinomethyl)cyclobutane; cis-1,2-bis(2-phospha-1,3,5-trimethyl-6,9,10-trioxatricyclo-{3.3.1.1[3.7]}decyl)cyclohexane; cis-1,2-bis(2-phospha-1,3,5-trimethyl-6,9,10-trioxatricyclo-{3.3.1.1[3.7]}decyl)cyclopentane; cis-1,2-bis(2-phospha-1,3,5-trimethyl-6,9,10-trioxatricyclo-{3.3.1.1[3.7]}decyl) cyclobutane; cis-1-(2-phospha-1,3,5-trimethyl-6,9,10-trioxatricyclo-{3.3.1.1[3.7]}decyl)-2-(di-t-butylphosphinomethyl)cyclohexane; cis-1-(2-phospha-1,3,5-trimethyl-6,9,10-trioxatricyclo-{3.3.1.1[3.7]}decyl)-2-(di-t-butylphosphinomethyl)cyclopentane; cis-1-(2-phospha-1,3,5-trimethyl-6,9,10-trioxatricyclo-{3.3.1.1[3.7]}decyl)-2-(di-t-butylphosphinomethyl)cyclobutane; cis-1-(2-phospha-1,3,5-trimethyl-6,9,10-trioxatricyclo-{3.3.1.1[3.7]}decyl)-2-(diadamantylphosphinomethyl)cyclohexane; cis-1-(2-phospha-1,3,5-trimethyl-6,9,10-trioxatricyclo-{3.3.1.1[3.7]}decyl)-2-(diadamantylphosphinomethyl)cyclopentane; cis-1-(2-phospha-1,3,5-trimethyl-6,9,10-trioxatricyclo-{3.3.1.1[3.7]}decyl)-2-(diadamantylphosphinomethyl)cyclobutane; cis-1,2-bis-perfluoro(2-phospha-1,3,5,7-tetramethyl-6,9,10-trioxatricyclo{3.3.1.1[3.7]}-decyl)cyclohexane; cis-1,2-bis-perfluoro(2-phospha-1,3,5,7-tetramethyl-6,9,10-trioxatricyclo{3.3.1.1[3.7]}decyl)cyclopentane; cis-1,2-bis-perfluoro(2-phospha-1,3,5,7-tetramethyl-6,9,10-trioxatricyclo{3.3.1.1[3.7]}decyl)cyclobutane; cis-1,2-bis-(2-phospha-1,3,5,7-tetra(trifluoromethyl)-6,9,10-trioxatricyclo{3.3.1.1[3.7]}decyl)cyclohexane; cis-1,2-bis-(2-phospha-1,3,5,7-tetra(trifluoromethyl)-6,9,10-trioxatricyclo{3.3.1.1[3.7]}decyl)cyclopentane; and cis-1,2-bis-(2-phospha-1,3,5,7-tetra(trifluoro-methyl)-6,9,10-trioxatricyclo{3.3.1.1[3.7]}decyl)cyclobutane and including all cis enantiomers of the foregoing where such enantiomers are possible.

Examples of norbornyl bridged ligands include:—

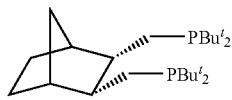

(2-exo, 3-exo)-bicyclo[2.2.1]heptane-2,3-bis(di-tert-butylphosphinomethyl)

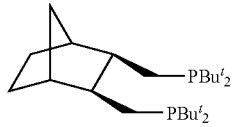

(2-endo, 3-endo)-bicyclo[2.2.1]heptane-2,3-bis(di-tert-butylphosphinomethyl)

Examples of substituted ligands include:—

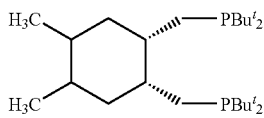

cis-1,2-bis(di-tert-butylphosphinomethyl), 4, 5 dimethylcyclohexane

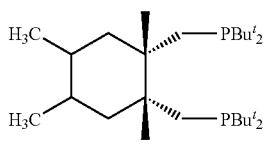

cis-1,2-bis(di-tert-butylphosphinomethyl), 1, 2, 4, 5 tetramethylcyclohexane

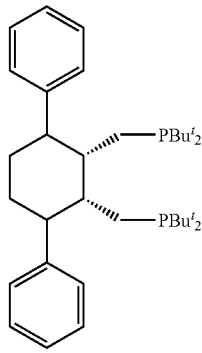

cis-1,2-bis(di-tert-butylphosphinomethyl), 3, 6, diphenylcyclohexane

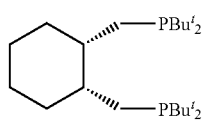

cis-1,2-bis(di-tert-butylphosphinomethyl)cyclohexane

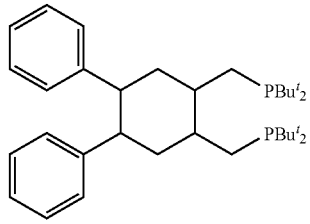

cis-1,2 bis(di-tert-butyl(phosphinomethyl)-4,5 diphenyl cyclohexane

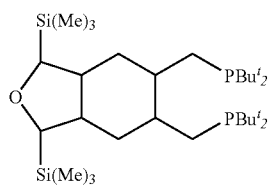

cis-5,6-bis(di-tert-butylphosphinomethyl)-1,3-bis(trimethylsilyl)-3a,4,5,6,7,7a-hexahydro-1,3H-isobenzofuran.

It will be appreciated by those skilled in the art that the compounds of formula (I), (II), (III), (IV) or (V) may function as ligands that coordinate with the Group 8, 9 or 10 metal compound to form the metal complexes for use in the invention. Typically, the Group 8, 9 or 10 metal coordinates to the one or more phosphorous, arsenic and/or antimony atoms of the compound of formula (I), (II), (III), (IV), or (V).

As mentioned herein, in a still further set of embodiments of the present invention, the ligand L is a bidentate ligand of general formula (IV)

  (IV)

wherein:

A and B each independently represent lower alkylene;

R represents a cyclic hydrocarbyl structure having at least one non-aromatic ring to which the $Q^1$ and $Q^2$ atoms are linked on available adjacent cyclic atoms of the at least one ring and which is substituted with at least one substituent on at least one further non-adjacent cyclic atom of the at least one ring;

wherein each adjacent cyclic atom to the said available adjacent cyclic atom is not substituted so as to form a further 3-8 atom ring structure via the other adjacent cyclic atom to the said available adjacent cyclic atoms in the at least one ring or via an atom adjacent to the said other adjacent atom but outside the at least one ring;

the groups X1, X2, X3 and X4 independently represent univalent radicals up to 30 atoms having at least one tertiary carbon atom or X1 and X2 and/or X3 and X4 together form a bivalent radical of up to 40 atoms having at least two tertiary carbon atoms wherein each said univalent or bivalent radical is joined via said at least one or two tertiary carbon atoms respectively to the appropriate atom $Q^1$ or $Q^2$; and $Q^1$ and $Q^2$ each independently represent phosphorous, arsenic or antimony.

By the term one further non-adjacent cyclic atom is meant any further cyclic atom in the ring which is not adjacent to any one of said available adjacent cyclic atoms to which the $Q^1$ and $Q^2$ atoms are linked.

Advantageously, the ring structure of the R group in the present invention prevents undue rigidity by avoiding ring structures or bridges involving the cyclic atoms immediately adjacent to the said available adjacent cyclic atoms or a non-ring atom adjacent to such adjacent atoms. Surprisingly, the inventors have discovered that introducing rigidity into the ring structure so close to the active site is disadvantageous and that beneficial effects are observed through more flexible steric influences (supplied by appropriate ring substitution) than through further proximate rigidity in the ring. This may be due to the relatively flexible constraints supplied by steric influences compared with inflexible ring rigidity. Such flexible steric constraints may allow the incoming metal atom to adopt the most favourable interaction position which would be denied by further ring rigidity close to the said available adjacent cyclic atoms. Accordingly, excluded from this aspect of the invention are norbornyl type bridges at the ring atoms adjacent to the available adjacent ring atoms or the like such as 1,8 Cineolyl. These structures introduce too much rigidity into the ring close to the active site.

Accordingly, the cyclic atoms adjacent to the said available adjacent cyclic atoms may be themselves substituted as long as they do not form part of further adjacent ring structures as defined herein. Suitable substituents may otherwise be selected from those defined for the said at least one further non-adjacent cyclic atom(s) defined herein.

For the avoidance of doubt, references to the cyclic atoms adjacent to the said available adjacent cyclic atoms or the like is not intended to refer to one of the said two available adjacent cyclic atoms themselves. As an example, a cyclohexyl ring joined to a $Q^1$ atom via position 1 on the ring and joined to a $Q^2$ atom via position 2 on the ring has two said further non adjacent cyclic atoms as defined at ring position 4 and 5 and two adjacent cyclic atoms to the said available cyclic atoms at positions 3 and 6.

The term a non-aromatic ring means that the at least one ring to which the $Q^1$ and $Q^2$ atom are linked via B & A respectively is non-aromatic, and aromatic should be interpreted broadly to include not only a phenyl type structure but other rings with aromaticity such as that found in the cyclopentadienyl ring of ferrocenyl, but, in any case, does not exclude aromatic substituents on this non-aromatic at least one ring.

References to ethylenically unsaturated compounds herein should be taken to include any one or more unsaturated C—C bond(s) such as those found in alkenes, alkynes, conjugated and unconjugated dienes, functional alkenes etc.

The substituents on the said at least one further non adjacent cyclic atom may be selected to encourage greater stability but not rigidity of conformation in the cyclic hydrocarbyl structure. The substituents are, therefore, selected to be of the appropriate size to discourage or lower the rate of non-aromatic ring conformation changes. Such groups may be independently selected from lower alkyl, aryl, het, hetero, halo, cyano, nitro, —OR$^{19}$, —OC(O)R$^{20}$, —C(O)R$^{21}$, —C(O)OR$^{22}$, —N(R$^{23}$)R$^{24}$, —C(O)N(R$^{25}$)R$^{26}$, —SR$^{29}$, —C(O)SR$^{30}$, —C(S)N(R$^{27}$)R$^{28}$ or —CF$_3$, more preferably, lower alkyl, or hetero most preferably, $C_1$-$C_6$ alkyl. Where there are two or more said further non-adjacent cyclic atoms in the at least one ring they may each be independently substituted as detailed herein. Accordingly, where two such further non adjacent cyclic atoms are substituted, the substituents may combine to form a further ring structure such as a 3-20 atom ring structure. Such a further ring structure may be saturated or unsaturated, unsubstituted or substituted by one or more substituents selected from halo, cyano, nitro, OR$^{19}$, OC(O)R$^{20}$, C(O)R$^{21}$, C(O)OR$^{22}$, NR$^{23}$R$^{24}$, C(O)NR$^{25}$R$^{26}$, SR$^{29}$, C(O)SR$^{30}$, C(S)NR$^{27}$R$^{28}$, unsubstituted or substituted aryl, lower alkyl (which alkyl group may itself be unsubstituted or substituted or terminated as defined herein) or unsubstituted or substituted Het, wherein R$^{19}$ to R$^{30}$ each independently represent hydrogen, unsubstituted or substituted aryl or unsubstituted or substituted lower alkyl, and/or be interrupted by one or more (preferably less than a total of 4) oxygen, nitrogen, sulphur, silicon atoms or by silano or dialkyl silicon groups or mixtures thereof.

Particularly preferred further non-adjacent cyclic atom substituents are methyl, ethyl, propyl, isopropyl, phenyl, oxo, hydroxy, mercapto, amino, cyano and carboxy. Particularly preferred substituents when two or more further non adjacent cyclic atoms are substituted are x,y-dimethyl, x,y-diethyl, x,y-dipropyl, x,y-di-isopropyl, x,y-diphenyl, x,y-methyl/ethyl, x,y-methyl/phenyl, saturated or unsaturated cyclopentyl, saturated or unsaturated cyclohexyl, 1,3 substituted or unsubstituted 1,3H-furyl, un-substituted cyclohexyl, x,y-oxo/ethyl, x,y-oxo/methyl, disubstitution at a single ring atom is also envisaged, typically, x,x-lower dialkyl. More typical substituents are methyl, ethyl, n-propyl, iso-propyl, n-butyl, isobutyl, t-butyl, or oxo, most typically methyl or ethyl, or oxo most typically, methyl; wherein x and y stand for atom positions in the at least one ring.

Preferably, further substitution of said cyclic hydrocarbyl structure is not on said available adjacent carbon atoms to which said $Q^1$ and $Q^2$ atoms are linked. The cyclic hydrocarbyl structure may be substituted at one or more said further cyclic atoms of the at least one ring but is preferably substituted at 1, 2, 3 or 4 such cyclic atoms, more preferably 1, 2 or 3, most preferably at 1 or 2 such cyclic atoms of the at least one ring. The substituted cyclic atoms may be carbon or hetero but are preferably carbon. For instance, in a ring of cyclic atoms wherein the $Q^1$ and $Q^2$ atoms are linked to cyclic atoms 1 and 2 respectively, substitution is preferably at one or more positions 4 to n-1 ie. positions 4 and/or 5 in a 6 membered ring (position 6 being n), positions 4, 5 and/or 6 in a seven membered ring and position 4 only in a 5 membered ring etc.

When there are two or more substituents on the said at least one ring they may meet to form a further ring structure unless excluded herein. However, it is preferred that substituents attached to said adjacent cyclic atoms to the said available adjacent cyclic atoms do not meet with substituents on the other said adjacent cyclic to form further ring structures at all as these may render the active site too rigid.

Preferably, the cyclic hydrocarbyl structure which is substituted by A and B at available adjacent positions on the at least one ring has a cis- conformation with respect to the relevant cyclic bond and the A and B substituents.

Preferably, the cyclic hydrocarbyl structure has from 5 up to 30 cyclic atoms, more preferably from 4 up to 18 cyclic atoms, most preferably from 4 up to 12 cyclic atoms and when monocyclic, especially 5 to 8 cyclic atoms and, in any case, may be monocyclic or polycyclic. The cyclic atoms may be carbon or hetero, wherein references to hetero herein are references to sulphur, oxygen and/or nitrogen. Typically, the cyclic hydrocarbyl structure has from 2 up to 30 cyclic carbon atoms, more preferably from 3 up to 18 cyclic carbon atoms, most preferably from 3 up to 12 cyclic carbon atoms and, when monocyclic, especially 3 to 8 cyclic carbon atoms and in any case, may be monocyclic or polycyclic and may or may not be interrupted by one or more hetero atoms. Typically, when the cyclic hydrocarbyl structure is polycylic it is preferably bicyclic or tricyclic. The cyclic hydrocarbyl structure as defined herein may include unsaturated bonds insofar as the said available adjacent cyclic atoms to which the $Q^1$ and $Q^2$ atoms are linked are saturated and references to unsaturated cyclic hydrocarbyl structures should be understood accordingly. By cyclic atom is meant an atom which forms part of a cyclic skeleton.

The cyclic hydrocarbyl structure, apart from that it may be interrupted with hetero atoms and, subject to the definitions herein, may be saturated or unsaturated.

The cyclic hydrocarbyl structure may be selected from 4 and/or 5 lower alkylcyclohexane-1,2-diyl, 4 lower alkylcyclopentane-1,2-diyl, 4, 5 and/or 6 lower alkylcycloheptane-1,2-diyl, 4, 5, 6 and/or 7 lower alkylcyclooctane-1,2-diyl, 4, 5, 6, 7 and/or 8 lower alkylcyclononane-1,2-diyl, 5 and/or 6 lower alkyl piperidinane-2,3-diyl, 5 and/or 6 lower alkyl morpholinane-2,3-diyl, O-2,3-isopropylidene-2,3-dihydroxyethane-2,3-diyl, cyclopentan-one-3,4-diyl, cyclohexanone-3,4-diyl, 6-lower alkyl cyclohexanone-3,4-diyl, 1-lower alkyl cyclopentene-3,4-diyl, 1 and/or 6 lower alkyl cyclohexene-3,4-diyl, 2 and/or 3 lower alkyl cyclohexadiene-5,6-diyl, 5 lower alkyl cyclohexen-4-one-1,2-diyl, adamantyl-1-2-diyl, 5 and/or 6 lower alkyl tetrahydropyran-2,3 diyl, 6-lower alkyl dihydropyran-2,3 diyl, 2-lower alkyl 1,3 dioxane-5,6-diyl, 5 and/or 6 lower alkyl-1,4 dioxane-2,3-diyl, 2-lower alkyl pentamethylene sulphide 4,5-diyl, 2-lower alkyl-1,3 dithiane-5,6-diyl, 2 and/or 3-lower alkyl 1,4 dithiane-5,6-diyl, tetrahydro-furan-2-one-4,5-diyl, delta-valero lactone 4,5-diyl, gamma-butyrolactone 3,4-diyl, 2H-dihydropyrone 5,6-diyl, glutaric anhydride 3,4-diyl, 1-lower alkyl pyrollidine-3,4-diyl, 2,3 di-lower alkyl piperazine-5,6-diyl, 2-lower alkyl dihydro imidazole-4,5-diyl, 2, 3, 5 and/or 6 lower alkyl-1,4,7 triazacyclononane-8,9-diyl, 2,3,4 and/or 10 lower alkyl-1,5,9 triazacyclodecane 6,7-diyl, 2,3-di-lower alkyl thiomorpholine-5,6-diyl, 2-lower alkyl-thiazolidine-4,5-diyl, 4,5-diphenyl-cyclohexane-1,2-diyl, 4 and/or 5-phenyl-cyclohexane-1, 2-diyl, 4,5-dimethyl-cyclohexane-1,2-diyl, 4 or 5-methylcyclohexane-1,2-diyl, 2, 3, 4 and/or 5 lower alkyl-decahydronaphthalene 8,9-diyl, bicyclo[4.3.0]nonane-3,4 diyl, 3a,4,5,6,7,7a-hexahydro-1H-inden-5,6-diyl, 1, 2 and/or 3 methyl-3a,4,5,6,7,7a hexahydro-1H-inden-5,6-diyl, Octahydro-4,7 methano-indene-1,2-diyl, 3a,4,7,7a-tetrahydro-1H-inden-5,6-diyl, 1, 2 and/or 3-dimethyl-3a,4,5,6,7,7a-hexahydro-1H-inden 5,6-diyls, 1,3-bis(trimethylsilyl)-3a,4, 5,6,7,7a-hexahydro-3H-isobenzofuran-5,6-diyl.

Some typical structures are shown below wherein R', R", R''', R"" etc are defined in the same way as the substituent on the at least one further non-adjacent cyclic atom above but may also be hydrogen, or represent the hetero atom being non substituted if linked directly to a hetero atom and may be the same or different and wherein at least one R' atom is not hydrogen or representing the hetero atom being non substituted if linked directly to a hetero atom. The diyl methylene linkages to the phosphorous (not shown) are shown in each case.

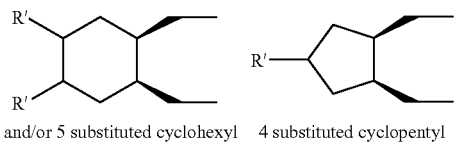

4 and/or 5 substituted cyclohexyl    4 substituted cyclopentyl

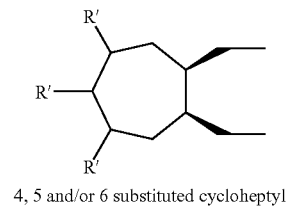

4, 5 and/or 6 substituted cycloheptyl

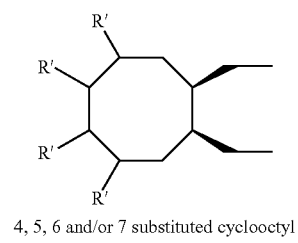

4, 5, 6 and/or 7 substituted cyclooctyl

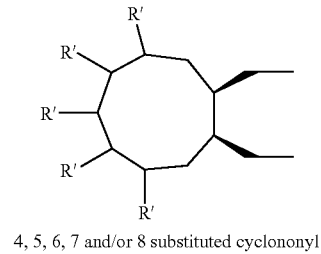

4, 5, 6, 7 and/or 8 substituted cyclononyl

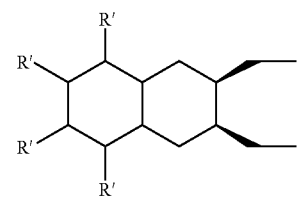

2, 3, 4, and/or 5 substituted decahydronaphthalene

-continued

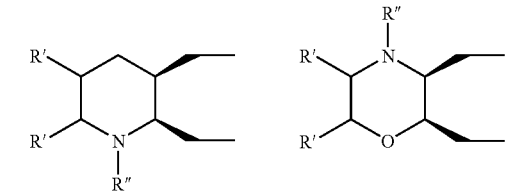

5 and/or 6 substituted piperidines    5 and/or 6 substituted morpholines

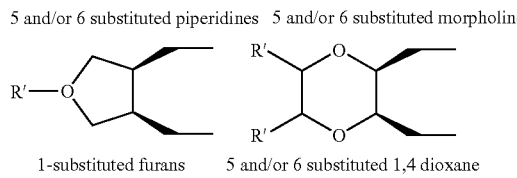

1-substituted furans    5 and/or 6 substituted 1,4 dioxane

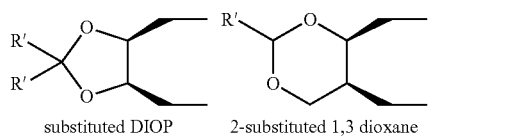

substituted DIOP    2-substituted 1,3 dioxane

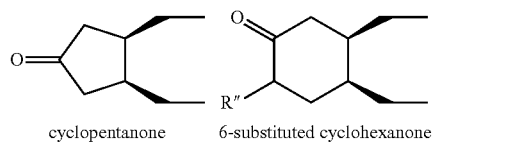

cyclopentanone    6-substituted cyclohexanone

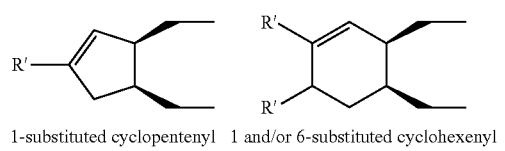

1-substituted cyclopentenyl    1 and/or 6-substituted cyclohexenyl

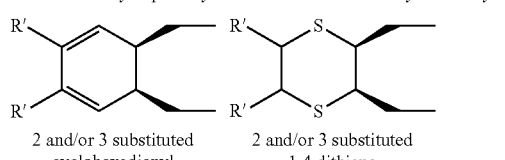

2 and/or 3 substituted cyclohexadienyl    2 and/or 3 substituted 1,4 dithiane

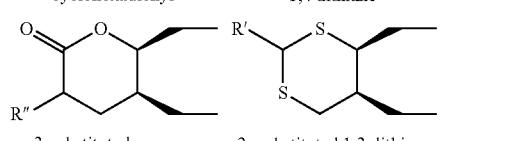

3-substituted pyrones    2-substituted 1,3 dithiane

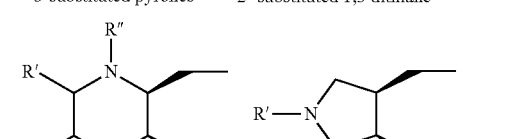

1, 2, 3, 4 substituted piperizine    1 substituted pyrollidine

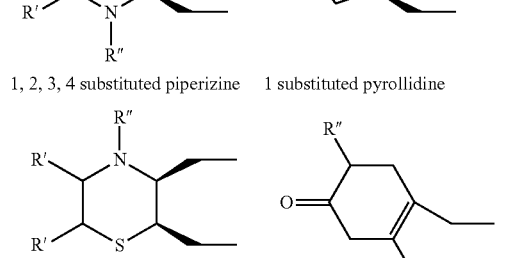

1, 2, 3 substituted thiomorphiline    5 substituted cyclohexen-4-one

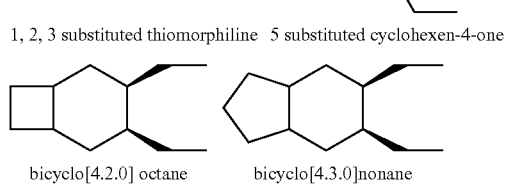

bicyclo[4.2.0] octane    bicyclo[4.3.0]nonane

-continued

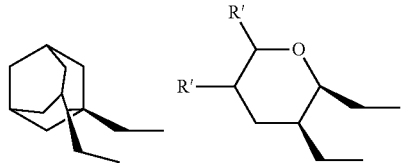

Adamantyl-1,2-diyl    substituted tetrahydropyran

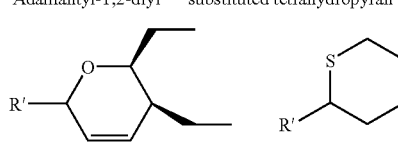

Substituted dihydropyran    substituted pentamethylene sulphide (substituted tetrahydro-thiopyran

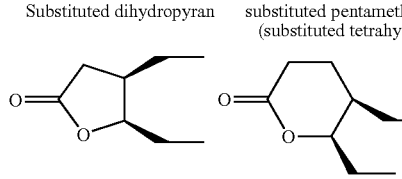

tetrahydro-furan-2-one    delta-valero lactone 4,5-diyl

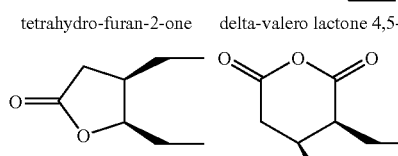

gamma-butyrolactone    glutaric anhydride

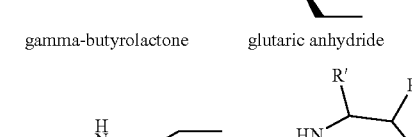

substituted dihydro imidazole    Substituted 1, 4, 7 triazacyclononane

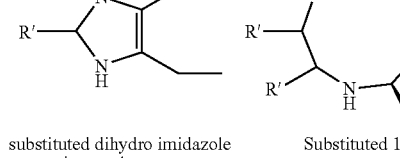

substituted 1, 5, 9 triazacyclodecane    substituted thiazolidine

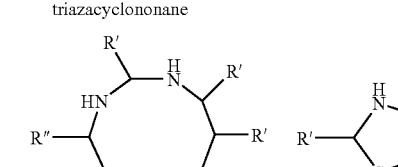

3a, 4, 5, 6, 7, 7a-hexahydro-1H-indene    substituted 3a, 4, 5, 6, 7, 7a hexahydro-1H-indene

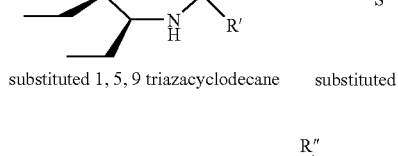

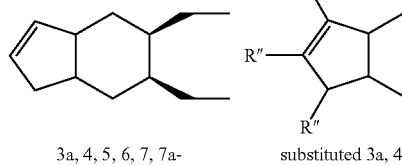

Octahydro-4, 7 methano-indene    3a, 4, 7, 7a-tetrahydro-1H-indene

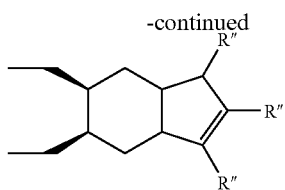

Substituted 3a, 4, 5, 6, 7, 7a-hexahydro-1H-indene

In the structures herein, where there is more than one stereisomeric form possible, all such stereoisomers are intended. However, it is preferable that the at least one substituent on at least one further non-adjacent cyclic atom of the at least one ring extends in a trans direction with respect to the A and or B atom ie. extends outwardly on the opposite side of the ring.

Preferably, the cyclic hydrocarbyl structure is associated with A and B as the cis-1,2-cyclic hydrocarbyl structure or, in any case, cis with respect to the bond between the two available adjacent cyclic atoms to which A and B are respectively attached.

Typically, the group $X^1$ represents $CR^1(R^2)(R^3)$, $X^2$ represents $CR^4(R^5)(R^6)$, $X^3$ represents $CR^7(R^8)(R^9)$ and $X^4$ represents $CR^{10}(R^{11})(R^{12})$, wherein $R^1$ to $R^{12}$ represent lower alkyl, aryl or het.

Particularly preferred is when the organic groups $R^1$-$R^3$, $R^4$-$R^6$, $R^7$-$R^9$ and/or $R^{10}$-$R^{12}$ or, alternatively, $R^1$-$R^6$ and/or $R^7$-$R^{12}$ when associated with their respective tertiary carbon atom(s) form composite groups which are at least as sterically hindering as t-butyl(s). Steric hindrance in this context is as discussed at page 14 et seq of "Homogenous Transition Metal Catalysis-A Gentle Art", by C Masters, published by Chapman and Hall 1981. These steric groups may be cyclic, part-cyclic or acyclic. When cyclic or part cyclic, the group may be substituted or unsubstituted or saturated or unsaturated. The cyclic or part cyclic groups may preferably contain, including the tertiary carbon atom(s), from $C_4$-$C_{34}$, more preferably $C_8$-$C_{24}$, most preferably $C_{10}$-$C_{20}$ carbon atoms in the cyclic structure. The cyclic structure may be substituted by one or more substituents selected from halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $SR^{29}$, $C(O)SR^{30}$, $C(S)NR^{27}R^{28}$, aryl or Het, wherein $R^{19}$ to $R^{30}$ each independently represent hydrogen, aryl or lower alkyl, and/or be interrupted by one or more oxygen or sulphur atoms, or by silano or dialkylsilcon groups.

In particular, when cyclic, $X^1$, $X^2$, $X^3$ and/or $X^4$ may represent congressyl, norbornyl, 1-norbornadienyl or adamantyl, or $X^1$ and $X^2$ together with $Q^2$ to which they are attached form an optionally substituted 2-$Q^2$-tricyclo[3.3.1.1{3,7}] decyl group or derivative thereof, or $X^1$ and $X^2$ together with $Q^2$ to which they are attached form a ring system of formula 1a

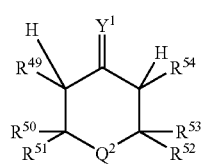

(1a)

Similarly, $X^3$ and $X^4$ together with $Q^1$ to which they are attached may form an optionally substituted 2-Q1-tricyclo [3.3.1.1{3,7}]decyl group or derivative thereof, or $X^3$ and $X^4$ together with $Q^1$ to which they are attached may form a ring system of formula 1b

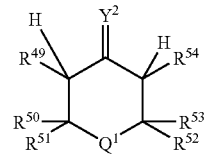

(1b)

Alternatively, one or more of the groups $X^1$, $X^2$, $X^3$ and/or $X^4$ may represent a solid phase to which the ligand is attached.

Particularly preferred is when $X^1$, $X^2$, $X^3$ and $X^4$ or $X^1$ and $X^2$ together with its respective $Q^2$ atom and $X^3$ and $X^4$ together with its respective $Q^1$ atom are the same or when $X^1$ and $X^3$ are the same whilst $X^2$ and $X^4$ are different but the same as each other.

$R^1$ to $R^{12}$ each independently represent lower alkyl, aryl or Het;

$R^{19}$ to $R^{30}$ each independently represent hydrogen, lower alkyl, aryl or Het and may be interrupted by one or more oxygen, sulphur, silicon atoms, or by silano or dialkylsilcon groups or mixtures thereof;

$R^{49}$, $R^{54}$ and $R^{55}$, when present, each independently represent hydrogen, lower alkyl or aryl;

$R^{50}$ to $R^{53}$, when present, each independently represent lower alkyl, aryl or Het;

$Y^1$, $Y^2$, $Y^3$, $Y^4$ and $Y^5$, when present, each independently represent oxygen, sulfur or N—$R^{55}$, wherein $R^{55}$ represents hydrogen, lower alkyl or aryl.

Preferably, $R^1$ to $R^{12}$ each independently represent lower alkyl or aryl. More preferably, $R^1$ to $R^{12}$ each independently represent $C_1$ to $C_6$ alkyl, $C_1$-$C_6$ alkyl phenyl (wherein the phenyl group is optionally substituted as defined herein) or phenyl (wherein the phenyl group is optionally substituted as aryl as defined herein). Even more preferably, $R^1$ to $R^{12}$ each independently represent $C_1$ to $C_6$ alkyl, which is optionally substituted as alkyl as defined herein. Most preferably, $R^1$ to $R^{12}$ each represent non-substituted $C_1$ to $C_6$ alkyl such as methyl, ethyl, n-propyl, iso-propyl, n-butyl, iso-butyl, tert-butyl, pentyl, hexyl and cyclohexyl, especially methyl.

In a particularly preferred embodiment of the present invention $R^1$, $R^4$, $R^7$ and $R^{10}$ each represent the same lower alkyl, aryl or Het moiety as defined herein, $R^2$, $R^5$, $R^8$ and $R^{11}$ each represent the same lower alkyl, aryl or Het moiety as defined herein, and $R^3$, $R^6$, $R^9$ and $R^{12}$ each represent the same lower alkyl, aryl or Het moiety as defined herein. More preferably $R^1$, $R^4$, $R^7$ and $R^{10}$ each represent the same $C_1$-$C_6$ alkyl, particularly non-substituted $C_1$-$C_6$ alkyl, such as methyl, ethyl, n-propyl, iso-propyl, n-butyl, iso-butyl, tert-butyl, pentyl, hexyl or cyclohexyl; $R^2$, $R^5$, $R^8$ and $R^{11}$ each independently represent the same $C_1$-$C_6$ alkyl as defined above; and $R^3$, $R^6$, $R^9$ and $R^{12}$ each independently represent the same $C_1$-$C_6$ alkyl as defined above. For example: $R^1$, $R^4$, $R^7$ and $R^{10}$ each represent methyl; $R^2$, $R^5$, $R^8$ and $R^{11}$ each represent ethyl; and, $R^3$, $R^6$, $R^9$ and $R^{12}$ each represent n-butyl or n-pentyl.

In an especially preferred embodiment of the present invention each $R^1$ to $R^{12}$ group represents the same lower alkyl, aryl, or Het moiety as defined herein. Preferably, when alkyl groups, each $R^1$ to $R^{12}$ represents the same $C_1$ to $C_6$ alkyl group, particularly non-substituted $C_1$-$C_6$ alkyl, such as methyl, ethyl, n-propyl, iso-propyl, n-butyl, iso-butyl, tert-butyl, pentyl, hexyl and cyclohexyl. More preferably, each $R^1$ to $R^{12}$ represents methyl or tert-butyl, most preferably, methyl.

The term "lower alkylene" which A and B represent in a compound of formula I, when used herein, includes $C_1$ to $C_{10}$ groups which can be bonded at two places on the group to thereby connect the group $Q^1$ or $Q^2$ to the R group, and is otherwise defined in the same way as "lower alkyl" below. Nevertheless, methylene is most preferred.

The term "lower alkyl" or "alkyl" when used herein, means $C_1$ to $C_{10}$ alkyl and includes methyl, ethyl, ethenyl, propyl, propenyl butyl, butenyl, pentyl, pentenyl, hexyl, hexenyl and heptyl groups. Unless otherwise specified, alkyl including lower alkyl groups may, when there is a sufficient number of carbon atoms, be linear or branched (particularly preferred branched groups include t-butyl and isopropyl), be saturated or unsaturated, be cyclic, acyclic or part cyclic/acyclic, be unsubstituted, substituted or terminated by one or more substituents selected from halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $SR^{29}$, $C(O)SR^{30}$, $C(S)NR^{27}R^{28}$, unsubstituted or substituted aryl, or unsubstituted or substituted Het, wherein $R^{19}$ to $R^{30}$ each independently represent hydrogen, halo, unsubstituted or substituted aryl or unsubstituted or substituted lower alkyl, or, in the case of $R^{21}$, halo, nitro, cyano and amino and/or be interrupted by one or more (preferably less than 4) oxygen, sulphur, silicon atoms, or by silano or dialkylsilcon groups, or mixtures thereof.

The term "Ar" or "aryl" when used herein, includes five- to-ten-membered, preferably five or six to ten membered, carbocyclic aromatic or pseudo aromatic groups, such as phenyl, cyclopentadienyl and indenyl anions and naphthyl, which groups may be unsubstituted or substituted with one or more substituents selected from unsubstituted or substituted aryl, lower alkyl (which group may itself be unsubstituted or substituted or terminated as defined herein), Het (which group may itself be unsubstituted or substituted or terminated as defined herein), halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $SR^{29}$, $C(O)SR^{30}$ or $C(S)NR^{27}R^{28}$ wherein $R^{19}$ to $R^{30}$ each independently represent hydrogen, unsubstituted or substituted aryl or lower alkyl (which alkyl group may itself be unsubstituted or substituted or terminated as defined herein), or, in the case of $R^{21}$, additionally, halo, nitro, cyano or amino.

The term "alkenyl" when used herein, means $C_2$ to $C_{10}$ alkenyl and includes ethenyl, propenyl, butenyl, pentenyl, and hexenyl groups. Unless otherwise specified, alkenyl groups may, when there is a sufficient number of carbon atoms, be linear or branched, be saturated or unsaturated, be cyclic, acyclic or part cyclic/acyclic, be unsubstituted, substituted or terminated by one or more substituents selected from halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $SR^{29}$, $C(O)SR^{30}$, $C(S)NR^{27}R^{28}$, unsubstituted or substituted aryl, or unsubstituted or substituted Het, wherein $R^{19}$ to $R^{30}$ are defined as for alkyl above and/or be interrupted by one or more (preferably less than 4) oxygen, sulphur, silicon atoms, or by silano or dialkylsilcon groups, or mixtures thereof.

The term "alkynyl" when used herein, means $C_2$ to $C_{10}$ alkynyl and includes ethynyl, propynyl, butynyl, pentynyl, and hexynyl groups. Unless otherwise specified, alkynyl groups may, when there is a sufficient number of carbon atoms, be linear or branched, be saturated or unsaturated, be cyclic, acyclic or part cyclic/acyclic, be unsubstituted, substituted or terminated by one or more substituents selected from halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $SR^{29}$, $C(O)SR^{30}$, $C(S)NR^{27}R^{28}$, unsubstituted or substituted aryl, or unsubstituted or substituted Het, wherein $R^{19}$ to $R^{30}$ are defined as for alkyl above and/or be interrupted by one or more (preferably less than 4) oxygen, sulphur, silicon atoms, or by silano or dialkylsilcon groups, or mixtures thereof.

The terms "alkylene", "aralkyl", "alkaryl", "arylenealkyl" or the like should, in the absence of information to the contrary, be taken to be in accordance with the above definition of "alkyl" as far as the alkyl or alk portion of the group is concerned.

The above Ar or aryl groups may be attached by one or more covalent bonds but references to "arylene" or "arylenealkyl" or the like herein should be understood as two covalent bond attachment but otherwise be defined as Ar or aryl above as far as the arylene portion of the group is concerned. References to "alkaryl", "aralkyl" or the like should be taken as references to Ar or aryl above as far as the Ar or aryl portion of the group is concerned.

Halo groups with which the above-mentioned groups may be substituted or terminated include fluoro, chloro, bromo and iodo.

The term "Het", when used herein, includes four- to twelve-membered, preferably four- to ten-membered ring systems, which rings contain one or more heteroatoms selected from nitrogen, oxygen, sulfur and mixtures thereof, and which rings contain no, one or more double bonds or may be non-aromatic, partly aromatic or wholly aromatic in character. The ring systems may be monocyclic, bicyclic or fused. Each "Het" group identified herein may be unsubstituted or substituted by one or more substituents selected from halo, cyano, nitro, oxo, lower alkyl (which alkyl group may itself be unsubstituted or substituted or terminated as defined herein) —$OR^{19}$, —$OC(O)R^{20}$, —$C(O)R^{21}$, —$C(O)OR^{22}$, —$N(R^{23})R^{24}$, —$C(O)N(R^{25})R^{26}$, —$SR^{29}$, —$C(O)SR^{30}$ or —$C(S)N(R^{27})R^{28}$ wherein $R^{19}$ to $R^{30}$ each independently represent hydrogen, unsubstituted or substituted aryl or lower alkyl (which alkyl group itself may be unsubstituted or substituted or terminated as defined herein) or, in the case of $R^{21}$, halo, nitro, amino or cyano. The term "Het" thus includes groups such as optionally substituted azetidinyl, pyrrolidinyl, imidazolyl, indolyl, furanyl, oxazolyl, isoxazolyl, oxadiazolyl, thiazolyl, thiadiazolyl, triazolyl, oxatriazolyl, thiatriazolyl, pyridazinyl, morpholinyl, pyrimidinyl, pyrazinyl, quinolinyl, isoquinolinyl, piperidinyl, pyrazolyl and piperazinyl. Substitution at Het may be at a carbon atom of the Het ring or, where appropriate, at one or more of the heteroatoms.

"Het" groups may also be in the form of an N oxide.

The term hetero as mentioned herein means nitrogen, oxygen, sulfur or mixtures thereof.

The adamantyl, congressyl, norbornyl or 1-norborndienyl group may optionally comprise, besides hydrogen atoms, one or more substituents selected from lower alkyl, —$OR^{19}$, —$OC(O)R^{20}$, halo, nitro, —$C(O)R^{21}$, —$C(O)OR^{22}$, cyano, aryl, —$N(R^{23})R^{24}$, —$C(O)N(R^{25})R^{26}$, —$C(S)(R^{27})R^{28}$, —$SR^{29}$, —$C(O)SR^{30}$, —$CF_3$, —$P(R^{56})R^{57}$, —$PO(R^{58})(R^{59})$, —$PO_3H_2$, —$PO(OR^{60})(OR^{61})$, or —$SO_3R^{62}$, wherein $R^{19}$-$R^{30}$, lower alkyl, halo, cyano and aryl are as defined herein and $R^{56}$ to $R^{62}$ each independently represent hydrogen, lower alkyl, aryl or Het.

Suitably, when the adamantyl, congressyl, norbornyl or 1-norborndienyl group is substituted with one or more substituents as defined above, highly preferred substituents include unsubstituted $C_1$ to C8 alkyl, —$OR^{19}$, —$OC(O)R^{20}$, phenyl, —$C(O)OR^{22}$, fluoro, —$SO_3H$, —$N(R^{23})R^{24}$, —$P(R^{56})R^{57}$, —$C(O)N(R^{25})R^{26}$ and —$PO(R^{58})(R^{59})$, —$CF_3$, wherein $R^{19}$ represents hydrogen, unsubstituted $C_1$-$C_8$ alkyl or phenyl, $R^{20}$, $R^{22}$, $R^{23}$, $R^{24}$, $R^{25}$, $R^{26}$ each independently represent hydrogen or unsubstituted $C_1$-$C_8$ alkyl, $R^{56}$ to $R^{59}$ each independently represent unsubstituted $C_1$-$C_8$ alkyl or phenyl. In a particularly preferred embodiment the substituents are $C_1$ to $C_8$ alkyl, more preferably, methyl such as found in 1,3 dimethyl adamantyl.

Suitably, the adamantyl, congressyl, norbornyl or 1-norborndienyl group may comprise, besides hydrogen atoms, up to 10 substituents as defined above, preferably up to 5 substituents as defined above, more preferably up to 3 substituents as defined above. Suitably, when the adamantyl, congressyl, norbornyl or 1-norborndienyl group comprises, besides hydrogen atoms, one or more substituents as defined herein, preferably each substituent is identical. Preferred substituents are unsubstituted $C_1$-$C_8$ alkyl and trifluoromethyl, particularly unsubstituted $C_1$-$C_8$ alkyl such as methyl. A highly preferred adamantyl, congressyl, norbornyl or 1-norborndienyl group comprises hydrogen atoms only i.e. the adamantyl congressyl, norbornyl or 1-norborndienyl group is not substituted.

Preferably, when more than one adamantyl, congressyl, norbornyl or 1-norborndienyl group is present in a compound of formula I, each such group is identical.

The 2-$Q^2$ (or $Q^1$)-tricyclo[3.3.1.1.{3,7}]decyl group (referred to hereinafter as a 2-meta-adamantyl group for convenience wherein 2-meta-adamantyl is a reference to $Q^1$ or $Q^2$ being an arsenic, antimony or phosphorous atom i.e. 2-arsa-adamantyl and/or 2-stiba-adamantyl and/or 2-phospha-adamantyl, preferably, 2-phospha-adamantyl) may optionally comprise, beside hydrogen atoms, one or more substituents. Suitable substituents include those substituents as defined herein in respect of the adamantyl group. Highly preferred substituents include lower alkyl, particularly unsubstituted $C_1$-$C_8$ alkyl, especially methyl, trifluoromethyl, —$OR^{19}$ wherein $R^{19}$ is as defined herein particularly unsubstituted $C_1$-$C_8$ alkyl or aryl, and 4-dodecylphenyl. When the 2-meta-adamantyl group includes more than one substituent, preferably each substituent is identical.

Preferably, the 2-meta-adamantyl group is substituted on one or more of the 1, 3, 5 or 7 positions with a substituent as defined herein. More preferably, the 2-meta-adamantyl group is substituted on each of the 1, 3 and 5 positions. Suitably, such an arrangement means the Q atom of the 2-meta-adamantyl group is bonded to carbon atoms in the adamantyl skeleton having no hydrogen atoms. Most preferably, the 2-meta-adamantyl group is substituted on each of the 1, 3, 5 and 7 positions. When the 2-meta-adamantyl group includes more than 1 substituent preferably each substituent is identical. Especially preferred substituents are unsubstituted $C_1$-$C_8$ alkyl and haloakyls, particularly unsubstituted $C_1$-$C_8$ alkyl such as methyl and fluorinated $C_1$-$C_8$ alkyl such as trifluoromethyl.

Preferably, 2-meta-adamantyl represents unsubstituted 2-meta-adamantyl or 2-meta-adamantyl substituted with one or more unsubstituted $C_1$-$C_8$ alkyl substituents, or a combination thereof.

Preferably, the 2-meta-adamantyl group includes additional heteroatoms, other than the 2-Q atom, in the 2-meta-adamantyl skeleton. Suitable additional heteroatoms include oxygen and sulphur atoms, especially oxygen atoms. More preferably, the 2-meta-adamantyl group includes one or more additional heteroatoms in the 6, 9 and 10 positions. Even more preferably, the 2-meta-adamantyl group includes an additional heteroatom in each of the 6, 9 and 10 positions. Most preferably, when the 2-meta-adamantyl group includes two or more additional heteroatoms in the 2-meta-adamantyl skeleton, each of the additional heteroatoms are identical. An especially preferred 2-meta-adamantyl group, which may optionally be substituted with one or more substituents as defined herein, includes an oxygen atom in each of the 6, 9 and 10 positions of the 2-meta-adamantyl skeleton.

Preferably, the 2-meta-adamantyl includes one or more oxygen atoms in the 2-meta-adamantyl skeleton.

Highly preferred 2-meta-adamantyl groups as defined herein include 2-phospha-1,3,5,7-tetramethyl-6,9,10-trioxadamantyl, 2-phospha-1,3,5-trimethyl-6,9,10-trioxadamantyl, 2-phospha-1,3,5,7-tetra(trifluoromethyl)-6,9,10-trioxadamantyl group, and 2-phospha-1,3,5-tri(trifluoromethyl)-6,9,10-trioxadamantyl group. Most preferably, the 2-phospha-adamantyl is selected from 2-phospha-1,3,5,7-tetramethyl-6,9,10-trioxadamantyl group or 2-phospha-1,3,5,-trimethyl-6,9,10-trioxadamantyl group.

Preferably, when more than one 2-meta-adamantyl group is present in a compound of formula I, each 2-meta-adamantyl group is identical.

The 2-meta-adamantyl group may be prepared by methods well known to those skilled in the art. Suitably, certain 2-phospha-adamantyl compounds are obtainable from Cytec Canada Inc, Canada. Likewise corresponding 2-meta-adamantyl compounds of formula I etc may be obtained from the same supplier or prepared by analogous methods.

Preferred embodiments of the present invention include those wherein:

$X^3$ represents $CR^7(R^8)(R^9)$, $X^4$ represents $CR^{10}(R^{11})(R^{12})$, $X^1$ represents $CR^1(R^2)(R^3)$ and $X^2$ represents $CR^4(R^5)(R^6)$;

$X^3$ represents $CR^7(R^8)(R^9)$, $X^4$ represents $CR^{10}(R^{11})(R^{12})$, and $X^1$ and $X^2$ together with $Q^2$ to which they are attached form a 2-phospha-adamantyl group;

$X^3$ represents $CR^7(R^8)(R^9)$, $X^4$ represents $CR^{10}(R^{11})(R^{12})$; and $X^1$ and $X^2$ together with $Q^2$ to which they are attached form a ring system of formula 1a;

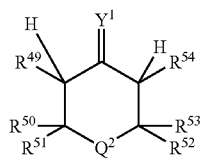

(1a)

$X^3$ represents $CR^7(R^8)(R^9)$, $X^4$ represents adamantyl, and $X^1$ and $X^2$ together with $Q^2$ to which they are attached form a 2-phospha-adamantyl group;

$X^3$ represents $CR^7(R^8)(R^9)$, $X^4$ represents adamantyl and $X^1$ and $X^2$ together with $Q^2$ to which they are attached form a ring system of formula 1a;

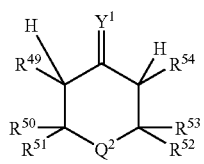

(1a)

$X^3$ represents $CR^7(R^8)(R^9)$, $X^4$ represents adamantyl, $X^1$ represents $CR^1(R^2)(R^3)$ and $X^2$ represents $CR^4(R^5)(R^6)$;

$X^3$ represents $CR^7(R^8)(R^9)$, $X^4$ represents congressyl, and $X^1$ and $X^2$ together with $Q^2$ to which they are attached form a 2-phospha-adamantyl group;

$X^3$ represents $CR^7(R^8)(R^9)$, $X^4$ represents congressyl, $X^1$ represents $CR^1(R^2)(R^3)$ and $X^2$ represents $CR^4(R^5)(R^6)$;

$X^3$ and $X^4$ independently represent adamantyl, and $X^1$ and $X^2$ together with $Q^2$ to which they are attached form a 2-phospha-adamantyl group;

$X^3$ and $X^4$ independently represent adamantyl, and $X^1$ and $X^2$ together with $Q^2$ to which they are attached form a ring system of formula 1a;

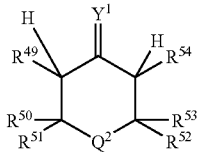

(1a)

$X^3$ and $X^4$ independently represent adamantyl, $X^1$ represents $CR^1(R^2)(R^3)$ and $X^2$ represents $CR^4(R^5)(R^6)$;

$X^1$, $X^2$, $X^3$ and $X^4$ represent adamantyl;

$X^3$ and $X^4$ together with $Q^1$ to which they are attached may form a ring system of formula 1b

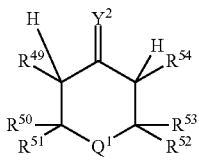

(1b)

and $X^1$ and $X^2$ together with $Q^2$ to which they are attached form a ring system of formula 1a;

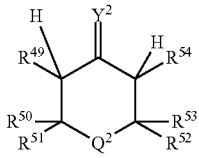

(1a)

$X^3$ and $X^4$ independently represent congressyl, and $X^1$ and $X^2$ together with $Q^2$ to which they are attached form a 2-phospha-adamantyl group;

$X^3$ and $X^4$ together with $Q^1$ to which they are attached may form a ring system of formula 1b

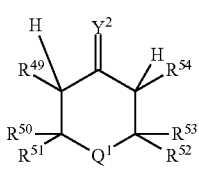

(1b)

and $X^1$ and $X^2$ together with $Q^2$, to which they are attached form a 2-phospha-adamantyl group;

$X^3$ and $X^4$ independently represent congressyl, and $X^1$ represents $CR^1(R^2)(R^3)$ and $X^2$ represents $CR^4(R^5)(R^6)$;

$X^3$ and $X^4$ together with $Q^1$ to which they are attached may form a ring system of formula 1b

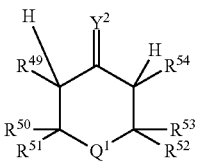

(1b)

$X^1$ represents $CR^1(R^2)(R^3)$ and $X^2$ represents $CR^4(R^5)(R^6)$;

$X^3$ and $X^4$ together with $Q^1$ to which they are attached form a 2-phospha-adamantyl group, and $X^1$ and $X^2$ together with $Q^2$ to which they are attached form a 2-phospha-adamantyl group Highly preferred embodiments of the present invention include those wherein:

$X^3$ represents $CR^7(R^8)(R^9)$, $X^4$ represents $CR^{10}(R^{11})(R^{12})$, $X^1$ represents $CR^1(R^2)(R^3)$ and $X^2$ represents $CR^4(R^5)(R^6)$; especially where $R^1$-$R^{12}$ are methyl.

Preferably in a compound of formula IV, $X^3$ is identical to $X^4$ and/or $X^1$ is identical to $X^2$.

Particularly preferred combinations in the present invention include those wherein:—

(1) $X^3$ represents $CR^7(R^8)(R^9)$, $X^4$ represents $CR^{10}(R^{11})(R^{12})$, $X^1$ represents $CR^1(R^2)(R^3)$ and $X^2$ represents $CR^4(R^5)(R^6)$;

A and B are the same and represent —$CH_2$—;

$Q^1$ and $Q^2$ both represent phosphorus linked to the R group at ring positions 1 and 2;

R represents 1,2 cis-5,6-dimethyl cyclohexyl.

(2) $X^3$ represents $CR^7(R^8)(R^9)$, $X^4$ represents $CR^{10}(R^{11})(R^{12})$, $X^1$ represents $CR^1(R^2)(R^3)$ and $X^2$ represents $CR^4(R^5)(R^6)$;

A and B are the same and represent —$CH_2$—;

$Q^1$ and $Q^2$ both represent phosphorus linked to the R group at ring positions 1 and 2;

R represents 1,2-cis-5-methyl cyclopentyl.

(3) $X^3$ and $X^4$ together with $Q^1$ to which they are attached form a 2-phospha-adamantyl group, and, $X^1$ and $X^2$ together with $Q^2$ to which they are attached form a 2-phospha-adamantyl group;

A and B are the same and represent —$CH_2$—;

$Q^1$ and $Q^2$ both represent phosphorus linked to the R group at ring positions 1 and 2;

R represents 1,2 cis-5,6-dimethyl cyclohexyl.

(4) $X^1$, $X^2$, $X^3$ and $X^4$ represent adamantyl;

A and B are the same and represent —$CH_2$—;

$Q^1$ and $Q^2$ both represent phosphorus linked to the R group at ring positions 1 and 2;

R represents 1,2 cis-5,6-dimethyl cyclohexyl.

Preferably, in the compounds of formula I-V, A and B each independently represents $C_1$ to $C_6$ alkylene which is optionally substituted as defined herein, for example with lower alkyl groups. Preferably, the lower alkylene groups which A and B represent are non-substituted. Particularly preferred lower alkylene which A and B may independently represent are —$CH_2$— or —$C_2H_4$—. Most preferably, each of A and B represent the same lower alkylene as defined herein, particularly —$CH_2$—.

Still further preferred compounds of formula I-V include those wherein:

R[1] to R[12] are alkyl and are the same and preferably, each represents $C_1$ to $C_6$ alkyl, particularly methyl.

Especially preferred specific compounds of formula (IV) include those wherein:

each R[1] to R[12] is the same and represents methyl;
A and B are the same and represent —$CH_2$—;
R represents 4,5 dimethyl-cis-1,2-cyclohexyl.

Examples of suitable bidentate ligands of formula IV are cis-1,2-bis(di-t-butylphosphinomethyl)-4,5-dimethyl cyclohexane; cis-1,2-bis(di-t-butylphosphinomethyl)-5-methylcyclopentane; cis-1,2-bis(2-phosphinomethyl-1,3,5,7-tetramethyl-6,9,10-trioxa-adamantyl)-4,5-dimethylcyclohexane; cis-1,2-bis(2-phosphinomethyl-1,3,5,7-tetramethyl-6,9,10-trioxa-adamantyl) 5-methylcyclopentane; cis-1,2-bis(di-adamantylphosphinomethyl)-4,5 dimethylcyclohexane; cis-1,2-bis(di-adamantylphosphinomethyl)-5-methyl cyclopentane; cis-1-(P,P adamantyl, t-butyl phosphinomethyl)-2-(di-t-butylphosphinomethyl)-4,5-dimethylcyclohexane; cis-1-(P,P adamantyl, t-butyl phosphinomethyl)-2-(di-t-butylphosphinomethyl)-5-methylcyclopentane; cis-1-(2-phosphinomethyl-1,3,5,7-tetramethyl-6,9,10-trioxa-adamantyl)-2-(di-t-butylphosphinomethyl) 4,5-dimethylcyclohexane; cis-1-(2-phosphinomethyl-1,3,5,7-tetramethyl-6,9,10-trioxa-adamantyl)-2-(di-t-butylphosphinomethyl)-5-methyl cyclopentane; cis-1-(2-phosphinomethyl-1,3,5,7-tetramethyl-6,9,10-trioxa-adamantyl)-2-(diadamantylphosphinomethyl)-5-methyl cyclohexane; cis-1-(2-phosphinomethyl-1,3,5,7-tetramethyl-6,9,10-trioxa-adamantyl)-2-(diadamantylphosphinomethyl)-5-methyl cyclopentane; cis-1-(2-phosphinomethyl-1,3,5,7-tetramethyl-6,9,10-trioxa-adamantyl)-2-(diadamantylphosphinomethyl)cyclobutane; cis-1-(di-t-butylphosphinomethyl)-2-(diadamantylphosphinomethyl)-4,5-dimethyl cyclohexane; cis-1-(di-t-butylphosphinomethyl)-2-(diadamantylphosphinomethyl)-5-methyl cyclopentane; cis-1,2-bis(2-phospha-1,3,5-trimethyl-6,9,10-trioxatricyclo-{3.3.1.1[3.7]}decyl)-4,5-dimethyl cyclohexane; cis-1,2-bis(2-phospha-1,3,5-trimethyl-6,9,10-trioxatricyclo-{3.3.1.1[3.7]}decyl)-5-methyl cyclopentane; cis-1-(2-phospha-1,3,5-trimethyl-6,9,10-trioxatricyclo-{3.3.1.1[3.7]}decyl)-2-(di-t-butylphosphinomethyl)-4,5-dimethyl cyclohexane; cis-1-(2-phospha-1,3,5-trimethyl-6,9,10-trioxatricyclo-{3.3.1.1[3.7]}decyl)-2-(di-t-butylphosphinomethyl)-5-methyl cyclopentane; cis-1-(2-phospha-1,3,5-trimethyl-6,9,10-trioxatricyclo-{3.3.1.1[3.7]}decyl)-2-(diadamantylphosphinomethyl)-4,5-dimethyl cyclohexane; cis-1-(2-phospha-1,3,5-trimethyl-6,9,10-trioxatricyclo-{3.3.1.1[3.7]}decyl)-2-(diadamantylphosphinomethyl)-5-methyl cyclopentane; cis-1,2-bis-perfluoro(2-phospha-1,3,5,7-tetramethyl-6,9,10-trioxatricyclo{3.3.1.1[3.7]}-decyl)-4,5-dimethyl cyclohexane; cis-1,2-bis-perfluoro(2-phospha-1,3,5,7-tetramethyl-6,9,10-trioxatricyclo{3.3.1.1[3.7]}decyl)-5-methyl cyclopentane; cis-1,2-bis-(2-phospha-1,3,5,7-tetra(trifluoro-methyl)-6,9,10-trioxatricyclo{3.3.1.1[3.7]}decyl)-4,5-dimethyl cyclohexane; cis-1,2-bis-(2-phospha-1,3,5,7-tetra(trifluoro-methyl)-6,9,10-trioxatricyclo{3.3.1.1 [3.7]}decyl)-5-methyl cyclopentane; and including all cis enantiomers of the foregoing where such enantiomers are possible.

Further examples of substituted ligands include:—

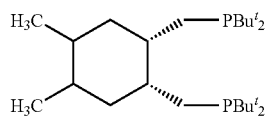

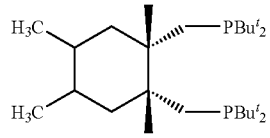

cis-1,2-bis(di-tert-butylphosphinomethyl), 4, 5 dimethylcyclohexane cis-1,2-bis(di-tert-butylphosphinomethyl), 1, 2, 4, 5 tetramethylcyclohexane

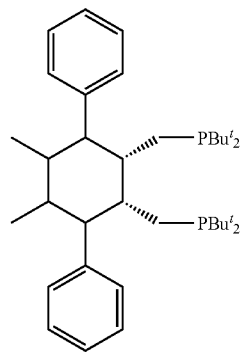

cis-1,2-bis(di-tert-butylphosphinomethyl), 3, 6, diphenyl-4, 5 dimethyl-cyclohexane

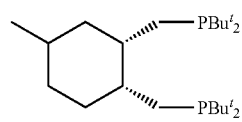

cis-1,2-bis (di-tert-butylphosphinomethyl) 5-methylcyclohexane

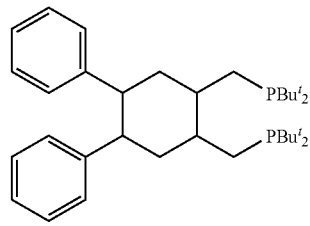

cis-1,2 bis(di-tert-butyl(phosphinomethyl)-4,5 diphenyl cyclohexane

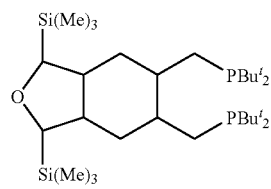

cis-5,6-bis(di-tert-butylphosphinomethyl)-1,3-bis(trimethylsilyl)-3a,4,5,6,7,7a-hexahydro-1,3H-isobenzofuran.

In a yet further set of embodiments the ligand L is a bidentate ligand of general formula (V)

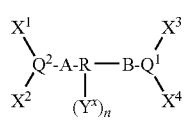

(V)

wherein:

A and B are as identified in formula (IV);

R represents a hydrocarbyl aromatic structure having at least one aromatic ring to which $Q^1$ and $Q^2$ are each linked, via the respective linking group, on available adjacent cyclic atoms of the at least one aromatic ring and which is substituted with one or more substituent(s) $Y^x$ on one or more further aromatic cyclic atom(s) of the aromatic structure;

wherein the substituent(s) $Y^x$ on the aromatic structure has a total $^{X=1-n}\Sigma tY^x$ of atoms other than hydrogen such that $^{X=1-n}\Sigma tY^x$ is $\geq 4$, where n is the total number of substituent(s) $Y^x$ and $tY^x$ represents the total number of atoms other than hydrogen on a particular substituent $Y^x$;

the groups $X^1$, $X^2$, $X^3$ and $X^4$ are as defined in formula (IV); and $Q^1$ and $Q^2$ are as defined in formula (IV).

The above novel bidentate ligands have been found to have surprisingly improved stability in carbonylation reactions. Typically, the turnover number (TON) (moles of metal/moles of product) for the carbonylation reaction, especially, hydroxy- or alkoxy-carbonylation is close to or greater than that for 1,3-bis(di-t-butylphosphino)propane reacted under the same conditions, more preferably, greater than 1,2-bis(di-t-butylphosphinomethyl)benzene reacted under the same conditions. Preferably, such conditions are in continuous reactions but batch reactions will also benefit.

Typically, when there is more than one substituent $Y^x$ hereinafter also referred to as simply Y, any two may be located on the same or different aromatic cyclic atoms of the aromatic structure. Preferably, there are $\leq 10$ Y groups ie n is 1 to 10, more preferably there are 1-6 Y groups, most preferably 1-4 Y groups on the aromatic structure and, especially, 1, 2 or 3 substituent Y groups on the aromatic structure. The substituted cyclic aromatic atoms may be carbon or hetero but are preferably carbon.

Preferably, $^{X=1-n}\Sigma tY^x$ is between 4-100, more preferably, 4-60, most preferably, 4-20, especially 4-12.

Preferably, when there is one substituent Y, Y represents a group which is at least as sterically hindering as phenyl and when there are two or more substituents Y they are each as sterically hindering as phenyl and/or combine to form a group which is more sterically hindering than phenyl.

By sterically hindering herein, whether in the context of the groups $R^1$-$R^{12}$ described hereinafter or the substituent Y, we mean the term as readily understood by those skilled in the art but for the avoidance of any doubt, the term more sterically hindering than phenyl can be taken to mean having a lower degree of substitution (DS) than $PH_2Ph$ when $PH_2Y$ (representing the group Y) is reacted with $Ni(0)(CO)_4$ in eightfold excess according to the conditions below. Similarly, references to more sterically hindering than t-butyl can be taken as references to DS values compared with $PH_2$t-Bu etc. If two Y groups are being compared and $PHY^1$ is not more sterically hindered than the reference then $PHY^1Y^2$ should be compared with the reference. Similarly, if three Y groups are being compared and $PHY^1$ or $PHY^1Y^2$ are not already determined to be more sterically hindered than the standard then $PY^1Y^2Y^3$ should be compared. If there are more than three Y groups they should be taken to be more sterically hindered than t-butyl.

Steric hindrance in the context of the invention herein is discussed on page 14 et seq of "Homogenous Transition Metal Catalysis-A Gentle Art", by C. Masters, published by Chapman and Hall 1981.

Tolman ("Phosphorus Ligand Exchange Equilibria on Zerovalent Nickel. A Dominant Role for Steric Effects", Journal of American Chemical Society, 92, 1970, 2956-2965) has concluded that the property of the ligands which primarily determines the stability of the Ni(O) complexes is their size rather than their electronic character.

To determine the relative steric hindrance of a group Y the method of Tolman to determine DS may be used on the phosphorous analogue of the group to be determined as set out above.

Toluene solutions of $Ni(CO)_4$ were treated with an eightfold excess of phosphorous ligand; substitution of CO by ligand was followed by means of the carbonyl stretching vibrations in the infrared spectrum. The solutions were equilibriated by heating in sealed tubes for 64 hr at 100°. Further heating at 100° for an additional 74 hrs did not significantly change the spectra. The frequencies and intensities of the carbonyl stretching bands in the spectra of the equilibriated solutions are then determined. The degree of substitution can be estimated semiquantitatively from the relative intensities and the assumption that the extinction coefficients of the bands are all of the same order of magnitude. For example, in the case of $P(C_6H_{11})_3$ the $A_1$ band of $Ni(CO)_3L$ and the $B_1$ band of $Ni(CO)_2L_2$ are of about the same intensity, so that the degree of substitution is estimated at 1.5. If this experiment fails to distinguish the respective ligands then the diphenyl phosphorous $PPh_2H$ or di-t-butyl phosphorous should be compared to the $PY_2H$ equivalent as the case may be. Still further, if this also fails to distinguish the ligands then the $PPh_3$ or $P(tBu)_3$ ligand should be compared to $PY_3$, as the case may be. Such further experimentation may be required with small ligands which fully substitute the $Ni(CO)_4$ complex.

The group Y may also be defined by reference to its cone angle which can be defined in the context of the invention as the apex angle of a cylindrical cone centred at the midpoint of the aromatic ring. By midpoint is meant a point in the plane of the ring which is equidistant from the cyclic ring atoms.

Preferably, the cone angle of the at least one group Y or the sum of the cone angles of two or more Y groups is at least 10°, more preferably, at least 20°, most preferably, at least 30°. Cone angle should be measured according to the method of Tolman {C. A. Tolman Chem. Rev. 77, (1977), 313-348} except that the apex angle of the cone is now centred at the midpoint of the aromatic ring. This modified use of Tolman cone angles has been used in other systems to measure steric effects such as those in cyclopentadienyl zirconium ethene polymerisation catalysts (Journal of Molecular Catalysis: Chemical 188,(2002), 105-113).

The substituents Y are selected to be of the appropriate size to provide steric hindrance with respect to the active site between the $Q^1$ and $Q^2$ atoms. However, it is not known whether the substituent is preventing the metal leaving, directing its incoming pathway, generally providing a more stable catalytic confirmation, or acting otherwise.

A particularly preferred ligand is found when Y represents —SR$^{90}$R$^{91}$R$^{92}$ wherein S represents Si, C, N, S, O or aryl and R$^{90}$R$^{91}$R$^{92}$ are as defined hereinafter. Preferably each Y and/or combination of two or more Y groups is at least as sterically hindering as t-butyl.

More preferably, when there is only one substituent Y, it is at least as sterically hindering as t-butyl whereas where there are two or more substituents Y, they are each at least as sterically hindering as phenyl and at least as sterically hindering as t-butyl if considered as a single group.

Preferably, when S is aryl, R$^{90}$, R$^{91}$ and R$^{92}$ are independently hydrogen, alkyl, —BQ$^3$-X$^3$(X$^4$) (wherein B, X$^3$ and X$^4$ are as defined herein and Q$^3$ is defined as Q$^1$ or Q$^2$ above), phosphorous, aryl, arylene, alkaryl, arylenalkyl, alkenyl, alkynyl, het, hetero, halo, cyano, nitro, —OR$^{19}$, —OC(O)R$^{20}$, —C(O)R$^{21}$, —C(O)OR$^{22}$, —N(R$^{23}$)R$^{24}$, —C(O)N(R$^{25}$)R$^{26}$, —SR$^{29}$, —C(O)SR$^{30}$, —C(S)N(R$^{27}$)R$^{28}$, —CF$_3$, —SiR$^{71}$R$^{72}$R$^{73}$ or alkylphosphorous.

R$^{19}$-R$^{30}$ referred to herein may independently be generally selected from hydrogen, unsubstituted or substituted aryl or unsubstituted or substituted alkyl, in addition R$^{21}$ may be nitro, halo, amino or thio.

Preferably, when S is Si, C, N, S or O, R$^{90}$, R$^{91}$ and R$^{92}$ are independently hydrogen, alkyl, phosphorous, aryl, arylene, alkaryl, aralkyl, arylenalkyl, alkenyl, alkynyl, het, hetero, halo, cyano, nitro, —OR$^{19}$, —OC(O)R$^{20}$, —C(O)R$^{21}$, —C(O)OR$^{22}$, —N(R$^{23}$)R$^{24}$, —C(O)N(R$^{25}$)R$^{26}$, —SR$^{29}$, —C(O)SR$^{30}$, —C(S)N(R$^{27}$)R$^{28}$, —CF$_3$, —SiR$^{71}$R$^{72}$R$^{73}$, or alkylphosphorous wherein at least one of R$^{90}$-R$^{92}$ is not hydrogen and wherein R$^{19}$-R$^{30}$ are as defined herein,; and R$^{71}$-R$^{73}$ are defined as R$^{90}$-R$^{92}$ but are preferably C$_1$-C$_4$ alkyl or phenyl.

Preferably, S is Si, C or aryl. However, N, S or O may also be preferred as one or more of the Y groups in combined or in the case of multiple Y groups. For the avoidance of doubt, as oxygen or sulphur can be bivalent, R$^{90}$-R$^{92}$ can also be lone pairs.

Preferably, in addition to group Y, the aromatic structure may be unsubstituted or, when possible be further substituted with groups selected from Y (on the non-aromatic cyclic atoms), alkyl, aryl, arylene, alkaryl, aralkyl, arylenalkyl, alkenyl, alkynyl, het, hetero, halo, cyano, nitro, —OR$^{19}$, —OC(O)R$^{20}$, —C(O)R$^{21}$, —C(O)OR$^{22}$, —N(R$^{23}$)R$^{24}$, —C(O)N(R$^{25}$)R$^{26}$, —SR$^{29}$, —C(O)SR$^{30}$, —C(S)N(R$^{27}$)R$^{28}$, —CF$_3$, —SiR$^{71}$R$^{72}$R$^{73}$, or alkylphosphorous wherein R$^{19}$-R$^{30}$ are as defined herein and in the case of Y or a group fulfilling the definition of Y of the first aspect the attachment is to a non-cyclic aromatic atom of the aromatic structure; and R$^{71}$-R$^{73}$ are defined as R$^{90}$-R$^{92}$ but are preferably C$_1$-C$_4$ alkyl or phenyl. In addition, the at least one aromatic ring can be part of a metallocene complex, for instance when R is a cyclopentadienyl or indenyl anion it may form part of a metal complex such as ferrocenyl, ruthenocyl, molybdenocenyl or indenyl equivalents.

Such complexes should be considered as aromatic structures within the context of the present invention so that, when they include more than one aromatic ring, the substituent(s) Y$^x$ may be on the same aromatic ring as that to which the Q$^1$ and Q$^2$ atoms are linked or a further aromatic ring of the structure. For instance, in the case of a metallocene, the substituent Y$^x$ may be on any one or more rings of the metallocene structure and this may be the same or a different ring to which Q$^1$ and Q$^2$ are linked.

Suitable metallocene type ligands which may be substituted with a group Y as defined herein will be known to the skilled person and are extensively defined in WO 04/024322. A particularly preferred Y substituent for such aromatic anions is when S is Si.

In general, however, when S is aryl, the aryl may be further unsubstituted or substituted with, in addition to R$^{90}$, R$^{91}$, R$^{92}$, any of the further substituents defined for the aromatic structure above.

More preferred Y substituents in the present invention may be selected from t-alkyl or t-alkyl,aryl such as -t-butyl or 2-phenylprop-2-yl, —SiMe$_3$, -phenyl, alkylphenyl-, phenylalkyl- or phosphinoalkyl- such as phosphinomethyl.

Preferably, when S is Si or C and one or more of R$^{90}$-R$^{92}$ are hydrogen, at least one of R$^{90}$-R$^{92}$ should be sufficiently bulky to give the required steric hindrance and such groups are preferably phosphorous, phosphinoalkyl-, a tertiary carbon bearing group such as -t-butyl, -aryl, -alkaryl, -aralkyl or tertiary silyl.

Preferably, the hydrocarbyl aromatic structure has, including substituents, from 5 up to 70 cyclic atoms, more preferably, 5 to 40 cyclic atoms, most preferably, 5-22 cyclic atoms, especially 5 or 6 cyclic atoms, if not a metallocene complex.

Preferably, the aromatic hydrocarbyl structure may be monocyclic or polycyclic. The cyclic aromatic atoms may be carbon or hetero, wherein references to hetero herein are references to sulphur, oxygen and/or nitrogen. However, it is preferred that the Q$^1$ and Q$^2$ atoms are linked to available adjacent cyclic carbon atoms of the at least one aromatic ring. Typically, when the cyclic hydrocarbyl structure is polycylic it is preferably bicyclic or tricyclic. The further cycles in the aromatic structure may or may not themselves be aromatic and aromatic structure should be understood accordingly. A non-aromatic cyclic ring(s) as defined herein may include unsaturated bonds. By cyclic atom is meant an atom which forms part of a cyclic skeleton.

Preferably, the bridging group —R(Y$^x$)$_n$, whether further substituted or otherwise preferably comprises less than 200 atoms, more preferably, less than 150 atoms, more preferably, less than 100 atoms.

By the term one further aromatic cyclic atom of the aromatic structure is meant any further aromatic cyclic atom in the aromatic structure which is not an available adjacent cyclic atom of the at least one aromatic ring to which the Q$^1$ or Q$^2$ atoms are linked, via the linking group.

As mentioned above, the immediate adjacent cyclic atoms on either side of the said available adjacent cyclic atoms are preferably not substituted. As an example, an aromatic phenyl ring joined to a Q$^1$ atom via position 1 on the ring and joined to a Q$^2$ atom via position 2 on the ring has preferably one or more said further aromatic cyclic atoms substituted at ring position 4 and/or 5 and two immediate adjacent cyclic atoms to the said available adjacent cyclic atoms not substituted at positions 3 and 6. However, this is only a preferred substituent arrangement and substitution at ring positions 3 and 6, for example, is possible.

The term aromatic ring means that the at least one ring to which the Q$^1$ and Q$^2$ atom are linked via B & A respectively is aromatic, and aromatic should preferably be interpreted broadly to include not only a phenyl, cyclopentadienyl anion, pyrollyl, pyridinyl, type structures but other rings with aromaticity such as that found in any ring with delocalised Pi electrons able to move freely in the said ring.

Preferred aromatic rings have 5 or 6 atoms in the ring but rings with 4n+2 pi electrons are also possible such as [14] annulene, [18] annulene, etc The aromatic hydrocarbyl structure may be selected from 4 and/or 5 t-alkylbenzene-1,2-diyl, 4,5-diphenyl-benzene-1,2-diyl, 4 and/or 5-phenyl-benzene-1,2-diyl, 4,5-di-t-butyl-benzene-1,2-diyl, 4 or 5-t-butylbenzene-1,2-diyl, 2, 3, 4 and/or 5 t-alkyl-naphthalene-8,9-diyl, 1H-inden-5,6-diyl, 1, 2 and/or 3 methyl-1H-inden-5,6-diyl, 4,7 methano-1H-indene-1,2-diyl, 1, 2 and/or 3-dimethyl-1H-inden 5,6-diyls, 1,3-bis(trimethylsilyl)-isobenzofuran-5,6-diyl, 4-(trimethylsilyl)benzene-1,2 diyl, 4-phosphinomethyl benzene-1,2 diyl, 4-(2'-phenylprop-2'-yl)benzene-1,2 diyl, 4-dimethylsilylbenzene-1,2diyl, 4-di-t-butyl,methylsilyl benzene-1,2diyl, 4-(t-butyldimethylsilyl)-benzene-1,2diyl, 4-t-butylsilyl-benzene-1,2diyl, 4-(tri-t-butylsilyl)-benzene-1,2diyl, 4-(2'-tert-butylprop-2'-yl)benzene-1,2 diyl, 4-(2',2',3',4',4' pentamethyl-pent-3'-yl)-benzene-1,2diyl, 4-(2',2',4',4'-tetramethyl,3'-t-butyl-pent-3'-yl)-benzene-1,2 diyl, 4-(or 1')t-alkylferrocene-1,2-diyl, 4,5-diphenyl-ferrocene-1,2-diyl, 4-(or 1')phenyl-ferrocene-1,2-diyl, 4,5-di-t-butyl-ferrocene-1,2-diyl, 4- (or 1')t-butylferrocene-1,2-diyl, 4-(or 1')(trimethylsilyl)ferrocene-1,2 diyl, 4- (or 1')phosphinomethyl ferrocene-1,2 diyl, 4- (or 1')(2'-phenylprop-2'-yl)ferrocene-1,2 diyl, 4- (or 1')dimethylsilylferrocene-1,2diyl, 4- (or 1')di-t-butyl,methylsilyl ferrocene-1,2diyl, 4- (or 1')(t-butyldimethylsilyl)-ferrocene-1,2diyl, 4- (or 1')t-butylsilyl-ferrocene-1,2diyl, 4- (or 1')(tri-t-butylsilyl)-ferrocene-1,2diyl, 4- (or 1')(2'-tert-butylprop-2'-yl)ferrocene-1,2 diyl, 4- (or 1')(2',2',3',4',4' pentamethyl-pent-3'-yl)-ferrocene-1,2diyl, 4- (or 1')(2',2',4',4'-tetramethyl, 3'-t-butyl-pent-3'-yl)-ferrocene-1,2 diyl.

As mentioned above, in some embodiments, there may be two or more of said Y and/or non-Y substituents on further aromatic cyclic atoms of the aromatic structure. Optionally, the said two or more substituents may, especially when on neighbouring cyclic aromatic atoms, combine to form a further ring structure such as a cycloaliphatic ring structure.

Such cycloaliphatic ring structures may be saturated or unsaturated, bridged or unbridged, substituted with alkyl, Y groups as defined herein, aryl, arylene, alkaryl, aralkyl, arylenalkyl, alkenyl, alkynyl, het, hetero, halo, cyano, nitro, —$OR^{19}$, —$OC(O)R^{20}$, —$C(O)R^{21}$, —$C(O)OR^{22}$, —$N(R^{23})R^{24}$, —$C(O)N(R^{25})R^{26}$, —$SR^{29}$, —$C(O)SR^{30}$, —$C(S)N(R^{27})R^{28}$, —$CF_3$, —$SiR^{71}R^{72}R^{73}$, or phosphinoalkyl wherein, when present, at least one of $R^{90}$-$R^{92}$ is not hydrogen and wherein $R^{19}$-$R^{30}$ are as defined herein; and $R^{71}$-$R^{73}$ are defined as $R^{90}$-$R^{92}$ but are preferably $C_1$-$C_4$ alkyl or phenyl and/or be interrupted by one or more (preferably less than a total of 4) oxygen, nitrogen, sulphur, silicon atoms or by silano or dialkyl silicon groups or mixtures thereof.

Examples of such structures include piperidine, pyridine, morpholine, cyclohexane, cycloheptane, cyclooctane, cyclononane, furan, dioxane, alkyl substituted DIOP, 2-alkyl substituted 1,3 dioxane, cyclopentanone, cyclohexanone, cyclopentene, cyclohexene, cyclohexadiene, 1,4 dithiane, piperizine, pyrollidine, thiomorpholine, cyclohexenone, bicyclo[4.2.0]octane, bicyclo[4.3.0]nonane, adamantane, tetrahydropyran, dihydropyran, tetrahydrothiopyran, tetrahydro-furan-2-one, delta valerolactone, gamma-butyrolactone, glutaric anhydride, dihydroimidazole, triazacyclononane, triazacyclodecane, thiazolidine, hexahydro-1H-indene (5,6 diyl), octahydro-4,7 methano-indene (1,2 diyl) and tetrahydro-1H-indene (5,6 diyl) all of which may be unsubstituted or substituted as defined for aryl herein.

However, whether forming combined groups or otherwise, it is preferred that the immediate adjacent aromatic cyclic atoms, on either side of the said available adjacent cyclic atoms to which $Q^1$ and $Q^2$ are linked, via the said linking group, are less preferably substituted and preferable substitution is elsewhere on the at least one aromatic ring or elsewhere in the aromatic structure when the aromatic structure comprises more than one aromatic ring and the preferred position of combined Y substituents should be understood accordingly.

In formula 1a & 1b above representing groups $X^3$ and $X^4$ or $X^1$ and $X^2$ together with the $Q^1$ or $Q^2$ atom, group $Y^1$ or $Y^2$ should be substituted with the groups $YY^1$ or $YY^2$ respectively.

$YY^1$ and $YY^2$, when present, each independently represent oxygen, sulfur or N—$R^{55}$, wherein $R^{55}$ represents hydrogen, alkyl or aryl.

Particularly preferred combinations of formula V in the present invention include those wherein:—

(1) $X^3$ represents $CR^7(R^8)(R^9)$, $X^4$ represents $CR^{10}(R^{11})(R^{12})$, $X^1$ represents $CR^1(R^2)(R^3)$ and $X^2$ represents $CR^4(R^5)(R^6)$;
A and B are the same and represent —$CH_2$—;
$Q^1$ and $Q^2$ both represent phosphorus linked to the R group at ring positions 1 and 2;
R represents 4-(trimethylsilyl)-benzene-1,2-diyl (2) $X^3$ represents $CR^7(R^8)(R^9)$, $X^4$ represents $CR^{10}(R^{11})(R^{12})$, $X^1$ represents $CR^1(R^2)(R^3)$ and $X^2$ represents $CR^4(R^5)(R^6)$;
A and B are the same and represent —$CH_2$—;
$Q^1$ and $Q^2$ both represent phosphorus linked to the R group at ring positions 1 and 2;
R represents 4-t-butyl-benzene-1,2-diyl.

(3) $X^3$ and $X^4$ together with $Q^1$ to which they are attached form a 2-phospha-adamantyl group, and, $X^1$ and $X^2$ together with $Q^2$ to which they are attached form a 2-phospha-adamantyl group;
A and B are the same and represent —$CH_2$—;
$Q^1$ and $Q^2$ both represent phosphorus linked to the R group at ring positions 1 and 2;
R represents 4-(trimethylsilyl)-benzene-1,2-diyl.

(4) $X^1$, $X^2$, $X^3$ and $X^4$ represent adamantyl;
A and B are the same and represent —$CH_2$—;
$Q^1$ and $Q^2$ both represent phosphorus linked to the R group at ring positions 1 and 2;
R represents 4-(trimethylsilyl)-benzene-1,2-diyl.

Especially preferred specific compounds of formula V include those wherein:
each $R^1$ to $R^{12}$ is the same and represents methyl;
A and B are the same and represent —$CH_2$—;
R represents 4-t-butyl-benzene-1,2-diyl or 4(trimethylsilyl)-benzene-1,2-diyl.

Examples of suitable bidentate ligands are 1,2-bis(di-t-butylphosphinomethyl)-4,5-diphenyl benzene; 1,2-bis(di-t-butylphosphinomethyl)-4-phenylbenzene; 1,2-bis(di-t-butylphosphinomethyl)-4,5-bis-(trimethylsilyl)benzene; 1,2-bis(di-t-butylphosphinomethyl)-4-(trimethylsilyl)benzene; 1,2-bis(2-phosphinomethyl-1,3,5,7-tetramethyl-6,9,10-trioxa-adamantyl)-4,5-diphenylbenzene; 1,2-bis(2-phosphinomethyl-1,3,5,7-tetramethyl-6,9,10-trioxa-adamantyl)-4-phenylbenzene; 1,2-bis(2-phosphinomethyl-1,3,5,7-tetramethyl-6,9,10-trioxa-adamantyl)-4,5-bis-(trimethylsilyl)benzene; 1,2-bis(2-phosphinomethyl-1,3,5,7-tetramethyl-6,9,10-trioxa-adamantyl)-4-(trimethylsilyl)benzene; 1,2-bis(di-adamantylphosphinomethyl)-4,5 diphenylbenzene; 1,2-bis(di-adamantylphosphinomethyl)-4-phenyl benzene; 1,2-bis(di-adamantylphosphinomethyl)-4,5 bis-(trimethylsilyl)benzene; 1,2-bis(di-adamantylphosphinomethyl)-4-(trimethylsilyl)benzene; 1-(P,P adamantyl, t-butyl phosphinomethyl)-2-(di-t-butylphosphinomethyl)-4,5-diphenylbenzene; 1-(P,P adamantyl, t-butyl phosphinomethyl)-2-(di-t-butylphosphinomethyl)-4-phenylbenzene; 1-(P,P adamantyl, t-butyl phosphinomethyl)-2-(di-t-butylphosphinomethyl)-4,5- bis-(trimethylsilyl)benzene;

1-(P,P adamantyl, t-butyl phosphinomethyl)-2-(di-t-butylphosphinomethyl)-4-(trimethylsilyl)benzene; 1-(2-phosphinomethyl-1,3,5,7-tetramethyl-6,9,10-trioxa-adamantyl)-2-(di-t-butylphosphinomethyl)4,5-diphenylbenzene; 1-(2-phosphinomethyl-1,3,5,7-tetramethyl-6,9,10-trioxa-adamantyl)-2-(di-t-butylphosphinomethyl)-4-phenyl benzene; 1-(2-phosphinomethyl-1,3,5,7-tetramethyl-6,9,10-trioxa-adamantyl)-2-(di-t-butylphosphinomethyl)4,5-bis-(trimethylsilyl)benzene; 1-(2-phosphinomethyl-1,3,5,7-tetramethyl-6,9,10-trioxa-adamantyl)-2-(di-t-butylphosphinomethyl)-4-(trimethylsilyl)benzene; 1-(2-phosphinomethyl-1,3,5,7-tetramethyl-6,9,10-trioxa-adamantyl)-2-(diadamantylphosphinomethyl)-4, 5-diphenyl benzene; 1-(2-phosphinomethyl-1,3,5,7-tetramethyl-6,9,10-trioxa-adamantyl)-2-(diadamantylphosphinomethyl)-4-phenyl benzene; 1-(2-phosphinomethyl-1,3,5,7-tetramethyl-6,9,10-trioxa-adamantyl)-2-(diadamantylphosphinomethyl)-4,5-bis-(trimethylsilyl)benzene; 1-(2-phosphinomethyl-1,3,5,7-tetramethyl-6,9,10-trioxa-adamantyl)-2-(diadamantylphosphinomethyl)-4-(trimethylsilyl)benzene; 1-(di-t-butylphosphinomethyl)-2-(diadamantylphosphinomethyl)-4,5-diphenyl benzene; 1-(di-t-butylphosphinomethyl)-2-(diadamantylphosphinomethyl)-4-phenyl benzene; 1-(di-t-butylphosphinomethyl)-2-(diadamantylphosphinomethyl)-4,5-bis-(trimethylsilyl)benzene; 1-(di-t-butylphosphinomethyl)-2-(diadamantylphosphinomethyl)-4-(trimethylsilyl)benzene; 1,2-bis(2-phosphinomethyl-1,3,5-trimethyl-6,9,10-trioxatricyclo-{3.3.1.1[3.7]}decyl)-4,5-diphenyl benzene; 1,2-bis(2-phosphinomethyl-1,3,5-trimethyl-6,9,10-trioxatricyclo-{3.3.1.1[3.7]}decyl)-4-phenyl benzene; 1,2-bis(2-phosphinomethyl-1,3,5-trimethyl-6,9,10-trioxatricyclo-{3.3.1.1[3.7]}decyl)-4,5-bis-(trimethylsilyl)benzene; 1,2-bis(2-phosphinomethyl-1,3,5-trimethyl-6,9,10-trioxatricyclo-{3.3.1.1[3.7]}decyl)-4-(trimethylsilyl)benzene; 1-(2-phosphinomethyl-1,3,5-trimethyl-6,9,10-trioxatricyclo-{3.3.1.1[3.7]}decyl)-2-(di-t-butylphosphinomethyl)-4,5-diphenyl benzene; 1-(2-phosphinomethyl-1,3,5-trimethyl-6,9,10-trioxatricyclo-{3.3.1.1[3.7]}decyl)-2-(di-t-butylphosphinomethyl)-4-phenyl benzene; 1-(2-phosphinomethyl-1,3,5-trimethyl-6,9,10-trioxatricyclo-{3.3.1.1[3.7]}decyl)-2-(di-t-butylphosphinomethyl)-4,5-bis-(trimethylsilyl)benzene; 1-(2-phosphinomethyl-1,3,5-trimethyl-6,9,10-trioxatricyclo-{3.3.1.1[3.7]}decyl)-2-(di-t-butylphosphinomethyl)-4-(trimethylsilyl)benzene; 1-(2-phosphinomethyl-1,3,5-trimethyl-6,9,10-trioxatricyclo-{3.3.1.1[3.7]}decyl)-2-(diadamantylphosphinomethyl)-4,5-diphenyl benzene; 1-(2-phosphinomethyl-1,3,5-trimethyl-6,9,10-trioxatricyclo-{3.3.1.1[3.7]}decyl)-2-(diadamantylphosphinomethyl)-4-phenyl benzene; 1-(2-phosphinomethyl-1,3,5-trimethyl-6,9,10-trioxatricyclo-{3.3.1.1[3.7]}decyl)-2-(diadamantylphosphinomethyl)-4,5-bis-(trimethylsilyl)benzene; 1-(2-phosphinomethyl-1,3,5-trimethyl-6,9,10-trioxatricyclo-{3.3.1.1[3.7]}decyl)-2-(diadamantylphosphinomethyl)-4-(trimethylsilyl)benzene; 1,2-bis-perfluoro(2-phosphinomethyl-1,3,5,7-tetramethyl-6,9,10-trioxatricyclo{3.3.1.1[3.7]}-decyl)-4,5-diphenyl benzene; 1,2-bis-perfluoro(2-phosphinomethyl-1,3,5,7-tetramethyl-6,9,10-trioxatricyclo{3.3.1.1[3.7]}decyl)-4-phenyl benzene; 1,2-bis-perfluoro(2-phosphinomethyl-1,3,5,7-tetramethyl-6,9,10-trioxatricyclo{3.3.1.1[3.7]}-decyl)-4,5-bis-(trimethylsilyl)benzene; 1,2-bis-perfluoro(2-phosphinomethyl-1,3,5,7-tetramethyl-6,9,10-trioxatricyclo{3.3.1.1[3.7]}decyl)-4-(trimethylsilyl)benzene; 1,2-bis-(2-phosphinomethyl-1,3,5,7-tetra(trifluoro-methyl)-6,9,10-trioxatricyclo{3.3.1.1[3.7]}decyl)-4,5-diphenyl benzene; 1,2-bis-(2-phosphinomethyl-1,3,5,7-tetra(trifluoro-methyl)-6,9,10-trioxatricyclo{3.3.1.1[3.7]}decyl)-4-phenyl benzene; 1,2-bis-(2-phosphinomethyl-1,3,5,7-tetra(trifluoro-methyl)-6,9,10-trioxatricyclo{3.3.1.1[3.7]}decyl)-4,5-bis-(trimethylsilyl)benzene; 1,2-bis-(2-phosphinomethyl-1,3,5,7-tetra(trifluoro-methyl)-6,9,10-trioxatricyclo{3.3.1.1[3.7]}decyl)-4-(trimethylsilyl)benzene; 1,2-bis(di-t-butylphosphinomethyl)-4,5-di-(2'-phenylprop-2'-yl)benzene; 1,2-bis(di-t-butylphosphinomethyl)-4-(2'-phenylprop-2'-yl)benzene; 1,2-bis(di-t-butylphosphinomethyl)-4,5-di-t-butyl benzene; 1,2-bis(di-t-butylphosphinomethyl)-4-t-butylbenzene; 1,2-bis(2-phosphinomethyl-1,3,5,7-tetramethyl-6,9,10-trioxa-adamantyl)-4,5-di-(2'-phenylprop-2'-yl)benzene; 1,2-bis(2-phosphinomethyl-1,3,5,7-tetramethyl-6,9,10-trioxa-adamantyl)-4-(2'-phenylprop-2'-yl)benzene; 1,2-bis(2-phosphinomethyl-1,3,5,7-tetramethyl-6,9,10-trioxa-adamantyl)-4,5-(di-t-butyl)benzene; 1,2-bis(2-phosphinomethyl-1,3,5,7-tetramethyl-6,9,10-trioxa-adamantyl)-4-t-butylbenzene; 1,2-bis(di-adamantylphosphinomethyl)-4,5-di-(2'-phenylprop-2'-yl)benzene; 1,2-bis(di-adamantylphosphinomethyl)-4-(2'-phenylprop-2'-yl)benzene; 1,2-bis(di-adamantylphosphinomethyl)-4,5-(di-t-butyl)benzene; 1,2-bis(di-adamantylphosphinomethyl)-4-t-butyl benzene; 1-(P,P adamantyl, t-butyl phosphinomethyl)-2-(di-t-butylphosphinomethyl)-4,5-di-(2'-phenylprop-2'-yl)benzene; 1-(P,P adamantyl, t-butyl phosphinomethyl)-2-(di-t-butylphosphinomethyl)-4-(2'-phenylprop-2'-yl)benzene; 1-(P,P adamantyl, t-butyl phosphinomethyl)-2-(di-t-butylphosphinomethyl)-4,5-(di-t-butyl)benzene; 1-(P,P adamantyl, t-butyl phosphinomethyl)-2-(di-t-butylphosphinomethyl)-4-t-butylbenzene; 1-(2-phosphinomethyl-1,3,5,7-tetramethyl-6,9,10-trioxa-adamantyl)-2-(di-t-butylphosphinomethyl)4,5-di-(2'-phenylprop-2'-yl)benzene; 1-(2-phosphinomethyl-1,3,5,7-tetramethyl-6,9,10-trioxa-adamantyl)-2-(di-t-butylphosphinomethyl)-4-(2'-phenylprop-2'-yl)benzene; 1-(2-phosphinomethyl-1,3,5,7-tetramethyl-6,9,10-trioxa-adamantyl)-2-(di-t-butylphosphinomethyl)4,5-(di-t-butyl)benzene; 1-(2-phosphinomethyl-1,3,5,7-tetramethyl-6,9,10-trioxa-adamantyl)-2-(di-t-butylphosphinomethyl)-4-t-butyl benzene; 1-(2-phosphinomethyl-1,3,5,7-tetramethyl-6,9,10-trioxa-adamantyl)-2-(diadamantylphosphinomethyl)-4,5-di-(2'-phenylprop-2'-yl)benzene; 1-(2-phosphinomethyl-1,3,5,7-tetramethyl-6,9,10-trioxa-adamantyl)-2-(diadamantylphosphinomethyl)-4-(2'-phenylprop-2'-yl) benzene; 1-(2-phosphinomethyl-1,3,5,7-tetramethyl-6,9,10-trioxa-adamantyl)-2-(diadamantylphosphinomethyl)-4,5-(di-t-butyl)benzene; 1-(2-phosphinomethyl-1,3,5,7-tetramethyl-6,9,10-trioxa-adamantyl)-2-(diadamantylphosphinomethyl)-4-t-butyl benzene; 1-(di-t-butylphosphinomethyl)-2-(diadamantylphosphinomethyl)-4,5-di-(2'-phenylprop-2'-yl)benzene; 1-(di-t-butylphosphinomethyl)-2-(diadamantylphosphinomethyl)-4-(2'-phenylprop-2'-yl)benzene; 1-(di-t-butylphosphinomethyl)-2-(diadamantylphosphinomethyl)-4,5-(di-t-butyl)benzene; 1-(di-t-butylphosphinomethyl)-2-(diadamantylphosphinomethyl)-4-t-butyl benzene; 1,2-bis(2-phosphinomethyl-1,3,5-trimethyl-6,9,10-trioxatricyclo-{3.3.1.1[3.7]}decyl)-4,5-di-(2'-phenylprop-2'-yl)benzene; 1,2-bis(2-phosphinomethyl-1,3,5-trimethyl-6,9,10-trioxatricyclo-{3.3.1.1[3.7]}decyl)-4-(2'-phenylprop-2'-yl)benzene; 1,2-bis(2-phosphinomethyl-1,3,5-trimethyl-6,9,10-trioxatricyclo-{3.3.1.1[3.7]}decyl)-4,5-(di-t-butyl)benzene; 1,2-bis(2-phosphinomethyl-1,3,5-trimethyl-6,9,10-trioxatricyclo-{3.3.1.1[3.7]}decyl)-4-t-butyl benzene; 1-(2-phosphinomethyl-1,3,5-trimethyl-6,9,10-trioxatricyclo-{3.3.1.1[3.7]}decyl)-2-(di-t-butylphosphinomethyl)-4,5-di-(2'-phenylprop-2'-yl)benzene; 1-(2-phosphinomethyl-1,3,5- trimethyl-6,9,10-trioxatricyclo-{3.3.1.1[3.7]}decyl)-2-(di-t-butylphosphinomethyl)-4-(2'-phenylprop-2'-yl)benzene; 1-(2-phosphinomethyl-1,3,5-trimethyl-6,9,10-trioxatricyclo-{3.3.1.1[3.7]}decyl)-2-(di-t-butylphosphinomethyl)-4,5-(di-t-butyl)benzene; 1-(2-phosphinomethyl-1,3,5-trimethyl-6,9,10-trioxatricyclo-{3.3.1.1[3.7]}decyl)-2-(di-t-butylphosphinomethyl)-4-t-butyl benzene; 1-(2-phosphinomethyl-1,3,5-trimethyl-6,9,10-trioxatricyclo-{3.3.1.1[3.7]}decyl)-2-(diadamantylphosphinomethyl)-4,5-di-(2'-phenylprop-2'-yl)benzene; 1-(2-phosphinomethyl-1,3,5-trimethyl-6,9,10-trioxatricyclo-{3.3.1.1[3.7]}decyl)-2-(diadamantylphosphinomethyl)-4-(2'-phenylprop-2'-yl)benzene; 1-(2-phosphinomethyl-1,3,5-trimethyl-6,9,10-trioxatricyclo-{3.3.1.1[3.7]}decyl)-2-(diadamantylphosphinomethyl)-4,5-(di-t-butyl)benzene; 1-(2-phosphinomethyl-1,3,5-trimethyl-6,9,10-trioxatricyclo-{3.3.1.1[3.7]}decyl)-2-(diadamantylphosphinomethyl)-4-t-butyl benzene; 1,2-bis-perfluoro(2-phosphinomethyl-1,3,5,7-tetramethyl-6,9,10-trioxatricyclo{3.3.1.1[3.7]}-decyl)-4,5-di-(2'-phenylprop-2'-yl)benzene; 1,2-bis-perfluoro(2-phosphinomethyl-1,3,5,7-tetramethyl-6,9,10-trioxatricyclo{3.3.1.1[3.7]}decyl)-4-(2'-phenylprop-2'-yl)benzene; 1,2-bis-perfluoro(2-phosphinomethyl-1,3,5,7-tetramethyl-6,9,10-trioxatricyclo{3.3.1.1[3.7]}-decyl)-4,5-(di-t-butyl)benzene; 1,2-bis-perfluoro(2-phosphinomethyl-1,3,5,7-tetramethyl-6,9,10-trioxatricyclo{3.3.1.1[3.7]}decyl)-4-t-butyl benzene; 1,2-bis-(2-phosphinomethyl-1,3,5,7-tetra(trifluoro-methyl)-6,9,10-trioxatricyclo{3.3.1.1[3.7]}decyl)-4,5-di-(2'-phenylprop-2'-yl)benzene; 1,2-bis-(2-phosphinomethyl-1,3,5,7-tetra(trifluoro-methyl)-6,9,10-trioxatricyclo{3.3.1.1[3.7]}decyl)-4-(2'-phenylprop-2'-yl)benzene; 1,2-bis-(2-phosphinomethyl-1,3,5,7-tetra(trifluoro-methyl)-6,9,10-trioxatricyclo{3.3.1.1[3.7]}decyl)-4,5-(di-t-butyl)benzene; 1,2-bis-(2-phosphinomethyl-1,3,5,7-tetra(trifluoro-methyl)-6,9,10-trioxatricyclo{3.3.1.1[3.7]}decyl)-4-t-butyl benzene.

Examples of suitable bidentate ferrocene type ligands are 1,2-bis(di-t-butylphosphinomethyl)-4,5-diphenyl ferrocene; 1,2-bis(di-t-butylphosphinomethyl)-4- (or 1')phenylferrocene; 1,2-bis(di-t-butylphosphinomethyl)-4,5- bis-(trimethylsilyl)ferrocene; 1,2-bis(di-t-butylphosphinomethyl)-4- (or 1')(trimethylsilyl)ferrocene; 1,2-bis(2-phosphinomethyl-1,3,5,7-tetramethyl-6,9,10-trioxa-adamantyl)-4,5-diphenylferrocene; 1,2-bis(2-phosphinomethyl-1,3,5,7-tetramethyl-6,9,10-trioxa-adamantyl) 4- (or 1')phenylferrocene; 1,2-bis(2-phosphinomethyl-1,3,5,7-tetramethyl-6,9,10-trioxa-adamantyl)-4,5-bis-(trimethylsilyl)ferrocene; 1,2-bis(2-phosphinomethyl-1,3,5,7-tetramethyl-6,9,10-trioxa-adamantyl) 4- (or 1')(trimethylsilyl)ferrocene; 1,2-bis(di-adamantylphosphinomethyl)-4,5 diphenylferrocene; 1,2-bis(di-adamantylphosphinomethyl)-4- (or 1')phenyl ferrocene; 1,2-bis(di-adamantylphosphinomethyl)-4,5 bis-(trimethylsilyl)ferrocene; 1,2-bis(di-adamantylphosphinomethyl)-4- (or 1')(trimethylsilyl)ferrocene; 1-(P,P adamantyl, t-butyl phosphinomethyl)-2-(di-t-butylphosphinomethyl)-4,5-diphenyl-ferrocene; 1-(P,P adamantyl, t-butyl phosphinomethyl)-2-(di-t-butylphosphinomethyl)-4- (or 1')phenylferrocene; 1-(P,P adamantyl, t-butyl phosphinomethyl)-2-(di-t-butylphosphinomethyl)-4,5- bis-(trimethylsilyl)ferrocene; 1-(P,P adamantyl, t-butyl phosphinomethyl)-2-(di-t-butylphosphinomethyl)-4- (or 1')(trimethylsilyl)ferrocene; 1-(2-phosphinomethyl-1,3,5,7-tetramethyl-6,9,10-trioxa-adamantyl)-2-(di-t-butylphosphinomethyl)4,5-diphenylferrocene; 1-(2-phosphinomethyl-1,3,5,7-tetramethyl-6,9,10-trioxa-adamantyl)-2-(di-t-butylphosphinomethyl)-4- (or 1')phenyl ferrocene; 1-(2-phosphinomethyl-1,3,5,7-tetram-ethyl-6,9,10-trioxa-adamantyl)-2-(di-t-butylphosphinom-ethyl)4,5-bis-(trimethylsilyl)ferrocene; 1-(2-phosphinom-ethyl-1,3,5,7-tetramethyl-6,9,10-trioxa-adamantyl)-2-(di-t-butylphosphinomethyl)-4- (or 1')(trimethylsilyl)ferrocene; 1-(2-phosphinomethyl-1,3,5,7-tetramethyl-6,9,10-trioxa-adamantyl)-2-(diadamantylphosphinomethyl)-4,5-diphenyl ferrocene; 1-(2-phosphinomethyl-1,3,5,7-tetramethyl-6,9,10-trioxa-adamantyl)-2-(diadamantylphosphinomethyl)-4- (or 1')phenyl ferrocene; 1-(2-phosphinomethyl-1,3,5,7-tetramethyl-6,9,10-trioxa-adamantyl)-2-(diadamantylphosphinomethyl)-4,5-bis-(trimethylsilyl)ferrocene; 1-(2-phosphinomethyl-1,3,5,7-tetramethyl-6,9,10-trioxa-adamantyl)-2-(diadamantylphosphinomethyl)-4- (or 1')(trimethylsilyl)ferrocene; 1-(di-t-butylphosphinomethyl)-2-(diadamantylphosphinomethyl)-4,5-diphenyl ferrocene; 1-(di-t-butylphosphinomethyl)-2-(diadamantylphosphinomethyl)-4- (or 1')phenyl ferrocene; 1-(di-t-butylphosphinomethyl)-2-(diadamantylphosphinomethyl)-4,5-bis-(trimethylsilyl)ferrocene; 1-(di-t-butylphosphinomethyl)-2-(diadamantylphosphinomethyl)-4- (or 1')(trimethylsilyl)ferrocene; 1,2-bis(2-phosphinomethyl-1,3,5-trimethyl-6,9,10-trioxatricyclo-{3.3.1.1[3.7]}decyl)-4,5-diphenyl ferrocene; 1,2-bis(2-phosphinomethyl-1,3,5-trimethyl-6,9,10-trioxatricyclo-{3.3.1.1[3.7]}decyl)-4- (or 1')phenyl ferrocene; 1,2-bis-(2-phosphinomethyl-1,3,5-trimethyl-6,9,10-trioxatricyclo-{3.3.1.1[3.7]}decyl)-4,5-bis-(trimethylsilyl)ferrocene; 1,2-bis(2-phosphinomethyl-1,3,5-trimethyl-6,9,10-trioxatricyclo-{3.3.1.1[3.7]}decyl)-4- (or 1')(trimethylsilyl)ferrocene; 1-(2-phosphinomethyl-1,3,5-trimethyl-6,9,10-trioxatricyclo-{3.3.1.1[3.7]}decyl)-2-(di-t-butylphosphinomethyl)-4,5-diphenyl ferrocene; 1-(2-phosphinomethyl-1,3,5-trimethyl-6,9,10-trioxatricyclo-{3.3.1.1[3.7]}decyl)-2-(di-t-butylphosphinomethyl)-4- (or 1')phenyl ferrocene; 1-(2-phosphinomethyl-1,3,5-trimethyl-6,9,10-trioxatricyclo-{3.3.1.1[3.7]}decyl)-2-(di-t-butylphosphinomethyl)-4,5-bis-(trimethylsilyl)ferrocene; 1-(2-phosphinomethyl-1,3,5-trimethyl-6,9,10-trioxatricyclo-{3.3.1.1[3.7]}decyl)-2-(di-t-butylphosphinomethyl)-4- (or 1')(trimethylsilyl)ferrocene; 1-(2-phosphinomethyl-1,3,5-trimethyl-6,9,10-trioxatricyclo-{3.3.1.1[3.7]}decyl)-2-(diadamantylphosphinomethyl)-4,5-diphenyl ferrocene; 1-(2-phosphinomethyl-1,3,5-trimethyl-6,9,10-trioxatricyclo-{3.3.1.1[3.7]}decyl)-2-(diadamantylphosphinomethyl)-4- (or 1')phenyl ferrocene; 1-(2-phosphinomethyl-1,3,5-trimethyl-6,9,10-trioxatricyclo-{3.3.1.1[3.7]}decyl)-2-(diadamantylphosphinomethyl)-4,5-bis-(trimethylsilyl)ferrocene; 1-(2-phosphinomethyl-1,3,5-trimethyl-6,9,10-trioxatricyclo-{3.3.1.1[3.7]}decyl)-2-(diadamantylphosphinomethyl)-4- (or 1')(trimethylsilyl)ferrocene; 1,2-bis-perfluoro(2-phosphinomethyl-1,3,5,7-tetramethyl-6,9,10-trioxatricyclo{3.3.1.1[3.7]}-decyl)-4,5-diphenyl ferrocene; 1,2-bis-perfluoro(2-phosphinomethyl-1,3,5,7-tetramethyl-6,9,10-trioxatricyclo{3.3.1.1[3.7]}decyl)-4- (or 1')phenyl ferrocene; 1,2-bis-perfluoro(2-phosphinomethyl-1,3,5,7-tetramethyl-6,9,10-trioxatricyclo{3.3.1.1[3.7]}-decyl)-4,5-bis-(trimethylsilyl)ferrocene; 1,2-bis-perfluoro(2-phosphinomethyl-1,3,5,7-tetramethyl-6,9,10-trioxatricyclo{3.3.1.1[3.7]}decyl)-4- (or 1')(trimethylsilyl)ferrocene; 1,2-bis-(2-phosphinomethyl-1,3,5,7-tetra(trifluoro-methyl)-6,9,10-trioxatricyclo{3.3.1.1[3.7]}decyl)-4,5-diphenyl ferrocene; 1,2-bis-(2-phosphinomethyl-1,3,5,7-tetra(trifluoro-methyl)-6,9,10-trioxatricyclo{3.3.1.1[3.7]}decyl)-4- (or 1')phenyl ferrocene; 1,2-bis-(2-phosphinomethyl-1,3,5,7-tetra(trifluoro-methyl)-6,9,10-trioxatricyclo{3.3.1.1[3.7]}decyl)-4,5-bis-(trimethylsilyl) ferrocene; 1,2-bis-(2-phosphinomethyl-1,3,5,7-tetra(trifluoro-methyl)-6,9,10-trioxatricyclo{3.3.1.1[3.7]}decyl)-4- (or 1')(trimethylsilyl)ferrocene; 1,2-bis(dit-butylphosphinomethyl)-4,5-di-(2'-phenylprop-2'-yl)ferrocene; 1,2-bis(di-t-butylphosphinomethyl)-4- (or 1')(2'-phenylprop-2'-yl)ferrocene; 1,2-bis(di-t-butylphosphinomethyl)-4,5-di-t-butyl ferrocene; 1,2-bis(di-t-butylphosphinomethyl)-4- (or 1')t-butylferrocene; 1,2-bis (2-phosphinomethyl-1,3,5,7-tetramethyl-6,9,10-trioxa-adamantyl)-4,5-di-(2'-phenylprop-2'-yl)ferrocene; 1,2-bis(2-phosphinomethyl-1,3,5,7-tetramethyl-6,9,10-trioxa-adamantyl)-4- (or 1')(2'-phenylprop-2'-yl)ferrocene; 1,2-bis (2-phosphinomethyl-1,3,5,7-tetramethyl-6,9,10-trioxa-adamantyl)-4,5-(di-t-butyl)ferrocene; 1,2-bis(2-phosphinomethyl-1,3,5,7-tetramethyl-6,9,10-trioxa-adamantyl)-4- (or 1')t-butylferrocene; 1,2-bis(di-adamantylphosphinomethyl)-4,5-di-(2'-phenylprop-2'-yl) ferrocene; 1,2-bis(di-adamantylphosphinomethyl)-4- (or 1') (2'-phenylprop-2'-yl)ferrocene; 1,2-bis(di-adamantylphosphinomethyl)-4,5-(di-t-butyl)ferrocene; 1,2-bis(di-adamantylphosphinomethyl)-4- (or 1')t-butyl ferrocene; 1-(P,P adamantyl, t-butyl phosphinomethyl)-2-(di-t-butylphosphinomethyl)-4,5-di-(2'-phenylprop-2'-yl) ferrocene; 1-(P,P adamantyl, t-butyl phosphinomethyl)-2-(di-t-butylphosphinomethyl)-4- (or 1')(2'-phenylprop-2'-yl) ferrocene; 1-(P,P adamantyl, t-butyl phosphinomethyl)-2-(di-t-butylphosphinomethyl)-4,5-(di-t-butyl)ferrocene; 1-(P,P adamantyl, t-butyl phosphinomethyl)-2-(di-t-butylphosphinomethyl)-4- (or 1')t-butylferrocene; 1-(2-phosphinomethyl-1,3,5,7-tetramethyl-6,9,10-trioxa-adamantyl)-2-(di-t-butylphosphinomethyl)4,5-di-(2'-phenylprop-2'-yl) ferrocene; 1-(2-phosphinomethyl-1,3,5,7-tetramethyl-6,9,10-trioxa-adamantyl)-2-(di-t-butylphosphinomethyl)-4- (or 1')(2'-phenylprop-2'-yl)ferrocene; 1-(2-phosphinomethyl-1,3,5,7-tetramethyl-6,9,10-trioxa-adamantyl)-2-(di-t-butylphosphinomethyl)4,5-(di-t-butyl)ferrocene; 1-(2-phosphinomethyl-1,3,5,7-tetramethyl-6,9,10-trioxa-adamantyl)-2-(di-t-butylphosphinomethyl)-4- (or 1')t-butyl ferrocene; 1-(2-phosphinomethyl-1,3,5,7-tetramethyl-6,9,10-trioxa-adamantyl)-2-(diadamantylphosphinomethyl)-4,5-di-(2'-phenylprop-2'-yl)ferrocene; 1-(2-phosphinomethyl-1,3,5,7-tetramethyl-6,9,10-trioxa-adamantyl)-2-(diadamantylphosphinomethyl)-4- (or 1')(2'-phenylprop-2'-yl)ferrocene; 1-(2-phosphinomethyl-1,3,5,7-tetramethyl-6,9,10-trioxa-adamantyl)-2-(diadamantylphosphinomethyl)-4,5-(di-t-butyl)ferrocene; 1-(2-phosphinomethyl-1,3,5,7-tetramethyl-6,9,10-trioxa-adamantyl)-2-(diadamantylphosphinomethyl)-4- (or 1')t-butyl ferrocene; 1-(di-t-butylphosphinomethyl)-2-(diadamantylphosphinomethyl)-4,5-di-(2'-phenylprop-2'-yl)ferrocene; 1-(di-t-butylphosphinomethyl)-2-(diadamantylphosphinomethyl)-4- (or 1')(2'-phenylprop-2'-yl)ferrocene; 1-(di-t-butylphosphinomethyl)-2-(diadamantylphosphinomethyl)-4,5-(di-t-butyl)ferrocene; 1-(di-t-butylphosphinomethyl)-2-(diadamantylphosphinomethyl)-4- (or 1')t-butyl ferrocene; 1,2-bis(2-phosphinomethyl-1,3,5-trimethyl-6,9,10-trioxatricyclo-{3.3.1.1[3.7]}decyl)-4,5-di-(2'-phenylprop-2'-yl)ferrocene; 1,2-bis(2-phosphinomethyl-1,3,5-trimethyl-6,9,10-trioxatricyclo-{3.3.1.1[3.7]}decyl)-4- (or 1')(2'-phenylprop-2'-yl)ferrocene; 1,2-bis(2-phosphinomethyl-1,3,5-trimethyl-6,9,10-trioxatricyclo-{3.3.1.1[3.7]}decyl)-4,5-(di-t-butyl) ferrocene; 1,2-bis(2-phosphinomethyl-1,3,5-trimethyl-6,9,10-trioxatricyclo-{3.3.1.1[3.7]}decyl)-4- (or 1')t-butyl ferrocene; 1-(2-phosphinomethyl-1,3,5-trimethyl-6,9,10-trioxatricyclo-{3.3.1.1[3.7]}decyl)-2-(di-t-butylphosphinomethyl)-4,5-di-(2'-phenylprop-2'-yl)ferrocene; 1-(2-phosphinomethyl-1,3,5-trimethyl-6,9,10-trioxatricyclo-{3.3.1.1 [3.7]}decyl)-2-(di-t-butylphosphinomethyl)-4- (or 1')(2'-phenylprop-2'-yl)ferrocene; 1-(2-phosphinomethyl-1,3,5-trimethyl-6,9,10-trioxatricyclo-{3.3.1.1[3.7]}decyl)-2-(di-t-butylphosphinomethyl)-4,5-(di-t-butyl)ferrocene; 1-(2-phosphinomethyl-1,3,5-trimethyl-6,9,10-trioxatricyclo-{3.3.1.1[3.7]}decyl)-2-(di-t-butylphosphinomethyl)-4- (or 1')t-butyl ferrocene; 1-(2-phosphinomethyl-1,3,5-trimethyl-6,9,10-trioxatricyclo-{3.3.1.1[3.7]}decyl)-2-(diadamantylphosphinomethyl)-4,5-di-(2'-phenylprop-2'-yl)ferrocene; 1-(2-phosphinomethyl-1,3,5-trimethyl-6,9,10-trioxatricyclo-{3.3.1.1[3.7]}decyl)-2-(diadamantylphosphinomethyl)-4- (or 1')(2'-phenylprop-2'-yl)ferrocene; 1-(2-phosphinomethyl-1,3,5-trimethyl-6,9,10-trioxatricyclo-{3.3.1.1 [3.7]}decyl)-2-(diadamantylphosphinomethyl)-4,5-(di-t-butyl)ferrocene; 1-(2-phosphinomethyl-1,3,5-trimethyl-6,9,10-trioxatricyclo-{3.3.1.1[3.7]}decyl)-2-(diadamantylphosphinomethyl)-4- (or 1')t-butyl ferrocene; 1,2-bis-perfluoro(2-phosphinomethyl-1,3,5,7-tetramethyl-6,9,10-trioxatricyclo{3.3.1.1[3.7]}-decyl)-4,5-di-(2'-phenylprop-2'-yl)ferrocene; 1,2-bis-perfluoro(2-phosphinomethyl-1,3,5,7-tetramethyl-6,9,10-trioxatricyclo{3.3.1.1[3.7]}decyl)-4- (or 1')(2'-phenylprop-2'-yl)ferrocene; 1,2-bis-perfluoro(2-phosphinomethyl-1,3,5,7-tetramethyl-6,9,10-trioxatricyclo{3.3.1.1[3.7]}-decyl)-4,5-(di-t-butyl)ferrocene; 1,2-bis-perfluoro(2-phosphinomethyl-1,3,5,7-tetramethyl-6,9,10-trioxatricyclo{3.3.1.1[3.7]}decyl)-4- (or 1')t-butyl ferrocene; 1,2-bis-(2-phosphinomethyl-1,3,5,7-tetra(trifluoro-methyl)-6,9,10-trioxatricyclo{3.3.1.1[3.7]}decyl)-4,5-di-(2'-phenylprop-2'-yl)ferrocene; 1,2-bis-(2-phosphinomethyl-1,3,5,7-tetra(trifluoro-methyl)-6,9,10-trioxatricyclo{3.3.1.1[3.7]}decyl)-4- (or 1')(2'-phenylprop-2'-yl)ferrocene; 1,2-bis-(2-phosphinomethyl-1,3,5,7-tetra(trifluoro-methyl)-6,9,10-trioxatricyclo{3.3.1.1[3.7]}decyl)-4,5-(di-t-butyl)ferrocene; 1,2-bis-(2-phosphinomethyl-1,3,5,7-tetra(trifluoro-methyl)-6,9,10-trioxatricyclo{3.3.1.1[3.7]}decyl)-4- (or 1')t-butyl ferrocene.

Selected structures of ligands of formula V of the invention include:—

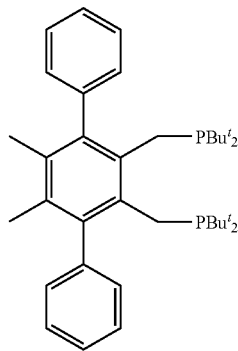

1,2-bis(di-tert-butylphosphinomethyl)-3,6-diphenyl-4,5-dimethyl benzene

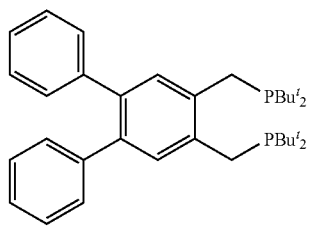

65

1,2bis(di-tert-butyl(phosphinomethyl)-4,5-diphenyl benzene

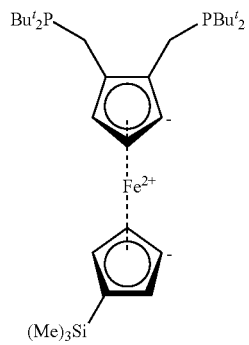

1,2-bis(di-tert-butylphospinomethyl)-1'-trimethylsilyl ferrocene

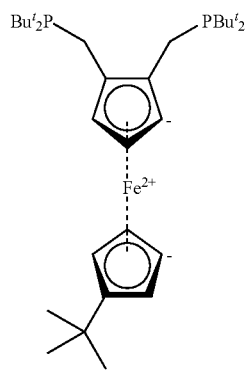

1,2-bis(di-tert-butylphospinomethyl)-1'-tert-butyl ferrocene

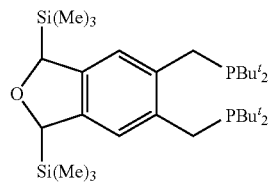

5,6-bis(di-tert-butylphosphinomethyl)-1,3-bis-trimethylsilyl-1,3-dihydroisobenzofuran

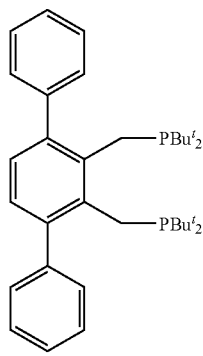

66

1,2-bis(di-tert-butylphosphinomethyl)-3,6-diphenyl benzene

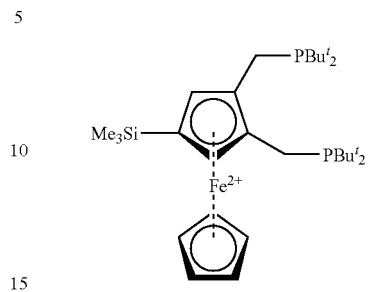

1,2-bis(di-tert-butylphospinomethyl)-4-trimethylsilyl ferrocene

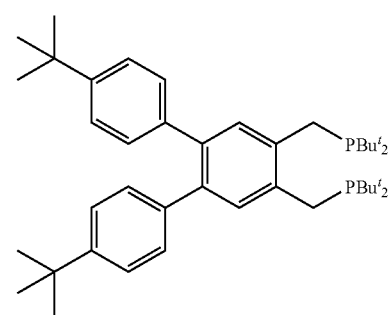

1,2 bis(di-tert-butyl(phosphinomethyl))-4,5-di(4'-tert butyl phenyl)benzene

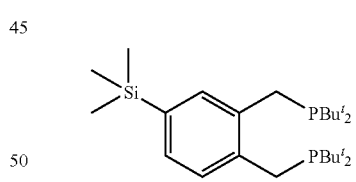

1,2-bis(di-tert-butyl(phosphinomethyl))-4-trimethylsilyl benzene

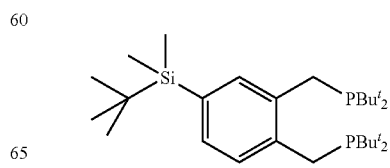

| 67 | 68 |
|---|---|
| 1,2-bis(di-tert-butyl(phosphinomethyl))-4-(tert-butyldimethylsilyl)benzene | 1,2-bis(di-tert-butyl(phosphinomethyl))-4-(tri-tert-butylsilyl)benzene |

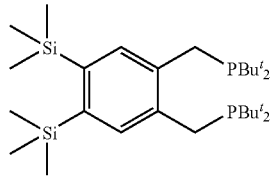

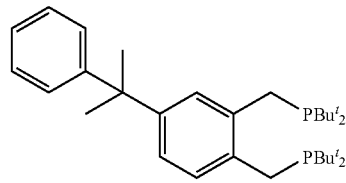

1,2-bis(di-tert-butyl(phosphinomethyl))-4,5-bis(trimethylsilyl)benzene 1,2-bis(di-tert-butyl(phosphinomethyl))-4-(2'-phenylprop-2'-yl)benzene

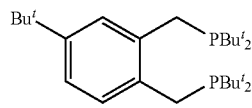

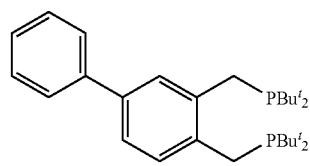

1,2-bis(di-tert-butyl(phosphinomethyl))-4-tert-butyl benzene 1,2-bis(di-tert-butyl(phosphinomethyl))-4-phenyl benzene

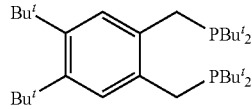

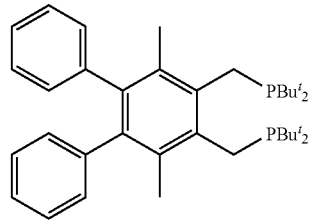

1,2-bis(di-tert-butyl(phosphinomethyl))-4,5-di-tert-butyl benzene 1,2-bis(di-tert-butyl(phosphinomethyl))-3,6-dimethyl-4,5-diphenyl benzene

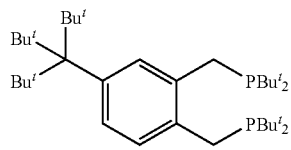

1,2-bis(di-tert-butyl(phosphinomethyl))-4-(tri-tert-butylmethyl)benzene

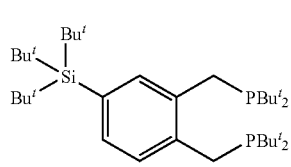

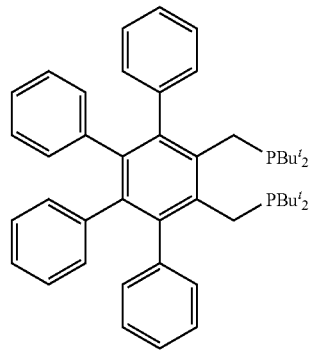

1,2-bis(di-tert-butyl(phosphinomethyl))-3,4,5,6-tetraphenyl benzene

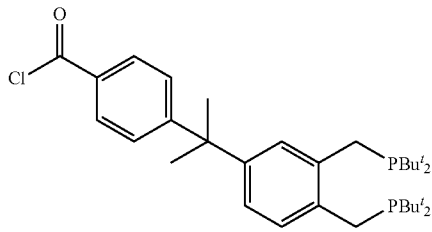

4-(1-{3,4-Bis-[(di-tert-butyl-phosphanyl)-methyl]-phenyl}-1-methyl-ethyl)-benzoyl chloride

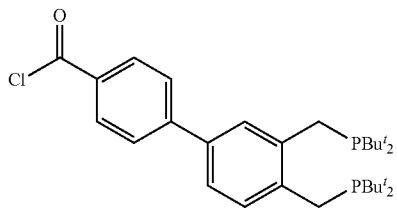

1,2-bis(di-tert-butyl(phosphinomethyl))-4-(4'-chlorocarbonyl-phenyl)benzene

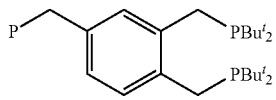

1,2-bis(di-tert-butyl(phosphinomethyl))-4-(phosphinomethyl)benzene

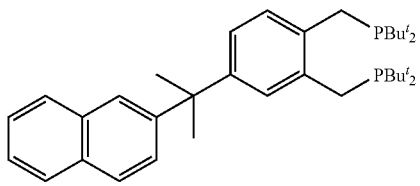

1,2-bis(di-tert-butyl(phosphinomethyl))-4-(2'-naphthylprop-2'-yl)benzene

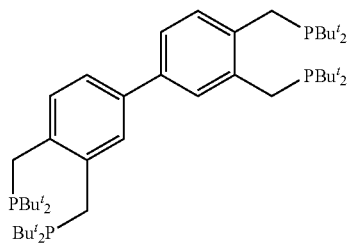

1,2-bis(di-tert-butyl(phosphinomethyl))-4-(3',4'-bis(di-tert-butyl(phosphinomethyl))phenyl)benzene

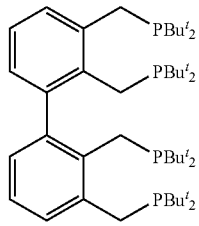

1,2-bis(di-tert-butyl(phosphinomethyl))-3-(2',3'-bis(di-tert-butyl(phosphinomethyl))phenyl)benzene

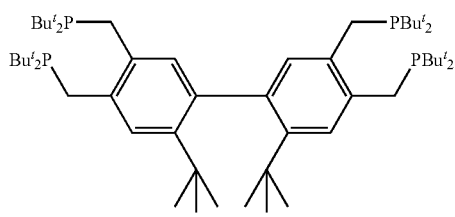

1,2-bis(di-tert-butyl(phosphinomethyl))-4-tertbutyl-5-(2'-tertbutyl-4',5'-bis(di-tert-butyl(phosphinomethyl))phenyl)benzene In the above example, structures of ligands of general formula (V), one or more of the $X^1$-$X^4$ tertiary carbon bearing groups, t-butyl, attached to the $Q^1$ and/or $Q^2$ group, phosphorous, may be replaced by a suitable alternative. Preferred alternatives are adamantyl, 1,3 dimethyl adamantyl, congressyl, norbornyl or 1-norbondienyl, or $X^1$ and $X^2$ together and/or $X^3$ and $X^4$ together form together with the phosphorous a 2-phospha-tricyclo[3.3.1.1{3,7}decyl group such as 2-phospha-1,3,5,7-tetramethyl-6,9,10-trioxadamantyl or 2-phospha-1,3,5-trimethyl-6,9,10-trioxadamantyl.

In most formula (I)-(V) embodiments, it is preferred that the $X^1$-$X^4$ groups or the combined $X^1/X^2$ and $X^3/X^4$ groups or equivalent formula (I) groups are the same but it may also be advantageous to use different groups to produce asymmetry around the active site in these selected ligands and generally in this invention.

Preferably, $Q^2$ is phosphorous and preferably, $Q^1$ is independently, phosphorous.

Preferably, the bidentate ligand is a bidentate phosphine, arsine or stibine ligand, preferably, a phosphine ligand.

The palladium complexes of the present invention are useful as pre-catalysts in the carbonylation of ethylenically unsaturated compounds. Suitable ethylenically unsaturated compounds for the non-ethylenically specific aspects of the invention are ethylenically unsaturated compounds having from 2 to 50 carbon atoms per molecule, or mixtures thereof. Suitable ethylenically unsaturated compounds may have one or more isolated or conjugated unsaturated bonds per molecule. Preferred are compounds having from 2 to 20 carbon atoms, or mixtures thereof, yet more preferred are compounds having at most 18 carbon atoms, yet more at most 16 carbon atoms, again more preferred compounds have at most 10 carbon atoms. The ethylenically unsaturated compound may further comprise functional groups or heteroatoms, such as nitrogen, sulphur or oxide. Examples include carboxylic acids, esters or nitriles as functional groups. In a preferred embodiment, the ethylenically unsaturated compound is an olefin or a mixture of olefins. Such olefins can be converted by reaction with carbon monoxide and a co-reactant with a high regioselectivity, where appropriate, towards the linear carbonylation product. Suitable ethylenically unsaturated compounds include acetylene, methyl acetylene, propyl acetylene, butadiene, ethylene, propylene, butylene, isobutylene, pentene, pentene nitriles, alkyl pentenoates such as methyl 3-pentenoates, pentene acids (such as 2-and 3-pentenoic acid), vinyl acetate, octenes.

Particularly preferred ethylenically unsaturated compounds are ethylene, vinyl acetate, butadiene, alkyl pentenoates, pentenenitriles, pentene acids (such as 3 pentenoic acid), acetylene and propylene.

Especially preferred are ethylene, vinyl acetate, butadiene and pentene nitrites.

The metal complex production reaction is preferably carried out at a temperature in the range from 20° C. to 120° C., more preferably from 20° C. to 90° C., especially from 50° C. to 80° C. It is preferred that the reaction temperature is maintained below the decomposition temperature and so when the metal phosphine is known to decompose within the temperature ranges given above, the reaction temperature should be maintained at least 10° C. (and preferably at least 20° C.) below the decomposition temperature.

Preferably, in the production of the metal complex, the complexing compound is present in the reaction mixture in stoichiometric excess. Preferably the amount of complexing compound in the reaction mixture is calculated to provide a molar excess of at least 10% over the amount required for the stoichiometric reaction, more preferably an excess of at least 50%, especially at least 90%. When the ligand L is a phosphine, we prefer to use an excess of phosphine of 10-25%. When the palladium is reduced in the formation of the product palladium complex, the reduction may be effected by the complexing compound and some excess complexing compound is preferably available in the reaction mixture to accomplish this.

The metal complex production reaction may be carried out in the presence of a solvent. When water is used as a solvent the pH of the solution may be controlled. The concentration of the metal ammine compound in the solvent is preferably equivalent to from 5-25 g of Pd per liter of solution. The pH of the reaction mixture is preferably adjusted and maintained to within a range from 2 to 7. A buffer solution may be added to the reaction mixture. Alternative solvents include alcohols (e.g. methanol, ethanol, propanol, methylated spirits) acetonitrile, tetrahydrofuran, toluene, aliphatic esters such as ethyl acetate and ketones such as methylethyl ketone. Organic solvents are required when the complexing compound is a phosphine.

The reactants may be added in any suitable order, but in a preferred process of the invention the metal ammine compound is placed in a reaction vessel, together with a solvent (if used), an alkali (if used) and a buffer solution (if used), heated if necessary and then the complexing compound is added.

The reaction may be continued for a period of from 30 minutes to several hours, but is normally complete within about four hours. On completion the product metal complex is separated from the reaction mixture by any appropriate method which is dependent upon the physical form of the product.

The catalyst system of the present invention may be used homogeneously or heterogeneously. Preferably, the catalyst system is used homogeneously.

Where a compound of a formula herein contains an alkenyl group or a cycloalkyl moiety as defined, cis (E) and trans (Z) isomerism may also occur. The present invention includes the individual stereoisomers of the compounds of any of the formulas defined herein and, where appropriate, the individual tautomeric forms thereof, together with mixtures thereof. Separation of diastereoisomers or cis and trans isomers may be achieved by conventional techniques, e.g. by fractional crystallisation, chromatography or H.P.L.C. of a stereoisomeric mixture of a compound one of the formulas or a suitable salt or derivative thereof. An individual enantiomer of a compound of one of the formulas may also be prepared from a corresponding optically pure intermediate or by resolution, such as by H.P.L.C. of the corresponding racemate using a suitable chiral support or by fractional crystallisation of the diastereoisomeric salts formed by reaction of the corresponding racemate with a suitable optically active acid or base, as appropriate.

All stereoisomers are included within the scope of the process of the invention.

It will be appreciated by those skilled in the art that the compounds of formulas (I)-(V) may function as ligands that coordinate with the Group 8, 9 or 10 metal or compound thereof to form the compounds for use in the invention. Typically, the Group 8, 9 or 10 metal or compound thereof coordinates to the one or more phosphorous, arsenic and/or antimony atoms of the compound of formula (I).

As mentioned above, the present invention provides a process for the carbonylation of ethylenically unsaturated compound comprising contacting an ethylenically unsaturated compound with carbon monoxide and a source of hydroxyl groups such as water or an alkanol in the presence of a catalyst compound as defined in the present invention.

Suitably, the source of hydroxyl groups includes an organic molecule having an hydroxyl functional group. Preferably, the organic molecule having a hydroxyl functional group may be branched or linear, and comprises an alkanol, particularly a C1-C30 alkanol, including aryl alkanols, which may be optionally substituted with one or more substituents selected from alkyl, aryl, Het, halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $C(S)R^{27}R^{28}$, $SR^{29}$ or $C(O)SR^{30}$ as defined herein. Highly preferred alkanols are $C_1$-$C_8$ alkanols such as methanol, ethanol, propanol, iso-propanol, iso-butanol, t-butyl alcohol, n-butanol, phenol and chlorocapryl alcohol. Although the monoalkanols are most preferred, poly-alkanols, preferably, selected from di-octa ols such as diols, triols, tetra-ols and sugars may also be utilised. Typically, such polyalkanols are selected from 1,2-ethanediol, 1,3-propanediol, glycerol, 1,2,4 butanetriol, 2-(hydroxymethyl)-1,3-propanediol, 1,2,6 trihydroxyhexane, pentaerythritol, 1,1,1 tri(hydroxymethyl)ethane, nannose, sorbase, galactose and other sugars. Preferred sugars include sucrose, fructose and glucose. Especially preferred alkanols are methanol and ethanol. The most preferred alkanol is methanol.

The amount of alcohol is not critical. Generally, amounts are used in excess of the amount of substrate to be carbonylated. Thus the alcohol may serve as the reaction solvent as well, although, if desired, separate solvents may also be used.

It will be appreciated that the end product of the reaction is determined at least in part by the source of alkanol used. For instance, use of methanol produces the corresponding methyl ester. Conversely, use of water produces the corresponding acids. Accordingly, the invention provides a convenient way of adding the group —C(O)O C$_1$-C$_{30}$ alkyl or aryl or —C(O) OH across the ethylenically unsaturated bond.

In the process according to the second aspect of the present invention, the carbon monoxide may be used in pure form or diluted with an inert gas such as nitrogen, carbon dioxide or a noble gas such as argon. Small amounts of hydrogen, typically less than 5% by volume, may also be present.

The ratio (volume/volume) of ethylenically unsaturated compounds to hydroxyl group source in a liquid phase reaction medium may vary between wide limits and suitably lies in the range of 1:0.1 to 1:10, preferably from between 2:1 to 1:2 and up to a large excess of alkanol or water when the latter is also the reaction solvent such as up to a 100:1 excess of alkanol or water. However, if the ethylenically unsaturated compound is a gas at the reaction temperature it may be present at lower levels in the liquid phase reaction medium such as at a ratio to hydroxyl group source of 1:20,000 to 1:10 more preferably, 1:10,000 to 1:50, most preferably, 1:5000 to 1:500

The amount of the catalyst of the invention used in the carbonylation process is not critical. Good results may be obtained when, preferably, the amount of Group 8, 9 or 10 metal is in the range $10^{-7}$ to $10^{-1}$, more preferably, $10^{-6}$ to $10^{-2}$, most preferably, $10^{-5}$ to $10^{-2}$ moles per mole of ethylenically unsaturated compound in the liquid phase carbonylation reaction medium.

Suitably, although non-essential to the invention, the carbonylation of ethylenically unsaturated compound as defined herein may be performed in one or more aprotic solvents. Suitable solvents include ketones, such as for example methylbutylketone; ethers, such as for example anisole (methyl phenyl ether), 2,5,8-trioxanonane(diglyme), diethyl ether, dimethyl ether, tetrahydrofuran, diphenylether, diisopropylether and the dimethylether of di-ethylene-glycol; esters, such as for example methylacetate, dimethyladipate methyl benzoate, dimethyl phthalate and butyrolactone; amides, such as for example dimethylacetamide, N-methylpyrrolidone and dimethyl formamide; sulfoxides and sulphones, such as for example dimethylsulphoxide, di-isopropylsulphone, sulfolane(tetrahydrothiophene-2,2-dioxide), 2-methylsulfolane, diethyl sulphone, tetrahydrothiophene 1,1-dioxide and 2-methyl-4-ethylsulfolane; aromatic compounds, including halo variants of such compounds e.g. benzene, toluene, ethyl benzene o-xylene, m-xylene, p-xylene, chlorobenzene, o-dichlorobenzene, m-dichlorobenzene: alkanes, including halo variants of such compounds egg, hexane, heptane, 2,2,3-trimethylpentane, methylene chloride and carbon tetrachloride; nitriles e.g. benzonitrile and acetonitrile.

Very suitable are aprotic solvents having a dielectric constant that is below a value of 50, more preferably in the range of 3 to 8, at 298.15 K and $1 \times 10^5$ Nm$^{-2}$. In the present context, the dielectric constant for a given solvent is used in its normal meaning of representing the ratio of the capacity of a condenser with that substance as dielectric to the capacity of the same condenser with a vacuum for dielectric. Values for the dielectric constants of common organic liquids can be found in general reference books, such as the Handbook of Chemistry and Physics, 76$^{th}$ edition, edited by David R. Lide et al, and published by CRC press in 1995, and are usually quoted for a temperature of about 20° C. or 25° C., i.e. about 293.15k or 298.15 K, and atmospheric pressure, i.e. about $1 \times 10^5$ Nm$^2$, or can readily be converted to that temperature and pressure using the conversion factors quoted. If no literature data for a particular compound is available, the dielectric constant may be readily measured using established physico-chemical methods.

Measurement of a dielectric constant of a liquid can easily be performed by various sensors, such as immersion probes, flow-through probes, and cup-type probes, attached to various meters, such as those available from the Brookhaven Instruments Corporation of Holtsville, N.Y. (e.g., model BI-870) and the Scientifica Company of Princeton, N.J. (e.g. models 850 and 870). For consistency of comparison, preferably all measurements for a particular filter system are performed at substantially the same sample temperature, e.g., by use of a water bath. Generally, the measured dielectric constant of a substance will increase at lower temperatures and decrease at higher temperatures. The dielectric constants falling within any ranges herein, may be determined in accordance with ASTM D924.

However, if there is doubt as to which technique to use to determine the dielectric constant a Scientifica Model 870 Dielectric Constant Meter with a 1-200 ε range setting should be used.

For example, the dielectric constant of anisole is 4.3 (at 294.2 K), of diethyl ether is 4.3 (at 293.2 K), of sulfolane is 43.4 (at 303.2 K), of methylpentanoate is 5.0 (at 293.2 K), of diphenylether is 3.7 (at 283.2 K), of dimethyladipate is 6.8 (at 293.2 K), of tetrahydrofuran is 7.5 (at 295.2 K), of methylnonanoate is 3.9 (at 293.2 K), of methyl-tert-butyl ether is 4.34 (at 293 K), of dioxane is 2.21 (at 298 K), of toluene is 2.38 (at 298 K) and of acetonitrile is 37.5 (at 298 K). The dielectric values are taken from the handbook of chemistry and physics and the temperature of the measurement is given. A preferred aprotic solvent is anisole.

In the presence of an alkanol, an aprotic solvent will be generated by the reaction as the ester carbonylation product of the ethylenically unsaturated compound, carbon monoxide and the alkanol is an aprotic solvent.

The process may be carried out in an excess of aprotic solvent, i.e. at a ratio (v/v) of aprotic solvent to alkanol of at least 1:1. Preferably, this ratio ranges from 1:1 to 10:1 and more preferably from 1:1 to 5:1. Most preferably the ratio (v/v) ranges from 1.5:1 to 3:1.

Despite the foregoing it is preferred that the reaction is carried out in the absence of any external added aprotic solvent i.e. in the absence of an aprotic solvent not generated by the reaction itself.

Alternatively, a protic co-solvent may be used. The protic co-solvent may include a further carboxylic acid or an alcohol. Suitable protic co-solvents include the conventional protic solvents known to the person skilled in the art, such as water, lower alcohols, such as, for example, methanol, ethanol and isopropanol, and primary and secondary amines.

During hydroxycarbonylation, the presence of a protic solvent is also preferred. The protic solvent may include a carboxylic acid or an alcohol. Mixtures of the aprotic and protic solvents may also be employed.

By protic co-solvent is meant any solvent that carries a donatable hydrogen ion such as those attached to oxygen as in a hydroxyl group or nitrogen as in a amine group. By aprotic co-solvent is meant a type of solvent which neither donates nor accepts protons.

Hydrogen may be added to the carbonylation reaction to improve reaction rate. Suitable levels of hydrogen when utilised may be in the ratio of between 0.1 and 20% vol/vol of the carbon monoxide, more preferably, 1-20% vol/vol of the carbon monoxide, more preferably, 2-15% vol/vol of the carbon monoxide, most preferably 3-10% vol/vol of carbon monoxide.

The catalyst compounds of the present invention may act as a "heterogeneous" catalyst or a "homogeneous" catalyst, preferably, a homogenous catalyst.

By the term "homogeneous" catalyst we mean a catalyst, i.e. a compound of the invention, which is not supported but is simply admixed or formed in-situ with the reactants of the carbonylation reaction (e.g. the ethylenically unsaturated compound, the hydroxyl containing compound and carbon monoxide), preferably in a suitable solvent as described herein.

By the term "heterogeneous" catalyst we mean a catalyst, i.e. the compound of the invention, which is carried on a support.

Thus according to a further aspect, the present invention provides a process for the carbonylation of ethylenically unsaturated compounds as defined herein wherein the process is carried out with the catalyst comprising a support, preferably an insoluble support.

Preferably, the support comprises a polymer such as a polyolefin, polystyrene or polystyrene copolymer such as a divinylbenzene copolymer or other suitable polymers or copolymers known to those skilled in the art; a silicon derivative such as a functionalised silica, a silicone or a silicone rubber; or other porous particulate material such as for example inorganic oxides and inorganic chlorides.

Preferably the support material is porous silica which has a surface area in the range of from 10 to 700 $m^2/g$, a total pore volume in the range of from 0.1 to 4.0 cc/g and an average particle size in the range of from 10 to 500 μm. More preferably, the surface area is in the range of from 50 to 500 $m^2/g$, the pore volume is in the range of from 0.5 to 2.5 cc/g and the average particle size is in the range of from 20 to 200 μm. Most desirably the surface area is in the range of from 100 to 400 $m^2/g$, the pore volume is in the range of from 0.8 to 3.0 cc/g and the average particle size is in the range of from 30 to 100 μm. The average pore size of typical porous support materials is in the range of from 10 to 1000 Å. Preferably, a support material is used that has an average pore diameter of from 50 to 500 Å, and most desirably from 75 to 350 Å. It may be particularly desirable to dehydrate the silica at a temperature of from 100° C. to 800° C. anywhere from 3 to 24 hours.

Suitably, the support may be flexible or a rigid support, the insoluble support is coated and/or impregnated with the compounds of the process of the invention by techniques well known to those skilled in the art.

Alternatively, the compounds of the process of the invention are fixed to the surface of an insoluble support, optionally via a covalent bond, and the arrangement optionally includes a bifunctional spacer molecule to space the compound from the insoluble support.

The compounds of the invention may be fixed to the surface of the insoluble support by promoting reaction of a functional group present in the ligands, for example a substituent of the aromatic structure, with a complimentary reactive group present on or previously inserted into the support. The combination of the reactive group of the support with a complimentary substituent of the compound of the invention provides a heterogeneous catalyst where the compound of the invention and the support are linked via a linkage such as an ether, ester, amide, amine, urea, keto group.

The choice of reaction conditions to link a compound of the process of the present invention to the support depends upon the ethylenically unsaturated compound and the groups of the support. For example, reagents such as carbodiimides, 1,1'-carbonyldiimidazole, and processes such as the use of mixed anhydrides, reductive amination may be employed.

According to a further aspect, the present invention provides the use of the process or ligand catalyst composition of any aspect of the invention wherein the catalyst is attached to a support.

Additionally, the bidentate phosphine may be bonded to a suitable polymeric substrate via at least one of the bridge substituents, the bridging group R, the linking group A or the linking group B e.g. 1,2 bis(di-t-butylphosphinomethyl)-4-t-butyl-benzene may be bonded, preferably, via the 3, 5 or 6 cyclic carbons of the benzene group to polystyrene to give an immobile heterogeneous catalyst.

The amount of ligand used can vary within wide limits. Preferably, when excess bidentate ligand is added, the bidentate ligand is present in an amount such that the ratio of the number of moles of the bidentate ligand present to the number of moles of the Group 8, 9 or 10 metal present is from 1 to 50 e.g. 1 to 15 and particularly from 1 to 10 mol per mol of metal. More preferably, the mol:mol range of ligands to Group 8, 9 or 10 metal is in the range of 1:1 to 20:1, most preferably in the range of 1:1 to 10:1 or even 1:1 to 1.5:1. Conveniently, the possibility of applying these low molar ratios is advantageous, as it avoids the use of excess ligand and hence minimises the consumption of these usually expensive compounds. Suitably, the catalysts of the invention are prepared in a separate step preceding their use in-situ in the carbonylation reaction.

Conveniently, the process of the invention may be carried out by dissolving the Group 8, 9 or 10 metal complex as defined herein in a suitable solvent such as one of the alkanols or aprotic solvents previously described (a particularly preferred solvent would be the ester or acid product of the specific carbonylation reaction e.g. 2-acetoxymethylpropionate or 3-acetoxymethylpropionate for vinyl acetate carbonylation or methyl propionate for ethylene carbonylation).

The carbon monoxide may be used in the presence of other gases which are inert in the reaction. Examples of such gases include hydrogen, nitrogen, carbon dioxide and the noble gases such as argon.

The product of the reaction may be separated from the other components by any suitable means. However, it is an advantage of the present process that significantly fewer by-products are formed thereby reducing the need for further purification after the initial separation of the product. A further advantage is that the other components which contain the catalyst system which may be recycled and/or reused in further reactions with minimal supplementation of fresh catalyst.

A particular advantage is the absence of metal anion in the case of $HCO_3^-$ and $CO_3^{2-}$ which are liberated as $CO_2$ and water.

Preferably, the carbonylation is carried out at temperatures of between −30 to 170° C., more preferably −10° C. to 160° C., most preferably 20° C. to 150° C. An especially preferred temperature is one chosen between 40° C. to 150° C. Advantageously, the carbonylation can be carried out at moderate temperatures, it is particularly advantageous to be able to carry out the reaction at room temperature (20° C.).

Preferably, when operating a low temperature carbonylation, the carbonylation is carried out between −30° C. to 49° C., more preferably, −10° C. to 45° C., still more preferably 0° C. to 45° C., most preferably 10° C. to 45° C. Especially preferred is a range of 10 to 35° C.

Preferably, the carbonylation is carried out at a CO partial pressure of between $0.80 \times 10^5$ $N.m^{-2}$-$90 \times 10^6$ $N.m^{-2}$, more preferably $1 \times 10^5$ $N.m^2$-$65 \times 10^5$ $N.m^2$, most preferably 1-50× $10^5$ $N.m^2$. Especially preferred is a CO partial pressure of 5 to $45 \times 10^5$ $N.m^{-2}$.

Preferably, a low pressure carbonylation is also envisaged. Preferably, when operating a low pressure carbonylation the carbonylation is carried out at a CO partial pressure of between 0.1 to $5 \times 10^5$ N.m$^{-2}$, more preferably 0.2 to $2 \times 10^5$ N.m$^{-2}$, most preferably 0.5 to $1.5 \times 10^5$ N.m$^2$.

There is no particular restriction on the duration of the carbonylation except that carbonylation in a timescale which is commercially acceptable is obviously preferred. Carbonylation in a batch reaction may take place in up to 48 hours, more typically, in up to 24 hours and most typically in up to 12 hours. Typically, carbonylation is for at least 5 minutes, more typically, at least 30 minutes, most typically, at least 1 hour. In a continuous reaction such time scales are obviously irrelevant and a continuous reaction can continue as long as the TON is commercially acceptable before catalyst requires replenishment.

The catalyst system of the present invention is preferably constituted in the liquid phase which may be formed by one or more of the reactants or by the use of a suitable solvent.

The use of stabilising compounds with the catalyst system may also be beneficial in improving recovery of metal which has been lost from the catalyst system. When the catalyst system is utilized in a liquid reaction medium such stabilizing compounds may assist recovery of the group 8, 9 or 10 metal.

Preferably, therefore, the catalyst system includes in a liquid reaction medium a polymeric dispersant dissolved in a liquid carrier, said polymeric dispersant being capable of stabilising a colloidal suspension of particles of the group 8, 9 or 10 metal or metal compound of the catalyst system within the liquid carrier.

The liquid reaction medium may be a solvent for the reaction or may comprise one or more of the reactants or reaction products themselves. The reactants and reaction products in liquid form may be miscible with or dissolved in a solvent or liquid diluent.

The polymeric dispersant is soluble in the liquid reaction medium, but should not significantly increase the viscosity of the reaction medium in a way which would be detrimental to reaction kinetics or heat transfer. The solubility of the dispersant in the liquid medium under the reaction conditions of temperature and pressure should not be so great as to deter significantly the adsorption of the dispersant molecules onto the metal particles.

The polymeric dispersant is capable of stabilising a colloidal suspension of particles of said group 8, 9 or 10 metal or metal compound within the liquid reaction medium such that the metal particles formed as a result of catalyst degradation are held in suspension in the liquid reaction medium and are discharged from the reactor along with the liquid for reclamation and optionally for re-use in making further quantities of catalyst. The metal particles are normally of colloidal dimensions, e.g. in the range 5-100 nm average particle size although larger particles may form in some cases. Portions of the polymeric dispersant are adsorbed onto the surface of the metal particles whilst the remainder of the dispersant molecules remain at least partially solvated by the liquid reaction medium and in this way the dispersed group 8, 9 or 10 metal particles are stabilised against settling on the walls of the reactor or in reactor dead spaces and against forming agglomerates of metal particles which may grow by collision of particles and eventually coagulate. Some agglomeration of particles may occur even in the presence of a suitable dispersant but when the dispersant type and concentration is optimised then such agglomeration should be at a relatively low level and the agglomerates may form only loosely so that they may be broken up and the particles redispersed by agitation.

The polymeric dispersant may include homopolymers or copolymers including polymers such as graft copolymers and star polymers.

Preferably, the polymeric dispersant has sufficiently acidic or basic functionality to substantially stabilise the colloidal suspension of said group 8, 9 or 10 metal or metal compound.

By substantially stabilise is meant that the precipitation of the group 8, 9 or 10 metal from the solution phase is substantially avoided.

Particularly preferred dispersants for this purpose include acidic or basic polymers including carboxylic acids, sulphonic acids, amines and amides such as polyacrylates or heterocycle, particularly nitrogen heterocycle, substituted polyvinyl polymers such as polyvinyl pyrrolidone or copolymers of the aforesaid.

Examples of such polymeric dispersants may be selected from polyvinylpyrrolidone, polyacrylamide, polyacrylonitrile, polyethylenimine, polyglycine, polyacrylic acid, polymethacrylic acid, poly(3-hydroxybutyricacid), poly-L-leucine, poly-L-methionine, poly-L-proline, poly-L-serine, poly-L-tyrosine, poly(vinylbenzenesulphonic acid) and poly (vinylsulphonic acid), acylated polyethylenimine. Suitable acylated polyethylenimines are described in BASF patent publication EP1330309 A1 and U.S. Pat. No. 6,723,882.

Preferably, the polymeric dispersant incorporates acidic or basic moieties either pendant or within the polymer backbone. Preferably, the acidic moieties have a dissociation constant ($pK_a$) of less than 6.0, more preferably, less than 5.0, most preferably less than 4.5. Preferably, the basic moieties have a base dissociation constant ($pK_b$) being of less than 6.0, more preferably less than 5.0 and most preferably less than 4.5, $pK_a$ and $pK_b$ being measured in dilute aqueous solution at 25° C.

Suitable polymeric dispersants, in addition to being soluble in the reaction medium at reaction conditions, contain at least one acidic or basic moiety, either within the polymer backbone or as a pendant group. We have found that polymers incorporating acid and amide moieties such as polyvinylpyrollidone (PVP) and polyacrylates such as polyacrylic acid (PAA) are particularly suitable. The molecular weight of the polymer which is suitable for use in the invention depends upon the nature of the reaction medium and the solubility of the polymer therein. We have found that normally the average molecular weight is less than 100,000. Preferably, the average molecular weight is in the range 1,000-200,000, more preferably, 5,000-100,000, most preferably, 10,000-40,000 e.g. Mw is preferably in the range 10,000-80,000, more preferably 20,000-60,000 when PVP is used and of the order of 1,000-10,000 in the case of PAA.

The effective concentration of the dispersant within the reaction medium should be determined for each reaction/catalyst system which is to be used.

The dispersed group 8, 9 or 10 metal may be recovered from the liquid stream removed from the reactor e.g. by filtration and then either disposed of or processed for re-use as a catalyst or other applications. In a continuous process the liquid stream may be circulated through an external heat-exchanger and in such cases it may be convenient to locate filters for the palladium particles in these circulation apparatus.

Preferably, the polymer:metal mass ratio in g/g is between 1:1 and 1000:1, more preferably, between 1:1 and 400:1, most preferably, between 1:1 and 200:1. Preferably, the polymer:metal mass ratio in g/g is up to 1000, more preferably, up to 400, most preferably, up to 200.

It will be appreciated that any of the features set forth in the first aspect of the invention may be regarded as preferred features of the second, third, fourth, fifth or other aspect of the present invention and vice versa.

The invention not only extends to novel complexes but also novel catalyst systems incorporating such complexes.

Production of a metal complexes and their catalytic activity in accordance with the invention is described in the following non-limiting examples and with reference to figure 1 in which:—

FIG. 1 is a molecular diagram of a metal complex in accordance with this invention.

EXAMPLE 1

Palladium tetraammine di(hydrogen carbonate) and 1 mole equivalent of 1,2-bis(di-tertbutylphosphinomethyl)benzene were suspended in methanol at reflux for 6 hrs. A basic gas (believed to be ammonia) was evolved during the reaction. The product was filtered off at room temperature and dried. This product was recrystallised from hot methanol and the crystals characterised by single crystal X-ray diffraction. The product was identified as Pd(1,2-bis(di-tertbutylphosphinomethyl)benzene) $(CO_3)$.$2CH_3OH$ (see FIG. 1). The dried product contained 18.82% Pd by standard wet chemical analysis which was consistent with the identification of the compound as Pd(1,2-bis(di-tertbutylphosphinomethyl)benzene)$(CO_3)$. Further supportive identification by infra-red spectroscopy was also obtained.

EXAMPLE 2

Palladium tetraammine di(hydrogen carbonate) and 1 mole equivalent of 1,2-bis(di-tertbutylphosphinomethyl)ferrocene were suspended in methanol at reflux for 6 hrs. A basic gas (believed to be ammonia) was evolved during the reaction. The product was filtered off at room temperature and dried. The product contained 15.95% Pd by standard wet chemical analysis which was consistent with the identification of the compound as Pd(1,2-bis(di-tertbutylphosphinomethyl)ferrocene) $(CO_3)$. Further supportive identification by infra-red spectroscopy was also obtained.

EXAMPLE 3

Palladium tetraammine di(hydrogen carbonate) and 1 mole equivalent of 1,2-bis(di-3,5,dimethyladamantylphosphinomethyl)ferrocene were suspended in methanol at reflux for 6 hrs. A basic gas (believed to be ammonia) was evolved during the reaction. The product was filtered off at room temperature and dried. The product contained 9.60% Pd by standard wet chemical analysis which was consistent with the identification of the compound as Pd(1,2-bis((di-3,5,dimethyladamantyl)phosphinomethyl)ferrocene) $(CO_3)$. Further supportive identification by infra-red spectroscopy was also obtained.

EXAMPLE 4

Palladium tetraammine di(hydrogen carbonate) and 1 mole equivalent of cis-1,2-bis(di-t-butylphosphinomethyl)4,5-dimethyl cyclohexane were suspended in methanol at reflux for 6 hrs. A basic gas (believed to be ammonia) was evolved during the reaction. The product was filtered off at room temperature and dried. The product contained 17.72% Pd by standard wet chemical analysis which was consistent with the identification of the compound as Pd(cis-1,2-bis(di-t-butylphosphinomethyl)4,5-dimethyl cyclohexane $(CO_3)$. Further supportive identification by infra-red spectroscopy was also obtained.

Catalyst Testing
Test Complex 1

Solutions for catalyst testing were prepared as follows, using standard Schlenk line techniques. In a nitrogen purge glove box, 10.58 mg of (L-L)PdCO$_3$ ($1.45*10^{-5}$ moles) complex (L-L)=1,2-bis(di-tert-butylphosphinomethyl)ferrocene and 5 equivalents of phosphine ligand (L-L) ($7.25*10^{-5}$ moles), were weighed into a 500 ml round bottom flask. The flask was then transferred to a Schlenk line. The palladium complex and excess ligand were then dissolved in 125 ml of degassed methyl propionate followed by 175 ml of degassed methyl propionate/methanol mixture (50% by weight methanol, 50% by weight methyl propionate). Addition of methane sulfonic acid (MSA), 420 µl, completes the preparation of the catalyst solution in a much shorter period of time compared to comparative tests 1 and 2 below. In addition, addition of the acid liberates carbon dioxide gas and water which do not contaminate the reaction system. The final composition of the solution is approximately 70 wt % methylpropionate, 30 wt % methanol.

The catalytic solution was added to the pre-evacuated autoclave and heated to 100° C. The autoclave was then pressured with 8 bars of ethene above vapour pressure giving a total pressure of 10.2 bars at 100° C. Next the autoclave was pressured to 12.2 bars with addition of CO: ethene (1:1 gas) charged from the 10 liter reservoir. A regulatory valve ensures that the pressure of the autoclave is maintained throughout the reaction at 12.2 bars through constant injection of gas from the 10 liter reservoir. The pressure of the reservoir as well as the reactor temperature was logged throughout the reaction period of 3 hrs.

The moles produced at any point in either reaction are calculated from the drop in reservoir pressure by assuming ideal gas behaviour and 100% selectivity for methyl propionate, which allowed reaction TON and rate to be obtained. The results are shown in Table 1.

Test Complex 2

The solutions for catalyst testing were prepared as for example ligand 1 using standard Schlenk line techniques. In a nitrogen purge glove box, 16.73 mg of (L-L)PdCO$_3$ ($1.45*10^{-5}$ moles) complex (L-L)=1,2-bis(di-1-(3,5-dimethyladamantyl)phosphinomethyl)ferrocene and 5 equivalents of phosphine ligand (L-L) ($7.25*10^{-5}$ moles), were weighed into a 500 ml round bottom flask. The flask was then transferred to a Schlenk line. The palladium complex and excess ligand were then dissolved in 125 ml of degassed methyl propionate followed by 175 ml of degassed methyl propionate/methanol mixture (50% by weight methanol, 50% by weight methyl propionate). Addition of methane sulfonic acid (MSA), 420 µl, completes the preparation of the catalyst solution in a much shorter period of time compared to comparative tests 1 and 2 below. In addition, addition of the acid liberates carbon dioxide gas and water which do not contaminate the reaction system. The final composition of the solution is approximately 70 wt % methylpropionate, 30 wt % methanol.

The catalytic solution was added to the pre-evacuated autoclave and heated to 100° C. The autoclave was then pressured with 8 bars of ethene above vapour pressure giving a total pressure of 10.2 bars at 100° C. Next the autoclave was pressured to 12.2 bars with addition of CO: ethene (1:1 gas) charged from the 10 liter reservoir. A regulatory valve ensures that the pressure of the autoclave is maintained throughout the reaction at 12.2 bars through constant injection of gas from the 10 liter reservoir. The pressure of the reservoir as well as the reactor temperature was logged throughout the reaction period of 3 hrs.

The moles produced at any point in either reaction are calculated from the drop in reservoir pressure by assuming ideal gas behaviour and 100% selectivity for methyl propionate, which allowed reaction TON and rate to be obtained. The results are shown in Table 1.

Comparative Test Complex 1 Using Pd(dba).

The solutions for catalyst testing were prepared using standard Schlenk line techniques. In a nitrogen purge glove box, 7.8 mg of $Pd_2dba_3$ ($1.45*10^{-5}$ moles) and 6 equivalents of phosphine ligand 1 (L-L)=1,2-bis(di-tert-butylphosphinomethyl)ferrocene ($8.7*10^{-5}$ moles), were weighed into a 500 ml round bottom flask. The flask was then transferred to a Schlenk line. The ligand and palladium were then dissolved in 125 ml of degassed methyl propionate. In order to aid complexation, the palladium and ligand were dissolved initially in methyl propionate and stirred for a period of 45 minutes, before addition of further solvents to the solution. This allows for the in situ formation of a neutral, trigonal planar Pd (0) complex [Pd(ligand)(dba)].

After complexation, 175 ml of methyl propionate/methanol mixture (50% by weight methanol, 50% by weight methyl propionate) was degassed and added to the flask. Addition of methane sulfonic acid (MSA), 420 μl, completes the preparation of the catalyst solution. However, dba is still present in the system. The final composition of the solution is approximately 70 wt % methylpropionate, 30 wt % methanol.

The catalytic solution was added to the pre-evacuated autoclave and heated to 100° C. The autoclave was then pressured with 8 bars of ethene above vapour pressure giving a total pressure of 10.2 bars at 100° C. Next the autoclave was pressured to 12.2 bars with addition of CO: ethene (1:1 gas) charged from the 10 liter reservoir. A regulatory valve ensures that the pressure of the autoclave is maintained throughout the reaction at 12.2 bars through constant injection of gas from the 10 liter reservoir. The pressure of the reservoir as well as the reactor temperature was logged throughout the reaction period of 3 hrs.

The moles produced at any point in either reaction are calculated from the drop in reservoir pressure by assuming ideal gas behaviour and 100% selectivity for methyl propionate, which allowed reaction TON and rate to be obtained. The results are shown in Table 1.

Comparative Test 2 Using Pd(dba).

The solutions for catalyst testing were prepared using standard Schlenk line techniques. In a nitrogen purge glove box, 7.8 mg of $Pd_2dba_3$ ($1.45*10^{-5}$ moles) and 6 equivalents of phosphine ligand 2 (L-L)=1,2-bis(di-1-(3,5-dimethyladamantyl)phosphinomethyl)ferrocene ($8.7*10^{-5}$ moles), where weighed into a 500 ml round bottom flask. The flask was then transferred to a Schlenk line. The ligand and palladium were then dissolved in 125 ml of degassed methyl propionate. In order to aid complexation, the palladium and ligand were dissolved initially in methyl propionate and stirred for a period of 45 minutes, before addition of further solvents to the solution. This allows for the in situ formation of a neutral, trigonal planar Pd (0) complex [Pd(ligand)(dba)].

After complexation, 175 ml of methyl propionate/methanol mixture (50% by weight methanol, 50% by weight methyl propionate) was degassed and added to the flask. Addition of methane sulfonic acid (MSA), 420 μl, completes the preparation of the catalyst solution. However, dba is still present in the system. The final composition of the solution is approximately 70 wt % methylpropionate, 30 wt % methanol.

The catalytic solution was added to the pre-evacuated autoclave and heated to 100° C. The autoclave was then pressured with 8 bars of ethene above vapour pressure giving a total pressure of 10.2 bars at 100° C. Next the autoclave was pressured to 12.2 bars with addition of CO: ethene (1:1 gas) charged from the 10 liter reservoir. A regulatory valve ensures that the pressure of the autoclave is maintained throughout the reaction at 12.2 bars through constant injection of gas from the 10 liter reservoir. The pressure of the reservoir as well as the reactor temperature was logged throughout the reaction period of 3 hrs.

The moles produced at any point in either reaction are calculated from the drop in reservoir pressure by assuming ideal gas behaviour and 100% selectivity for methyl propionate, which allowed reaction TON and rate to be obtained. The results are shown in Table 1.

TABLE 1

| Ligand | TON (moles MeP/Mole Pd) |
|---|---|
| 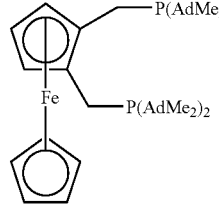 Using Pd(dba) | 90834 |
| 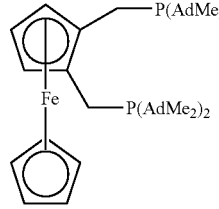 Using Pd(dba) | 92546 |
| 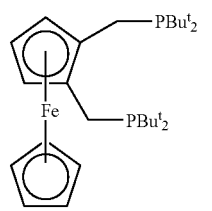 | 84772 |
| 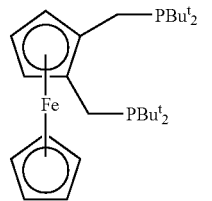 Using Pd(dba) | 85110 |

In the above batch examples the ligand is added in a proportion of 6 equivalents to metal and the acid is then added in a proportion of 450 equivalents to metal. With such a large excess of acid there is no need to equilibrate the system and the metal will easily be oxidised in both systems.

However, in a continuous process such a large excess of acid is not tenable and will cause corrosion to the reactor and pipe work. Similarly, ligand is an expensive commodity and a large excess of such ligand would add to the expense of the continuous industrial process. With much lower levels of ligand equilibration of the complex will take even longer with the dba based system whereas the system of the invention will reach rapid equilibration. Similarly, using less acid in the continuous system means a much longer period of oxidation of the metal from the Pd(0) to Pd(II) oxidation state. In the system of the invention the metal is already in the active oxidation state so does not require equilibration. Therefore, the second stage of catalyst preparation is also dramatically speeded up by using the metal complexes of the present invention.

The reader's attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings), may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

The invention claimed is:

1. A metal complex $ML_nX_m$, where M is a metal of group 8, 9 or 10, L is a bidentate phosphine ligand of formula (I), (II), (III), (IV) or (V) as set out below, X is $HCO_3^-$, or $CO_3^{2-}$, n is a number equal to or less than the coordination number of the metal, m is 1 or 2 and is equal to the oxidation state of the metal:

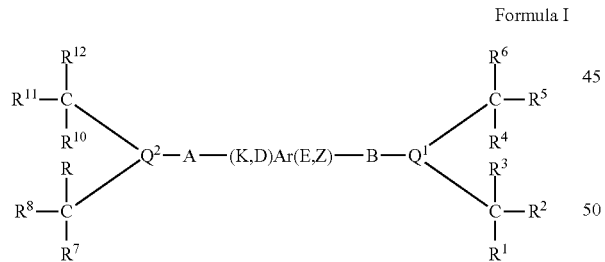

Formula I wherein:
Ar is a bridging group comprising an optionally substituted aryl moiety to which the phosphorus atoms are linked on available adjacent carbon atoms;

A and B each independently represent lower alkylene;

K, D, E and Z are substituents of the aryl moiety (Ar) and each independently represent hydrogen, lower alkyl, aryl, Het, halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $C(S)R^{25}R^{26}$, $SR^{27}$, $C(O)SR^{27}$, or $-J-Q^3(CR^{13}(R^{14})(R^{15})CR^{16}(R^{17})(R^{18})$ where J represents lower alkylene; or two adjacent groups selected from K, Z, D and E together with the carbon atoms of the aryl ring to which they are attached form a further phenyl ring, which is optionally substituted by one or more substituents selected from hydrogen, lower alkyl, halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $C(S)R^{25}R^{26}$, $SR^{27}$ or $C(O)SR^{27}$;

$R^{13}$ to $R^{18}$ each independently represent hydrogen, lower alkyl, aryl, or Het, preferably each independently represent lower alkyl, aryl, or Het;

$R^{19}$ to $R^{27}$ each independently represent hydrogen, lower alkyl, aryl or Het;

$R^1$ to $R^{12}$ each independently represent hydrogen, lower alkyl, aryl, or Het, preferably each independently represent lower alkyl, aryl, or Het;

$Q^1$, $Q^2$ and $Q^3$ (when present) each independently represent phosphorous, arsenic or antimony and in the latter two cases references to phosphine or phosphorous above are amended accordingly;

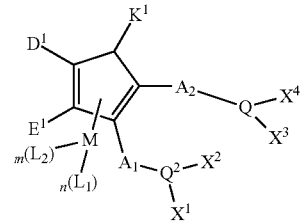

Formula II wherein:
$A_1$ and $A_2$, and $A_3$, $A_4$ and $A_5$ (when present), each independently represent lower alkylene;

$K^1$ is selected from the group consisting of hydrogen, lower alkyl, aryl, Het, halo, cyano, nitro, $—OR^{19}$, $—OC(O)R^{20}$, $—C(O)R^{21}$, $—C(O)OR^{22}$, $—N(R^{23})R^{24}$, $—C(O)N(R^{25})R^{26}$, $—C(S)(R^{27})R^{28}$, $—SR^{29}$, $—C(O)SR^{30}$, $—CF_3$ or $-A_3-Q^3(X^5)X^6$;

$D^1$ is selected from the group consisting of hydrogen, lower alkyl, aryl, Het, halo, cyano, nitro, $—OR^{19}$, $—OC(O)R^{20}$, $—C(O)R^{21}$, $—C(O)OR^{22}$, $—N(R^{23})R^{24}$, $—C(O)N(R^{25})R^{26}$, $—C(S)(R^{27})R^{28}$, $—SR^{29}$, $—C(O)SR^{30}$, $—CF_3$ or $-A_4-Q^4(X^7)X^8$;

$E^1$ is selected from the group consisting of hydrogen, lower alkyl, aryl, Het, halo, cyano, nitro, $—OR^{19}$, $—OC(O)R^{20}$, $—C(O)R^{21}$, $—C(O)OR^{22}$, $—N(R^{23})R^{24}$, $—C(O)N(R^{25})R^{26}$, $—C(S)(R^{27})R^{28}$, $—SR^{29}$, $—C(O)SR^{30}$, $—CF_3$ or $-A_5-Q^5(X^9)X^{10}$;

or both $D^1$ and $E^1$ together with the carbon atoms of the cyclopentadienyl ring to which they are attached form an optionally substituted phenyl ring:

$X^1$ represents $CR^1(R^2)(R^3)$, congressyl or adamantyl, $X^2$ represents $CR^4(R^5)(R^6)$, congressyl or adamantyl, or $X^1$ and $X^2$ together with $Q^2$ to which they are attached form an optionally substituted 2-phospha-tricyclo[3.3.1.1{3,7}]decyl group or derivative thereof, or $X^1$ and $X^2$ together with $Q^2$ to which they are attached form a ring system of formula IIIa

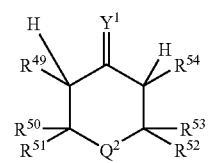

(IIIa)

$X^3$ represents $CR^7(R^8)(R^9)$, congressyl or adamantyl, $X^4$ represents $CR^{10}(R^{11})(R^{12})$, congressyl or adamantyl, or $X^3$ and $X^4$ together with $Q^1$ to which they are attached form an optionally substituted 2-phospha-tricyclo[3.3.1.1{3,7}]decyl group or derivative thereof, or $X^3$ and $X^4$ together with $Q^1$ to which they are attached form a ring system of formula IIIb

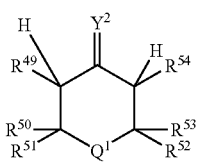
(IIIb)

$X^5$ represents $CR^{13}(R^{14})(R^{15})$, congressyl or adamantyl, $X^6$ represents $CR^{16}(R^{17})(R^{18})$, congressyl or adamantyl, or $X^5$ and $X^6$ together with $Q^3$ to which they are attached form an optionally substituted 2-phospha-tricyclo[3.3.1.1{3,7}]decyl group or derivative thereof, or $X^5$ and $X^6$ together with $Q^3$ to which they are attached form a ring system of formula IIIc

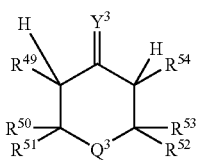
(IIIc)

$X^7$ represents $CR^{31}(R^{32})(R^{33})$, congressyl or adamantyl, $X^8$ represents $CR^{34}(R^{35})(R^{36})$, congressyl or adamantyl, or $X^7$ and $X^8$ together with $Q^4$ to which they are attached form an optionally substituted 2-phospha-tricyclo[3.3.1.1{3,7}]decyl group or derivative thereof, or $X^7$ and $X^8$ together with $Q^4$ to which they are attached form a ring system of formula IIId

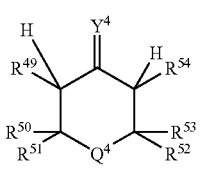
(IIId)

$X^9$ represents $CR^{37}(R^{38})(R^{39})$, congressyl or adamantyl, $X^{10}$ represents $CR^{40}(R^{41})(R^{42})$, congressyl or adamantyl, or $X^9$ and $X^{10}$ together with $Q^5$ to which they are attached form an optionally substituted 2-phospha-tricyclo[3.3.1.1.{3,7}]decyl group or derivative thereof, or $X^9$ and $X^{10}$ together with $Q^5$ to which they are attached form a ring system of formula IIIe

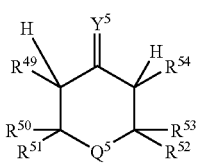
(IIIe)

and in this yet further embodiment, $Q^1$ and $Q^2$, and $Q^3$, $Q^4$ and $Q^5$ (when present), each independently represent phosphorus, arsenic or antimony;

M represents a Group VIB or VIIIB metal or metal cation thereof;

$L_1$ represents an optionally substituted cyclopentadienyl, indenyl or aryl group;

$L_2$ represents one or more ligands each of which are independently selected from hydrogen, lower alkyl, alkylaryl, halo, CO, $P(R^{43})(R^{44})R^{45}$ or $N(R^{46})(R^{47})R^{48}$;

$R^1$ to $R^{18}$ and $R^{31}$ to $R^{42}$, when present, each independently represent hydrogen, lower alkyl, aryl, halo or Het;

$R^{19}$ to $R^{30}$ and $R^{43}$ to $R^{48}$, when present, each independently represent hydrogen, lower alkyl, aryl or Het;

$R^{49}$, $R^{54}$ and $R^{55}$, when present, each independently represent hydrogen, lower alkyl or aryl;

$R^{50}$ to $R^{53}$, when present, each independently represent hydrogen, lower alkyl, aryl or Het;

$Y^1$, $Y^2$, $Y^3$, $Y^4$ and $Y^5$, when present, each independently represent oxygen, sulfur or N—$R^{55}$;

n=0 or 1;

and m=0 to 5;

provided that when n=1 then m equals 0, and when n equals 0 then m does not equal 0;

$$X^1(X^2)\text{-}Q^2\text{-}A\text{-}R\text{—}B\text{-}Q^1\text{-}X^3(X^4) \quad \text{Formula III}$$

wherein:

A and B are as defined for formula (IV) hereinafter

R represents an optionally substituted cycloalkyl moiety to which the $Q^1$ and $Q^2$ atoms are linked on available adjacent cyclic carbon atoms;

the groups $X^1$, $X^2$, $X^3$ and $X^4$ are as defined for formula (IV) hereinafter;

$Q^1$ and $Q^2$ are as defined for formula (IV) hereinafter;

$$X1(X2)\text{-}Q^2\text{-}A\text{-}R\text{—}B\text{-}Q^1\text{-}X3(X4) \quad \text{Formula IV}$$

wherein:

A and B each independently represent lower alkylene;

R represents a cyclic hydrocarbyl structure having at least one non-aromatic ring to which the $Q^1$ and $Q^2$ atoms are linked on available adjacent cyclic atoms of the at least one ring and which is substituted with at least one substituent on at least one further non-adjacent cyclic atom of the at least one ring;

wherein each adjacent cyclic atom to the said available adjacent cyclic atom is not substituted so as to form a further 3-8 atom ring structure via the other adjacent cyclic atom to the said available adjacent cyclic atoms in the at least one ring or via an atom adjacent to the said other adjacent atom but outside the at least one ring;

the groups X1, X2, X3 and X4 independently represent univalent radicals up to 30 atoms having at least one tertiary carbon atom or X1 and X2 and/or X3 and X4 together form a bivalent radical of up to 40 atoms having at least two tertiary carbon atoms wherein each said univalent or bivalent radical is joined via said at least one or two tertiary carbon atoms respectively to the appropriate atom $Q^1$ or $Q^2$; and $Q^1$ and $Q^2$ each independently represent phosphorous, arsenic or antimony;

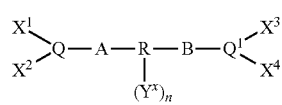
Formula V wherein:

A and B are as identified in formula (IV);

R represents a hydrocarbyl aromatic structure having at least one aromatic ring to which $Q^1$ and $Q^2$ are each linked, via the respective linking group, on available adjacent cyclic atoms of the at least one aromatic ring and which is substituted with one or more substituent(s) $Y^x$ on one or more further aromatic cyclic atom(s) of the aromatic structure;

wherein the substituent(s) $Y^x$ on the aromatic structure has a total $^{X=1-n}\Sigma tY^x$ of atoms other than hydrogen such that $^{X=1-n}\Sigma tY^x$ is $\geq 4$, where n is the total number of substituent(s) $Y^x$ and $tY^x$ represents the total number of atoms other than hydrogen on a particular substituent $Y^x$;

the groups $X^1, X^2, X^3$ and $X^4$ are as defined in formula (IV); and $Q^1$ and $Q^2$ are as defined in formula (IV).

2. A metal complex according to claim 1, wherein the ligand L is a phosphine selected from the group consisting of 1,2-bis-(di-tert-butylphosphinomethyl)benzene, 1,2-bis-(di-tert-pentylphosphinomethyl)benzene, 1,2-bis-(di-tert-butylphosphinomethyl)naphthalene, 1,2bis(diadamantylphosphinomethyl)benzene, 1,2bis(di-3,5-dimethyladamantylphosphinomethyl)benzene, 1,2bis(di-5-tert-butyladamantylphosphinomethyl)benzene, 1,2bis(1-adamantyl tert-butyl-phosphinomethyl)benzene, 1-(diadamantylphosphinomethyl)-2-(di-tert-butylphosphinomethyl)benzene, 1-(di-tert-butylphosphinomethyl)-2-(di-congressylphosphinomethyl)benzene, 1-(di-tert-butylphosphinomethyl)-2-(phospha-adamantyl-P-methyl)benzene, 1-(diadamantylphosphinomethyl)-2-(phospha-adamantyl-P-methyl)benzene, 1-(tert-butyladamantylphosphinomethyl)-2-(di-adamantylphosphinomethyl)benzene and 1-[(P-(2,2,6,6,-tetra-methylphosphinan-4-one)phosphinomethyl)]-2-(phospha-adamantyl-P-methyl)benzene, wherein "phospha-adamantyl" is selected from 2-phospha-1,3,5,7-tetramethyl-6,9,10-trioxadamantyl, 2-phospha-1,3,5-trimethyl-6,9,10trioxadamantyl, 2-phospha-1,3,5,7-tetra(trifluoromethyl)-6,9,10-trioxadamantyl or 2-phospha-1,3,5-tri(trifluoromethyl)-6,9,10-trioxadamantyl; 1,2-bis-(dimethylaminomethyl)ferrocene, 1,2-bis-(ditertbutylphosphinomethyl)ferrocene, 1-hydroxymethyl-2-dimethylaminomethylferrocene, 1,2-bis-(ditertbutylphosphinomethyl)ferrocene, 1-hydroxymethyl-2,3-bis-(dimethylaminomethyl)ferrocene, 1,2,3-tris-(ditertbutylphosphinomethyl)ferrocene, 1,2-bis-(dicyclohexylphosphinomethyl)ferrocene, 1,2-bis-(di-isobutylphosphinomethyl)ferrocene, 1,2-bis-(dicyclopentylphosphinomethyl)ferrocene, 1,2-bis-(diethylphosphinomethyl)ferrocene, 1,2-bis-(di-isopropylphosphinomethyl)ferrocene, 1,2-bis-(dimethylphosphinomethyl)ferrocene, 1,2-bis-(di-(1,3,5,7-tetramethyl-6,9,10-trioxa-2-phospha-adamantylmethyl))ferrocene, 1,2-bis-(dimethylaminomethyl)ferrocene-bismethyl iodide, 1,2-bis(dihydroxymethylphosphinomethyl)ferrocene, 1,2-bis(diphosphinomethyl)ferrocene, 1,2-bis-α,α-(P-(2,2,6,6,-tetramethylphosphinan-4-one))dimethylferrocene, and 1,2-bis-(di-1,3,5,7-tetramethyl-6,9,10-trioxa-2-phospha-adamantylmethyl))benzene; cis-1,2-bis(di-t-butylphosphinomethyl)-4,5-dimethyl cyclohexane; cis-1,2-bis(di-t-butylphosphinomethyl)-5-methylcyclopentane; cis-1,2-bis(2-phosphinomethyl-1,3,5,7-tetramethyl-6,9,10-trioxa-adamantyl)-4,5-dimethylcyclohexane; cis-1,2-bis(2-phosphinomethyl-1,3,5,7-tetramethyl-6,9,10-trioxa-adamantyl) 5-methylcyclopentane; cis-1,2-bis(di-adamantylphosphinomethyl)-4,5dimethylcyclohexane; cis-1,2-bis(di-adamantylphosphinomethyl)-5-methyl cyclopentane; cis-1-(P,P adamantyl, t-butyl phosphinomethyl)-2-(di-t-butylphosphinomethyl)-4,5-dimethylcyclohexane; cis-1-(P,P adamantyl, t-butyl phosphinomethyl)-2-(di-t-butylphosphinomethyl)-5-methylcyclopentane; cis-1-(2-phosphinomethyl-1,3,5,7-tetramethyl-6,9,10-trioxa-adamantyl)-2-(di-t-butylphosphinomethyl)4,5-dimethylcyclohexane; cis-1-(2-phosphinomethyl-1,3,5,7-tetramethyl-6,9,10-trioxa-adamantyl)-2-(di-t-butylphosphinomethyl)-5-methyl cyclopentane; cis-1-(2-phosphinomethyl-1,3,5,7-tetramethyl-6,9,10-trioxa-adamantyl)-2-(diadamantylphosphinomethyl)-5-methyl cyclohexane; cis-1-(2-phosphinomethyl-1,3,5,7-tetramethyl-6,9,10-trioxa-adamantyl)-2-(diadamantylphosphinomethyl)-5-methyl cyclopentane; cis-1-(2-phosphinomethyl-1,3,5,7-tetramethyl-6,9,10-trioxa-adamantyl)-2-(diadamantylphosphinomethyl)cyclobutane; cis-1-(di-t-butylphosphinomethyl)-2-(diadamantylphosphinomethyl)-4,5-dimethyl cyclohexane; cis-1-(di-t-butylphosphinomethyl)-2-(diadamantylphosphinomethyl)-5-methyl cyclopentane; cis-1,2-bis(2-phospha-1,3,5-trimethyl-6,9,10-trioxatricyclo-{3.3.1.1[3.7]}decyl)-4,5-dimethyl cyclohexane; cis-1,2-bis(2-phospha-1,3,5-trimethyl-6,9,10-trioxatricyclo-{3.3.1.1[3 .7]}decyl)-5-methyl cyclopentane; cis-1-(2-phospha-1,3,5-trimethyl-6,9,10-trioxatricyclo-{3.3.1.1[3.7]}decyl)-2-(di-t-butylphosphinomethyl)-4,5-dimethyl cyclohexane; cis-1-(2-phospha-1,3,5-trimethyl-6,9,10-trioxatricyclo-{3.3.1.1[3.7]}decyl)-2-(di-t-butylphosphinomethyl)-5-methyl cyclopentane; cis-1-(2-phospha-1,3,5-trimethyl-6,9,10-trioxatricyclo-{3.3.1.1[3.7]}decyl)-2-(diadamantylphosphinomethyl)-4,5-dimethyl cyclohexane; cis-1-(2-phospha-1,3,5-trimethyl-6,9,10-trioxatricyclo-{3.3.1.1[3.7]}decyl)-2-(diadamantylphosphinomethyl)-5-methyl cyclopentane; cis-1,2-bis-perfluoro(2-phospha-1,3,5,7-tetramethyl-6,9,10-trioxatricyclo{3.3.1.1[3.7]}-decyl)-4,5-dimethyl cyclohexane; cis-1,2-bis-perfluoro(2-phospha-1,3,5,7-tetramethyl-6,9,10-trioxatricyclo{3.3.1.1[3.7]}decyl)-5-methyl cyclopentane; cis-1,2-bis-(2-phospha-1,3,5,7-tetra(trifluoro-methyl)-6,9,10-trioxatricyclo{3.3.1.1[3.7]}decyl)-4,5-dimethyl cyclohexane; cis-1,2-bis-(2-phospha-1,3,5,7-tetra(trifluoro-methyl)-6,9,10-trioxatricyclo{3.3.1.1[3.7]}decyl)-5-methyl cyclopentane; cis-1,2-bis(di-t-butylphosphinomethyl)cyclohexane; cis-1,2-bis(di-t-butylphosphinomethyl)cyclopentane; cis-1,2-bis(di-t-butylphosphinomethyl)cyclobutane; cis-1,2-bis(2-phosphinomethyl-1,3,5,7-tetramethyl-6,9,10-trioxa-adamantyl)cyclohexane; cis-1,2-bis(2-phosphinomethyl-1,3,5,7-tetramethyl-6,9,10-trioxa-adamantyl)cyclopentane; cis-1,2-bis(2-phosphinomethyl-1,3,5,7-tetramethyl-6,9,10-trioxa-adamantyl)cyclobutane; cis-1,2-bis(di-adamantylphosphinomethyl)cyclohexane; cis-1,2-bis(di-adamantylphosphinomethyl)cyclopentane; cis-1,2-bis(di-adamantylphosphinomethyl)cyclobutane; cis-1-(P,P-adamantyl, t-butyl-phosphinomethyl)-2-(di-t-butylphosphinomethyl)cyclohexane; cis-1-(P,P-adamantyl, t-butyl-phosphinomethyl)-2-(di-t-butylphosphinomethyl)cyclopentane; cis-1-(P,P-adamantyl, t-butyl-phosphinomethyl)-2-(di-t-butylphosphinomethyl)cyclobutane; cis-1-(2-phosphinomethyl-1,3,5,7-tetramethyl-6,9, 10-trioxa-adamantyl)-2-(di-t-butylphosphinomethyl)cyclohexane; cis-1-(2-phosphinomethyl-1,3,5,7-tetramethyl-6,9,10-trioxa-adamantyl)-2-(di-t-butylphosphinomethyl)cyclopentane; cis-1-(2-phosphinomethyl-1,3,5,7-tetramethyl-6,9,10-trioxa-adamantyl)-2-(di-t-butylphosphinomethyl)cyclobutane; cis-1-(2-phosphinomethyl-1,3,5,7-tetramethyl-6,9,10-trioxa-adamantyl)-2-(diadamantylphosphinomethyl)cyclohexane; cis-1-(2-phosphinomethyl-1,3,5,7-tetramethyl-6,9,10-trioxa-adamantyl)-2-(diadamantylphosphinomethyl)cyclopentane; cis-1-(2-phosphinomethyl-1,3,5,7-tetramethyl-6,9,10-trioxa-adamantyl)-2-(diadamantylphosphinomethyl)cyclobutane; cis-1-(di-t-butylphosphinomethyl)-2-(diadamantylphosphinomethyl)cyclohexane; cis-1-(di-t-butylphosphinomethyl)-2-(diadamantylphosphinomethyl)cyclopentane; cis-1-(di-t-butylphosphinomethyl)-2-(diadamantylphosphinomethyl)cyclobutane; cis-1,2-bis(2-phospha-1,3,5-trimethyl-6,9,10-trioxatricyclo-{3.3.1.1[3.7]}decyl)cyclohexane; cis-1,2-bis(2-phospha-1,3,5-trimethyl-6,9,10-trioxatricyclo-{3.3.1.1[3.7]}decyl)cyclopentane; cis-1,2-bis(2-phospha-1,3,5-trimethyl-6,9,10-trioxatricyclo-{3.3.1.1[3.7]}decyl)cyclobutane; cis-1-(2-phospha-1,3,5-trimethyl-6,9,10-trioxatricyclo-{3.3.1.1[3.7]}decyl)-2-(di-t-butylphosphinomethyl)cyclohexane; cis-1-2-phospha-1,3,5-trimethyl-6,9,10-trioxatricyclo-{3.3.1.1[3.7]}decyl)-2-(di-t-butylphosphinomethyl)cyclopentane; cis-1-(2-phospha-1,3,5-trimethyl-6,9,10-trioxatricyclo-{3.3.1.1[3.7]}decyl)-2-(di-t-butylphosphinomethyl)cyclobutane; cis-1-(2-phospha-1,3,5-trimethyl-6,9,10-trioxatricyclo-{3.3.1.1[3.7]}decyl)-2-(diadamantylphosphinomethyl)cyclohexane; cis-1-(2-phospha-1,3,5-trimethyl-6,9,10-trioxatricyclo-{3.3.1.1[3.7]}decyl)-2-(diadamantylphosphinomethyl)cyclopentane; cis-1-(2-phospha-1,3,5-trimethyl-6,9,10-trioxatricyclo-{3.3.1.1[3.7]}decyl)-2-(diadamantylphosphinomethyl)cyclobutane; cis-1,2-bis-perfluoro(2-phospha-1,3,5,7-tetramethyl-6,9,10-trioxatricyclo{3.3.1.1[3.7]}-decyl)cyclohexane; cis-1,2-bis-perfluoro(2-phospha-1,3,5,7-tetramethyl-6,9,10-trioxatricyclo{3.3.1.1[3.7]}decyl)cyclopentane; cis-1,2-bis-perfluoro(2-phospha-1,3,5,7-tetramethyl-6,9,10-trioxatricyclo{3.3.1.1[3.7]}decyl)cyclobutane; cis-1,2-bis-(2-phospha-1,3,5,7-tetra(trifluoro-methyl)-6,9,10-trioxatricyclo{3.3.1.1[3.7]}decyl)cyclohexane; cis-1,2-bis-(2-phospha-1,3,5,7-tetra(trifluoro-methyl)-6,9,10-trioxatricyclo{3.3.1.1[3.7]}decyl)cyclopentane; cis-1,2-bis-(2-phospha-1,3,5,7-tetra(trifluoro-methyl)-6,9,10-trioxatricyclo{3.3.1.1[3.7]}decyl)cyclobutane; (2-exo, 3-exo)-bicyclo[2.2.1]heptane-2,3-bis(di-tert-butylphosphinomethyl); (2-endo, 3-endo)-bicyclo[2.2.1]heptane-2,3-bis(di-tert-butylphosphinomethyl); 1,2-bis(di-t-butylphosphinomethyl)-4,5-diphenylbenzene; 1,2-bis(di-t-butylphosphinomethyl)-4-phenylbenzene; 1,2-bis(di-t-butylphosphinomethyl)-4,5-bis(trimethylsilyl)benzene; 1,2-bis(di-t-butylphosphinomethyl)-4-(trimethylsilyl)benzene; 1,2-bis(2-phosphinomethyl-1,3,5,7-tetramethyl-6,9,10-trioxa-adamantyl)-4,5-diphenylbenzene; 1,2-bis(2-phosphinomethyl-1,3,5,7-tetramethyl-6,9,10-trioxa-adamantyl)-4-phenylbenzene; 1,2-bis(2-phosphinomethyl-1,3,5,7-tetramethyl-6,9,10-trioxa-adamantyl)-4,5-bis-(trimethylsilyl)benzene; 1,2-bis(2-phosphinomethyl-1,3,5,7-tetramethyl-6,9,10-trioxa-adamantyl)-4-(trimethylsilyl)benzene; 1,2-bis(di-adamantylphosphinomethyl)-4,5diphenylbenzene; 1,2-bis(di-adamantylphosphinomethyl)-4-phenylbenzene; 1,2-bis(di-adamantylphosphinomethyl)-4,5bis-(trimethylsilyl)benzene; 1,2-bis(di-adamantylphosphinomethyl)-4-(trimethylsilyl)benzene; 1-(P,P adamantyl, t-butyl phosphinomethyl)-2-(di-t-butylphosphinomethyl)-4,5-diphenylbenzene; 1-(P,P adamantyl, t-butyl phosphinomethyl)-2-(di-t-butylphosphinomethyl)-4-phenylbenzene; 1-(P,P adamantyl, t-butyl phosphinomethyl)-2-(di-t-butylphosphinomethyl)-4,5-bis-(trimethylsilyl)benzene; 1-(P,P adamantyl, t-butyl phosphinomethyl)-2-(di-t-butylphosphinomethyl)-4-(trimethylsilyl)benzene; 1-(2-phosphinomethyl-1,3,5,7-tetramethyl-6,9,10-trioxa-adamantyl)-2-(di-t-butylphosphinomethyl)4,5-diphenylbenzene; 1-(2-phosphinomethyl-1,3,5,7-tetramethyl-6,9,10-trioxa-adamantyl)-2-(di-t-butylphosphinomethyl)-4-phenylbenzene; 1-(2-phosphinomethyl-1,3,5,7-tetramethyl-6,9,10-trioxa-adamantyl)-2-(di-t-butylphosphinomethyl)4,5-bis-(trimethylsilyl)benzene; 1-(2-phosphinomethyl-1,3,5,7-tetramethyl-6,9,10-trioxa-adamantyl)-2-(di-t-butylphosphinomethyl)-4-(trimethylsilyl)benzene; 1-(2-phosphinomethyl-1,3,5,7-tetramethyl-6,9,10-trioxa-adamantyl)-2-(diadamantylphosphinomethyl)-4,5-diphenylbenzene; 1-(2-phosphinomethyl-1,3,5,7-tetramethyl-6,9,10-trioxa-adamantyl)-2-(diadamantylphosphinomethyl)-4-phenylbenzene; 1-(2-phosphinomethyl-1,3,5,7-tetramethyl-6,9,10-trioxa-adamantyl)-2-(diadamantylphosphinomethyl)-4,5-bis-(trimethylsilyl)benzene; 1-(2-phosphinomethyl-1,3 5,7-tetramethyl-6,9,10-trioxa-adamantyl)-2-(diadamantylphosphinomethyl)-4-(trimethylsilyl)benzene; 1-(di-t-butylphosphinomethyl)-2-(diadamantylphosphinomethyl)-4,5-diphenylbenzene; 1-(di-t-butylphosphinomethyl)-2-(diadamantylphosphinomethyl)-4-phenylbenzene; 1-(di-t-butylphosphinomethyl)-2-(diadamantylphosphinomethyl)-4,5-bis-(trimethylsilyl)benzene; 1-(di-t-butylphosphinomethyl)-2-(diadamantylphosphinomethyl)-4-(trimethylsilyl)benzene; 1,2-bis(2-phosphinomethyl-1,3,5-trimethyl-6,9,10-trioxatricyclo-{3.3.1.1[3.7]}decyl)-4,5-diphenylbenzene; 1,2-bis(2-phosphinomethyl-1,3,5-trimethyl-6,9,10-trioxatricyclo-{3.3.1.1[3.7]}decyl)-4-phenylbenzene; 1,2-bis(2-phosphinomethyl-1,3,5-trimethyl-6,9,10-trioxatricyclo-{3.3.1.1[3.7]}decyl)-4,5-bis-(trimethylsilyl)benzene; 1,2-bis(2-phosphinomethyl-1,3,5-trimethyl-6,9,10-trioxatricyclo-{3.3.1.1[3.7]}decyl)-4-(trimethylsilyl)benzene; 1-(2-phosphinomethyl-1,3,5-trimethyl-6,9,10-trioxatricyclo-{3.3.1.1[3.7]}decyl)-2-(di-t-butylphosphinomethyl)-4,5-diphenylbenzene; 1-(2-phosphinomethyl-1,3,5-trimethyl-6,9,10-trioxatricyclo-{3.3.1.1[3.7]}decyl)-2-(di-t-butylphosphinomethyl)-4-phenylbenzene; 1-(2-phosphinomethyl-1,3,5-trimethyl-6,9,10-trioxatricyclo-{3.3.1.1[3.7]}decyl)-2-(di-t-butylphosphinomethyl)-4,5-bis-(trimethylsilyl)benzene; 1-(2-phosphinomethyl-1,3,5-trimethyl-6,9,10-trioxatricyclo-{3.3.1.1[3.7]}decyl)-2-(di-t-butylphosphinomethyl)-4-(trimethylsilyl)benzene; 1-(2-phosphinomethyl-1,3,5-trimethyl-6,9,10-trioxatricyclo-{3.3.1.1[3.7]}decyl)-2-(diadamantylphosphinomethyl)-4,5-diphenylbenzene; 1-(2-phosphinomethyl-1,3,5-trimethyl-6,9,10-trioxatricyclo-{3.3.1.1[3.7]}decyl)-2-(diadamantylphosphinomethyl)-4-phenylbenzene; 1-(2-phosphinomethyl-1,3,5-trimethyl-6,9,10-trioxatricyclo-{3.3.1.1[3.7]}decyl)-2-(diadamantylphosphinomethyl)-4,5-bis-(trimethylsilyl)benzene; 1-(2-phosphinomethyl-1,3,5-trimethyl-6,9,10-trioxatricyclo-{3.3.1.1[3.7]}decyl)-2-(diadamantylphosphinomethyl)-4-(trimethylsilyl)benzene; 1,2-bis-perfluoro(2-phosphinomethyl-1,3,5,7-tetramethyl-6,9,10-trioxatricyclo{3.3.1.1[3.7]}-decyl)-4,5-diphenyl benzene; 1,2-bis-perfluoro(2-phosphinomethyl-1,3,5,7-tetramethyl-6,9,10-trioxatricyclo{3.3.1.1[3.7]}decyl)-4-phenylbenzene; 1,2-bis-perfluoro(2-phosphinomethyl-1,3,5,7-tetramethyl-6,9,10-trioxatricyclo{3.3.1.1[3.7]}-decyl)-4,5-bis-(trimethylsilyl)benzene; 1,2-bis-perfluoro(2-phosphinomethyl-1,3,5,7-tetramethyl-6,9,10-trioxatricyclo{3.3.1.1[3.7]}decyl)-4-(trimethylsilyl)benzene; 1,2-bis-(2-phosphinomethyl-1,3,5,7-tetra(trifluoro-methyl)-6,9,10-trioxatricyclo{3.3.1.1[3.7]}decyl)-4,5-diphenylbenzene; 1,2-bis-(2-phosphinomethyl-1,3,5,7-tetra(trifluoro-methyl)-6,9,10-trioxatricyclo{3.3.1.1[3.7]}decyl)-4-phenylbenzene; 1,2-bis-(2-phosphinomethyl-1,3,5,7-tetra(trifluoro-methyl)-6,9,10-trioxatricyclo{3.3.1.1[3.7]}decyl)-4,-bis-(trimethylsilyl)benzene; 1,2-bis-(2-phosphinomethyl-1,3,5,7-tetra(trifluoro-methyl)-6,9,10-trioxatricyclo{3.3.1.1[3.7]}decyl)-4-(trimethylsilyl)benzene; 1,2-bis(di-t-butylphosphinomethyl)-4,5-di-(2'-phenylprop-2'-yl)benzene; 1,2-bis(di-t-butylphosphinomethyl)-4-(2'-phenylprop-2'-yl)benzene; 1,2-bis(di-t-butylphosphinomethyl)-4,5-di-t-butylbenzene; 1,2-bis(di-t-butylphosphinomethyl)-4-t-butylbenzene; 1,2-bis(2-phosphinomethyl-1,3,5,7-tetramethyl-6,9,10-trioxa-adamantyl)-4,5-di-(2'-phenylprop-2'-yl)benzene; 1,2-bis(2-phosphinomethyl-1,3,5,7-tetramethyl-6,9,10-trioxa-adamantyl)-4-(2'-phenylprop-2'-yl)benzene; 1,2-bis(2-phosphinomethyl-1,3,5,7-tetramethyl-6,9,10-trioxa-adamantyl)-4,5-(di-t-butyl)benzene; 1,2-bis(2-phosphinomethyl-1,3,5,7-tetramethyl-6,9,10-trioxa-adamantyl)-4-t-butylbenzene; 1,2-bis(di-adamantylphosphinomethyl)-4,5-di-(2'-phenylprop-2'-yl)benzene; 1,2-bis(di-adamantylphosphinomethyl)-4-(2'-phenylprop-2'-yl)benzene; 1,2-bis(di-adamantylphosphinomethyl)-4,5-(di-t-butyl)benzene; 1,2-bis(di-adamantylphosphinomethyl)-4-t-butylbenzene; 1-(P,P adamantyl, t-butyl phosphinomethyl)-2-(di-t-butylphosphinomethyl)-4,5-di-(2'-phenylprop-2'-yl)benzene; 1-(P,P adamantyl, t-butyl phosphinomethyl)-2-(di-t-butylphosphinomethyl)-4-(2'-phenylprop-2'-yl)benzene; 1-(P,P adamantyl, t-butyl phosphinomethyl)-2-(di-t-butylphosphinomethyl)-4,5-(di-t-butyl)benzene; 1-(P,P adamantyl, t-butyl phosphinomethyl)-2-(di-t-butylphosphinomethyl)-4-t-butylbenzene; 1-(2-phosphinomethyl-1,3,5,7-tetramethyl-6,9,10-trioxa-adamantyl)-2-(di-t-butylphosphinomethyl)4,5-di-(2'-phenylprop-2'-yl)benzene; 1-(2-phosphinomethyl-1,3,5,7-tetramethyl-6,9,10-trioxa-adamantyl)-2-(di-t-butylphosphinomethyl)-4-(2'-phenylprop-2'-yl)benzene; 1-(2-phosphinomethyl-1,3,5,7-tetramethyl-6,9,10-trioxa-adamantyl)-2-(di-t-butylphosphinomethyl)4,5-(di-t-butyl)benzene; 1-(2-phosphinomethyl-1,3 5,7-tetramethyl-6,9,10-trioxa-adamantyl)-2-(di-t-butylphosphinomethyl)-4-t-butylbenzene; 1-(2-phosphinomethyl-1,3,5,7-tetramethyl-6,9,10-trioxa-adamantyl)-2-(diadamantylphosphinomethyl)-4,5-di-(2'-phenylprop-2'-yl)benzene; 1-(2-phosphinomethyl-1,3,5,7-tetramethyl-6,9,10-trioxa-adamantyl)-2-(diadamantylphosphinomethyl)-4-(2'-phenylprop-2'-yl)benzene; 1-(2-phosphinomethyl-1,3,5,7-tetramethyl-6,9,10-trioxa-adamantyl)-2-(diadamantylphosphinomethyl)-4,5-(di-t-butyl)benzene; 1-(2-phosphinomethyl-1,3,5,7-tetramethyl-6,9,10-trioxa-adamantyl)-2-(diadamantylphosphinomethyl)-4-t-butylbenzene; 1-(di-t-butylphosphinomethyl)-2-(diadamantylphosphinomethyl)-4,5-di-(2'-phenylprop-2'-yl)benzene; 1-(di-t-butylphosphinomethyl)-2-(diadamantylphosphinomethyl)-4-(2'-phenylprop-2'-yl)benzene; 1-(di-t-butylphosphinomethyl)-2-(diadamantylphosphinomethyl)-4,5-(di-t-butyl)benzene; 1-(di-t-butylphosphinomethyl)-2-(diadamantylphosphinomethyl)-4-t-butylbenzene; 1,2-bis(2-phosphinomethyl-1,3,5-trimethyl-6,9,10-trioxatricyclo-{3.3.1.1[3.7]}decyl)-4,5-di-(2'-phenylprop-2'-yl)benzene; 1,2-bis(2-phosphinomethyl-1,3,5-trimethyl-6,9,10-trioxatricyclo-{3.3.1.1[3.7]}decyl)-4-(2'-phenylprop-2'-yl)benzene; 1,2-bis(2-phosphinomethyl-1,3,5-trimethyl-6,9,10-trioxatricyclo-{3.3.1.1[3.7]}decyl)-4,5-(di-t-butyl)benzene; 1,2-bis(2-phosphinomethyl-1,3,5-trimethyl-6,9,10-trioxatricyclo-{3.3.1.1[3.7]}decyl)-4-t-butylbenzene; 1-(2-phosphinomethyl-1,3,5-trimethyl-6,9,10-trioxatricyclo-{3.3.1.1[3.7]}decyl)-2-(di-t-butylphosphinomethyl)-4,5-di-(2'-phenylprop-2'-yl)benzene; 1-(2-phosphinomethyl-1,3,5-trimethyl-6,9,10-trioxatricyclo-{3.3.1.1[3.7]}decyl)-2-(di-t-butylphosphinomethyl)-4-(2'-phenylprop-2'-yl)benzene; 1-(2-phosphinomethyl-1,3,5-trimethyl-6,9,10-trioxatricyclo-{3.3.1.1[3.7]}decyl)-2-(di-t-butylphosphinomethyl)-4,5-(di-t-butyl)benzene; 1-(2-phosphinomethyl-1,3,5-trimethyl-6,9,10-trioxatricyclo-{3.3.1.1[3.7]}decyl)-2-(di-t-butylphosphinomethyl)-4-t-butylbenzene; 1-(2-phosphinomethyl-1,3,5-trimethyl-6,9,10-trioxatricyclo-{3.3.1.1[3.7]}decyl)-2-(diadamantylphosphinomethyl)-4,5-di-(2'-phenylprop-2'-yl)benzene; 1-(2-phosphinomethyl-1,3,5-trimethyl-6,9,10-trioxatricyclo-{3.3.1.1[3.7]}decyl)-2-(diadamantylphosphinomethyl)-4-(2'-phenylprop-2'-yl)benzene; 1-(2-phosphinomethyl-1,3,5-trimethyl-6,9,10-trioxatricyclo-{3.3.1.1[3.7]}decyl)-2-(diadamantylphosphinomethyl)-4,5-(di-t-butyl)benzene; 1-(2-phosphinomethyl-1,3,5-trimethyl-6,9,10-trioxatricyclo-{3.3.1.1[3.7]}decyl)-2-(diadamantylphosphinomethyl)-4-t-butylbenzene; 1,2-bis-perfluoro(2-phosphinomethyl-1,3,5,7-tetramethyl-6,9,10-trioxatricyclo{3.3.1.1[3.7]}-decyl)-4,5-di-(2'-phenylprop-2'-yl)benzene; 1,2-bis-perfluoro(2-phosphinomethyl-1,3,5,7-tetramethyl-6,9,10-trioxatricyclo{3.3.1.1[3.7]}decyl)-4-(2'-phenylprop-2'-yl)benzene; 1,2-bis-perfluoro(2-phosphinomethyl-1,3,5,7-tetramethyl-6,9,10-trioxatricyclo{3.3.1.1[3.7]}-decyl)-4,5-(di-t-butyl)benzene; 1,2-bis-perfluoro(2-phosphinomethyl-1,3,5,7-tetramethyl-6,9,10-trioxatricyclo{3.3.1.1[3.7]}decyl)-4-t-butylbenzene; 1,2-bis-(2-phosphinomethyl-1,3,5,7-tetra(trifluoro-methyl)-6,9,10-trioxatricyclo{3.3.1.1[3.7]}decyl)-4,5-di-(2'-phenylprop-2'-yl)benzene; 1,2-bis-(2-phosphinomethyl-1,3,5,7-tetra(trifluoro-methyl)-6,9,10-trioxatricyclo{3.3.1.1[3.7]}decyl)-4-(2'-phenylprop-2'-yl)benzene; 1,2-bis-(2-phosphinomethyl-1,3,5,7-tetra(trifluoro-methyl)-6,9,10-trioxatricyclo{3.3.1.1[3.7]}decyl)-4,5-(di-t-butyl)benzene; 1,2-bis-(2-phosphinomethyl-1,3,5,7-tetra(trifluoro-methyl)-6,9,10-trioxatricyclo{3.3.1.1[3.7]}decyl)-4-t-butylbenzene; 1,2-bis(di-t-butylphosphinomethyl)-4,5-diphenylferrocene; 1,2-bis(di-t-butylphosphinomethyl)-4-(or 1')phenylferrocene; 1,2-bis(di-t-butylphosphinomethyl)-4,5-bis-(trimethylsilyl)ferrocene; 1,2-bis(di-t-butylphosphinomethyl)-4-(or 1')(trimethylsilyl)ferrocene; 1,2-bis(2-phosphinomethyl-1,3,5,7-tetramethyl-6,9,10-trioxa-adamantyl)-4,5-diphenylferrocene; 1,2-bis(2-phosphinomethyl-1,3,5,7-tetramethyl-6,9,10-trioxa-adamantyl) 4-(or 1')phenylferrocene; 1,2-bis(2-phosphinomethyl-1,3,5,7-tetramethyl-6,9,10-trioxa-adamantyl)-4,5-bis-(trimethylsilyl)ferrocene; 1,2-bis(2-phosphinomethyl-1,3,5,7-tetramethyl-6,9,10-trioxa-adamantyl)4-(or 1')(trimethylsilyl)ferrocene; 1,2-bis(di-adamantylphosphinomethyl)-4,5diphenylferrocene; 1,2-bis(di-adamantylphosphinomethyl)-4-(or 1')phenylferrocene; 1,2-bis(di-adamantylphosphinomethyl)-4,5bis-(trimethylsilyl)ferrocene; 1,2-bis(di-adamantylphosphinomethyl)-4-(or 1')(trimethylsilyl)ferrocene; 1-(P,P adamantyl, t-butyl phosphinomethyl)-2-(di-t-butylphosphinomethyl)-4,5-diphenylferrocene; 1-(P,P adamantyl, t-butyl phosphinomethyl)-2-(di-t-butylphosphinomethyl)-4-(or 1')phenylferrocene; 1-(P,P adamantyl, t-butyl phosphinomethyl)-2-(di-t-butylphosphinomethyl)-4,5-bis-(trimethylsilyl)ferrocene; 1-(P,P adamantyl, t-butyl phosphinomethyl)-2-(di-t-butylphosphinomethyl)-4-(or 1')(trimethylsilyl)ferrocene; 1-(2-phosphinomethyl-1,3,5,7-tetramethyl-6,9,10-trioxa-adamantyl)-2-(di-t-butylphosphinomethyl)4,5-diphenylferrocene; 1-(2-phosphinomethyl-1,3,5,7-tetramethyl-6,9,10-trioxa-adamantyl)-2-(di-t-butylphosphinomethyl)-4-(or 1')phenylferrocene; 1-(2-phosphinomethyl-1,3,5,7-tetramethyl-6,9,10-trioxa-adamantyl)-2-(di-t-butylphosphinomethyl)4,5-bis-(trimethylsilyl)ferrocene; 1-(2-phosphinomethyl-1,3,5,7- tetramethyl-6,9,10-trioxa-adamantyl)-2-(di-t-butylphosphinomethyl)-4-(or 1')(trimethylsilyl)ferrocene; 1-(2-phosphinomethyl-1,3,5,7-tetramethyl-6,9,10-trioxa-adamantyl)-2-(diadamantylphosphinomethyl)-4,5-diphenylferrocene; 1-(2-phosphinomethyl-1,3,5,7-tetramethyl-6,9,10-trioxa-adamantyl)-2-(diadamantylphosphinomethyl)-4-(or 1')phenylferrocene; 1-(2-phosphinomethyl-1,3,5,7-tetramethyl-6,9,10-trioxa-adamantyl)-2-(diadamantylphosphinomethyl)-4,5-bis-(trimethylsilyl)ferrocene; 1-(2-phosphinomethyl-1,3,5,7-tetramethyl-6,9,10-trioxa-adamantyl)-2-(diadamantylphosphinomethyl)-4-(or 1')(trimethylsilyl)ferrocene; 1-(di-t-butylphosphinomethyl)-2-(diadamantylphosphinomethyl)-4,5-diphenylferrocene; 1-(di-t-butylphosphinomethyl)-2-(diadamantylphosphinomethyl)-4-(or 1')phenylferrocene; 1-(di-t-butylphosphinomethyl)-2-(diadamantylphosphinomethyl)-4,5-bis-(trimethylsilyl)ferrocene; 1-(di-t-butylphosphinomethyl)-2-(diadamantylphosphinomethyl)-4-(or 1')(trimethylsilyl)ferrocene; 1,2-bis(2-phosphinomethyl-1,3,5-trimethyl-6,9,10-trioxatricyclo-{3.3.1.1[3.7]}decyl)-4,5-diphenylferrocene; 1,2-bis(2-phosphinomethyl-1,3,5-trimethyl-6,9,10-trioxatricyclo-{3.3.1.1[3.7]}decyl)-4-(or 1')phenylferrocene; 1,2-bis(2-phosphinomethyl-1,3,5-trimethyl-6,9,10-trioxatricyclo-{3.3.1.1[3.7]}decyl)-4,5-bis-(trimethylsilyl)ferrocene; 1,2-bis(2-phosphinomethyl-1,3,5-trimethyl-6,9,10-trioxatricyclo-{3.3.1.1[3.7]}decyl)-4-(or 1')(trimethylsilyl)ferrocene; 1-(2-phosphinomethyl-1,3,5-trimethyl-6,9,10-trioxatricyclo-{3.3.1.1[3.7]}decyl)-2-(di-t-butylphosphinomethyl)-4,5-diphenylferrocene; 1-(2-phosphinomethyl-1,3,5-trimethyl-6,9,10-trioxatricyclo-{3.3.1.1[3.7]}decyl)-2-(di-t-butylphosphinomethyl)-4-(or 1')phenylferrocene; 1-(2-phosphinomethyl-1,3,5-trimethyl-6,9,10-trioxatricyclo-{3.3.1.1[3.7]}decyl)-2-(di-t-butylphosphinomethyl)-4,5-bis-(trimethylsilyl)ferrocene; 1-(2-phosphinomethyl-1,3,5-trimethyl-6,9,10-trioxatricyclo-{3.3.1.1[3.7]}decyl)-2-(di-t-butylphosphinomethyl)-4-(or 1')(trimethylsilyl)ferrocene; 1-(2-phosphinomethyl-1,3,5-trimethyl-6,9,10-trioxatricyclo-{3.3.1.1[3.7]}decyl)-2-(diadamantylphosphinomethyl)-4,5-diphenylferrocene; 1-(2-phosphinomethyl-1,3,5-trimethyl-6,9,10-trioxatricyclo-{3.3.1.1[3.7]}decyl)-2-(diadamantylphosphinomethyl)-4-(or 1')phenylferrocene; 1-(2-phosphinomethyl-1,3,5-trimethyl-6,9,10-trioxatricyclo-{3.3.1.1[3.7]}decyl)-2-(diadamantylphosphinomethyl)-4,5-bis-(trimethylsilyl)ferrocene; 1-(2-phosphinomethyl-1,3,5-trimethyl-6,9,10-trioxatricyclo-{3.3.1.1[3.7]}decyl)-2-diadamantylphosphinomethyl)-4-(or 1')(trimethylsilyl)ferrocene; 1,2-bis-perfluoro(2-phosphinomethyl-1,3,5,7-tetramethyl-6,9,10-trioxatricyclo{3.3.1.1[3.7]}-decyl)-4,5-diphenylferrocene; 1,2-bis-perfluoro(2-phosphinomethyl-1,3,5,7-tetramethyl-6,9,10-trioxatricyclo{3.3.1.1[3.7]}decyl)-4-(or 1')phenylferrocene; 1,2-bis-perfluoro(2-phosphinomethyl-1,3,5,7-tetramethyl-6,9,10-trioxatricyclo{3.3.1.1[3.7]}-decyl)-4,5-bis-(trimethylsilyl)ferrocene; 1,2-bis-perfluoro(2-phosphinomethyl-1,3,5,7-tetramethyl-6,9,10-trioxatricyclo{3.3.1.1[3.7]}decyl)-4-(or 1')(trimethylsilyl)ferrocene; 1,2-bis-(2-phosphinomethyl-1,3,5,7-tetra(trifluoro-methyl)-6,9,10-trioxatricyclo{3.3.1.1[3.7]}decyl)-4,5-diphenylferrocene; 1,2-bis-(2-phosphinomethyl-1,3,5,7-tetra(trifluoro-methyl)-6,9,10-trioxatricyclo{3.3.1.1[3.7]}decyl)-4-(or 1')phenylferrocene; 1,2-bis-(2-phosphinomethyl-1,3,5,7-tetra(trifluoro-methyl)-6,9,10-trioxatricyclo{3.3.1.1[3.7]}decyl)-4,5-bis-(trimethylsilyl)ferrocene; 1,2-bis-(2-phosphinomethyl-1,3,5,7-tetra(trifluoro-methyl)-6,9,10-trioxatricyclo{3.3.1.1[3.7]}decyl)-4-(or 1')(trimethylsilyl)ferrocene; 1,2-bis(di-t-butylphosphinomethyl)-4,5-di-(2'-phenylprop-2'-yl)ferrocene; 1,2-bis(di-t-butylphosphinomethyl)-4-(or 1')(2'-phenylprop-2'-yl)ferrocene; 1,2-bis(di-t-butylphosphinomethyl)-4,5-di-t-butylferrocene; 1,2-bis(di-t-butylphosphinomethyl)-4-(or 1')t-butylferrocene; 1,2-bis(2-phosphinomethyl-1,3,5,7-tetramethyl-6,9,10-trioxa-adamantyl)-4,5-di-(2'-phenylprop-2'-yl)ferrocene; 1,2-bis(2-phosphinomethyl-1,3,5,7-tetramethyl-6,9,10-trioxa-adamantyl)-4-(or 1')(2'-phenylprop-2'-yl)ferrocene; 1,2-bis(2-phosphinomethyl-1,3,5,7-tetramethyl-6,9,10-trioxa-adamantyl)-4,5-(di-t-butyl)ferrocene; 1,2-bis(2-phosphinomethyl-1,3,5,7-tetramethyl-6,9,10-trioxa-adamantyl)-4-(or 1')t-butylferrocene; 1,2-bis(di-adamantylphosphinomethyl)-4,5-di-(2'-phenylprop-2'-yl)ferrocene; 1,2-bis(di-adamantylphosphinomethyl)-4-(or 1')(2'-phenylprop-2'-yl)ferrocene; 1,2-bis(di-adamantylphosphinomethyl)-4,5-(di-t-butyl)ferrocene; 1,2-bis(di-adamantylphosphinomethyl)-4-(or 1')t-butylferrocene; 1-(P,P adamantyl, t-butyl phosphinomethyl)-2-(di-t-butylphosphinomethyl)-4,5-di-(2'-phenylprop-2'-yl)ferrocene; 1-(P,P adamantyl, t-butyl phosphinomethyl)-2-(di-t-butylphosphinomethyl)-4-(or 1')(2'-phenylprop-2'-yl)ferrocene; 1-(P,P adamantyl, t-butyl phosphinomethyl)-2-(di-t-butylphosphinomethyl)-4,5-(di-t-butyl)ferrocene; 1-(P,P adamantyl, t-butyl phosphinomethyl)-2-(di-t-butylphosphinomethyl)-4-(or 1')t-butylferrocene; 1-(2-phosphinomethyl-1,3,5,7-tetramethyl-6,9,10-trioxa-adamantyl)-2-di-t-butylphosphinomethyl)4,5-di-(2'-phenylprop-2'-yl)ferrocene; 1-(2-phosphinomethyl-1,3,5,7-tetramethyl-6,9,10-trioxa-adamantyl)-2-(di-t-butylphosphinomethyl)-4-(or 1')(2'-phenylprop-2'-yl)ferrocene; 1-(2-phosphinomethyl-1,3,5,7-tetramethyl-6,9,10-trioxa-adamantyl)-2-(di-t-butylphosphinomethyl)4,5-(di-t-butyl)ferrocene; 1-(2-phosphinomethyl-1,3,5,7-tetramethyl-6,9,10-trioxa-adamantyl)-2-(di-t-butylphosphinomethyl)-4-(or 1')t-butylferrocene; 1-(2-phosphinomethyl-1,3,5,7-tetramethyl-6,9,10-trioxa-adamantyl)-2-(diadamantylphosphinomethyl)-4,5-di-(2'-phenylprop-2'-yl)ferrocene; 1-(2-phosphinomethyl-1,3,5,7-tetramethyl-6,9,10-trioxa-adamantyl)-2-(diadamantylphosphinomethyl)-4-(or 1')(2'-phenylprop-2'-yl)ferrocene; 1-(2-phosphinomethyl-1,3,5,7-tetramethyl-6,9,10-trioxa-adamantyl)-2-(diadamantylphosphinomethyl)-4,5-(di-t-butyl)ferrocene; 1-(2-phosphinomethyl-1,3,5,7-tetramethyl-6,9,10-trioxa-adamantyl)-2-(diadamantylphosphinomethyl)-4-(or 1')t-butylferrocene; 1-(di-t-butylphosphinomethyl)-2-(diadamantylphosphinomethyl)-4,5-di-(2'-phenylprop-2'-yl)ferrocene; 1-(di-t-butylphosphinomethyl)-2-(diadamantylphosphinomethyl)-4-(or 1')(2'-phenylprop-2'-yl)ferrocene; 1-(di-t-butylphosphinomethyl)-2-(diadamantylphosphinomethyl)-4,5-(di-t-butyl)ferrocene; 1-(di-t-butylphosphinomethyl)-2-(diadamantylphosphinomethyl)-4-(or 1')t-butylferrocene; 1,2-bis(2-phosphinomethyl-1,3,5-trimethyl-6,9,10-trioxatricyclo-{3.3.1.1[3.7]}decyl)-4,5-di-(2'-phenylprop-2'-yl)ferrocene; 1,2-bis(2-phosphinomethyl-1,3,5-trimethyl-6,9,10-trioxatricyclo-{3.3.1.1[3.7]}decyl)-4-(or 1')(2'-phenylprop-2'-yl)ferrocene; 1,2-bis(2-phosphinomethyl-1,3,5-trimethyl-6,9,10-trioxatricyclo-{3.3.1.1[3.7]}decyl)-4,5-(di-t-butyl)ferrocene; 1,2-bis(2-phosphinomethyl-1,3,5-trimethyl-6,9,10-trioxatricyclo-{3.3.1.1[3.7]}decyl)-4-(or 1')t-butylferrocene; 1-(2-phosphinomethyl-1,3,5-trimethyl-6,9,10-trioxatricyclo-{3.3.1.1[3.7]}decyl)-2-(di-t-butylphosphinomethyl)-4,5-di-(2'-phenylprop-2'-yl)ferrocene; 1-(2-phosphinomethyl-1,3,5-trimethyl-6,9,10-trioxatricyclo-{3.3.1.1[3.7]}decyl)-2-(di-t-butylphosphinomethyl)-4-(or 1')(2'-phenylprop-2'-yl)ferrocene; 1-(2-phosphinomethyl-1,3,5-trimethyl-6,9,10- trioxatricyclo-{3.3.1.1[3.7]}decyl)-2-(di-t-butylphosphinomethyl)-4,5-(di-t-butyl)ferrocene; 1-(2-phosphinomethyl-1,3,5-trimethyl-6,9,10-trioxatricyclo-{3.3.1.1[3.7]}decyl)-2-(di-t-butylphosphinomethyl)-4-(or 1')t-butylferrocene; 1-(2-phosphinomethyl-1,3,5-trimethyl-6,9,10-trioxatricyclo-{3.3.1.1[3.7]}decyl)-2-(diadamantylphosphinomethyl)-4,5-di-(2'-phenylprop-2'-yl)ferrocene; 1-(2-phosphinomethyl-1,3,5-trimethyl-6,9,10-trioxatricyclo-{3.3.1.1[3.7]}decyl)-2-(diadamantylphosphinomethyl)-4-(or 1')(2'-phenylprop-2'-yl)ferrocene; 1-(2-phosphinomethyl-1,3,5-trimethyl-6,9,10-trioxatricyclo-{3.3.1.1[3.7]}decyl)-2-(diadamantylphosphinomethyl)-4,5-(di-t-butyl)ferrocene; 1-(2-phosphinomethyl-1,3,5-trimethyl-6,9,10-trioxatricyclo-{3.3.1.1[3.7]}decyl)-2-(diadamantylphosphinomethyl)-4-(or 1')t-butylferrocene; 1,2-bis-perfluoro(2-phosphinomethyl-1,3,5,7-tetramethyl-6,9,10-trioxatricyclo{3.3.1.1[3.7]}-decyl)-4,5-di-(2'-phenylprop-2'-yl)ferrocene; 1,2-bis-perfluoro(2-phosphinomethyl-1,3,5,7-tetramethyl-6,9,10-trioxatricyclo{3.3.1.1[3.7]}decyl)-4-(or 1')(2'-phenylprop-2'-yl)ferrocene; 1,2-bis-perfluoro(2-phosphinomethyl-1,3,5,7-tetramethyl-6,9,10-trioxatricyclo{3.3.1.1[3.7]}-decyl)-4,5-(di-t-butyl)ferrocene; 1,2-bis-perfluoro(2-phosphinomethyl-1,3,5,7-tetramethyl-6,9,10-trioxatricyclo{3.3.1.1[3.7]}decyl)-4-(or 1')t-butylferrocene; 1,2-bis-(2-phosphinomethyl-1,3,5,7-tetra(trifluoro-methyl)-6,9,10-trioxatricyclo{3.3.1.1[3.7]}decyl)-4,5-di-(2'-phenylprop-2'-yl)ferrocene; 1,2-bis-(2-phosphinomethyl-1,3,5,7-tetra(trifluoro-methyl)-6,9,10-trioxatricyclo{3.3.1.1[3.7]}decyl)-4-(or 1')(2'-phenylprop-2'-yl)ferrocene; 1,2-bis-(2-phosphinomethyl-1,3,5,7-tetra(trifluoro-methyl)-6,9,10-trioxatricyclo{3.3.1.1[3.7]}decyl)-4,5-(di-t-butyl)ferrocene; and 1,2-bis-(2-phosphinomethyl-1,3,5,7-tetra(trifluoro-methyl)-6,9,10-trioxatricyclo{3.3.1.1[3.7]}decyl)-4-(or 1')t-butylferrocene.

3. A catalyst system capable of carbonylating an ethylenically unsaturated compound comprising a metal complex according to claim 1.

4. A process for the preparation of a metal complex according to claim 1, comprising reacting an amine compound of metal M with a complexing compound of formula L as defined in claim 1.

5. A metal complex as claimed in claim 1, wherein said metal M comprises a precious metal selected from Ru, Rh, Os, Ir, Pt and Pd.

6. A metal complex as claimed in claim 5, wherein said metal M comprises Ru, Pt or Pd.

7. A process as claimed in claim 4, wherein said phosphine is selected from the group consisting of 1,2-bis-(di-tert-butylphosphinomethyl)benzene, 1,2-bis-(di-tert-pentylphosphinomethyl)benzene, 1,2-bis-(di-tert-butylphosphinomethyl)naphthalene, 1,2bis(diadamantylphosphinomethyl)benzene, 1,2bis(di-3,5-dimethyladamantylphosphinomethyl)benzene, 1,2bis(di-5-tert-butyladamantylphosphinomethyl)benzene, 1,2bis(1-adamantyl tert-butyl-phosphinomethyl)benzene, 1-(diadamantylphosphinomethyl)-2-(di-tert-butylphosphinomethyl)benzene, 1-(di-tert-butylphosphinomethyl)-2-(di-congressylphosphinomethyl)benzene, 1-(di-tert-butylphosphinomethyl)-2-(phospha-adamantyl-P-methyl)benzene, 1-(diadamantylphosphinomethyl)-2-(phospha-adamantyl-P-methyl)benzene, 1-(tert-butyladamantylphosphinomethyl)-2-(di-adamantylphosphinomethyl)benzene and 1-[(P-(2,2,6,6,-tetra-methylphosphinan-4-one)phosphinomethyl)]-2-(phospha-adamantyl-P-methyl)benzene, wherein "phospha-adamantyl" is selected from 2-phospha-1,3,5,7-tetramethyl-6,9,10-trioxadamantyl, 2-phospha-1,3,5-trimethyl-6,9,10trioxadamantyl, 2-phospha-1,3,5,7-tetra(trifluoromethyl)-6,9,10-trioxadamantyl or 2-phospha-1,3,5-tri(trifluoromethyl)-6,9,10-trioxadamantyl; 1,2-bis-(dimethylaminomethyl)ferrocene, 1,2-bis-(ditertbutylphosphinomethyl)ferrocene, 1-hydroxymethyl-2-dimethylaminomethylferrocene, 1,2-bis-(ditertbutylphosphinomethyl)ferrocene, 1-hydroxymethyl-2,3-bis-(dimethylaminomethyl)ferrocene, 1,2,3-tris-(ditertbutylphosphinomethyl)ferrocene, 1,2-bis-(dicyclohexylphosphinomethyl)ferrocene, 1,2-bis-(di-isobutylphosphinomethyl)ferrocene, 1,2-bis-(dicyclopentylphosphinomethyl)ferrocene, 1,2-bis-(diethylphosphinomethyl)ferrocene, 1,2-bis(di-isopropylphosphinomethyl)ferrocene, 1,2-bis-(dimethylphosphinomethyl)ferrocene, 1,2-bis-(di-(1,3,5,7-tetramethyl-6,9,10-trioxa-2-phospha-adamantylmethyl))ferrocene, 1,2-bis-(dimethylaminomethyl)ferrocene-bismethyl iodide, 1,2-bis(dihydroxymethylphosphinomethyl)ferrocene,1,2-bis(diphosphinomethyl)ferrocene, 1,2-bis-α,α-(P-(2,2,6,6,-tetramethylphosphinan-4-one))dimethylferrocene, and 1,2-bis-(di-1,3,5,7-tetramethyl-6,9,10-trioxa-2-phospha-adamantylmethyl))benzene; cis-1,2-bis(di-t-butylphosphinomethyl)-4,5-dimethylcyclohexane; cis-1,2-bis(di-t-butylphosphinomethyl)-5-methylcyclopentane; cis-1,2-bis(2-phosphinomethyl-1,3,5,7-tetramethyl-6,9,10-trioxa-adamantyl)-4,5-dimethylcyclohexane; cis-1,2-bis(2-phosphinomethyl-1,3,5,7-tetramethyl-6,9,10-trioxa-adamantyl)5-methylcyclopentane; cis-1,2-bis(di-adamantylphosphinomethyl)-4,5dimethylcyclohexane; cis-1,2-bis(di-adamantylphosphinomethyl)-5-methylcyclopentane; cis-1-(P,P adamantyl, t-butyl phosphinomethyl)-2-(di-t-butylphosphinomethyl)-4,5-dimethylcyclohexane; cis-1-(P,P adamantyl, t-butyl phosphinomethyl)-2-(di-t-butylphosphinomethyl)-5-methylcyclopentane; cis-1-(2-phosphinomethyl-1,3,5,7-tetramethyl-6,9,10-trioxa-adamantyl)-2-(di-t-butylphosphinomethyl)4,5-dimethylcyclohexane; cis-1-(2-phosphinomethyl-1,3,5,7-tetramethyl-6,9,10-trioxa-adamantyl)-2-(di-t-butylphosphinomethyl)-5-methylcyclopentane; cis-1-(2-phosphinomethyl-1,3,5,7-tetramethyl-6,9,10-trioxa-adamantyl)-2-(diadamantylphosphinomethyl)-5-methylcyclohexane; cis-1-(2-phosphinomethyl-1,3,5,7-tetramethyl-6,9,10-trioxa-adamantyl)-2-(diadamantylphosphinomethyl)-5-methylcyclopentane; cis-1-(2-phosphinomethyl-1,3,5,7-tetramethyl-6,9,10-trioxa-adamantyl)-2-(diadamantylphosphinomethyl)cyclobutane; cis-1-(di-t-butylphosphinomethyl)-2-(diadamantylphosphinomethyl)-4,5-dimethylcyclohexane; cis-1-(di-t-butylphosphinomethyl)-2-(diadamantylphosphinomethyl)-5-methylcyclopentane; cis-1,2-bis(2-phospha-1,3,5-trimethyl-6,9,10-trioxatricyclo-{3.3.1.1[3.7]}decyl)-4,5-dimethylcyclohexane; cis-1,2-bis(2-phospha-1,3,5-trimethyl-6,9,10-trioxatricyclo-{3.3.1.1[3.7]}decyl)-5-methylcyclopentane; cis-1-(2-phospha-1,3,5-trimethyl-6,9,10-trioxatricyclo-{3.3.1.1[3.7]}decyl)-2-(di-t-butylphosphinomethyl)-4,5-dimethylcyclohexane; cis-1-(2-phospha-1,3,5-trimethyl-6,9,10-trioxatricyclo-{3.3.1.1[3.7]}decyl)-2-(di-t-butylphosphinomethyl)-5-methylcyclopentane; cis-1-(2-phospha-1,3,5-trimethyl-6,9,10-trioxatricyclo-{3.3.1.1[3.7]}decyl)-2-(diadamantylphosphinomethyl)-4,5-dimethylcyclohexane; cis-1-(2-phospha-1,3,5-trimethyl-6,9,10-trioxatricyclo-{3.3.1.1[3.7]}decyl)-2-(diadamantylphosphinomethyl)-5-methylcyclopentane; cis-1,2-bis-perfluoro(2-phospha-1,3,5,7-tetramethyl-6,9,10-trioxatricyclo{3.3.1.1[3.7]}-decyl)-4,5-dimethylcyclohexane; cis-1,2-bis-perfluoro(2-phospha-1,3, 5,7-tetramethyl-6,9,10-trioxatricyclo{3.3.1.1[3.7]}decyl)-5-methylcyclopentane; cis-1,2-bis-(2-phospha-1,3,5,7-tetra(trifluoro-methyl)-6,9,10-trioxatricyclo{3.3.1.1[3.7]}decyl)-4,5-dimethylcyclohexane; cis-1,2-bis-(2-phospha-1,3,5,7-tetra(trifluoro-methyl)-6,9,10-trioxatricyclo{3.3.1.1[3.7]}decyl)-5-methylcyclopentane; cis-1,2-bis(di-t-butylphosphinomethyl)cyclohexane; cis-1,2-bis(di-t-butylphosphinomethyl)cyclopentane; cis-1,2-bis(di-t-butylphosphinomethyl)cyclobutane; cis-1,2-bis(2-phosphinomethyl-1,3,5,7-tetramethyl-6,9,10-trioxa-adamantyl)cyclohexane; cis-1,2-bis(2-phosphinomethyl-1,3,5,7-tetramethyl-6,9,10-trioxa-adamantyl)cyclopentane; cis-1,2-bis(2-phosphinomethyl-1,3,5,7-tetramethyl-6,9,10-trioxa-adamantyl)cyclobutane; cis-1,2-bis (di-adamantylphosphinomethyl)cyclohexane; cis-1,2-bis(di-adamantylphosphinomethyl)cyclopentane; cis-1,2-bis(di-adamantylphosphinomethyl)cyclobutane; cis-1-(P,P-adamantyl, t-butyl-phosphinomethyl)-2-(di-t-butylphosphinomethyl)cyclohexane; cis-1-(P,P-adamantyl, t-butyl-phosphinomethyl)-2-(di-t-butylphosphinomethyl)cyclopentane; cis-1-(P,P-adamantyl, t-butyl-phosphinomethyl)-2-(di-t-butylphosphinomethyl)cyclobutane; cis-1-(2-phosphinomethyl-1,3,5,7-tetramethyl-6,9,10-trioxa-adamantyl)-2-(di-t-butylphosphinomethyl)cyclohexane; cis-1-(2-phosphinomethyl-1,3,5,7-tetramethyl-6,9,10-trioxa-adamantyl)-2-(di-t-butylphosphinomethyl)cyclopentane; cis-1-(2-phosphinomethyl-1,3,5,7-tetramethyl-6,9,10-trioxa-adamantyl)-2-(di-t-butylphosphinomethyl)cyclobutane; cis-1-(2-phosphinomethyl-1,3,5,7-tetramethyl-6,9,10-trioxa-adamantyl)-2-(diadamantylphosphinomethyl)cyclohexane; cis-1-(2-phosphinomethyl-1,3,5,7-tetramethyl-6,9,10-trioxa-adamantyl)-2-(diadamantylphosphinomethyl)cyclopentane; cis-1-(2-phosphinomethyl-1,3,5,7-tetramethyl-6,9,10-trioxa-adamantyl)-2-(diadamantylphosphinomethyl)cyclobutane; cis-1-(di-t-butylphosphinomethyl)-2-(diadamantylphosphinomethyl)cyclohexane; cis-1-(di-t-butylphosphinomethyl)-2-(diadamantylphosphinomethyl)cyclopentane; cis-1-(di-t-butylphosphinomethyl)-2-(diadamantylphosphinomethyl)cyclobutane; cis-1,2-bis(2-phospha-1,3,5-trimethyl-6,9,10-trioxatricyclo-{3.3.1.1[3.7]}decyl)cyclohexane; cis-1,2-bis(2-phospha-1,3,5-trimethyl-6,9,10-trioxatricyclo-{3.3.1.1[3.7]}decyl)cyclopentane; cis-1,2-bis(2-phospha-1,3,5-trimethyl-6,9,10-trioxatricyclo-{3.3.1.1[3.7]}decyl)cyclobutane; cis-1-(2-phospha-1,3,5-trimethyl-6,9,10-trioxatricyclo-{3.3.1.1[3.7]}decyl)-2-(di-t-butylphosphinomethyl)cyclohexane; cis-1-(2-phospha-1,3,5-trimethyl-6,9,10-trioxatricyclo-{3.3.1.1[3.7]}decyl)-2-(di-t-butylphosphinomethyl)cyclopentane; cis-1-(2-phospha-1,3,5-trimethyl-6,9,10-trioxatricyclo-{3.3.1.1[3.7]}decyl)-2-(di-t-butylphosphinomethyl)cyclobutane; cis-1-(2-phospha-1,3,5-trimethyl-6,9,10-trioxatricyclo-{3.3.1.1[3.7]}decyl)-2-(diadamantylphosphinomethyl)cyclohexane; cis-1-(2-phospha-1,3,5-trimethyl-6,9,10-trioxatricyclo-{3.3.1.1[3.7]}decyl)-2-(diadamantylphosphinomethyl)cyclopentane; cis-1-(2-phospha-1,3,5-trimethyl-6,9,10-trioxatricyclo-{3.3.1.1[3.7]}decyl)-2-(diadamantylphosphinomethyl)cyclobutane; cis-1,2-bis-perfluoro(2-phospha-1,3,5,7-tetramethyl-6,9,10-trioxatricyclo{3.3.1.1[3.7]}-decyl)cyclohexane; cis-1,2-bis-perfluoro(2-phospha-1,3,5,7-tetramethyl-6,9,10-trioxatricyclo{3.3.1.1[3.7]}decyl)cyclopentane; cis-1,2-bis-perfluoro(2-phospha-1,3,5,7-tetramethyl-6,9,10-trioxatricyclo{3.3.1.1[3.7]}decyl)cyclobutane; cis-1,2-bis-(2-phospha-1,3,5,7-tetra(trifluoro-methyl)-6,9,10-trioxatricyclo{3.3.1.1[3.7]}decyl)cyclohexane; cis-1,2-bis-(2-phospha-1,3,5,7-tetra(trifluoro-methyl)-6,9,10-trioxatricyclo{3.3.1.1[3.7]}decyl)cyclopentane; cis-1,2-bis-(2-phospha-1,3,5,7-tetra(trifluoro-methyl)-6,9,10-trioxatricyclo{3.3.1.1[3.7]}decyl)cyclobutane; (2-exo, 3-exo)-bicyclo[2.2.1]heptane-2,3-bis(di-tert-butylphosphinomethyl); (2-endo, 3-endo)-bicyclo[2.2.1]heptane-2,3-bis(di-tert-butylphosphinomethyl); 1,2-bis(di-t-butylphosphinomethyl)-4,5-diphenylbenzene; 1,2-bis(di-t-butylphosphinomethyl)-4-phenylbenzene; 1,2-bis(di-t-butylphosphinomethyl)-4,5-bis-(trimethylsilyl)benzene; 1,2-bis(di-t-butylphosphinomethyl)-4-(trimethylsilyl)benzene; 1,2-bis(2-phosphinomethyl-1,3,5,7-tetramethyl-6,9,10-trioxa-adamantyl)-4,5-diphenylbenzene; 1,2-bis(2-phosphinomethyl-1,3,5,7-tetramethyl-6,9,10-trioxa-adamantyl)-4-phenylbenzene; 1,2-bis(2-phosphinomethyl-1,3,5,7-tetramethyl-6,9,10-trioxa-adamantyl)-4,5-bis-(trimethylsilyl)benzene; 1,2-bis(2-phosphinomethyl-1,3,5,7-tetramethyl-6,9,10-trioxa-adamantyl)-4-(trimethylsilyl)benzene; 1,2-bis(di-adamantylphosphinomethyl)-4,5diphenylbenzene; 1,2-bis(di-adamantylphosphinomethyl)-4-phenylbenzene; 1,2-bis(di-adamantylphosphinomethyl)-4,5bis-(trimethylsilyl)benzene; 1,2-bis(di-adamantylphosphinomethyl)-4-(trimethylsilyl)benzene; 1-(P,P adamantyl, t-butyl phosphinomethyl)-2-(di-t-butylphosphinomethyl)-4,5-diphenylbenzene; 1-(P,P adamantyl, t-butyl phosphinomethyl)-2-(di-t-butylphosphinomethyl)-4-phenylbenzene; 1-(P,P adamantyl, t-butyl phosphinomethyl)-2-(di-t-butylphosphinomethyl)-4,5-bis-(trimethylsilyl)benzene; 1-(P,P adamantyl, t-butyl phosphinomethyl)-2-(di-t-butylphosphinomethyl)-4-(trimethylsilyl)benzene; 1-(2-phosphinomethyl-1,3,5,7-tetramethyl-6,9,10-trioxa-adamantyl)-2-(di-t-butylphosphinomethyl)4,5-diphenylbenzene; 1-(2-phosphinomethyl-1,3,5,7-tetramethyl-6,9,10-trioxa-adamantyl)-2-(di-t-butylphosphinomethyl)-4-phenyl benzene; 1-(2-phosphinomethyl-1,3,5,7-tetramethyl-6,9,10-trioxa-adamantyl)-2-(di-t-butylphosphinomethyl)4,5-bis-(trimethylsilyl)benzene; 1-(2-phosphinomethyl-1,3,5,7-tetramethyl-6,9,10-trioxa-adamantyl)-2-(di-t-butylphosphinomethyl)-4-(trimethylsilyl)benzene; 1-(2-phosphinomethyl-1,3,5,7-tetramethyl-6,9,10-trioxa-adamantyl)-2-(diadamantylphosphinomethyl)-4,5-diphenylbenzene; 1-(2-phosphinomethyl-1,3,5,7-tetramethyl-6,9,10-trioxa-adamantyl)-2-(diadamantylphosphinomethyl)-4-phenylbenzene; 1-(2-phosphinomethyl-1,3,5,7-tetramethyl-6,9,10-trioxa-adamantyl)-2-(diadamantylphosphinomethyl)-4,5-bis-(trimethylsilyl)benzene; 1-(2-phosphinomethyl-1,3,5,7-tetramethyl-6,9,10-trioxa-adamantyl)-2-(diadamantylphosphinomethyl)-4-(trimethylsilyl)benzene; 1-(di-t-butylphosphinomethyl)-2-(diadamantylphosphinomethyl)-4,5-diphenylbenzene; 1-(di-t-butylphosphinomethyl)-2-(diadamantylphosphinomethyl)-4-phenylbenzene; 1-(di-t-butylphosphinomethyl)-2-(diadamantylphosphinomethyl)-4,5-bis-(trimethylsilyl)benzene; 1-(di-t-butylphosphinomethyl)-2-(diadamantylphosphinomethyl)-4-(trimethylsilyl)benzene; 1,2-bis(2-phosphinomethyl-1,3,5-trimethyl-6,9,10-trioxatricyclo-{3.3.1.1[3.7]}decyl)-4,5-diphenylbenzene; 1,2-bis(2-phosphinomethyl-1,3,5-trimethyl-6,9,10-trioxatricyclo-{3.3.1.1[3.7]}decyl)-4-phenylbenzene; 1,2-bis(2-phosphinomethyl-1,3,5-trimethyl-6,9,10-trioxatricyclo-{3.3.1.1[3.7]}decyl)-4,5-bis-(trimethylsilyl)benzene; 1,2-bis(2-phosphinomethyl-1,3,5-trimethyl-6,9,10-trioxatricyclo-{3.3.1.1[3.7]}decyl)-4-(trimethylsilyl)benzene; 1-(2-phosphinomethyl-1,3,5-trimethyl-6,9,10-trioxatricyclo-{3.3.1.1[3.7]}decyl)-2-(di-t-butylphosphinomethyl)-4,5-diphenylbenzene; 1-(2- phosphinomethyl-1,3,5-trimethyl-6,9,10-trioxatricyclo-{3.3.1.1[3.7]}decyl)-2-(di-t-butylphosphinomethyl)-4-phenylbenzene; 1-(2-phosphinomethyl-1,3,5-trimethyl-6,9,10-trioxatricyclo-{3.3.1.1[3.7]}decyl)-2-(di-t-butylphosphinomethyl)-4,5-bis-(trimethylsilyl)benzene; 1-(2-phosphinomethyl-1,3,5-trimethyl-6,9,10-trioxatricyclo-{3.3.1.1[3.7]}decyl)-2-(di-t-butylphosphinomethyl)-4-(trimethylsilyl)benzene; 1-(2-phosphinomethyl-1,3,5-trimethyl-6,9,10-trioxatricyclo-{3.3.1.1[3.7]}decyl)-2-(diadamantylphosphinomethyl)-4,5-diphenylbenzene; 1-(2-phosphinomethyl-1,3,5-trimethyl-6,9,10-trioxatricyclo-{3.3.1.1[3.7]}decyl)-2-(diadamantylphosphinomethyl)-4-phenylbenzene; 1-(2-phosphinomethyl-1,3,5-trimethyl-6,9,10-trioxatricyclo-{3.3.1.1[3.7]}decyl)-2-(diadamantylphosphinomethyl)-4,5-bis-(trimethylsilyl)benzene; 1-(2-phosphinomethyl-1,3,5-trimethyl-6,9,10-trioxatricyclo-{3.3.1.1[3.7]}decyl)-2-(diadamantylphosphinomethyl)-4-(trimethylsilyl)benzene; 1,2-bis-perfluoro(2-phosphinomethyl-1,3,5,7-tetramethyl-6,9,10-trioxatricyclo{3.3.1.1[3.7]}-decyl)-4,5-diphenylbenzene; 1,2-bis-perfluoro(2-phosphinomethyl-1,3,5,7-tetramethyl-6,9,10-trioxatricyclo{3.3.1.1[3.7]}decyl)-4-phenylbenzene; 1,2-bis-perfluoro(2-phosphinomethyl-1,3,5,7-tetramethyl-6,9,10-trioxatricyclo{3.3.1.1[3.7]}-decyl)-4,5-bis-(trimethylsilyl)benzene; 1,2-bis-perfluoro(2-phosphinomethyl-1,3,5,7-tetramethyl-6,9,10-trioxatricyclo{3.3.1.1[3.7]}decyl)-4-(trimethylsilyl)benzene; 1,2-bis-(2-phosphinomethyl-1,3,5,7-tetra(trifluoro-methyl)-6,9,10-trioxatricyclo{3.3.1.1[3.7]}decyl)-4,5-diphenylbenzene; 1,2-bis-(2-phosphinomethyl-1,3,5,-tetra(trifluoro-methyl)-6,9,10-trioxatricyclo{3.3.1.1[3.7]}decyl)-4-phenylbenzene; 1,2-bis-(2-phosphinomethyl-1,3,5,7-tetra(trifluoro-methyl)-6,9,10-trioxatricyclo{3.3.1.1[3.7]}decyl)-4,5-bis-(trimethylsilyl)benzene; 1,2-bis-(2-phosphinomethyl-1,3,5,7-tetra(trifluoro-methyl)-6,9,10-trioxatricyclo{3.3.1.1[3.7]}decyl)-4-(trimethylsilyl)benzene; 1,2-bis(di-t-butylphosphinomethyl)-4,5-di-(2'-phenylprop-2'-yl)benzene; 1,2-bis(di-t-butylphosphinomethyl)-4-(2'-phenylprop-2'-yl)benzene; 1,2-bis(di-t-butylphosphinomethyl)-4,5-di-t-butylbenzene; 1,2-bis(di-t-butylphosphinomethyl)-4-t-butylbenzene; 1,2-bis(2-phosphinomethyl-1,3,5,7-tetramethyl-6,9,10-trioxa-adamantyl)-4,5-di-(2'-phenylprop-2'-yl)benzene; 1,2-bis(2-phosphinomethyl-1,3,5,7-tetramethyl-6,9,10-trioxa-adamantyl)-2-(2'-phenylprop-2'-yl)benzene; 1,2-bis(2-phosphinomethyl-1,3,5,7-tetramethyl-6,9,10-trioxa-adamantyl)-4,5-(di-t-butyl)benzene; 1,2-bis(2-phosphinomethyl-1,3,5,7-tetramethyl-6,9,10-trioxa-adamantyl)-4-t-butylbenzene; 1,2-bis(di-adamantylphosphinomethyl)-4,5-di-(2'-phenylprop-2'-yl)benzene; 1,2-bis(di-adamantylphosphinomethyl)-4-(2'-phenylprop-2'-yl)benzene; 1,2-bis(di-adamantylphosphinomethyl)-4,5-(di-t-butyl)benzene; 1,2-bis(di-adamantylphosphinomethyl)-4-t-butylbenzene; 1-(P,P adamantyl, t-butyl phosphinomethyl)-2-(di-t-butylphosphinomethyl)-4,5-di-(2'-phenylprop-2'-yl)benzene; 1-(P,P adamantyl, t-butyl phosphinomethyl)-2-(di-t-butylphosphinomethyl)-4-(2'-phenylprop-2'-yl)benzene; 1-(P,P adamantyl, t-butyl phosphinomethyl)-2-(di-t-butylphosphinomethyl)-4,5-(di-t-butyl)benzene ; 1-(P,P adamantyl, t-butyl phosphinomethyl)-2-(di-t-butylphosphinomethyl)-4-t-butylbenzene; 1-(2-phosphinomethyl-1,3,5,7-tetramethyl-6,9,10-trioxa-adamantyl)-2-(di-t-butylphosphinomethyl)4,5-di-(2'-phenylprop-2'-yl)benzene; 1-(2-phosphinomethyl-1,3,5,7-tetramethyl-6,9,10-trioxa-adamantyl)-2-(di-t-butylphosphinomethyl)-4-(2'-phenylprop-2'-yl)benzene; 1-(2-phosphinomethyl-1,3,5,7-tetramethyl-6,9,10-trioxa-adamantyl)-2-(di-t-butylphosphinomethyl)4,5-(di-t-butyl)benzene; 1-(2-phosphinomethyl-1,3,5,7-tetramethyl-6,9,10-trioxa-adamantyl)-2-(di-t-butylphosphinomethyl)-4-t-butylbenzene; 1-(2-phosphinomethyl-1,3,5,7-tetramethyl-6,9,10-trioxa-adamantyl)-2-(diadamantylphosphinomethyl)-4,5-di-(2'-phenylprop-2'-yl) benzene; 1-(2-phosphinomethyl-1,3,5,7-tetramethyl-6,9,10-trioxa-adamantyl)-2-(diadamantylphosphinomethyl)-4-(2'-phenylprop-2'-yl)benzene; 1-(2-phosphinomethyl-1,3,5,7-tetramethyl-6,9,10-trioxa-adamantyl)-2-(diadamantylphosphinomethyl)-4,5-(di-t-butyl)benzene; 1-(2-phosphinomethyl-1,3,5,7-tetramethyl-6,9,10-trioxa-adamantyl)-2-(diadamantylphosphinomethyl)-4-t-butylbenzene; 1-(di-t-butylphosphinomethyl)-2-(diadamantylphosphinomethyl)-4,5-di-(2'-phenylprop-2'-yl)benzene; 1-(di-t-butylphosphinomethyl)-2-(diadamantylphosphinomethyl)-4-(2'-phenylprop-2'-yl)benzene; 1-(di-t-butylphosphinomethyl)-2-(diadamantylphosphinomethyl)-4,5-(di-t-butyl)benzene; 1-(di-t-butylphosphinomethyl)-2-(diadamantylphosphinomethyl)-4-t-butylbenzene; 1,2-bis(2-phosphinomethyl-1,3,5-trimethyl-6,9,10-trioxatricyclo-{3.3.1.1[3.7]}decyl)-4,5-di-(2'-phenylprop-2'-yl)benzene; 1,2-bis(2-phosphinomethyl-1,3,5-trimethyl-6,9,1-trioxatricyclo-{3.3.1.1[3.7]}decyl)-4-(2'-phenylprop-2'-yl)benzene; 1,2-bis(2-phosphinomethyl-1,3,5-trimethyl-6,9,10-trioxatricyclo-{3.3.1.1[3.7]}decyl)-4,5-(di-t-butyl)benzene; 1,2-bis(2-phosphinomethyl-1,3,5-trimethyl-6,9,10-trioxatricyclo-{3.3.1.1[3.7]}decyl)-4-t-butylbenzene; 1-(2-phosphinomethyl-1,3,5-trimethyl-6,9,10-trioxatricyclo-{3.3.1.1[3.7]}decyl)-2-(di-t-butylphosphinomethyl)-4,5-di-(2'-phenylprop-2'-yl)benzene; 1-(2-phosphinomethyl-1,3,5-trimethyl-6,9,10-trioxatricyclo-{3.3.1.1[3.7]}decyl)-2-(di-t-butylphosphinomethyl)-4-(2'-phenylprop-2'-yl)benzene; 1-(2-phosphinomethyl-1,3,5-trimethyl-6,9,10-trioxatricyclo-{3.3.1.1[3.7]}decyl)-2-(di-t-butylphosphinomethyl)-4,5-(di-t-butyl)benzene; 1-(2-phosphinomethyl-1,3,5-trimethyl-6,9,10-trioxatricyclo-{3.3.1.1[3.7]}decyl)-2-(di-t-butylphosphinomethyl)-4-t-butylbenzene; 1-(2-phosphinomethyl-1,3,5-trimethyl-6,9,10-trioxatricyclo-{3.3.1.1[3.7]}decyl)-2-(diadamantylphosphinomethyl)-4,5-di-(2'-phenylprop-2'-yl)benzene; 1-(2-phosphinomethyl-1,3,5-trimethyl-6,9,10-trioxatricyclo-{3.3.1.1[3.7]}decyl)-2-(diadamantylphosphinomethyl)-4-(2'-phenylprop-2'-yl)benzene; 1-(2-phosphinomethyl-1,3,5-trimethyl-6,9,10-trioxatricyclo-{3.3.1.1[3.7]}decyl)-2-(diadamantylphosphinomethyl)-4,5-(di-t-butyl)benzene; 1-(2-phosphinomethyl-1,3,5-trimethyl-6,9,10-trioxatricyclo-{3.3.1.1[3.7]}decyl)-2-(diadamantylphosphinomethyl)-4-t-butylbenzene; 1,2-bis-perfluoro(2-phosphinomethyl-1,3,5,7-tetramethyl-6,9,10-trioxatricyclo{3.3.1.1[3.7]}-decyl)-4,5-di-(2'-phenylprop-2'-yl)benzene; 1,2-bis-perfluoro(2-phosphinomethyl-1,3,5,7-tetramethyl-6,9,10-trioxatricyclo{3.3.1.1[3.7]}decyl)-4-(2'-phenylprop-2'-yl)benzene; 1,2-bis-perfluoro(2-phosphinomethyl-1,3,5,7-tetramethyl-6,9,10-trioxatricyclo{3.3.1.1[3.7]}-decyl)-4,5-(di-t-butyl)benzene; 1,2-bis-perfluoro(2-phosphinomethyl-1,3,5,7-tetramethyl-6,9,10-trioxatricyclo{3.3.1.1[3.7]}decyl)-4-t-butylbenzene; 1,2-bis-(2-phosphinomethyl-1,3,5,7-tetra(trifluoro-methyl)-6,9,10-trioxatricyclo{3.3.1.1[3.7]}decyl)-4,5-di-(2'-phenylprop-2'-yl)benzene; 1,2-bis-(2-phosophinomethyl-1,3,5,7-tetra(triflouro-methyl)-6,9,10-trioxatricyclo{3.3.1.1[3.7]}decyl)-4-(2'-phenylprop-2'-yl)benzene; 1,2-bis-(2-phosphinomethyl-1,3,5,7-tetra(trifluoro-methyl)-6,9,10-trioxatricyclo{3.3.1.1[3.7]}decyl)-4,5-(di-t-butyl)benzene; 1,2-bis-(2-phosphinomethyl-1,3,5,7-tetra(trifluoro-methyl)-6,9,10-trioxatricyclo{3.3.1.1[3.7]}decyl)-4-t-butylbenzene; 1,2-bis (di-t-butylphosphinomethyl)-4,5-diphenylferrocene; 1,2-bis (di-t-butylphosphinomethyl)-4-(or 1')phenylferrocene; 1,2-bis(di-t-butylphosphinomethyl)-4,5-bis-(trimethylsilyl)ferrocene; 1,2-bis(di-t-butylphosphinomethyl)-4-(or 1')(trimethylsilyl)ferrocene; 1,2-bis(2-phosphinomethyl-1,3,5,7-tetramethyl-6,9,10-trioxa-adamantyl)-4,5-diphenylferrocene; 1,2-bis(2-phosphinomethyl-1,3,5,7-tetramethyl-6,9,10-trioxa-adamantyl)4-(or 1')phenylferrocene; 1,2-bis(2-phosphinomethyl-1,3,5,7-tetramethyl-6,9,10-trioxa-adamantyl)-4,5-bis-(trimethylsilyl)ferrocene; 1,2-bis(2-phosphinomethyl-1,3,5,7-tetramethyl-6,9,10-trioxa-adamantyl)4-(or 1')(trimethylsilyl)ferrocene; 1,2-bis(di-adamantylphosphinomethyl)-4,5diphenylferrocene; 1,2-bis(di-adamantylphosphinomethyl)-4-(or 1')phenylferrocene; 1,2-bis(di-adamantylphosphinomethyl)-4,5bis-(trimethylsilyl)ferrocene; 1,2-bis(di-adamantylphosphinomethyl)-4-(or 1')(trimethylsilyl)ferrocene; 1-(P,P adamantyl, t-butyl phosphinomethyl)-2-(di-t-butylphosphinomethyl)-4,5-diphenylferrocene; 1-(P,P adamantyl, t-butyl phosphinomethyl)-2-(di-t-butylphosphinomethyl)-4-(or 1')phenylferrocene; 1-(P,P adamantyl, t-butyl phosphinomethyl)-2-(di-t-butylphosphinomethyl)-4,5-bis-(trimethylsilyl)ferrocene; 1-(P,P adamantyl, t-butyl phosphinomethyl)-2-(di-t-butylphosphinomethyl)-4-(or 1')(trimethylsilyl)ferrocene; 1-(2-phosphinomethyl-1,3,5,7-tetramethyl-6,9,10-trioxa-adamantyl)-2-(di-t-butylphosphinomethyl)4,5-diphenylferrocene; 1-(2-phosphinomethyl-1,3,5,7-tetramethyl-6,9,10-trioxa-adamantyl)-2-(di-t-butylphosphinomethyl)-4-(or 1')phenylferrocene; 1-(2-phosphinomethyl-1,3,5,7-tetramethyl-6,9,10-trioxa-adamantyl)-2-(di-t-butylphosphinomethyl)4,5-bis-(trimethylsilyl)ferrocene; 1-(2-phosphinomethyl-1,3,5,7-tetramethyl-6,9,10-trioxa-adamantyl)-2-(di-t-butylphosphinomethyl)-4-(or 1')(trimethylsilyl)ferrocene; 1-(2-phosphinomethyl-1,3,5,7-tetramethyl-6,9,10-trioxa-adamantyl)-2-(diadamantylphosphinomethyl)-4,5-diphenylferrocene; 1-(2-phosphinomethyl-1,3,5,7-tetramethyl-6,9,10-trioxa-adamantyl)-2-(diadamantylphosphinomethyl)-4-(or 1')phenylferrocene; 1-(2-phosphinomethyl-1,3,5,7-tetramethyl-6,9,10-trioxa-adamantyl)-2-(diadamantylphosphinomethyl)-4,5-bis-(trimethylsilyl)ferrocene; 1-(2-phosphinomethyl-1,3,5,7-tetramethyl-6,9,10-trioxa-adamantyl)-2-(diadamantylphosphinomethyl)-4-(or 1')(trimethylsilyl)ferrocene; 1-(di-t-butylphosphinomethyl)-2-(diadamantylphosphinomethyl)-4,5-diphenylferrocene; 1-(di-t-butylphosphinomethyl)-2-(diadamantylphosphinomethyl)-4-(or 1')phenylferrocene; 1-(di-t-butylphosphinomethyl)-2-(diadamantylphosphinomethyl)-4,5-bis-(trimethylsilyl)ferrocene; 1-(di-t-butylphosphinomethyl)-2-(diadamantylphosphinomethyl)-4-(or 1')(trimethylsilyl)ferrocene; 1,2-bis(2-phosphinomethyl-1,3,5-trimethyl-6,9,10-trioxatricyclo-{3.3.1.1[3.7]}decyl)-4,5-diphenylferrocene; 1,2-bis(2-phosphinomethyl-1,3,5-trimethyl-6,9,10-trioxatricyclo-{3.3.1.1[3.7]}decyl)-4-(or 1')phenylferrocene; 1,2-bis(2-phosphinomethyl-1,3,5-trimethyl-6,9,10-trioxatricyclo-{3.3.1.1[3.7]}decyl)-4,5-bis-(trimethylsilyl)ferrocene; 1,2-bis(2-phosphinomethyl-1,3,5-trimethyl-6,9,10-trioxatricyclo-{3.3.1.1[3.7]}decyl)-4-(or 1')(trimethylsilyl)ferrocene; 1-(2-phosphinomethyl-1,3,5-trimethyl-6,9,10-trioxatricyclo-{3.3.1.1[3.7]}decyl)-2-(di-t-butylphosphinomethyl)-4,5-diphenylferrocene; 1-(2-phosphinomethyl-1,3,5-trimethyl-6,9,10-trioxatricyclo-{3.3.1.1[3.7]}decyl)-2-(di-t-butylphosphinomethyl)-4-(or 1')phenylferrocene; 1-(2-phosphinomethyl-1,3,5-trimethyl-6,9,10-trioxatricyclo-{3.3.1.1[3.7]}decyl)-2-(di-t-butylphosphinomethyl)-4-(or 1')(trimethylsilyl)ferrocene; 1-(2-phosphinomethyl-1,3,5-trimethyl-6,9,10-trioxatricyclo-{3.3.1.1[3.7]}decyl)-2-(di-adamantylphosphinomethyl)-4,5-diphenylferrocene; 1-(2-phosphinomethyl-1,3,5-trimethyl-6,9,10-trioxatricyclo-{3.3.1.1[3.7]}decyl)-2-(diadamantylphosphinomethyl)-4-(or 1')phenylferrocene; 1-(2-phosphinomethyl-1,3,5-trimethyl-6,9,10-trioxatricyclo-{3.3.1.1[3.7]}decyl)-2-(diadamantylphosphinomethyl)-4,5-bis-(trimethylsilyl)ferrocene; 1-(2-phosphinomethyl-1,3,5-trimethyl-6,9,10-trioxatricyclo-{3.3.1.1[3.7]}decyl)-2-(diadamantylphosphinomethyl)-4-(or 1')(trimethylsilyl)ferrocene; 1,2-bis-perfluoro(2-phosphinomethyl-1,3,5,7-tetramethyl-6,9,10-trioxatricyclo{3.3.1.1[3.7]}-decyl)-4,5-diphenylferrocene; 1,2-bis-perfluoro(2-phosphinomethyl-1,3,5,7-tetramethyl-6,9,10-trioxatricyclo{3.3.1.1[3.7]}decyl)-4-(or 1')phenylferrocene; 1,2-bis-perfluoro(2-phosphinomethyl-1,3,5,7-tetramethyl-6,9,10-trioxatricyclo{3.3.1.1[3.7]}-decyl)-4,5-bis-(trimethylsilyl)ferrocene; 1,2-bis-perfluoro(2-phosphinomethyl-1,3,5,7-tetramethyl-6,9,10-trioxatricyclo{3.3.1.1[3.7]}decyl)-4-(or 1')(trimethylsilyl)ferrocene; 1,2-bis-(2-phosphinomethyl-1,3,5,7-tetra(trifluoro-methyl)-6,9,10-trioxatricyclo{3.3.1.1[3.7]}decyl)-4,5-diphenylferrocene; 1,2-bis-(2-phosphinomethyl-1,3,5,7-tetra(trifluoro-methyl)-6,9,10-trioxatricyclo{3.3.1.1[3.7]}decyl)-4-(or 1')phenylferrocene; 1,2-bis-(2-phosphinomethyl-1,3,5,7-tetra(trifluoro-methyl)-6,9,10-trioxatricyclo{3.3.1.1[3.7]}decyl)-4,5-bis-(trimethylsilyl)ferrocene; 1,2-bis-(2-phosphinomethyl-1,3,5,7-tetra(trifluoro-methyl)-6,9,10-trioxatricyclo{3.3.1.1[3.7]}decyl)-4-(or 1')(trimethylsilyl)ferrocene; 1,2-bis(di-t-butylphosphinomethyl)-4,5-di-(2'-phenylprop-2'-yl)ferrocene; 1,2-bis(di-t-butylphosphinomethyl)-4-(or 1')(2'-phenylprop-2'-yl)ferrocene; 1,2-bis(di-t-butylphosphinomethyl)-4,5-di-t-butylferrocene; 1,2-bis(di-t-butylphosphinomethyl)-4-(or 1')t-butylferrocene; 1,2-bis(2-phosphinomethyl-1,3,5,7-tetramethyl-6,9,10-trioxa-adamantyl)-4,5-di-(2'-phenylprop-2'-yl)ferrocene; 1,2-bis(2-phosphinomethyl-1,3,5,7-tetramethyl-6,9,10-trioxa-adamantyl)-4-(or 1')(2'-phenylprop-2'-yl)ferrocene; 1,2-bis(2-phosphinomethyl-1,3,5,7-tetramethyl-6,9,10-trioxa-adamantyl)-4,5-(di-t-butyl)ferrocene; 1,2-bis(2-phosphinomethyl-1,3,5,7-tetramethyl-6,9,10-trioxa-adamantyl)-4-(or 1')t-butylfeaocene; 1,2-bis (di-adamantylphosphinomethyl)-4,5-di-(2'-phenylprop-2'-yl)ferrocene; 1,2-bis(di-adamantylphosphinomethyl)-4-(or 1')(2'-phenylprop-2'-yl)ferrocene; 1,2-bis(di-adamantylphosphinomethyl)-4,5-(di-t-butyl)ferrocene; 1,2-bis(di-adamantylphosphinomethyl)-4-(or 1')t-butylferrocene; 1-(P,P adamantyl, t-butyl phosphinomethyl)-2-(di-t-butylphosphinomethyl)-4,5-di-(2'-phenylprop-2'-yl)ferrocene; 1-(P,P adamantyl, t-butyl phosphinomethyl)-2-(di-t-butylphosphinomethyl)-4-(or 1')(2'-phenylprop-2'-yl)ferrocene; 1-(P,P adamantyl, t-butyl phosphinomethyl)-2-(di-t-butylphosphinomethyl)-4,5-(di-t-butyl)ferrocene; 1-(P,P adamantyl, t-butyl phosphinomethyl)-2-(di-t-butylphosphinomethyl)-4-(or 1')t-butylferrocene; 1-(2-phosphinomethyl-1,3,5,7-tetramethyl-6,9,10-trioxa-adamantyl)-2-(di-t-butylphosphinomethyl)4,5-di-(2'-phenylprop-2'-yl)ferrocene; 1-(2-phosphinomethyl-1,3,5,7-tetramethyl-6,9,10-trioxa-adamantyl)-2-(di-t-butylphosphinomethyl)-4-(or 1')(2'-phenylprop-2'-yl)ferrocene; 1-(2-phosphinomethyl-1,3,5,7-tetramethyl-6,9,10-trioxa-adamantyl)-2-(di-t-butylphosphinomethyl)4,5-(di-t-butyl)ferrocene; 1-(2-phosphinomethyl-1,3,5,7-tetramethyl-6,9,10-trioxa-adamantyl)-2-(di-t-butylphosphinomethyl)-4-(or 1')t-butylferrocene; 1-(2-phosphinomethyl-1,3,5,7-tetramethyl- 6,9,10-trioxa-adamantyl)-2-(diadamantylphosphinomethyl)-4,5-di-(2'-phenylprop-2'-yl)ferrocene; 1-(2-phosphinomethyl-1,3,5,7-tetramethyl-6,9,10-trioxa-adamantyl)-2-(diadamantylphosphinomethyl)-4-(or 1')(2'-phenylprop-2'-yl)ferrocene; 1-(2-phosphinomethyl-1,3,5,7-tetramethyl-6,9,10-trioxa-adamantyl)-2-(diadamantylphosphinomethyl)-4,5-(di-t-butyl)ferrocene; 1-(2-phosphinomethyl-1,3,5,7-tetramethyl-6,9,10-trioxa-adamantyl)-2-(diadamantylphosphinomethyl)-4-(or 1')t-butylferrocene; 1-(di-t-butylphosphinomethyl)-2-(diadamantylphosphinomethyl)-4,5-di-(2'-phenylprop-2'-yl)ferrocene; 1-(di-t-butylphosphinomethyl)-2-(diadamantylphosphinomethyl)-4-(or 1')(2'-phenylprop-2'-yl)ferrocene; 1-(di-t-butylphosphinomethyl)-2-(diadamantylphosphinomethyl)-4,5-(di-t-butyl)ferrocene; 1-(di-t-butylphosphinomethyl)-2-(diadamantylphosphinomethyl)-4-(or 1')t-butylferrocene; 1,2-bis(2-phosphinomethyl-1,3,5-trimethyl-6,9,10-trioxatricyclo-{3.3.1.1[3.7]}decyl)-4,5-di-(2'-phenylprop-2'-yl)ferrocene; 1,2-bis(2-phosphinomethyl-1,3,5-trimethyl-6,9,10-trioxatricyclo-{3.3.1.1[3.7]}decyl)-4-(or 1')(2'-phenylprop-2'-yl)ferrocene; 1,2-bis(2-phosphinomethyl-1,3,5-trimethyl-6,9,10-trioxatricyclo-{3.3.1.1[3.7]}decyl)-4,5-(di-t-butyl)ferrocene; 1,2-bis(2-phosphinomethyl-1,3,5-trimethyl-6,9,10-trioxatricyclo-{3.3.1.1[3.7]}decyl)-4-(or 1')t-butylferrocene; 1-(2-phosphinomethyl-1,3,5-trimethyl-6,9,10-trioxatricyclo-{3.3.1.1[3.7]}decyl)-2-(di-t-butylphosphinomethyl)-4,5-di-(2'-phenylprop-2'-yl)ferrocene; 1-(2-phosphinomethyl-1,3,5-trimethyl-6,9,10-trioxatricyclo-{3.3.1.1[3.7]}decyl)-2-(di-t-butylphosphinomethyl)-4-(or 1')(2'-phenylprop-2'-yl)ferrocene; 1-(2-phosphinomethyl-1,3,5-trimethyl-6,9,10-trioxatricyclo-{3.3.1.1[3.7]}decyl)-2-(di-t-butylphosphinomethyl)-4,5-(di-t-butyl)ferrocene; 1-(2-phosphinomethyl-1,3,5-trimethyl-6,9,10-trioxatricyclo-{3.3.1.1[3.7]}decyl)-2-(di-t-butylphosphinomethyl)-4-(or 1')t-butylferrocene; 1-(2-phosphinomethyl-1,3,5-trimethyl-6,9,10-trioxatricyclo-{3.3.1.1[3.7]}decyl)-2-(diadamantylphosphinomethyl)4,5-di-(2'-phenylprop-2'-yl)ferrocene; 1-(2-phosphinomethyl-1,3,5-trimethyl-6,9,10-trioxatricyclo-{3.3.1.1[3.7]}decyl)-2-(diadamantylphosphinomethyl)-4-(or 1')(2'-phenylprop-2'-yl)ferrocene; 1-(2-phosphinomethyl-1,3,5-trimethyl-6,9,10-trioxatricyclo-{3.3.1.1[3.7]}decyl)-2-(diadamantylphosphinomethyl)-4,5-(di-t-butyl)ferrocene; 1-(2-phosphinomethyl-1,3,5-trimethyl-6,9,10-trioxatricyclo-{3.3.1.1[3.7]}decyl)-2-(diadamantylphosphinomethyl)-4-(or 1')t-butylferrocene; 1,2-bis-perfluoro(2-phosphinomethyl-1,3,5,7-tetramethyl-6,9,10-trioxatricyclo{3.3.1.1[3.7]}-decyl)-4,5-di-(2'-phenylprop-2'-yl)ferrocene; 1,2-bis-perfluoro(2-phosphinomethyl-1,3,5,7-tetramethyl-6,9,10-trioxatricyclo{3.3.1.1[3.7]}decyl)-4-(or 1')(2'-phenylprop-2'-yl)ferrocene; 1,2-bis-perfluoro(2-phosphinomethyl-1,3,5,7-tetramethyl-6,9,10-trioxatricyclo{3.3.1.1[3.7]}-decyl)-4,5-(di-t-butyl)ferrocene; 1,2-bis-perfluoro(2-phosphinomethyl-1,3,5,7-tetramethyl-6,9,10-trioxatricyclo{3.3.1.1[3.7]}decyl)-4-(or 1')t-butylferrocene; 1,2-bis-(2-phosphinomethyl-1,3,5,7-tetra(trifluoro-methyl)-6,9,10-trioxatricyclo{3.3.1.1[3.7]}decyl)-4,5-di-(2'-phenylprop-2'-yl)ferrocene; 1,2-bis-(2-phosphinomethyl-1,3,5,7-tetra(trifluoro-methyl)-6,9,10-trioxatricyclo{3.3.1.1[3.7]}decyl)-4-(or 1')(2'-phenylprop-2'-yl)ferrocene; 1,2-bis-(2-phosphinomethyl-1,3,5,7-tetra(trifluoro-methyl)-6,9,10-trioxatricyclo{3.3.1.1[3.7]}decyl)-4,5-(di-t-butyl)ferrocene; and 1,2-bis-(2-phosphinomethyl-1,3,5,7-tetra(trifluoro-methyl)-6,9,10-trioxatricyclo{3.3.1.1[3.7]}decyl)-4-(or 1')t-butylferrocene.

8. A process as claimed in claim 4, wherein the amount of complexing compound in the reaction mixture is calculated to provide a molar excess of at least 10% over the amount required for the stoichiometric reaction.

9. A process as claimed in claim 4, wherein the reaction is carried out in the presence of a solvent.

10. A process for the carbonylation of ethylenically unsaturated compounds comprising reacting said compound with carbon monoxide in the presence of a source of hydroxyl groups and of a catalyst system, the catalyst system comprising a metal complex according to claim 1.

11. A catalyst system as claimed in claim 3, wherein said metal M comprises a precious metal selected from the group consisting of Ru, Rh, Os, Ir, Pt and Pd.

12. A catalyst system as claimed in claim 11, wherein said metal M comprises Ru, Pt or Pd.

13. A process as claimed in claim 4, wherein said metal M comprises a precious metal selected from the group consisting of Ru, Rh, Os, Ir, Pt and Pd.

14. A process as claimed in claim 13, wherein said metal M comprises Ru, Pt or Pd.

15. A metal complex as claimed in claim 1, wherein $Q^1$ and $Q^2$ represent phosphorous.

16. A metal complex as claimed in claim 1, wherein $Q^3$ is present and represents phosphorous.

* * * * *